US010731187B2

(12) United States Patent
Jaeger et al.

(10) Patent No.: US 10,731,187 B2
(45) Date of Patent: Aug. 4, 2020

(54) RECOMBINANT STRAIN PRODUCING O-AMINOBENZOATE AND FERMENTATIVE PRODUCTION OF ANILINE FROM RENEWABLE RESOURCES VIA 2-AMINOBENZOIC ACID

(71) Applicant: Covestro Deutschland AG, Leverkusen (DE)

(72) Inventors: Gernot Jaeger, Erkelenz (DE); Jorgen Magnus, Dusseldorf (DE); Amgad Salah Moussa, Cologne (DE); Guenter Olf, Monheim (DE); Giulio Lolli, Cologne (DE); Swantje Behnken, Cologne (DE); Jung-Won Youn, Stuttgart (DE); Mohammad Yalfani, Aachen (DE); Georg Sprenger, Backnang (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/119,825

(22) PCT Filed: Feb. 19, 2015

(86) PCT No.: PCT/EP2015/053526
§ 371 (c)(1),
(2) Date: Aug. 18, 2016

(87) PCT Pub. No.: WO2015/124687
PCT Pub. Date: Aug. 27, 2015

(65) Prior Publication Data
US 2017/0152535 A1    Jun. 1, 2017

(30) Foreign Application Priority Data

Feb. 20, 2014  (EP) .................................... 14155936
Dec. 5, 2014   (EP) .................................... 14196432

(51) Int. Cl.
| | |
|---|---|
| *C12P 13/00* | (2006.01) |
| *C12P 13/02* | (2006.01) |
| *C12P 13/04* | (2006.01) |
| *C12N 15/78* | (2006.01) |
| *C12N 15/77* | (2006.01) |
| *C12N 15/70* | (2006.01) |
| *C12N 9/90* | (2006.01) |
| *C12N 9/10* | (2006.01) |
| *C12N 15/52* | (2006.01) |

(52) U.S. Cl.
CPC .......... *C12P 13/001* (2013.01); *C12N 9/1077* (2013.01); *C12N 9/90* (2013.01); *C12N 15/52* (2013.01); *C12N 15/70* (2013.01); *C12N 15/77* (2013.01); *C12N 15/78* (2013.01); *C12P 13/02* (2013.01); *C12P 13/04* (2013.01); *C12Y 204/02018* (2013.01); *C12Y 504/99005* (2013.01)

(58) Field of Classification Search
CPC ....... C12P 13/001; C12N 15/52; C12N 15/70; C12N 15/77; C12N 15/78; C12N 9/1077; C12N 9/90; C12Y 204/02018; C12Y 504/99005
See application file for complete search history.

(56) References Cited

U.S. PATENT DOCUMENTS

| | | | |
|---|---|---|---|
| 4,910,336 A | 3/1990 | Goodman | |
| 6,962,794 B2 * | 11/2005 | Valle ........................ | C12N 1/20 435/108 |
| 2011/0097767 A1 * | 4/2011 | Pharkya ................. | C12N 15/52 435/128 |
| 2013/0302860 A1 | 11/2013 | Yukawa et al. | |

FOREIGN PATENT DOCUMENTS

| | | | | |
|---|---|---|---|---|
| EP | 0549421 A1 * | 6/1993 | ............... | C12G 3/02 |
| EP | 2660313 A1 | 11/2013 | | |
| JP | 02-135093 | * 5/1990 | .............. | C12P 13/04 |

(Continued)

OTHER PUBLICATIONS

Balderas-Hernandez et al., Metabolic engineering for improving anthranilate synthesis from glucose in *Escherichia coli*. Microbial Cell Factories. 2009, vol. 8: 19, 12 pages (Year: 2009).*
Broun et al., Catalytic plasticity of fatty acid modification enzymes underlying chemical diversity of plant lipids. Science, 1998, vol. 282: 1315-1317. (Year: 1998).*
Devos et al., Practical limits of function prediction. Proteins: Structure, Function, and Genetics. 2000, vol. 41: 98-107. (Year: 2000).*
Katsumata et al., Hyperproduction of tryptophan in Corynebacterium glutamicum by pathway engineering. Nat. Bloterchnol., 1993, vol. 11: 921-925 (Year: 1993).*

(Continued)

*Primary Examiner* — Ganapathirama Raghu
(74) *Attorney, Agent, or Firm* — Jed C. Benson; Donald R. Palladino

(57) ABSTRACT

The invention provides a recombinant microbial host cell capable of converting a raw material comprising a fermentable carbon substrate to o-aminobenzoate biologically. The invention further provides a method for producing aniline, comprising the steps of: a) producing o-aminobenzoate by fermentation of a raw material comprising at least one fermentable carbon substrate using the recombinant microbial host cell of the capable of converting said raw material comprising at least one fermentable carbon substrate to o-aminobenzoate biologically, wherein said o-aminobenzoate comprises anthranilate anion, b) converting said o-aminobenzoate from said anthranilate anion to anthranilic acid by acid protonation, c) recovering said anthranilic acid by precipitation or by dissolving in an organic solvent, and d) converting said anthranilic acid to aniline by thermal decarboxylation in an organic solvent.

45 Claims, 39 Drawing Sheets

Specification includes a Sequence Listing.

(56) References Cited

FOREIGN PATENT DOCUMENTS

| JP | 02135093 A | | 5/1990 | |
|---|---|---|---|---|
| JP | 05-000094 | * | 1/1993 | ............ C12P 13/02 |
| JP | 05000094 A | | 1/1993 | |
| WO | 20070065767 A1 | | 6/2007 | |
| WO | 20130103894 A1 | | 7/2013 | |

OTHER PUBLICATIONS

Seffernick et al., Melamine deaminase and Atrazine chlorohydrolase: 98 percent identical but functionally different. J. Bacteriol., 2001, vol. 183 (8): 2405-2410. (Year: 2001).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Anthranilate; 3 pages downloaded from http://www.chemspider.com/Chemical-Structure.4573589.html, dated Nov. 7, 2018.*
Dewick PM., The biosynthesis of shikimate metabolites. Natural Product Repors, 1995: 101-133.*
Ikeda M., Towards bacterial strains overproducing L-tryptophan and other aromatics by metabolic engineering. Appl Microbiol Biotechnol., 2006, vol. 69: 615-626. (Year: 2006).*
Sasaki et al., Identification of mannose uptake and catabolism genes in Corynebacterium glutamicum and genetic engineering for simultaneous utilization of mannose and glucose. Appl Microbiol Biotechnol., 2011, vol. 89: 1905-1916. (Year: 2011).*
Bernasconi et al; "Functional Expression of *Arabidopsis thaliana* Anthranilate Synthase Subunit I in *Escherichia coli*"; Plant Physiol.; (1994); 106; pp. 353-358; Sandoz Agro Inc., Research Division, 975 California Avenue, Palo Alto, California 94304-1104.
Leuchtenberger et al; "Biotechnological production of amino acids and derivatives: current status and prospects"; Appl Microbiol Biotechnol; Published online: Sep. 30, 2005; 69: pp. 1-8; Springer-Verlag 2005; Dusseldorf, Germany.
Kalinowski et al; "The complete Corynebacterium glutamicum ATCC 13032 genome sequence and its impact on the production of L-aspartate-derived amino acids and vitamins"; Journal of Biotechnology 104 (2013); pp. 5-25; Elsevier; Hilden, Germany.
Ikeda et al; "A genome-based approach to create a minimally mutated, Corynebacterium glutamicum strain for efficient L-lysine production"; Journal of Industrial Microbiology & Biotechnology 33 (7): 610-615; Issue Date: Jul. 2006; Shinshu University Institutional Repository; Japan.
Ikeda et al; "The Corynebacterium glutamicum genome: features and impacts on biotechnological processes"; Appl Microbiol Biotechnol 62:99-109; Published online: May 13, 2003; Springer-Verlag 2003; Japan.
Li et al; "Genetic and biochemical identification of the chorismate mutase from Corynebacterium glutamicum"; Accepted: Jul. 3 2009; Microbiology (2009); 155, pp. 3382-3391; Great Britain.
Seo et al; "Synthesis and Single-crystal Structure of Fully Dehydrated Fully Ca2+-exchanged Zeolite Y (FAU), Ca35.5 [SI121AI71O384]-FAU; Crystal Structure of Ca2+-exchanged Zeolite Y; Bull. Korean Chem. Soc. 2009, vol. 30, No. 8; pp. 1703-1710; Accepted Jun. 8, 2009; Korea.
Wierckx et al; "Engineering of Solvent-Tolerant Pseudomonas putida S12 for Bioproduction of Phenol from Glucose"; Applied and Environmental Microbiology, Dec. 2005; vol. 71, No. 12; pp. 8221-8227; American Society for Microbiology.
Silva-Rocha et al; "The Standard European Vector Architecture (SEVA): a coherent platform for the analysis and deployment of complex prokaryotic phenotyes"; Nucleic Acids Research, 2013, vol. 41, Database issue, Published online Nov. 23, 2012; Published by Oxford University Press; Spain.
Choi et al; "A 10-min method for preparation of highly electrocompetent Pseudomonas aeruginosa cells: Application or DNA fragment transfer between chromosomes and plasmid transformation"; Journal of Microbiological Methods 64 (2006); pp. 391-397; Available online Jun. 28, 2005; Colorado State University; Fort Collins, Colorado, United States.
Martinez-Garcia et al; "pBAM1: an all-synthetic genetic tool for analysis and construction of complex bacterial phenotypes"; BioMed Central: BMC Microbiology 2011, 11:38; pp. 1-13; Spain.
Kubota et al; "Chorismate-dependent transcriptional regulation of quinate/shikimate utilization genes by LysR-type transcriptional regulator QsuR in Corynebacterium glutamicum: carbon flow control at metabolic branch point"; Molecular Microbiology; (2014); 92(2), pp. 356-368; First published online Mar. 10, 2014, John Wiley & Sons Ltd.; Research Institute of Innovative Technology for the Earth (RITE), Japan.
Tanaka et al; "Incorporation and remodeling of extracellular phosphatidylcholine with short acyl residues in *Saccharomyces cerevisiae*"; Biochimica et Biophysica Acta 1781 (2008); pp. 391-399; Elsevier; Japan.
Siebold et al; "Carbohydrate transporters of the bacterial phosphoenolpyruvate: sugar phosphotransferase system (PTS)"; First published online Jul. 26, 2001; FEBS Letters 504 (2001); pp. 104-111; Federation of European Biochemical Societies; Elsevier Science B.V.; Switzerland.
Sun et al; "A Novel Muconic Acid Biosynthesis Approach by Shunting Tryptophan Biosynthesis via Anthranilate"; Applied and Environmental Microbiology; pp. 4024-4030; Jul. 2013; vol. 79, No. 13; Copyright 2013, American Society for Microbiology.
Kwak et al; "Identification of Amino Acid Residues Involved in Feedback Inhibition of the Anthranilate Synthase in *Escherichia coli*"; Journal of Biochemistry and Molecular Biology, vol. 32, No. 1; Jan. 1999, pp. 20-24; Korea.
Matsui et al; "Two Single-Base-Pair Substitutions Causing Desensitization to Tryptophan Feedback Inhibition of Anthranilate Synthase and Enhanced Expression of Tryptophan Genes of Brevibacterium lactofermentum"; Journal of Bacteriology; vol. 169, No. 11; Copyright 1987, American Society for Microbiology; Japan.
Caligiuri et al; "Identification of Amino Acid Residues Involved in Feedback Regulation of the Anthranilate Synthase complex from Salmonella typhimurium"; The Journal of Biological Chemistry; Copyright 1991; The American Society for Biochemistry and Molecular Biology, Inc.; vol. 266, No. 13, Issue of May 5; pp. 8328-8335; Virginia, United States.
Schafer et al; "Small mobilizable multi-purpose cloning vectors derived from the *Escherichia coli* plasmids pK18 and pK19: selection of defined deletions in the chromosome of Corynebacterium glutamicum"; Gene, 145 (1994); pp. 69-73; Elsevier Science B.V.; Germany.
Eikmanns et al; "A family of Corynebacterium glutamicum / *Escherichia coli* shuttle vectors for cloning, controlled gene expression, and promoter probing" (Recombinant DNA; expression vector; promoter probe vector; co-transformation); Gene. 102 (1991); pp. 93-98; Accepted: Mar. 6, 1991; Munchen, Germany.

* cited by examiner

RECOMBINANT STRAIN PRODUCING O-AMINOBENZOATE AND FERMENTATIVE PRODUCTION OF ANILINE FROM RENEWABLE RESOURCES VIA 2-AMINOBENZOIC ACID

CROSS-REFERENCE TO RELATED APPLICATIONS

This Application is a National Phase Application of PCT/EP2015/053526, filed Feb. 19, 2015, which claims priority to European Application No. 14155936.9, filed Feb. 20, 2014 and European Application No. 14196432.0, filed Dec. 5, 2014, each of which being incorporated herein by reference.

FIELD

The invention relates to the field of producing aniline from raw material of renewable resources, such as e.g. biomass via a suitable microbial host followed by chemical conversion of an intermediate product to aniline.

REFERENCE TO A SEQUENCE LISTING

This application contains a Sequence Listing in computer readable form, which is herein incorporated by reference.

BACKGROUND

Aniline is currently produced at several million tonnes per year from fossil raw materials, e.g. to produce polyurethanes. An aniline source based on renewable resources, also called "bioaniline", is strongly desired for the chemical industry in order to become independent from fossil resources. More importantly, there is a strong desire to reduce carbon dioxide ($CO_2$) emissions both for the chemical processes as well as by increasing the use of renewable resources in the raw materials. Bioaniline has a high potential of saving $CO_2$ emissions.

The invention further relates to engineering of microorganisms and production of aromatic compounds therefrom. In particular, the invention relates to the field of producing o-aminobenzoate (oAB) from renewable sources, such as e.g. biomass in a suitable recombinant microbial host. Typically a source containing a significant proportion of fermentable sugars is used. These sugars may include polysaccharides such as disaccharides, e.g. sucrose, or trisaccharides, e.g. kestose, as well as C-6 monosaccharides such as glucose, fructose or mannose and C-5 monosaccharides such as xylose and arabinose. A recombinant microbial strain capable of converting sugar to o-aminobenzoate (2-aminobenzoate, ortho-aminobenzoate, o-aminobenzoate, oAB) would enable the production of o-aminobenzoate from a wide range of renewable resources including sugar beet and sugar cane, starch-containing plants such as corn, wheat and rye, as well as lignocellulose e.g. from straw, wood or bagasse.

Currently, there is no renewable or biologically derived source of o-aminobenzoate or the corresponding acid available commercially and no known example of the large-scale biological production of o-aminobenzoate has been described. o-Aminobenzoate is a natural intermediate of the shikimate acid pathway and a precursor for the biosynthesis of the aromatic amino acid L-tryptophane. The biosynthetic pathway to o-aminobenzoate is relatively well understood in both prokaryotes and eukaryotes. A chemical conversion of o-aminobenzoate to aniline can be achieved. Current production methods of aniline rely on chemical synthesis from petroleum-derived raw-materials. Such petroleum-derived raw materials are not renewable as opposed to raw materials which are renewable, such as the renewable resource "biomass". Several chemical steps involved in the chemical synthesis result in high production costs of the chemicals. The conventional chemical synthesis of aniline can be associated with hazardous intermediates, solvents, and waste products which can have substantial impacts on the environment. Non-specific side-reactions on the aromatic-ring result in the reduction of the product yield. Petroleum-derived raw materials are influenced by cost fluctuations resulting from the global petroleum price.

WO 2013/103894 A1 discloses a method of producing aromatic amines via biologically-derived p-aminobenzoic acid (4-aminobenzoate). However, this document discloses to produce the p-aminobenzoic acid in either *E. coli* or in *S. cerevisiae* and fails to recognize the advantages of *Corynebacterium glutamicum* as a host. In addition, this document does also not disclose how to successfully combine the fermentation process with the downstream chemical process of converting the biologically-derived p-aminobenzoic acid to aromatic amines.

A direct fermentation of sugar to aniline as a one-step conversion was thought to be most cost efficient if based on a biosynthesis pathway including an enzymatic, in vivo, decarboxylation of anthranilate to aniline as the final reaction step. Since an aminobenzoate decarboxylase could not successfully be identified or developed through protein engineering, the decarboxylation reaction of anthranilate to aniline could not be carried out by pure enzymatic means. Since such a one-step process was not technically feasible, process alternatives to perform the final reaction step of decarboxylating anthranilate to aniline as the final reaction step were taken into consideration, e.g. by a chemical step, as opposed to an enzymatic step.

Therefore, it has been the technical problem of the invention to provide a method of producing aniline based on renewable resources that is superior to existing fermentation and chemical methods and that achieves a large reduction in carbon dioxide emissions, independence from fossil resources, and similar or lower production cost compared to the established petroleum-based production processes.

SUMMARY

The invention has solved said problem by providing a recombinant microbial host cell capable of converting a raw material comprising a fermentable carbon substrate to o-aminobenzoate biologically.

The invention has further solved said problem by providing a method for producing aniline, comprising the steps of:
a) producing o-aminobenzoate by fermentation of a raw material comprising at least one fermentable carbon substrate using the recombinant microbial host cell of the invention as described herein and as claimed in the claims that is capable of converting said raw material comprising at least one fermentable carbon substrate to o-aminobenzoate biologically, wherein said o-aminobenzoate comprises anthranilate anion,
b) converting said o-aminobenzoate from said anthranilate anion to anthranilic acid by acid protonation,
c) recovering said anthranilic acid by precipitation or by dissolving in an organic solvent, and
d) converting said anthranilic acid to aniline by thermal decarboxylation in an organic solvent.

The change to aniline production based on renewable resources, e.g. biomass or fermentable carbon sources, offers the advantages of reducing $CO_2$ emissions significantly, allows for independence from fossil resources, and enables a possible reduction in production cost. A further advantage of the invention is that the use of hazardous chemicals and the resulting waste are kept to a minimum. Further, biologically derived o-aminobenzoate can be produced and converted to aniline in a process with much less overall impact on the environment.

DETAILED DESCRIPTION

In particular, the invention provides a recombinant microbial host cell capable of converting a raw material comprising a fermentable carbon substrate to o-aminobenzoate biologically. Such a recombinant microbial host according to the invention can be a genetically engineered microorganism for fermentative production of o-aminobenzoate from renewable sources, such as e.g. biomass. For example, the invention provides genetically engineered strains of *Corynebacterium glutamicum* as biocatalysts that are suitable for efficient fermentative production of o-aminobenzoate from fermentable carbon sources.

Figure 1:
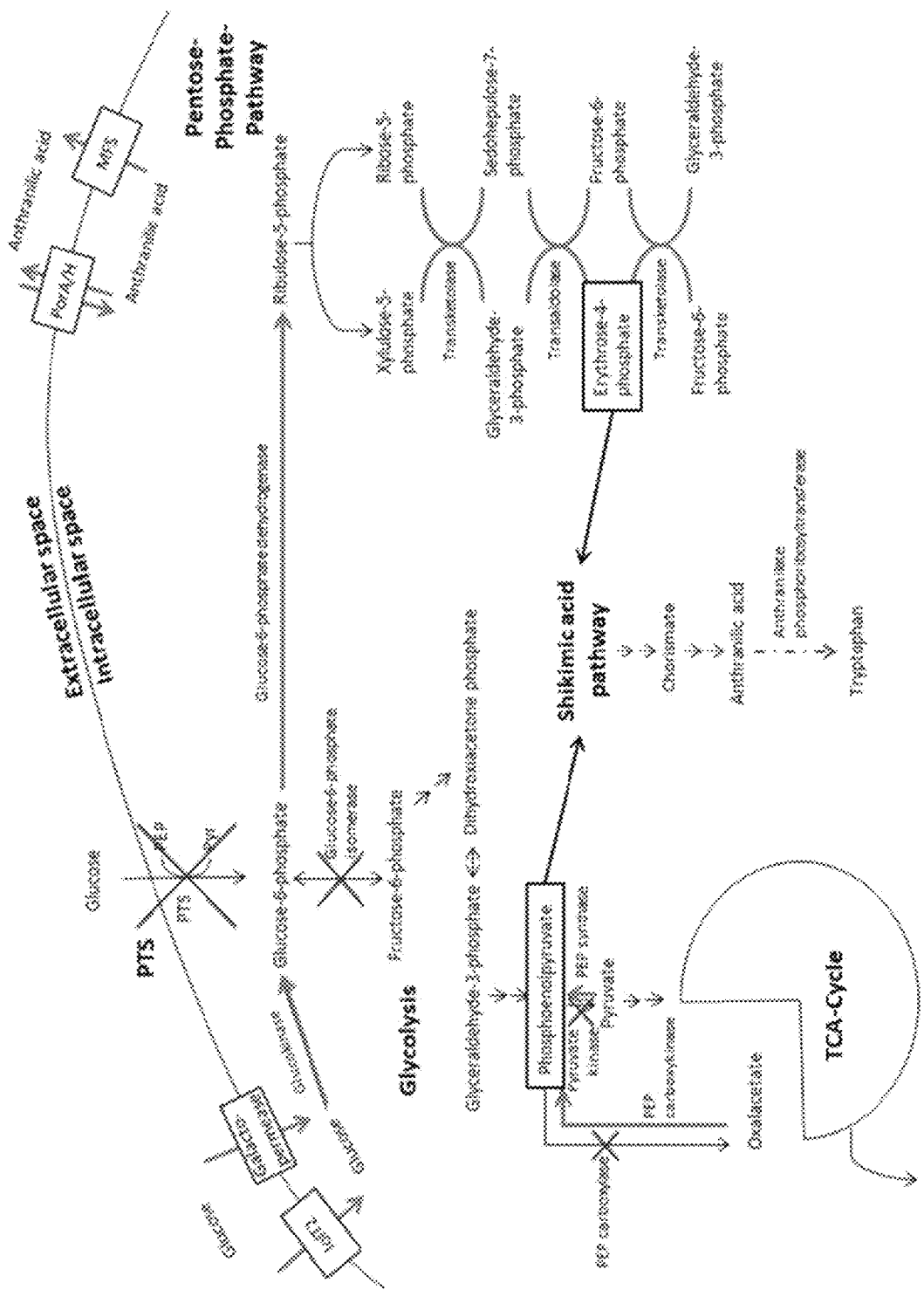
FIG. 1 shows a schematic overview display of biosynthetic pathway from glucose to oAB (anthranilate) in *C. glutamicum* showing the strategy to increase the precursor supply from the central metabolism (PTS: phosphotransferase system; PEP: phosphoenolpyruvate; TCA: tricarbonic acid; IolT2: inositolpermease unit T2; PorA/H: porine complex of PorA and PorH; MFS: mayor facilitating system) Thick arrows display biosynthetic steps that are enhanced and crosses mark biosynthetic steps that are interrupted.

*Corynebacterium glutamicum* is a soil-dwelling Gram-positive bacterium. It belongs to the high GC content Gram-positives actinobacteria. *C. glutamicum* is one of the biotechnologically most important bacterial species with an annual production of more than two million tons of amino acids, mainly L-glutamate and L-lysine. Due to this immense industrial importance, *C. glutamicum* has been studied extensively starting already shortly after its discovery in 1956. The genome of *C. glutamicum* was sequenced and published in 2003 (Ikeda M, Nakagawa S, Appl Microbiol Biotechnol, 2003, 62:99; Kalinowski J, Bathe B, Bartels D, Bischoff N, Bott M, Burkovski A, Dusch N, Eggeling L, Eikmanns B J, Gaigalat L, Goesmann A, Hartmann M, et al., J Biotechnol, 2003, 104: 5). *C. glutamicum* exhibits numerous ideal intrinsic attributes as a microbial factory to produce not only amino acids but also other chemicals. The deep fundamental knowledge of the corynebacteria physiology and the postgenomic tools to model processes or design synthetic pathways in combinatorial approaches constitute a foundational basis to design efficient and versatile corynebacterial biorefineries. The biosynthetic pathways of *C. glutamicum* leading to oAB have been extensively studied and can be divided into three main sections: the central metabolism, the common aromatic pathway, and the L-tryptophan branch pathway. oAB is an intermediate of L-tryptophan biosynthesis (FIG. 1). However, previous attempts at strain improvement for amino acid production relied mainly on classical random mutagenesis and screening procedures, aiming at deleting competing pathways and eliminating feedback regulations in the biosynthetic pathways. The classical approach has limited usefulness since complete deregulation of regulatory steps and enhancement of an appropriate biosynthetic enzyme activity are difficult to achieve. Furthermore random mutagenesis often produces unexpected mutations at some locations in the genome together with desirable ones. Since it is difficult to ascertain the influence of these unidentified mutations, further strain improvement would be affected. These problems widely exist in industrial strains constructed by random mutagenesis. On the basis of literature reported mainly during the last decade, the current production with strains generated by the classical approach yields towards sugar (wt %) approximately 20-23 for L-tryptophan and around 25 for L-phenylalanine. In contrast, far higher production yields towards sugar (wt %) have been reported for many other amino acids, e.g., L-lysine, 40-50; L-glutamate, 45-55; L-arginine, 30-40; L-threonine, 40-50, L-valine, 30-40; and L-alanine, 45-55 (Leuchtenberger W, Huthmacher K, Drauz K, Appl Microbiol Biotechnol, 2005, 69:1; Ikeda M, Nakagawa S, Appl Microbiol Biotechnol, 2003, 62:99).

Based on the recent advantages made in molecular biology and in the understanding of the functionality of the biosynthetic pathways leading from sugars to L-tryptophan (and oAB), the invention provides a recombinant microbial host cell capable of converting a raw material comprising a fermentable carbon substrate to o-aminobenzoate biologically, and more specifically, an oAB producer from *Corynebacterium glutamicum* ATCC13032 based on directed mutagenesis and the metabolic engineering approach. Certain gene targets for metabolic engineering to generate an oAB producer are located in the aromatic biosynthesis pathway leading to oAB and subsequent to L-tryptophan (FIG. 1). The biosynthesis of L-tryptophan is strictly controlled at several steps in *C. glutamicum*. Therefore, overproduction of oAB required the genetic removal of the metabolic controls existing both in the common aromatic pathway and in the L-tryptophan branch. In addition, amplification of the DAHP synthase, which initiates the aromatic pathway, was an important strategy to increase net carbon flow down the common pathway as a further embodiment of the invention. These mutations were combined with the generation of aromatic amino acid bradytroph strains to circumvent the constant need for aromatic amino acid supplementation. A balanced supply of precursors was addressed to achieve efficient production of the product, considering that biosynthesis of 1 mol of oAB from glucose requires 1 mol of erythrose-4-phosphate (E4P) and 2 mol phosphoenolpyruvate (PEP) as starting precursors and, in addition, consumes 1 mol of L-glutamine and releases 1 mol of pyruvate on its pathway.

In the following, the inventors focussed on *Corynebacterium glutamicum* as a recombinant microbial strain for producing o-aminobenzoate biologically. Therefore, the invention provides a recombinant microbial host cell capable of converting a raw material comprising a fermentable carbon substrate to o-aminobenzoate biologically. Said *Corynebacterium glutamicum* preferably is *Corynebacterium glutamicum* ATCC 13032, most preferably a recombinant *Corynebacterium glutamicum* ATCC 13032.

In further embodiments of the invention, the *Corynebacterium glutamicum* strain, preferably *Corynebacterium glutamicum* ATCC 13032 can comprise a genetic modification of the trpD gene (Cgl3032, SEQ ID NO: 1) encoding anthranilate phosphoribosyl transferase, wherein said genetic modification preferably is selected from the group consisting of SEQ ID NO: 2, SEQ ID NO: 3, SEQ ID NO: 4, SEQ ID NO: 5, SEQ ID NO: 6, SEQ ID NO: 7, and SEQ ID NO:8, which all have the effect of a reduced expression of the trpD gene to yield a tryptophan auxotrophic strain. A single one of the aforementioned genetic modifications already results in a recombinant *Corynebacterium glutamicum* ATCC 13032 strain that produces o-aminobenzoate (oAB).

In the following, a few terms used to describe the invention are defined.

The term "bioaniline" according to the invention refers to aniline that is based on raw material from renewable resources, such as sugar beet, sugar cane, starch-containing plants, preferably corn, wheat and rye, and lignocellulose, preferably straw, wood and bagasse, glycerol and C1-compounds, preferably CO, or such as fermentable sugars, preferably C-5 monosaccharides, C-6 monosaccharides, disaccharides, and tri-saccharides, wherein the C-5 monosaccharides preferably are xylose and arabinose, and wherein the C-6 monosaccharides preferably are glucose, fructose or mannose, and wherein the disaccharide preferably is saccharose, and wherein the trisaccharide preferably is kestose.

"o-aminobenzoate" according to the invention refers to ortho-aminobenzoate (o-aminobenzoate, "oAB"). o-aminobenzoate can be present in the form of the anthranilate salt comprising the anthranilate anion, $C_6H_4COO^-$, and a suitable cation, such as $NH_4^+$ or Na, or as anthranilic acid, which is the zwitter ion $C_6H_4COO^-$ $NH_3^+$ and $C_6H_4COO^-$ $NH_2$. "o-aminobenzoate" ("oAB") is different from "4-aminobenzoate" ("pAB") in that the amino group is attached to the benzene ring at the $C_4$-position (para) as opposed to the $C_2$-position (ortho) in the case of o-aminobenzoate ("oAB").

The term "host" within the meaning of the invention can comprise any host that is capable of producing o-aminobenzoate by fermentation, either naturally, or only after transformation as a "recombinant microbial host", or in addition to the naturally present o-aminobenzoate, either in the form of the anthranilate anion or as anthranilic acid, following transformation. A "microbial host" according to the invention can be selected from the group consisting of bacteria, yeast and fungi. Said host can be selected from the group consisting of bacteria, yeast and fungi, wherein said bacterium preferably is an *Escherichia coli* strain, a *Corynebacterium* strain or a *Pseudomonas* strain, wherein said *Corynebacterium* strain preferably is *Corynebacterium glutamicum* and wherein said *Pseudomonas* strain preferably is *Pseudomonas putida*. Preferably, said microbial host can be a recombinant microbial host. Such a recombinant microbial host can be *E. coli* W3110 trpD9923, as shown in Example 1. Such a recombinant host can be a *Pseudomonas putida* KT2440, as shown in Example 4. Such a recombinant host can also be a *Corynebacterium glutamicum* ATCC 13032, as shown in Example 3.

The term "genetic modification" within the meaning of the invention refers to changes in nucleic acid sequence of a given gene of a microbial host as compared to the wild-type sequence. Such a genetic modification can comprise deletions as well as insertions of one or more deoxyribo nucleic acids. Such a genetic modification can comprise partial or complete deletions as well as insertions introduced by transformations into the genome of a microbial host. Such a genetic modification can produce a recombinant microbial host, wherein said genetic modification can comprise changes of at least one, two, three, four or more single nucleotides as compared to the wild type sequence of the respective microbial host. For example, a genetic modification can be a deletion or insertion of at least one, two, three, four or more single nucleotides or a transformation of at least one, two, three, four or more single nucleotides. A genetic modification according to the invention can have the effect of e.g. a reduced expression of the respective gene or of e.g. an enhanced expression of the respective gene. In one example of such a genetic modification according to the invention, a recombinant microbial host, e.g. *Corynebacterium glutamicum*, can comprises a genetic modification of the trpD gene (Cgl3032, SEQ ID NO: 1) encoding the enzyme anthranilate phosphoribosyl transferase, wherein said genetic modification can have the effect of a reduced expression of the modified trpD gene. Such modified trpD gene can be selected from the group consisting of SEQ ID NO: 2, SEQ ID NO: 3, SEQ ID NO: 4, SEQ ID NO: 5, SEQ ID NO: 6, SEQ ID NO: 7, and SEQ ID NO: 8. A single one of the aforementioned genetic modifications already results in a recombinant *Corynebacterium glutamicum* ATCC 13032 strain showing a reduced expression of the modified trpD gene that produces o-aminobenzoate (oAB). In a further embodiment of the invention, such genetic modification can also be a deletion of the trpD gene, e.g. as in *Corynebacterium glutamicum* ΔtrpD.

The term "batch fermentation" within the meaning of the invention refers to a single fermentation reaction having a defined starting point and a defined end point. Batch fermentation can be used in step a) of the method according to the invention in cases where the production rates of the microorganisms cannot be maintained at a high rate in continuous fermentation mode.

The term "fed-batch fermentation" within the meaning of the invention Fed-batch fermentation refers to an operational technique in biotechnological processes where one or more nutrients (substrates) are fed (supplied) to the bioreactor during cultivation and in which the product(s) remain in the bioreactor until the end of the run. "Fed-batch fermentation" can be used in step a) of the method according to the invention in cases where the production rates of the microorganisms cannot be maintained at a high rate in continuous fermentation mode.

The term "continuous fermentation" within the meaning of the invention, refers to a fermentation method in which substrate is added and the product (i.e. o-aminobenzoate, oAB) is removed continuously during the fermentation in step a) of the method according to the invention.

In the following, the invention is described in more detail.

The invention provides a recombinant microbial host cell capable of converting a raw material comprising a fermentable carbon substrate to o-aminobenzoate (oAB) biologically.

Said microbial host cell can be selected from the group consisting of bacteria, yeast and fungi, wherein said bacterium preferably is an *Escherichia coli* strain, a *Corynebacterium* strain or a *Pseudomonas* strain, and wherein said *Corynebacterium* strain preferably is *Corynebacterium glutamicum*, more preferably *Corynebacterium glutamicum* ATCC 13032, and wherein said *Pseudomonas* strain preferably is *Pseudomonas putida*, more preferably *Pseudomonas putida* KT2440.

In a further embodiment of the recombinant microbial host cell of the invention, the recombinant microbial host cell can be *Corynebacterium glutamicum*. In more specific embodiments of the invention, *Corynebacterium glutamicum* ATCC13032 is the preferred recombinant microbial host for the production of o-aminobenzoate, since the inventors observed that the organism has a high tolerance for o-aminobenzoate, whereas for other microorganisms, e.g. *Escherichia coli* K12, already low concentrations of o-aminobenzoate are toxic.

Figure 3:
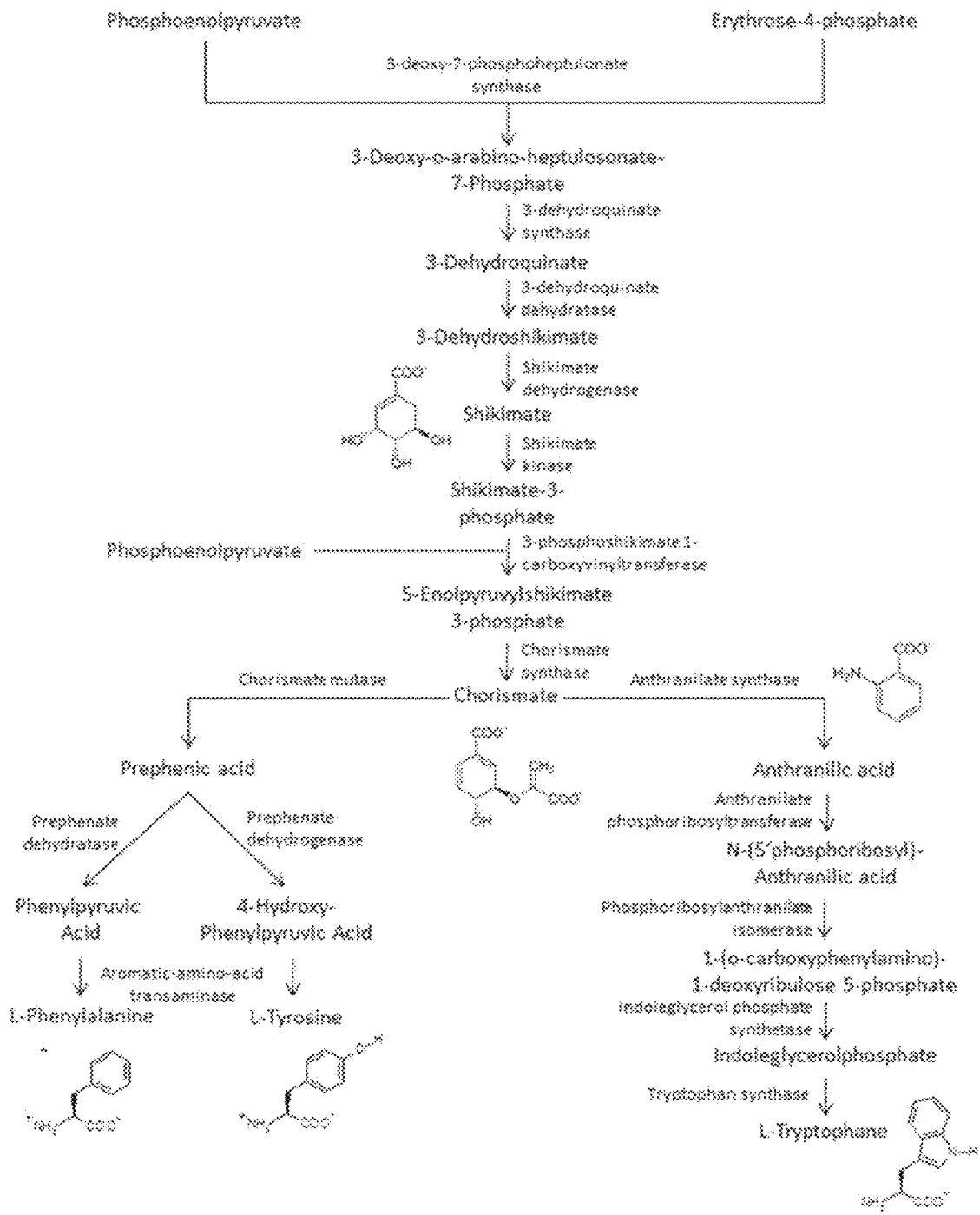
FIG. 3 is a schematic overview of the shikimic acid pathway in *C. glutamicum* from precursor molecules to the aromatic amino acids. The structural formulas of central intermediates are given.

In a further embodiment of the recombinant microbial host cell of the invention, said *Corynebacterium glutamicum*, preferably *Corynebacterium glutamicum* ATCC 13032, can comprise a genetic modification of the trpD gene encoding anthranilate phosphoribosyl transferase (FIG. 3).

Said genetic modification of the trpD gene (Cgl3032, SEQ ID NO: 1) encoding anthranilate phosphoribosyl transferase can be selected from the group consisting of SEQ ID NO: 2, SEQ ID NO: 3, SEQ ID NO: 4, SEQ ID NO: 5, SEQ ID NO: 6, SEQ ID NO: 7, and SEQ ID NO: 8, and wherein said genetic modification has the effect of a reduced expression of the trpD gene. More specifically, the mutations in the aforementioned sequences can change the spacer region between the ribosomal binding site and the start codon of the trpD gene as. In addition, an exchange of the natural start codon of the trpD gene can lead to a reduced translation of trpD and thus to a bradytroph strain towards L-tryptophan that produces o-aminobenzoate in a multi-gram scale without supplementation with L-tryptophan. It follows that such type of strain is particularly preferred as a recombinant microbial has according to the invention.

In further embodiments of the recombinant microbial host cell of invention, the microbial host cell can be *Corynebacterium glutamicum*, preferably *Corynebacterium glutamicum* ATCC 13032, wherein said *Corynebacterium glutamicum* or *Corynebacterium glutamicum* ATCC 13032 can comprise a genetic modification of the csm gene (Cgl0853, SEQ ID NO: 9) encoding chorismate mutase (FIG. 3), wherein said genetic modification preferably is selected from the group consisting of SEQ ID NO: 10, SEQ ID NO:11, SEQ ID NO:12, SEQ ID NO: 13, SEQ ID NO: 14, SEQ ID NO: 15 and SEQ ID NO:16, and wherein said genetic modification has the effect of a reduced expression of the csm gene. In particular, the csm gene can be manipulated to further improve o-aminobenzoate production rates by reduction of L-phenylalanine and L-tyrosine production rates to a minimum.

The effect of reducing the expression of the csm gene is that a bradytroph strain towards L-tyrosine and L-phenylalanine results, that produces o-aminobenzoate in a multi-gram scale without supplementation with L-tyrosine and L-phenylalanine. This circumvents the reduction of o-aminobenzoate production due to feedback-inhibition of enzymes catalyzing reactions in the aromatic acid pathway by L-tyrosine and/or L-phenylalanine, as possible in L-tyrosine and L-phenylalanine auxotrophic strains supplemented with L-tyrosine and/or L-phenylalanine. It follows that such type of strain is particularly preferred as a recombinant microbial has according to the invention. This effect can result in a higher production of o-aminobenzoate.

In further embodiments of the recombinant microbial host cell of invention, the *Corynebacterium glutamicum* microbial host cell, preferably *Corynebacterium glutamicum* ATCC 13032, can further comprise one or more deletions selected from the group consisting of hpr (Cgl1937—SEQ ID NO:17 or SEQ ID NO: 18), ptsG (Cgl1537—SEQ ID NO: 19 or SEQ ID NO: 20), pepco (Cgl1523—SEQ ID NO: 21 or SEQ ID NO: 22), pyk (Cgl2089—SEQ ID NO: 23 or SEQ ID NO: 24), and gpi (Cgl0851—SEQ ID NO: 27 or SEQ ID NO: 28).

Figure 2:
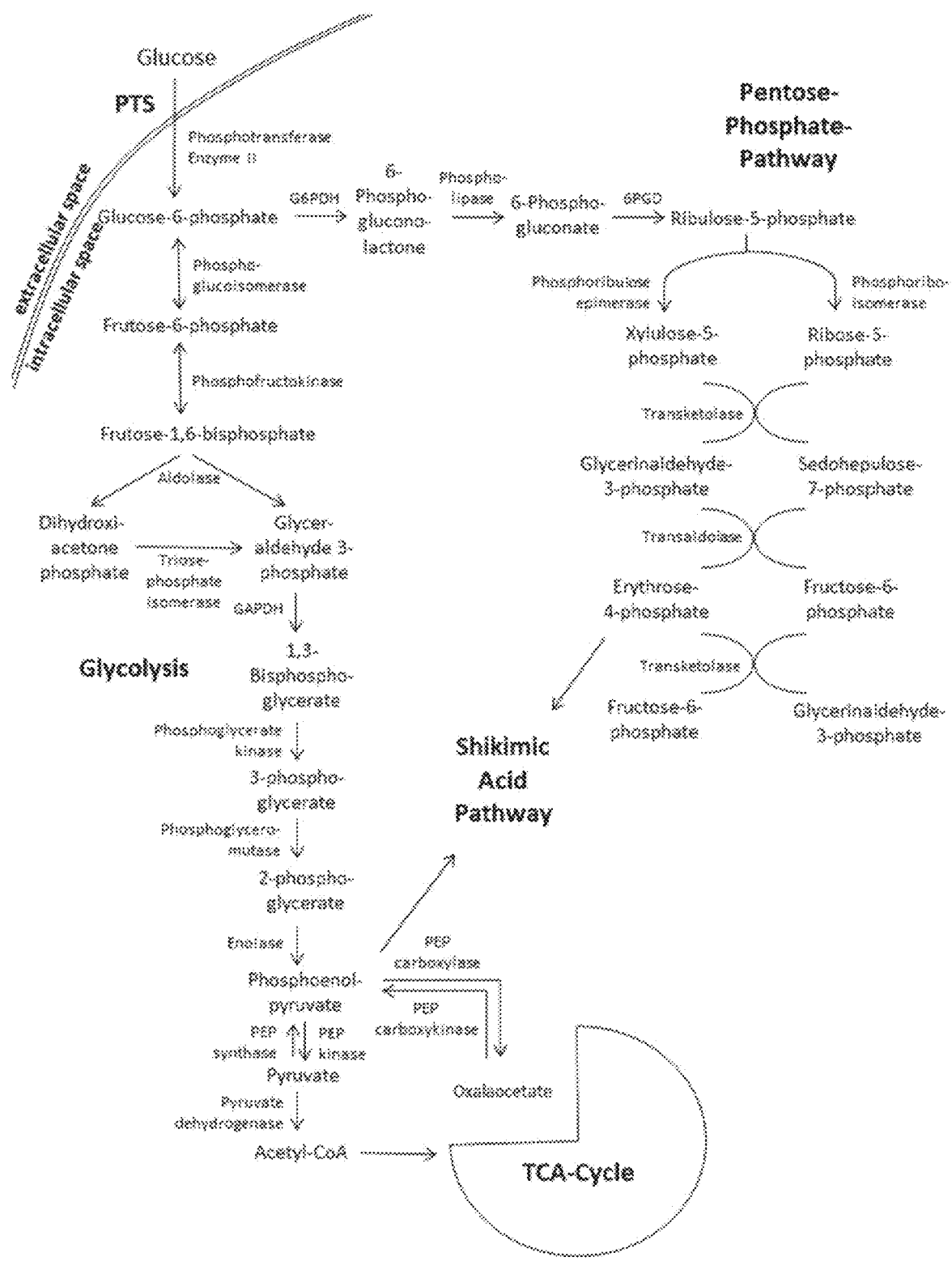
FIG. 2 is a schematic overview of the central carbon metabolism in *C. glutamicum*. Shown are the phosphotransferase system (PTS) for glucose uptake, the glycolysis, the pentose phosphate pathway and relevant anaplerotic reactions. The TCA (tricarbonic acid)-cycle and the shikimic acid pathway are indicated to explain the positioning and transitions into these pathways (GAPDH=glyceraldehyde-3-phosphate dehydrogenase; G6PDH=glucose-6-phosphate dehydrogenase; 6PGD=phosphogluconate dehydrogenase; PEP=phosphoenolpyruvate).

The gene hpr (Cgl1937—SEQ ID NO: 17 or SEQ ID NO: 18) and the gene ptsG (SEQ ID NO: 19 or SEQ ID NO: 20): each one of these genes encodes a unit of the multi-enzyme complex PEP-phosphotransferase system (PTS) (FIGS. 1, 2). Both units of PTS, Hpr and PtsG, of *C. glutamicum* were manipulated and compared with regard to the effects on growth, cell viability, as well as oAB production, as shown in Example 3.

The gene pepco (Cgl1523—SEQ ID NO: 21 or SEQ ID NO: 22) encodes the enzyme phosphoenolpyruvate-carboxylase. Phosphoenolpyruvate-carboxylase consumes PEP (phosphoenolpyruvate) by transforming it into oxaloacetate (FIGS. 1, 2). This reaction is the major anaplerotic reaction under oxygen deprivation, whereas under standard sufficient oxygen supply the pyruvate kinase consumes most of the PEP to generate pyruvate under gain of one ATP. The gene pepco of *C. glutamicum* was manipulated and compared with regard to the effects on growth, cell viability, as well as oAB production, with other *C. glutamicum* strains, as shown in Example 3.

The gene pyk (Cgl2089—SEQ ID NO: 23 or SEQ ID NO: 24) encode the enzyme pyruvate kinase. Pyruvate kinase consumes PEP (phosphoenolpyruvate) by production of pyruvate and ATP (FIGS. 1, 2). This reaction is part of the glycolysis in *C. glutamicum*. The Pyk-encoding gene, annotated in the genome of *C. glutamicum*, was deleted, as described in Example 3.

The gene gpi (Cgl0851—SEQ ID NO: 27 or SEQ ID NO: 28) encodes the enzyme glucose-6-phosphate isomerase. The enzyme catalyses the first step of the glycolysis transforming glucose-6-phosphat into fructose-6-phosphat (FIGS. 1, 2).

In more specific embodiments of the recombinant microbial host cell of invention, the *Corynebacterium glutamicum* microbial host cell, preferably *Corynebacterium glutamicum* ATCC 13032, can further overexpress one or more of the genes selected from the group consisting of galP (SEQ ID NO: 30), iolT2 (SEQ ID NO: 31), ppgk (SEQ ID NO: 32), pps (SEQ ID NO: 33-35), ppk (SEQ ID NO: 36), zwfl (SEQ ID NO: 37), opcA (SEQ ID NO: 38-39), tktCg (SEQ ID NO: 40), tktEc (SEQ ID NO: 41), talCg (SEQ ID NO: 42), tame (SEQ ID NO: 43), a gene encoding TrpEGS38F (trpEG$^{S38F}$, SEQ ID NO: 50), a gene encoding TrpEGS38R (trpEG$^{S38R}$, SEQ ID NO: 51), a gene encoding TrpEGS40R (trpEG$^{S40R}$, SEQ ID NO: 52), a gene encoding TrpEGS40F (trpEG$^{S40F}$, SEQ ID NO: 53), the gene encoding AroGD146N (aroG$^{D146N}$, SEQ ID NO: 55), aroL of *Escherichia coli* LJ110 (SEQ ID NO: 93), aroK (SEQ ID NO: 94), glnA (SEQ ID NO: 95), and qsuA (SEQ ID NO: 96).

The expression of feedback-resistant trpEG genes (anthranilate synthase genes), a gene encoding TrpEGS38F (trpEG$^{S38F}$—SEQ ID NO: 50), a gene encoding TrpEGS38R (trpEG$^{S38R}$—SEQ ID NO: 51), a gene encoding TrpEGS40R (trpEG$^{S40R}$—SEQ ID NO: 52), a gene encoding TrpEGS40F (trpEG$^{S40F}$—SEQ ID NO: 53), in the *Corynebacterium glutamicum* microbial host, preferably *Corynebacterium glutamicum* ATCC 13032, is a preferred embodiment of the invention, alone or in combination with any one of the other genetic modifications of the invention. The genes all share the common feature that they encode mutated versions of the anthranilate synthase unit, which releases a pyruvate molecule under formation of o-aminobenzoate and L-glutamate (FIG. 3). These are feedback-resistant versions of TrpEG, which is why the corresponding mutated genes are referred to as trpEG$^{fbr}$. The overexpression of feedback resistant aroG gene (3-deoxy-D-arabino-heptulosonate 7-phosphate synthase gene) in the *Corynebacterium glutamicum* microbial host, preferably *Corynebacterium glutamicum* ATCC 13032, such as the gene encoding AroGD146N (aroG$^{D146N}$—SEQ ID NO: 55), is another preferred embodiment of the invention, alone or in combination with any one of the other genetic modifications of the invention. The gene encoding AroGD146N (aroG$^{D146N}$—SEQ ID NO: 55) encodes a mutated version of AroG, which is an enzyme that catalyses the reaction from erythrose-4-phosphate (E4P) to 3-deoxy-D-arabino-heptulosonate-7-phosphate (DAHP) in *Escherichia coli* (FIG. 3).

The gene galP (Cgl2409—SEQ ID NO: 30) encoding the enzyme galactopermease. The glucose uptake can be restored after PTS disruption by expression of a galactopermease (FIGS. 1, 2). In *C. glutamicum* a gene was identified and annotated as galactopermease and is therefore a good candidates for such an expression. The candidate gene is expressed in *C. glutamicum* strains with disrupted. PTS, as shown in Example 3.

The gene iolT2 (Cgl3058—SEQ ID NO: 31) encodes the inositolpermease T2 unit. The glucose uptake can be restored after PTS disruption by expression of a inositolpermease T2 unit (FIGS. 1, 2). As an alternative approach to the overexpression of a galactopermease to restore glucose-uptake after PTS disruption in *C. glutamicum*, the overexpression of the inositolpermease T2 unit of the inositolpermease is performed. The resulting strain characteristics are compared to that of strains overexpressing a galactopermease, as shown in Example 3.

The gene ppgk (Cgl1910—SEQ ID NO: 32) encodes the enzyme polyphosphoglucokinase. The galactopermease, as well as the inositolpermease T2 unit, can only take up glucose, but they cannot phosphorylate the sugar molecule (FIGS. 1, 2). This phosphorylation, however, is essential to enable the metabolism of the glucose molecule. Therefore, expression of the different permeases is combined with expression of a glucose phosphorylating enzyme. This Ppgk is co-expressed in the different permease-expressing PTS deficient strains of the invention, as described in Example 3.

The genes pps (Cgl0551 and Cgl0552—SEQ ID NO: 33-35) encode the enzyme PEP (phosphoenolpyruvate) synthase. Apart from the disruption of reactions consuming PEP, biosynthetic steps leading to the generation of PEP are promoted. PEP synthase catalyses the formation of PEP by pyruvate recycling and consumption of ATP to AMP, as part of the gluconeogenesis in *C. glutamicum* (FIGS. 1, 2). Overexpression of the pps gene results in an increased oAB pool in *C. glutamicum* strains, as described in Example 3.

The gene ppk (Cgl2862—SEQ ID NO: 36) encodes the enzyme PEP carboxykinase. As part of the glyoxylate pathway oxaloacetate can be recycled into PEP by a PEP carboxykinase (FIGS. 1, 2). Overexpressing the gene can be another route to a larger PEP pool available for oAB biosynthesis, as described in Example 3.

The gene zwf1 (Cgl1576—SEQ ID NO: 37) and the gene (opcA (Cgl577—SEQ ID NO: 38-39) encode the enzyme glucose-6-phosphat dehydrogenase (FIGS. 1, 2). The enhanced production of the enzyme catalysing the first reaction of the pentose phosphate pathway (PPP) (formation of ribulose-5-phosphate from glucose-6-phosphate) (FIGS. 1, 2) can result in an increased flux into the PPP leading to the production of higher amounts of E4P and via fructose-6-phosphate (Frc-6-P) production and can furthermore increase the cells PEP pool, finally resulting in an increased oAB pool in *C. glutamicum* strains. This effect is achieved when this manipulation is applied to *C. glutamicum* strains and an expression of the Zop enzyme is performed, as described in Example 3.

The gene tktCG (Cgl1574—SEQ ID NO: 40) and the gene tktEC (ECDH10B_3110—SEQ ID NO: 41) encode the enzyme transketolase. An enhanced flux through the PPP and an increased E4P pool, and even an increased production of oAB and aromatic amino acids is observed by the expression of a transketolase in *C. glutamicum* strains (FIGS. 1, 2). A transketolase gene from *E. coli* was overexpressed as well as the transketolase encoded in *C. glutamicum*, as described in Example 3.

The gene talCG (Cgl1575—SEQ ID NO: 42) and the gene talEC (ECDH10B_2629—SEQ ID NO: 43) encode the enzyme transaldolase. A comparable favorable effect on E4P production as by transketolase overexpression can be observed for the overexpression of transaldolases in *E. coli* (FIGS. 1, 2). As the sequences of *E. coli* and *C. glutamicum* transaldolases differ significantly the inventors proceeded to express the described *E. coli* gene and the natural *C. glutamicum* gene in *C. glutamicum* strains of the invention, as described in Example 3. The transaldolase and the transketolase encoding genes are combined on one vector and co-expressed in *C. glutamicum* strains to further enhance oAB producer strain characteristics, as described in Example 3.

The gene qsnA (Cgr0492—SEQ ID NO: 96) encodes the drug resistance transporter protein QsuA. Expressing the gene in *C. glutamicum* strains results in an optimized of oAB transport, as described in Example 3.

The gene aroL (B0388—SEQ ID NO: 93) from *Escherichia coli* LJ110 encodes an enzyme that catalyses the reaction from shikimate (SHI) to shikimate-3-phosphate (SHI3P)) in *Escherichia coli*. The aroL gene from *E. coli* is expressed in *C. glutamicum* strains, as described in Example 3.

The gene aroK (Cgl1622—SEQ ID NO: 94) encodes an enzyme that catalyses the reaction from shikimate (SHI) to shikimate-3-phosphate (SHI3P) in *Corynebacterium glutamicum* ATCC 13032 (FIG. 3). The aroK gene is expressed in *C. glutamicum* strains, as described in Example 3.

The gene glnA (Cgl2214—SEQ ID NO: 95) encodes the enzyme glutamine syntethase in *Corynebacterium glutamicum* ATCC 13032 (FIG. 3). The glnA gene is expressed in *C. glutamicum* strains, as described in Example 3.

In particularly preferred embodiments of the invention, the recombinant microbial host cell can be *C. glutamicum* ΔtrpD, *C. glutamicum* ΔtrpD::trpD5, *C. glutamicum* ΔtrpD::trpD5Δpepco, *C. glutamicum* ΔtrpD::trpD5Δgpi, *C. glutamicum* ΔtrpD::trpD5Δpyk, *C. glutamicum* ΔtrpD::trpD5/pEKEx2-trpEG$^{S40F}$, *C. glutamicum* ΔtrpD::trpD5/pEKEx2-aroG$^{D146N}$, *C. glutamicum* ΔtrpD::trpD5/pEKEx2-aroG$^{D146N}$-trpEG$^{S40F}$, *C. glutamicum* ΔtrpD::trpD5/pEKEx2-aroL, *C. glutamicum* ΔtrpD::trpD5/pSB072, *C. glutamicum* ΔtrpD::trpD5/pSB073, *C. glutamicum* ΔtrpD::trpD5/pSB074, *C. glutamicum* ΔtrpD::trpD5/pSB075, *C. glutamicum* ΔtrpD::trpD5/pSB076, *C. glutamicum* ΔtrpD::trpD5/pSB077, *C. glutamicum* ΔtrpD::trpD5/pSB078, *C. glutamicum* ΔtrpD::trpD5/pSB085, or *C. glutamicum* ΔtrpD::trpD5/pSB096, as further described in Example 3 and in Table 4.

In the following further recombinant microbial hosts of the invention are described.

In yet another embodiment of the recombinant microbial host cell of the invention, the microbial host cell can be *Pseudomonas putida*, preferably *Pseudomonas putida* KT2440.

Figure 4:
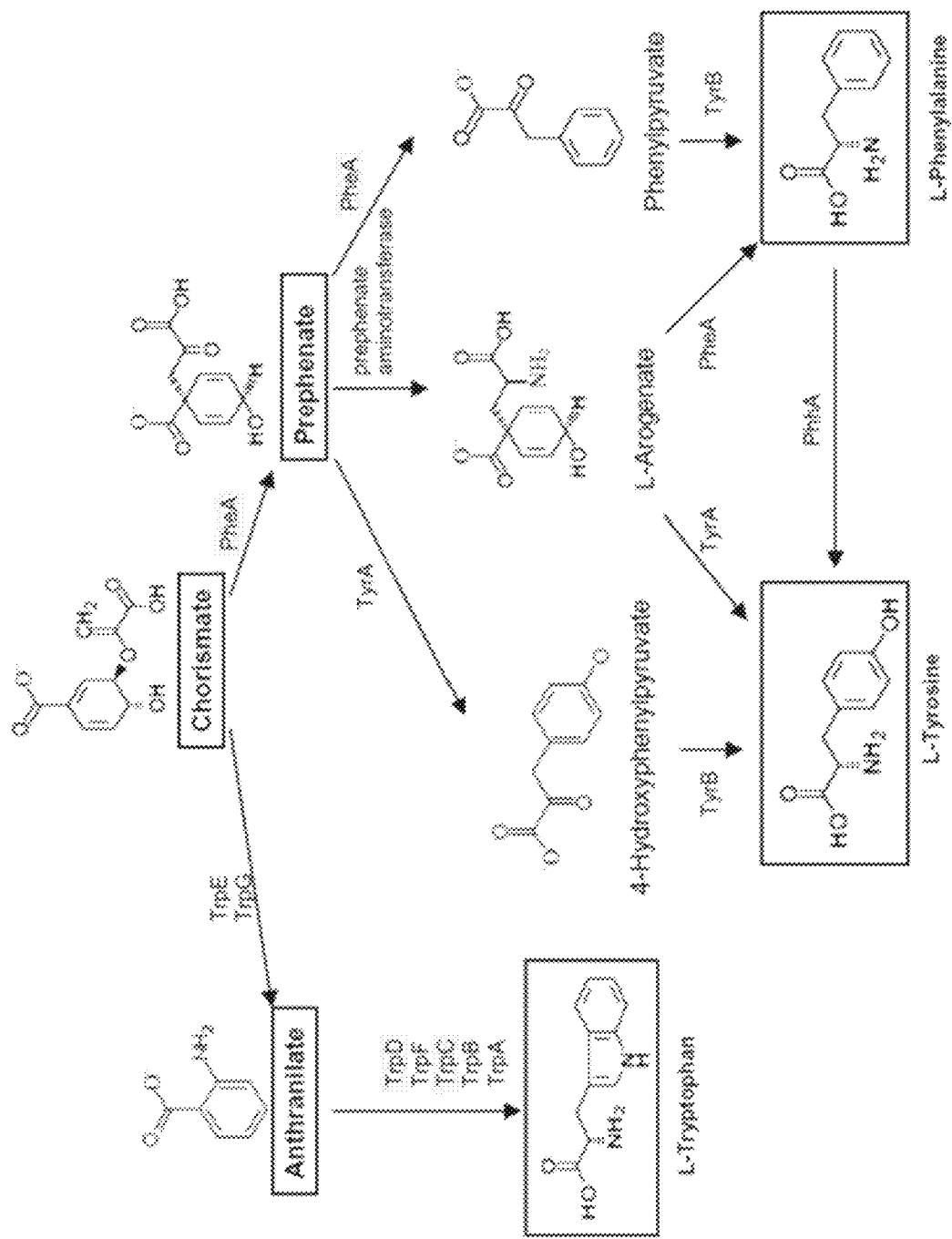
FIG. 4 shows the genetic background of aromatic amino acid biosynthesis in *P. putida* KT2440. Performed genetic manipulations are highlighted in grey.

In a further embodiment of the recombinant microbial host cell of the invention, said *Pseudomonas putida*, preferably *Pseudomonas putida* KT2440, can comprise a deletion of the trpDC gene encoding anthranilate phosphoribosyl transferase and indole-3-glycerol phosphate synthase (PP_0421 and PP_0422 SEQ ID NO: 63-64), or a deletion of the pheA gene encoding chorismate mutase and prephenate dehydratase (PP_1769 SEQ ID NO: 65-66), or both, as described in Example 4 (FIG. 4).

In a further embodiment of the recombinant microbial host cell of the invention, said *Pseudomonas putida*, preferably *Pseudomonas putida* KT2440, wherein said *Pseudomonas putida* or *Pseudomonas putida* KT2440 can express one or more of the genes selected from the group consisting of the gene encoding TrpEGS40F (trpEG$^{S40F}$—SEQ ID NO: 53) and the gene encoding AroGD146N (aroG$^{D146N}$—SEQ ID NO: 55) (FIG. 4). In certain embodiments of the recombinant microbial host cell of invention, the one or more expressed genes mentioned above can be integrated into said *P. putida* microbial host cells by plasmid transformation or by chromosomal transformation, as described in Example 4.

The raw material comprising a fermentable carbon substrate that is converted by the recombinant microbial host cell biologically to o-aminobenzoate (oAB) can be selected from the group consisting of sugar beet, sugar cane, starch-containing plants, preferably corn, wheat and rye, and lignocellulose, preferably straw, wood and bagasse, glycerol and C1-compounds, preferably CO.

In further embodiments of the invention, the fermentable carbon substrate that is comprised in the raw material, can be selected from the group consisting of C-5 monosaccharides, C-6 monosaccharides, disaccharides, and tri-saccharides, wherein the C-5 monosaccharides preferably are xylose and arabinose, and wherein the C-6 monosaccharides preferably are glucose, fructose or mannose, and wherein the disaccharide preferably is saccharose, and wherein the tri-saccharide preferably is kestose.

The invention has further solved the above problem by providing a method for producing aniline, comprising the steps of:
  a) producing o-aminobenzoate by fermentation of a raw material comprising at least one fermentable carbon substrate using the recombinant microbial host cell, as described herein and as claimed in the claims, capable of converting said raw material comprising at least one fermentable carbon substrate to o-aminobenzoate biologically, wherein said o-aminobenzoate comprises anthranilate anion,
  b) converting said o-aminobenzoate from said anthranilate anion to anthranilic acid by acid protonation,
  c) recovering said anthranilic acid by precipitation or by dissolving in an organic solvent, and d) converting said anthranilic acid to aniline by thermal decarboxylation in an organic solvent.

The method according to the invention provides the technical advantages of producing aniline whilst achieving a large reduction in $CO_2$ emissions as compared to methods that are based on fossil resources, independence of such fossil resources, as well as achieving similar or lower production costs as compared to the established petroleum based production processes for aniline.

The method according to the invention comprises two main parts, in which the first part, step a), is fermentation-based (biotechnological) and comprises a conversion of raw material comprising at least one fermentable carbon substrate to o-aminobenzoate by fermentation by a suitable recombinant microbial host, wherein said o-aminobenzoate comprises anthranilate anion ($C_6H_4COO^-NH_2$).

The second part is of a more chemical nature and follows downstream of step a), and comprises the following steps a) to d), and optionally e):
b) converting said o-aminobenzoate from said anthranilate anion to anthranilic acid by acid protonation,
c) recovering said anthranilic acid by precipitation or by dissolving in an organic solvent, and
d) converting said anthranilic acid to aniline by thermal decarboxylation in an organic solvent.

In summary, the invention therefore provides a method for producing aniline, which combines a first biotechnological fermentation step a) with a subsequent downstream, chemical process comprising at least the steps b), c) and d), with an optional step e).

Figure 5:
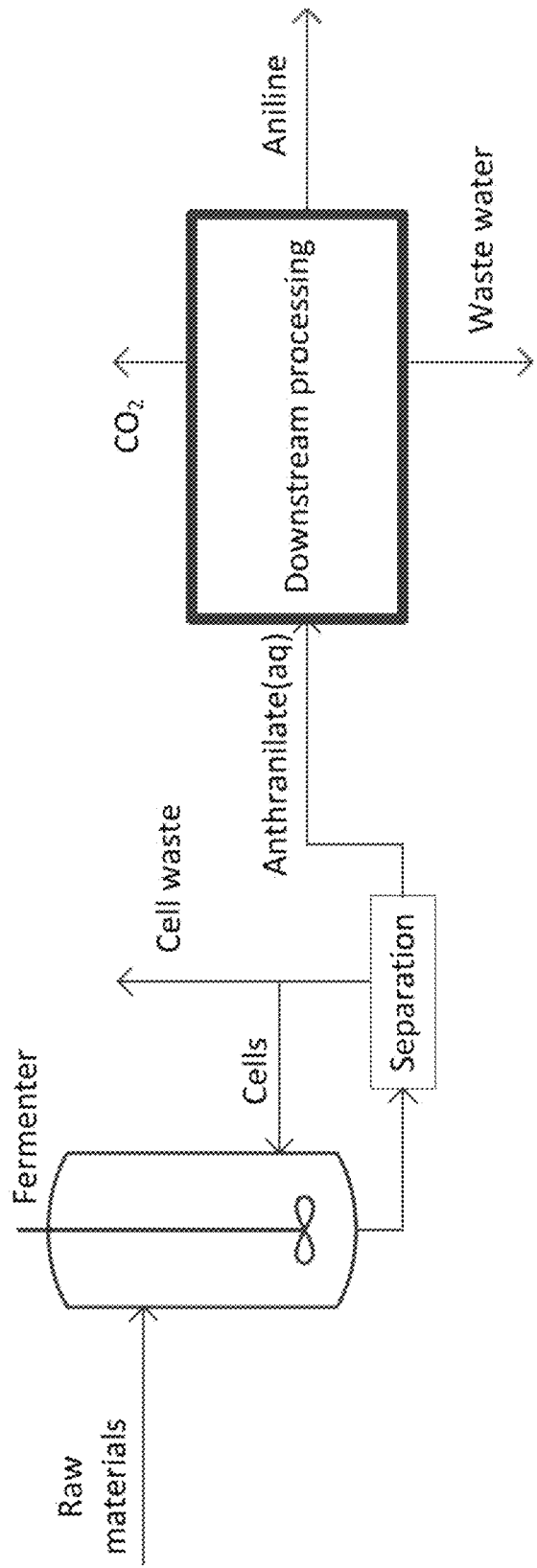
FIG. 5 shows the overall concept of the method according to the invention comprising the conversion of raw materials to anthranilate in the fermentation step followed by a chemical conversion and purification to aniline in the downstream processing.
Figure 6:
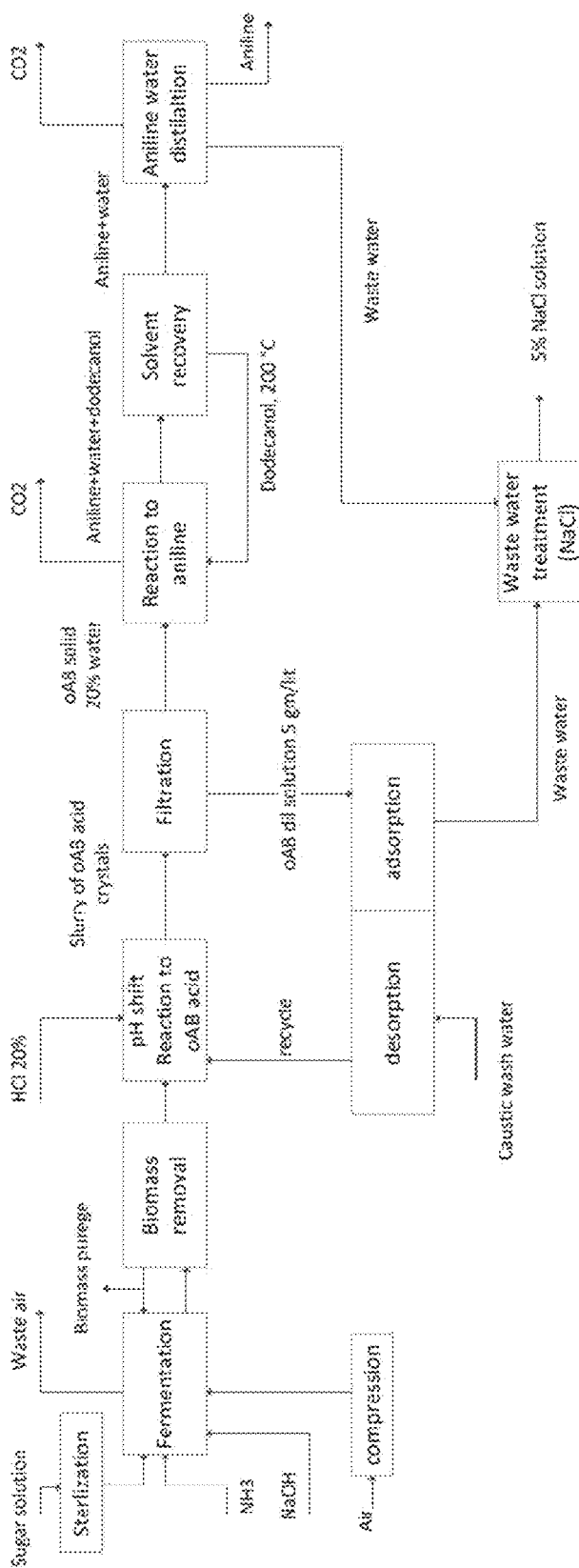
FIG. 6 shows the overall concept of the method according to the invention in more detail. Both of NaOH and $NH_3$ can be used as a buffer in the fermenter.

In the following, the invention is described in further detail. The overall concept of the method according to the invention is depicted in FIG. 5, and a more detailed overview is presented in FIG. 6.

The invention further provides a method for producing aniline, comprising the steps of:
a) producing o-aminobenzoate by fermentation of a raw material comprising at least one fermentable carbon substrate using the recombinant microbial host cell, as described herein and as claimed in the claims, capable of converting said raw material comprising at least one fermentable carbon substrate to o-aminobenzoate biologically, wherein said o-aminobenzoate comprises anthranilate anion,
b) converting said o-aminobenzoate from said anthranilate anion to anthranilic acid by acid protonation,
c) recovering said anthranilic acid by precipitation or by dissolving in an organic solvent, and
d) converting said anthranilic acid to aniline by thermal decarboxylation in an organic solvent.

The fermentation of step a) can be a batch fermentation, a fed-batch fermentation or a continuous fermentation. In the case of a continuous fermentation in step a), a cell retention device may be used to separate the host from a water phase used in fermentation step a) and to retain the host in a fermenter used for performing step a). The cell retention device may be incorporated in such a fermenter, or, as a preferred option, it can be located outside the fermenter as a separate device. Such a separation may be achieved by centrifugation, e.g. in a disc separator or a decanter, by gravity in a settling device, or by a filtration technique such as cross flow filtration. The separation can be designed with a limited retention time so that the host, e.g. cells of bacteria, yeast and fungi, spend a limited time outside of the fermenter and do not lose their ability to grow or produce anthranilate, while they are in the separation device. The continuous fermentation with cell retention allows the fermentation step a) to be run with a high cell density and thus a high space time yield. More importantly, the fermentation in step a) can be run with a very low growth rate. This results in a higher overall product yield (g of product per g of raw material) since less sugar is used for the production of biomass and more for the production of oAB.

A further advantage of the continuous fermentation over batch fermentation is that the so-called "down time" of the fermenter can be reduced to a minimum. A continuous fermentation has a much longer production phase than a batch fermentation so the time spent on cleaning, sterilization, filling and harvesting is proportionally much shorter. This aspect contributes to the increase the space time yield and therefore reduces the investment costs for a given plant capacity, which is used to run the method according to the invention.

If step a) of the method is run as a batch or a fed-batch fermentation the total fermentation capacity can be divided between several fermenters, and break tanks can be used to enable a continuous supply of fermentation material of step a) to the downstream section comprising steps b) to d), or even e). Batch or fed-batch fermentation can be used in step a) of the method according to the invention in cases where the production rates of the microorganisms cannot be maintained at a high rate in continuous fermentation mode.

Step a) of the method according to the invention provides o-aminobenzoate comprising anthranilate anion by fermentation of a raw material comprising fermentable sugars using a host, preferably a recombinant host that is capable of converting sugars to o-aminobenzoate by fermentation. Preferably, a fermentation reactor comprising such a host is cultivated with the addition of a carbon source, for example corn syrup, sugar can juice, molasses, and the like and a nitrogen source, for example ammonia gas, ammonium hydroxide solution, ammonium sulphate, ammonium nitrate, corn steep liquor, and the like, as well as the respective micro-nutrients needed for survival of the microorganism. The pH in the fermentation of step a) can be in the range of 3 to 9, preferably between pH 4 to 8, most preferably kept at a value between 6.5 and 7.5. The pH in step a) can be adjusted e.g. by the addition of a base, for example, ammonia gas, ammonium hydroxide or sodium hydroxide.

In a further embodiment of the method according to the invention, at least step a) of producing o-aminobenzoate by fermentation and step b) of converting said o-aminobenzoate from said anthranilate anion to anthranilic acid by acid protonation can be run continuously. In this embodiment, a fermenter in which step a) is performed is operated continuously, wherein a fermentation broth produced in step a) can be withdrawn continuously and processed through a device to separate the biomass comprising the host grown to a certain density, for example a filter, a centrifuge, membranes, etc. This biomass can be recycled to the fermenter used in the fermentation of step a) after purging a small portion the biomass comprising the recombinant microbial host. Such purge stream from the biomass can be useful in order to avoid biomass accumulation. A portion of microbial host cells that multiply in the fermenter and dead cells can thus be removed in order to keep the concentration of live host cells in the reactor of fermentation step a) within defined limits, most preferably constant. This can be different in the case of fed-batch fermentation, where the recombinant host cells and the fermentation product(s) remain in the bioreactor until the end of the run, which therefore is not a continuous fermentation but a fed-batch fermentation. Sufficient oxygen can be added to the reactor used in step a)

either as pure oxygen, as air, or as enriched air. The cell free fermentation broth of the fermentation step a) can essentially be a solution of an anthranilate salt comprising the anthranilate anion and a suitable counter cation, such as $NH_4^+$ or $Na^+$. The anthranilate solution produced in fermentation step a) can have a concentration between 5 g/L and 500 g/L, preferably between 20 g/L and 200 g/L, most preferably between 50 g/L and 150 g/L of anthranilate salt.

In a further embodiment of the method according to the invention, the recombinant microbial host used in the fermentation of step a) is removed prior to performing step b) of converting said o-aminobenzoate from said anthranilate anion to anthranilic acid. Preferably, the removed recombinant microbial host is re-fed to the fermentation of step a). This has the technical advantage of allowing a continuous fermentation process, which can be particularly efficient and cost-effective.

o-aminobenzoate (oAB) is an amino acid; thus its ionization state, and solubility in water, depends on the pH; with the zwitterion being the least soluble form. At pH 7, which prevails in the fermenter that can be used in fermentation step a), oAB exists as anions buffered with cations such as $Na^+$ or $NH_4^+$. Adding an acid, such as HCl, until the pH drops to the isoelectric point therefore causes precipitation of oAB crystals. Accordingly, method step b) of the method according to the invention comprises converting the anthranilate anion to anthranilic acid by acid protonation thereby forming a precipitate comprising anthranilic acid crystals. For this reason, method step b) can also be referred to as "crystallisation". Specifically, the anthranilate solution of step a) can be mixed with an acid, preferably HCl. Thus, the pH can be reduced to a value between 2 and 4, preferably between 3.2 and 3.6. This causes a change in solubility and results in the precipitation of the anthranilate crystals. The anthranilate crystals can be recovered, preferably by filtration, in the subsequent step c) ("recovery"). The residual moisture and inorganic salt contents in the precipitated anthranilate crystals ("cake") depends on the solid liquid separation operation.

When performing method step b), the anthranilate salt in the cell free aqueous fermentation broth produced in fermentation step a) is first protonated to anthranilic acid by reaction with the stronger acid, preferably HCl, wherein the anthranilic acid precipitates and is subsequently recovered as a solid material in method step c) ("recovery"). The anthranilic acid is then converted to aniline in a subsequent method step d) by thermal decarboxylation.

In a preferred embodiment of the method according to the invention, the conversion of o-aminobenzoate from anthranilate anion to anthranilic acid by acid protonation in method step b) can be done by adding HCl, preferably to a pH of 2.5 to 4.5, more preferably to a pH of 3 to 4, most preferably between 3.2 and 3.6.

In a further embodiment of the method according to the invention, the recovering of the anthranilic acid by precipitation in method step c) comprises filtration, thereby generating a slurry comprising said recovered anthranilic acid, wherein said slurry comprising said recovered anthranilic acid is preferably dissolved in an organic solvent. Preferably, the organic solvent used at this stage is aniline or 1-dodecanol or a mixture thereof.

In a further embodiment of the method according to the invention, the recovering of the anthranilic acid by dissolving said anthranilic acid in an organic solvent in method step c) comprises adding said organic solvent, preferably aniline or 1-dodecanol or a mixture thereof, to said anthranilic acid such that said anthranilic acid is recovered as a solute in the organic solvent.

Preferably, the recovery step c) of the method according to the invention can be followed by washing and drying the recovered anthranilic acid precipitate in advance of performing the thermal decarboxylation of step d).

In a further embodiment of the method according to the invention, thermal decarboxylation step d) can be performed in the presence of a catalyst. Such a catalyst that is preferred can be a zeolite catalyst, wherein said zeolite catalyst preferably is zeolite H—Y (e.g. as obtained from Zeolyst International, catalog number CBV600). The acid catalyst zeolite H-Y ($SiO_2/Al_2O_3$ can be between 5 and 7, preferably it is 5.5) has a particularly high acidic character and has a wider pore size (0.7-0.8 nm) than e.g. ZSM5-27 (e.g. as obtained from Clariant SuedChemie, catalog number MFI-27, $SiO_2/Al_2O_3$=27), which also possesses a strong acidic character, but which has smaller pore size (0.5 nm) so that AA molecules cannot effectively penetrate into them and consequently do not have easy access to the active sites of the acidic catalyst, thereby reducing its effectivity.

Method step d) comprises converting the anthranilic acid of step c) to aniline by thermal decarboxylation in an organic solvent. The anthranilic acid, e.g. in the form of anthranilate crystals, with or without residual moisture, is thermally decarboxylated, preferably by feeding the anthranilic acid to a decarboxylation reactor, in which step d) can be performed. The thermal decarboxylation of step d) can be operated at a temperature between 150° C. and 250° C., preferably between 160° C. and 220° C., more preferably between 180° C. and 200° C. The thermal decarboxylation of step d) can be run for sufficient time to react the anthranilic acid to aniline. Preferably, step d) can be run for 0.5 hours to 3 hours.

Thermal decarboxylation step d) can be performed in the presence of an acid catalyst in order to speed up the thermal decarboxylation.

Thermal decarboxylation step d) can be run in a solvent such as water, aniline, or in 1-dodecanol, preferably in 1-dodecanol, or in a mixture of 1-dodecanol and aniline.

Further, thermal decarboxylation step d) can be performed in a reactor, wherein the pressure in the reactor can be selected as a function of how much of the liquid phase is allowed to evaporate during the reaction and leave the reactor with the carbon dioxide ($CO_2$) that is a product of the decarboxylation.

Further, thermal decarboxylation step d) can produce an aniline organic solvent mixture, which can then be distilled with aniline and any water entrained or dissolved in it. Any organic solvent used in recovery step c) can be recovered as "overhead product". The solvent can then be cooled and be recycled for distillation. The overhead stream that contains aniline can then be fed to a distillation step, e.g. a heteroazeotropic distillation.

In a further embodiment of the method according to the invention, the thermal decarboxylation step d) can be followed by a further step e) of purifying the aniline, preferably by distillation.

In one embodiment of the method according to the invention, following recovery step c) the solution ("mother liquor") can still have up to 3-10 g/l anthranilate. Thus, in a further embodiment of the method according to the invention, following recovery step c) residual anthranilate anion can be recovered by adsorption to an ion exchange resin or an active carbon material or a zeolite, preferably a zeolite modified with $Fe^{3+}$ or $Ca^{2+}$, preferably a Fe—Y zeolite that can be produced by ion exchange of commercially available zeolite H—Y (e.g. as obtained from Zeolyst International—$CBV_{600}$), e.g. as described in Example 6, such as Fe—Y, followed by desorption of the recovered anthranilate anion, and re-feeding of said anthranilate anion to conversion step b) for acid protonation. The desorption of the recovered anthranilate anion can preferably be carried out at a pH of 5 to 10. For example, the desorption can be performed with water having a pH or 5 to 10, e.g. water with a neutral or alkaline pH can be used. The solution after desorption can be recycled upstream of the acid addition in conversion step b) and downstream of the biomass removal after fermentation step a).

Figure 7:
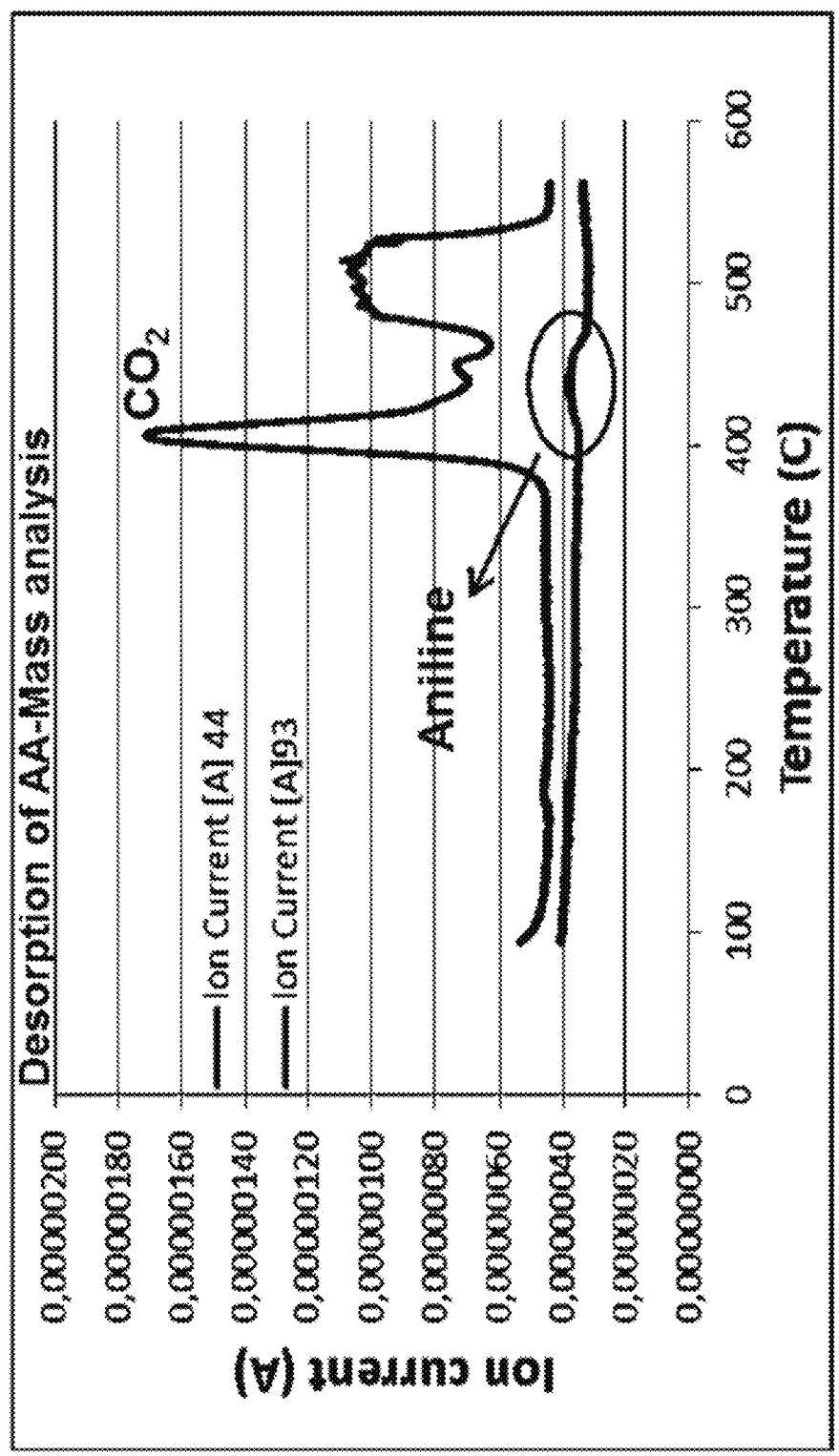
FIG. 7 shows a mass profile of anthranilic acid decomposition adsorbed on Fe—Y in the temperature range of 100-550° C.
Figure 8:
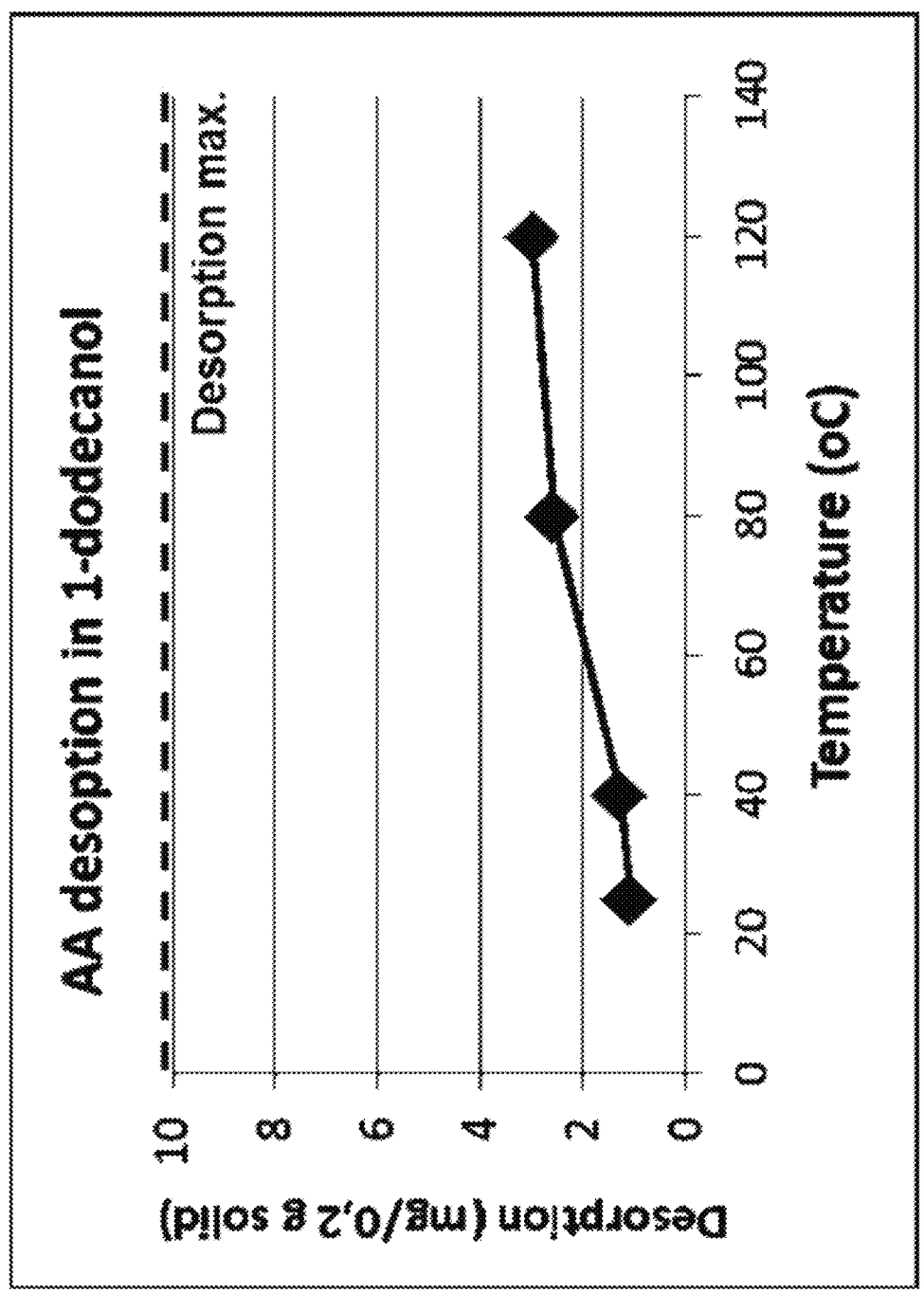
FIG. 8 shows the desorption of anthranilic acid from Fe—Y into 1-dodecanol. The experiment was performed by suspending 0.2 g Fe—Y containing 10.8 mg anthranilic acid in 2 mL 1-dodecanol. The slurry was stirred for 0.5 h at the temperature range of 25-120° C. The desorption results are shown in FIG. 2 in which maximum 27.8% anthranilic acid could be desorbed into 1-dodecanol phase at 120° C.
Figure 9:
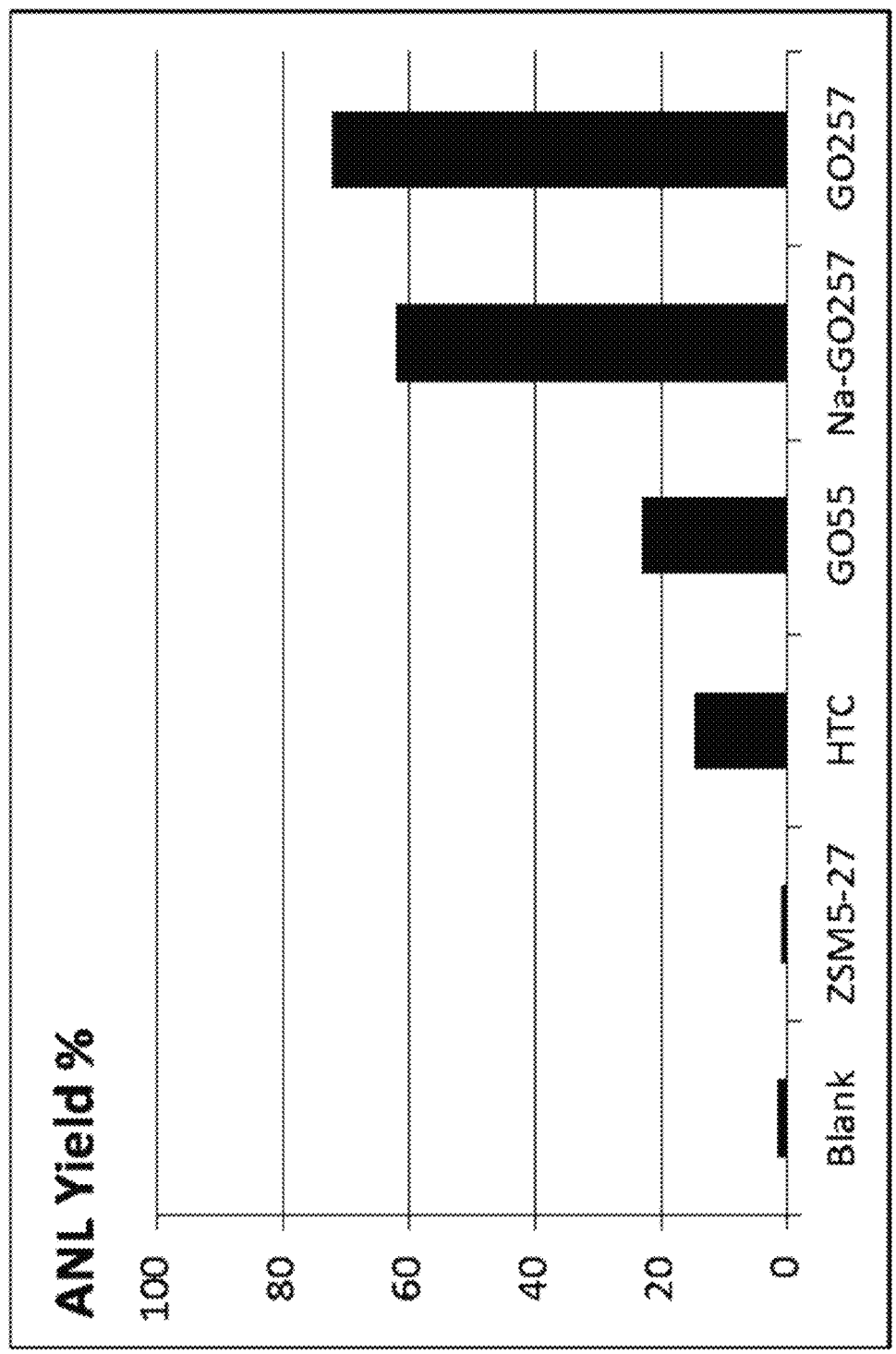
FIG. 9 shows the desorption of anthranilic acid from adsorbent into the liquid phase. The desorption test of anthranilic acid from Fe—Y into water showed that the adsorption of anthranilic acid by metal-exchanged zeolite in aqueous solution is reversible. The desorption of anthranilic acid into an organic solvent was tested. 1-dodecanol was selected as organic solvent due to high solubility of anthranilic acid in it and also its very low miscibility in water (0.004 g/L).

Following recovery step c) residual anthranilate anion can be recovered by adsorption to an ion exchange resin or an active carbon material or a zeolite. A preferred zeolite is modified with $Fe^{3+}$ or $Ca^{2+}$, preferably a Fe—Y zeolite. Such a Fe—Y can be prepared as described in Example 6. After adsorption of residual anthranilate anion, desorption of the recovered anthranilate anion into a liquid phase follows. Such desorption of the recovered anthranilate anion can be into an organic solvent phase or in a water phase. FIG. 7 shows a mass profile of AA decomposition adsorbed on the zeolite Fe—Y. FIG. 8 shows the desorption of AA from the zeolite Fe—Y into the organic solvent 1-dodecanol, which is the preferred organic solvent due to high solubility of AA in it and its low miscibility in water (0.004 g/L). FIG. 9 shows the desorption of anthranilic acid (AA) from the adsorbent into the liquid phase.

It is preferred that the recovered and desorbed residual anthranilate, anion is at least partially re-fed to conversion step b) for converting said anthranilate anion to anthranilic acid by acid protonation. This has the technical advantage of improving the efficiency of the method even further leading to the associated economic benefit.

In a particularly preferred embodiment of the method according to the invention, subsequent to the recovery of the residual anthranilate anion by adsorption following recovery step c), a water stream devoid of the adsorbed anthranilate anion can at least be partially re-fed to the fermentation of step a). Again, this has the technical advantage of improving the efficiency of the method even further.

In a preferred embodiment of the invention, steps a) through d) can be run continuously as an integrated process. In a further preferred embodiment of the invention, steps a) through e) can be run continuously as an integrated process. In such an integrated and continuous process, the fermentation of step a) can be run continuously with cell retention and continuous removal of anthranilate from the fermentation broth in the fermentation of step a), followed by continuous processing to aniline by thermal decarboxylation in the subsequent steps b) through d), or b) through e). The method according to the invention can therefore be an integrated and continuous process, which is optimized with respect to production cost. The method according to the invention therefore offers a significant technical advantages leading to a higher yield of aniline with the corresponding economic benefit, as compared to more traditional state of the art methods that run in a non-continuous fashion.

In a further embodiment of the method according to the invention, the raw material of fermentation step a) can be selected from the group consisting of sugar beet, sugar cane, starch-containing plants, preferably corn, wheat and rye, and lignocellulose, preferably straw, wood and bagasse, glycerol and C1-compounds, preferably CO.

In a further embodiment of the method according to the invention, said fermentable carbon substrate of fermentation step a) can be selected from the group consisting of C-5 monosaccharides, C-6 monosaccharides, disaccharides, and tri-saccharides, wherein the C-5 monosaccharides preferably are xylose and arabinose, and wherein the C-6 monosaccharides preferably are glucose, fructose or mannose, and wherein the disaccharide preferably is saccharose, and wherein the trisaccharide preferably is kestose.

In a further embodiment of the method according to the invention, said recombinant microbial host of fermentation step a) can be selected from the group consisting of bacteria, yeast and fungi, wherein said bacterium preferably is an *Escherichia coli* strain, a *Corynebacterium* strain or a *Pseudomonas* strain, and wherein said *Corynebacterium* strain preferably is *Corynebacterium glutamicum*, more preferably *Corynebacterium glutamicum* ATCC 13032, and wherein said *Pseudomonas* strain preferably is *Pseudomonas putida*, more preferably *Pseudomonas putida* KT2440. In essence, any of the recombinant microbial host cells of the invention described above can be used in the fermentation step a) of the method according to the invention.

In a different embodiment of the invention a further method for producing aniline is provided, comprising the steps of:
  a) providing o-aminobenzoate, wherein said o-aminobenzoate comprises anthranilate anion and a suitable cation,
  b) converting said anthranilate anion to aniline by thermal decarboxylation in the presence or absence of a catalyst,
  c) extracting the aniline produced in step b) in an organic solvent at least once, and
  d) purifying the aniline produced in steps b) and c) by distillation, wherein said distillation produces aniline and a water phase.

In this embodiment, said o-aminobenzoate in step a) can be provided chemically or produced biologically, preferably it is produced biologically by fermentation of a raw material comprising at least one fermentable carbon substrate using a recombinant microbial host cell capable of converting said raw material comprising a fermentable carbon substrate to o-aminobenzoate by fermentation, wherein said o-aminobenzoate comprises anthranilate anion and a suitable cation.

Said fermentation of step a) can be a batch fermentation, a fed-batch fermentation or a continuous fermentation. In a preferred embodiment, step a) to step d) can be run continuously. The suitable cation of step a) can be $NH_4^+$ or $Na^+$. The recombinant microbial host of step a) can be removed prior to the subsequent conversion of said anthranilate anion to aniline by thermal decarboxylation in step b), wherein said removed recombinant microbial host preferably can be re-fed to the fermentation of step a). The catalyst used in this embodiment of the invention can be a heterogeneous acid catalyst, preferably a zeolite, most preferably zeolite H—Y. However, said catalyst can also be a heterogeneous base catalyst, preferably a layered double hydroxide, most preferably Mg—Al hydrotalcite.

In a preferred embodiment of the further method according to the invention, the extraction of aniline in an organic solvent in step c) can be performed for more than one time for a further pre-concentration of aniline in advance of distillation.

In a preferred embodiment of the further method according to the invention, the method can comprise recovering the organic solvent used in the extraction of step c), wherein said recovering can preferably be done by distillation, wherein said recovered organic solvent preferably can be re-fed to step c) to be re-used again for extracting the aniline produced in step b). Said organic solvent can be selected from the group consisting of alcohols, phenols, amides, ethers and aromatic hydrocarbons, wherein said alcohol preferably is 1-dodecanol. In another embodiment, this further method of the invention can comprise a further step e) of re-feeding the water-phase of the extraction performed in step c) and/or of re-feeding the water-phase of the distillation performed in step d) to the fermentation of step a). The $NH_4^+$ cation can be recovered as $NH_3$ subsequent to the distillation of step d) and can be re-fed to the fermentation of step a).

Lastly, the invention also provides the use of the aniline produced according to the method of the invention, wherein the aniline produced in step d) and/or e) is further converted to methylenedianiline (MDA) with formaldehyde in the presence of water and catalyst. The MDA produced in this way can be further converted to methylenediisocyanate (MDI) with phosgene. It will be apparent to those skilled in the art that various modifications can be made to the methods and recombinant host strains of the invention. Thus, it is intended that the present invention covers such modifications and variations, provided they come within the scope of the appended claims and their equivalents.

List of Tables

Table 1 shows vectors and plasmids used and/or generated in this study.

Table 2 shows bacterial strains used and/or generated in this study.

Table 3 shows primers used in this study.

Table 4 shows characteristics towards oAB production of bacterial strains used and/or generated in this study (CDW: cell dry weight; Y: yield; $\mu_{max}$: maximal growth rate; STY: space time yield).

Table 5 shows biochemical characteristics of *C. glutamicum* ΔtrpD raw extracts producing different variants of TrpEG towards TrpEG activity.

Table 6 shows the adsorption of AA 0.5% in water by HAP, zeolite Y (G0257 and G055) and ZSM5 (ZSM5-27 and ZSM5-55), as described in Example 6.

Table 7 shows the AA adsorption capacities of metal-exchanged zeolite G0257 in g AA/kg adsorbent in distilled water and buffered aqueous solution after 10 and 60 minutes, as described in Example 6.

EXAMPLES

Example 1—Production of o-Aminobenzoate with *E. coli*

The strain *E. coli* W3110 trpD9923 (*Escherichia coli*:: trpD9923; Table 2) was purchased from the *E. coli* Genetic Resource Center at Yale University. The strain had been created by random mutagenesis and contained a mutated trpD gene called trpD9923. An inactivation of the enzyme was achieved by a random point mutation (G→T) in the related gene, resulting in a nonsense mutation in the transferase activity encoding region. As the result only seven amino acids of the original transferase domain are translated (Ikeda M, Appl Microbiol Biotechnol, 2006, 69:615). The related truncated enzyme of the trpD9923 gene looses its ability to catalyse the reaction of anthranilate phosphoribosyl transferase, but maintains its anthranilate synthase activity. The strain can therefore synthesize anthranilate, but cannot metabolize it further to L-tryptophan and is thus L-tryptophan auxotroph. This leads to an accumulation of anthranilate.

The strain was grown in 50 mL shake flasks with a 10 mL culture volume at 28° C. at 140 rpm. The medium used was the mineral medium M9 (1 g/L $(NH_4)_2Cl$, 0.5 g/L NaCl, 0.05 g/L thiamin, 1 g/L $KH_2PO_4$, 1 g/L $K_2HPO_4$, 0.247 g/L $MgSO_4.7H_2O$ (Merck, Darmstadt), 0.015 g/L $CaCl_2$, and 10 g/L glucose. The pH was adjusted to 7 with 5 mol/L sodium hydroxide solution.) with 20 mg/L L-tryptophan. The strain produced 60 mg/L anthranilate after 25.5 h as measured by HPLC-DAD (254 nm) (Table 4 and Example 3). The strain was further optimized by inactivating the phosphotransferase system (PTS) using knockout deletion. Accordingly, a the resulting PTS-deficient strain *Escherichia coli*:: trpD9923Δhpr (Table 2) was generated and adapted to growth on glucose and tested for anthranilate production using a 25 mL shake flask fermentation at 37° C. at 150 rpm with a culture volume of 10 mL. The same medium as for the pts positive strain was used. It produced 69 mg/L of anthranilate after 25 hours as measured by HPLC-DAD (254 nm) (Table 4 and Example 3).

Example 2—Strain Selection for Developing a Microbial Strain that Produces o-Aminobenzoate Several strains commonly used industrial biotechnology were investigated regarding their natural tolerance towards oAB and to organic solvents in question for later product extraction (e.g. 1-dodecanol or octanol). Furthermore, the influence of the used pH value was investigated. It was known from previous experiments that at least for *E. coli* the toxicity of aromatic compounds depends strongly on the pH value, probably because protonated acids can much more efficiently penetrate the cell membrane and accordingly their toxicity rises severely. The extraction of oAB in an organic phase is supposed to work best at low pH values, close to the isoelectric point of oAB. The most relevant host strains considered were: *Escherichia coli* K12, *Corynebacterium glutamicum* DSM 20300 (=ATCC 13032), *Pseudomonas putida* KT2440, *Bacillus subtilis* subsp. 168, *Saccharomyces cerevisiae* DSM 70449, and *Pichia pastoris* X33 (DSM 70382).

To investigate the chosen strains towards the mentioned characteristics shake flasks and small scale fermentation experiments were performed and the organisms were supplemented with the toxic substances (aminobenzoates, solvents) at differed concentrations, different pH values, and the behaviour of the strains was studied.

The organisms (commercially obtained from ordered from the DSMZ, German collection of Microorganisms and cell cultures, Braunschweig) were firstly cultivated in shake flasks and in each of them in suiting, published standard minimal medium in order to characterize their growth under standard cultivation conditions (*C. glutamicum*: Preculture: BHI medium (37 g/L; Brain-Heart-Infusion; Becton Dickenson and Company, Heidelberg); Main culture pH 7: CGXII-MOPS medium (42 g/L MOPS buffer, 20 g/L $(NH_4)_2SO_4$, 5 g/L urea (Fisher Scientific, Schwerte), 1 g/L $KH_2PO_4$, 1 g/L $K_2HPO_4$, 0.25 g/L $MgSO_4.7H_2O$ (Merck, Darmstadt), 0.01 g/L $CaCl_2$, and 10 g/L glucose (autoclaved separately). The pH was adjusted to 7 with 5 mol/L sodium hydroxide solution. The following components were added after sterile filtration: 2 mg/L biotin, 0.01 g/L $MnSO_4.H_2O$ (Merck, Darmstadt), 0.01 g/L $FeSO_4.7H_2O$ (Merck, Darmstadt), 1 mg/L $ZnSO_4.7H_2O$, 0.2 mg/L $CuSO_4.5H_2O$ (Merck, Darmstadt), 0.02 mg/L $NiCl_2.6H_2O$ (Merck, Darmstadt), and 0.03 g/L 3.4-dihydroxybenzoic acid (Acros Organics, Nidderau); Main culture pH 5: CGXII-MES medium (39 g/L MES buffer, 20 g/L $(NH_4)_2SO_4$, 5 g/L urea (Fisher Scientific, Schwerte), 1 g/L $KH_2PO_4$, 1 g/L $K_2HPO_4$, 0.25 g/L $MgSO_4.7H_2O$ (Merck, Darmstadt), 0.01 g/L $CaCl_2$, and 10 g/L glucose (autoclaved separately). The pH was adjusted to 5 with 5 mol/L sodium hydroxide solution. The following components were added after sterile filtration: 2 mg/L biotin, 0.01 g/L $MnSO_4.H_2O$ (Merck, Darmstadt), 0.01 g/L $FeSO_4.7H_2O$ (Merck, Darmstadt), 1 mg/L $ZnSO_4.7H_2O$, 0.2 mg/L $CuSO_4.5H_2O$ (Merck, Darmstadt), 0.02 mg/L $NiCl_2.6H_2O$ (Merck, Darmstadt), and 0.03 g/L 3.4-dihydroxybenzoic acid (Acros Organics, Nidderau); *E. coli*: Preculture: LB medium (Luria-Bertani; Roth, Karlsruhe); Main culture pH 7: M9 medium (1 g/L $(NH_4)_2Cl$, 0.5 g/L NaCl, 0.05 g/L Thiamin chloride, 1 g/L $KH_2PO_4$, 1 g/L K2HPO4, 0.247 g/L $MgSO_4.7H_2O$ (Merck, Darmstadt), 0.015 g/L $CaCl_2$, and 10 g/L glucose. The pH was adjusted to 7 with 5 mol/L sodium hydroxide solution.); Main culture pH 5: M9-MES medium (19.5 g/L MES buffer, 1 g/L $(NH_4)_2Cl$, 0.5 g/L NaCl, 0.05 g/L Thiamin chloride, 1 g/L $KH_2PO_4$, 1 g/L $K_2HPO_4$, 0.247 g/L $MgSO_4.7H_2O$ (Merck, Darmstadt), 0.015 g/L $CaCl_2$, and 10 g/L glucose. The pH was adjusted to 7 with 5 mol/L sodium hydroxide solution.); *B. subtilis*: Preculture: LB medium; Main culture pH 7: M9-SL medium (1 g/L $(NH_4)_2Cl$, 0.5 g/L NaCl, 0.05 g/L thiamin, 1 g/L $KH_2PO_4$, 1 g/L $K_2HPO_4$, 0.247 g/L $MgSO_4.7H_2O$, 0.015 g/L $CaCl_2$, 1.0 mg/L $MnCl.H_2O$, 1.35 mg/L $FeCl.6H_2O$, 1.7 mg/L $ZnSO_4.7H_2O$, 0.04 mg/L $CuCl.2H_2O$, 0.06 mg/L $CoCl_2.6H_2O$, 0.06 mg/L $Na_2MoO_4.2H_2O$, and 10 g/L glucose. The pH was adjusted to 7 with 5 mol/L sodium hydroxide solution.); Main culture pH 5: M9-SL-MES medium (19.5 g/L MES buffer, 1 g/L $(NH_4)_2Cl$, 0.5 g/L NaCl, 0.05 g/L thiamin, 1 g/L $KH_2PO_4$, 1 g/L $K_2HPO_4$, 0.247 g/L $MgSO_4.7H_2O$, 0.015 g/L $CaCl_2$, 1.0 mg/L $MnCl.H_2O$, 1.35 mg/L $FeCl.6H_2O$, 1.7 mg/L $ZnSO_4.7H_2O$, 0.04 mg/L $CuCl.2H_2O$, 0.06 mg/L $CoCl_2.6H_2O$, 0.06 mg/L $Na_2MoO_4.2H_2O$, and 10 g/L glucose. The pH was adjusted to 5 with 5 mol/L sodium hydroxide solution.); *P. putida*: Preculture: LB medium; Main culture pH 7: Brunner medium (0.5 g/L $(NH_4)_2SO_4$, 1 g/L $KH_2PO_4$, 1 g/L $K_2HPO_4$, 0.2 g/L $MgSO_4.7H_2O$, 0.05 g/L $CaCl_2$, 5.0 mg/L EDTA, 2.0 mg/L $FeSO_4.7H_2O$, 0.03 mg/L $MnCl.H_2O$, 0.1 mg/L $ZnSO_4.7H_2O$, 0.01 mg/L $CuCl.2H_2O$, 0.2 mg/L $CoCl_2.6H_2O$, 0.03 mg/L $Na_2MoO_4.2H_2O$, 0.3 mg/L $H_3BO_3$, 0.02 mg/L $NiCl_2.6H_2O$, and 10 g/L glucose. The pH was adjusted to 7 with 5 mol/L sodium hydroxide solution.); Main culture pH 5: Brunner-MES medium (19.5 g/L MES buffer, 0.5 g/L $(NH_4)_2SO_4$, 1 g/L $KH_2PO_4$, 1 g/L $K_2HPO_4$, 0.2 g/L $MgSO_4.7H_2O$, 0.05 g/L $CaCl_2$, 5.0 mg/L EDTA, 2.0 mg/L $FeSO_4.7H_2O$, 0.03 mg/L $MnCl.H_2O$, 0.1 mg/L $ZnSO_4.7H_2O$, 0.01 mg/L $CuCl.2H_2O$, 0.2 mg/L $CoCl_2.6H_2O$, 0.03 mg/L $Na_2MoO_4.2H_2O$, 0.3 mg/L $H_3BO_3$, 0.02 mg/L $NiCl_2.6H_2O$, and 10 g/L glucose. The pH was adjusted to 5 with 5 mol/L sodium hydroxide solution.); *S. cerevisiae*: Preculture: YPD medium (10 g/L yeast extract, 20 g/L peptone, 20 g/L glucose); Main culture pH 5: SCM medium (5 g/L $(NH_4)_2SO_4$, 3 g/L $KH_2PO_4$, 2.5 g/L $MgSO_4.7H_2$), 0.5 g/L NaCl, 20 mg/L inositol, 5 mg/L thiamin, 1.32 mg/L riboflavin, 17.8 mg/L calcium pantothenat, 18.4 mg/L nicotinic acid, 5.16 mg/L pyridoxine-HCl, 0.18 mg/L biotin, 0.12 mg/L folic acid, 40.6 mg/L $FeCl_3.6H_2O$, 6.0 mg/L $ZnCl_2.4H_2O$, 3.0 mg/L $CaCl_2.2H_2O$, 5.76 mg/L $CuSO_4.5H_2O$, 6.0 mg/L $CoCl_2.6H_2O$, 6.0 mg/L $Na_2MoO_4.2H_2O$, 1.56 mg/L $H_3BO_3$, and 5 g/L glucose. The pH was adjusted to 5 with 5 mol/L sodium hydroxide solution.) (Sambrock J; Fritsch, E F, and Maniatis, T: Molecular Cloning—a laboratory manual. Cold Spring Larbor Laboratory Press; 1989; New York; Harwood C R, Cutting S M: Molecular biological methods for *Bacillus*. Chichester, England: John Wiley & Sons Ltd; 1990; Keilhauer, C, Eggeling, L, Sahm, H: J Bacteriol, 1993, 175(17): 5595). These experiments were performed with a medium pH of 7 and pH 5 to evaluate the difference in toxicity of aminobenzoate at low pH values. The yeast strains were only investigated at pH values below 7 (5.5 and 3.5). The different pH values were stabilized by addition of different buffer systems (MOPS, MES).

Figure 11:
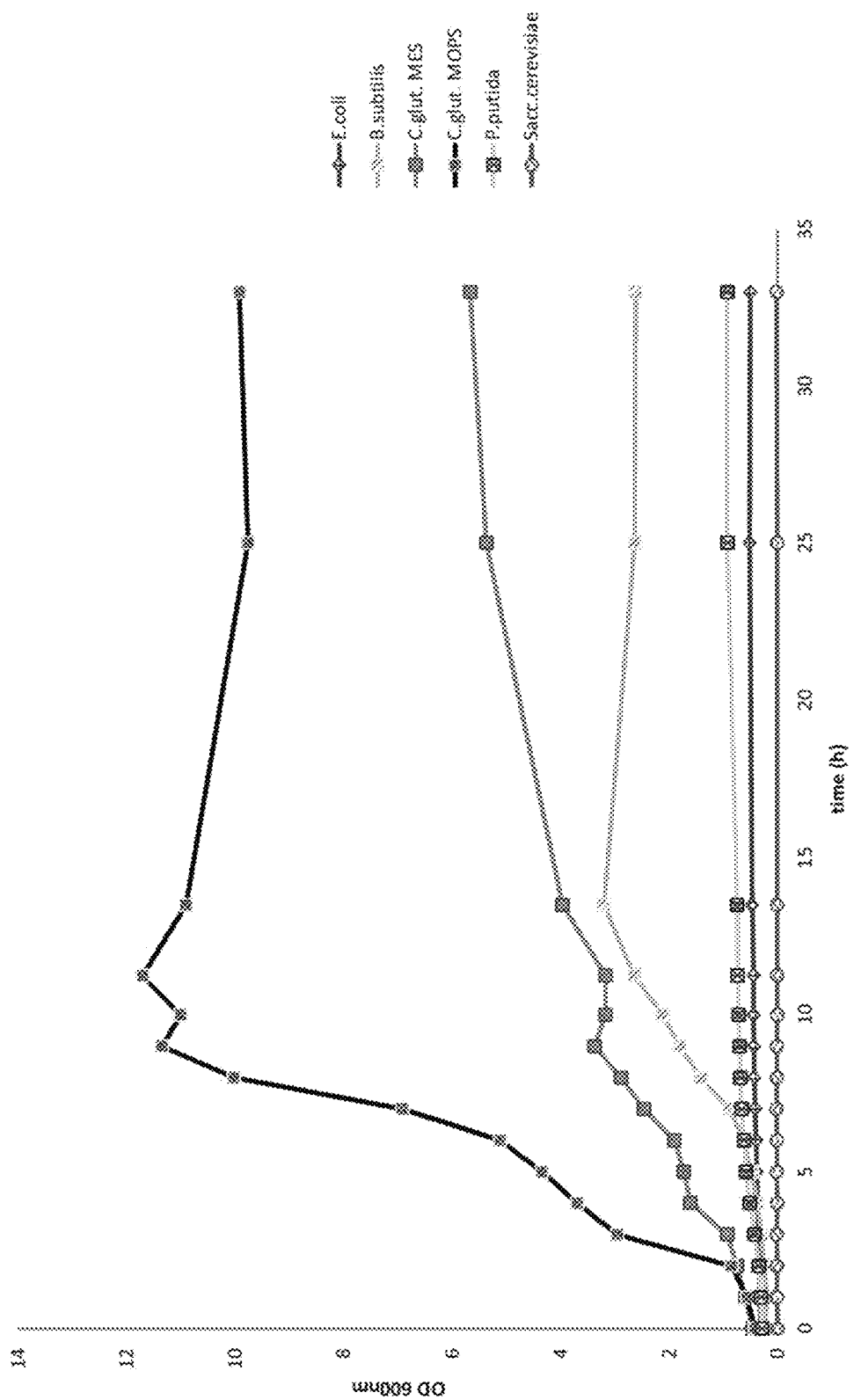
FIG. 11 shows the optical density at 600 nm ($OD_{600}$) followed over 33 h (triple determination) of 100-mL-shake flask cultures at pH 5 (with MES buffer) of the strains *Escherichia coli, Bacillus subtilis, Corynebacterium glutamicum, Pseudomonas putida*, and *Saccharomyces cerevisiae*. *C. glutamicum* was additionally cultivated at pH 7 (supplemented with MOPS buffer).

100-mL-shake flask cultures of the strains (pH 5 (with MES buffer) were incubated for 33 h and the growth was followed by measurement of the optical density at 600 nm ($OD_{600}$) over the time (triple determination). *C. glutamicum* was additionally cultivated at pH 7 (with MOPS buffer). FIG. 11 shows the results.

Figure 12:
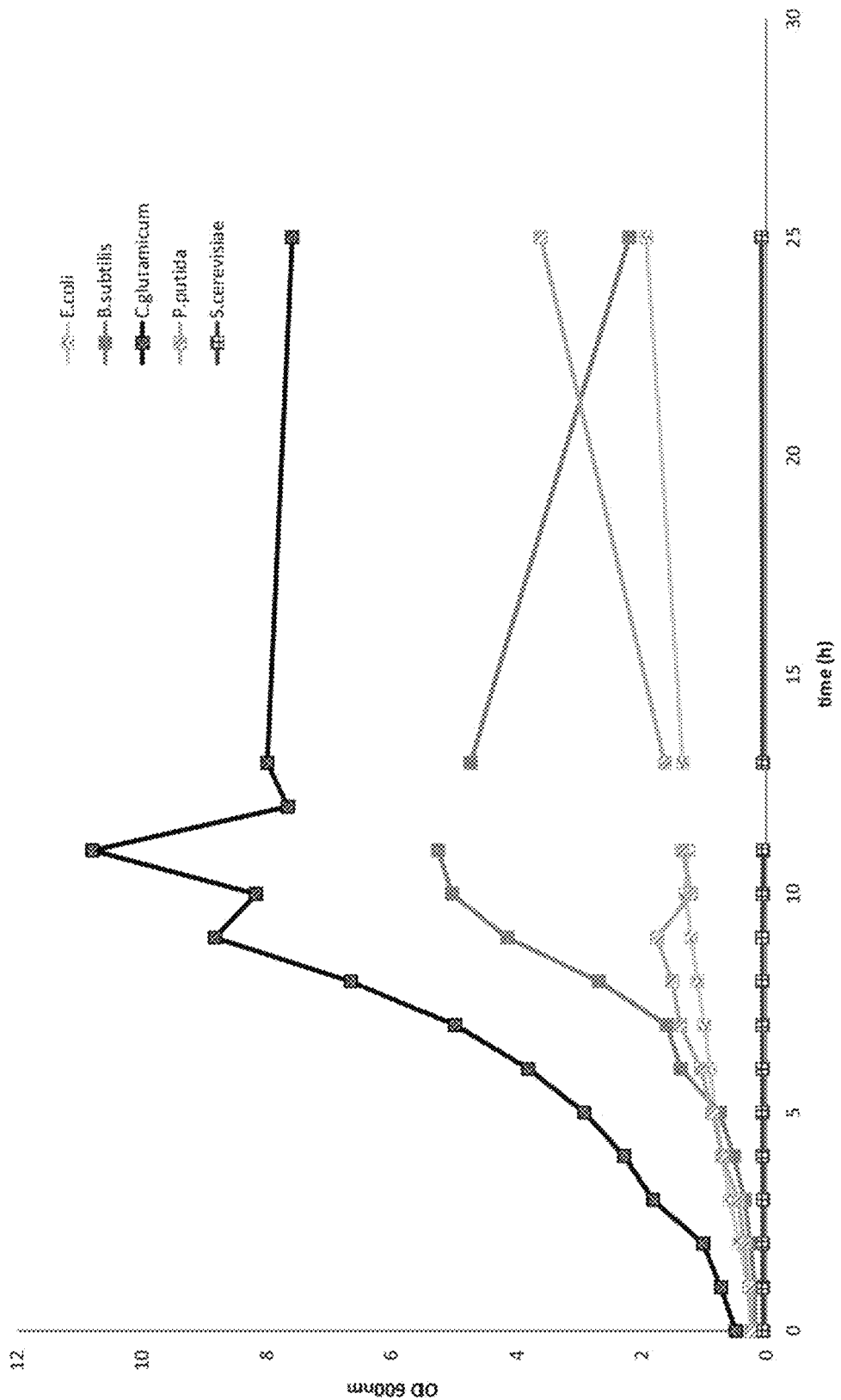
FIG. 12 shows the optical density at 600 nm ($OD_{600}$) followed over 25 h (double determination) of 100-mL-shake flask cultures at pH 7 (with MOPS buffer) of the strains *Escherichia coli, Bacillus subtilis, Corynebacterium glutamicum, Pseudomonas putida*, and *Saccharomyces cerevisiae*.
Figure 13:
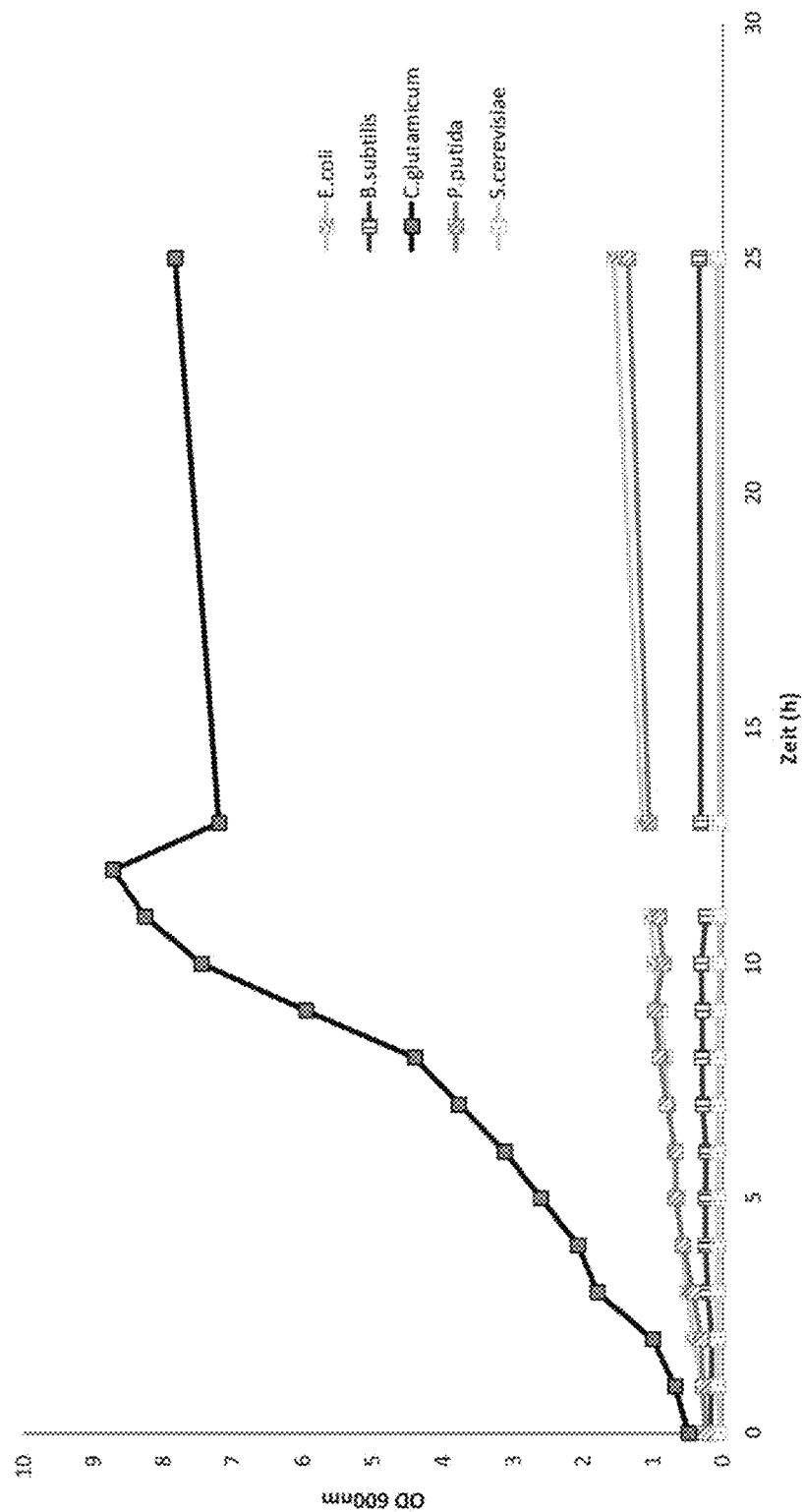
FIG. 13 shows the optical density at 600 nm ($OD_{600}$) followed over 25 h (double determination) of 100-mL-shake flask cultures at pH 7 (with MOPS buffer) supplemented with 3 g/L oAB of the strains *Escherichia coli, Bacillus subtilis, Corynebacterium glutamicum, Pseudomonas putida*, and *Saccharomyces cerevisiae*.
Figure 14:
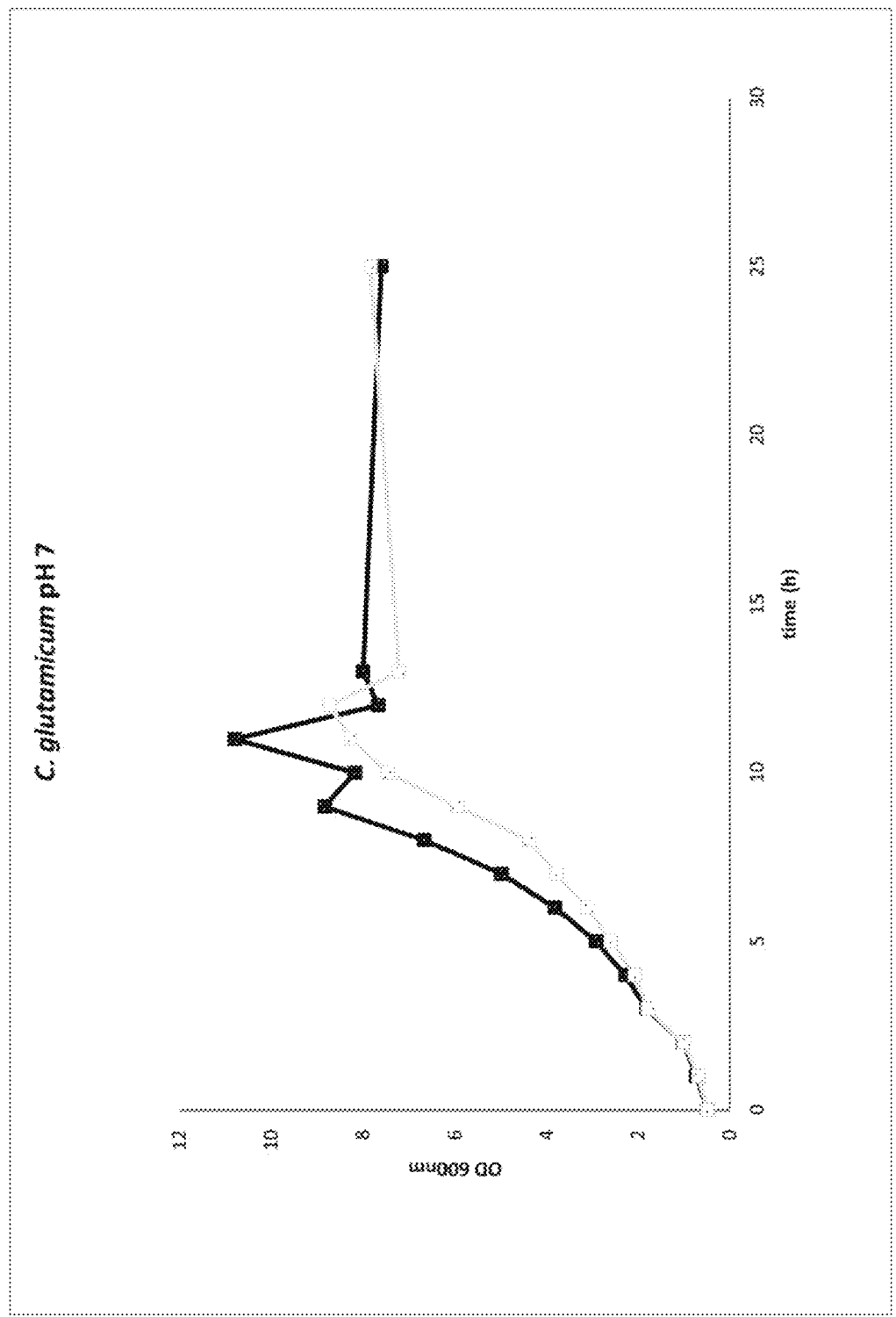
FIG. 14 shows the optical density at 600 nm ($OD_{600}$) followed over 25 h (double determination) of 100-mL-shake flask cultures at pH 7 (with MOPS buffer) not supplemented (black) or supplemented with 3 g/L oAB (grey) of the strain *Corynebacterium glutamicum*.
Figure 15:
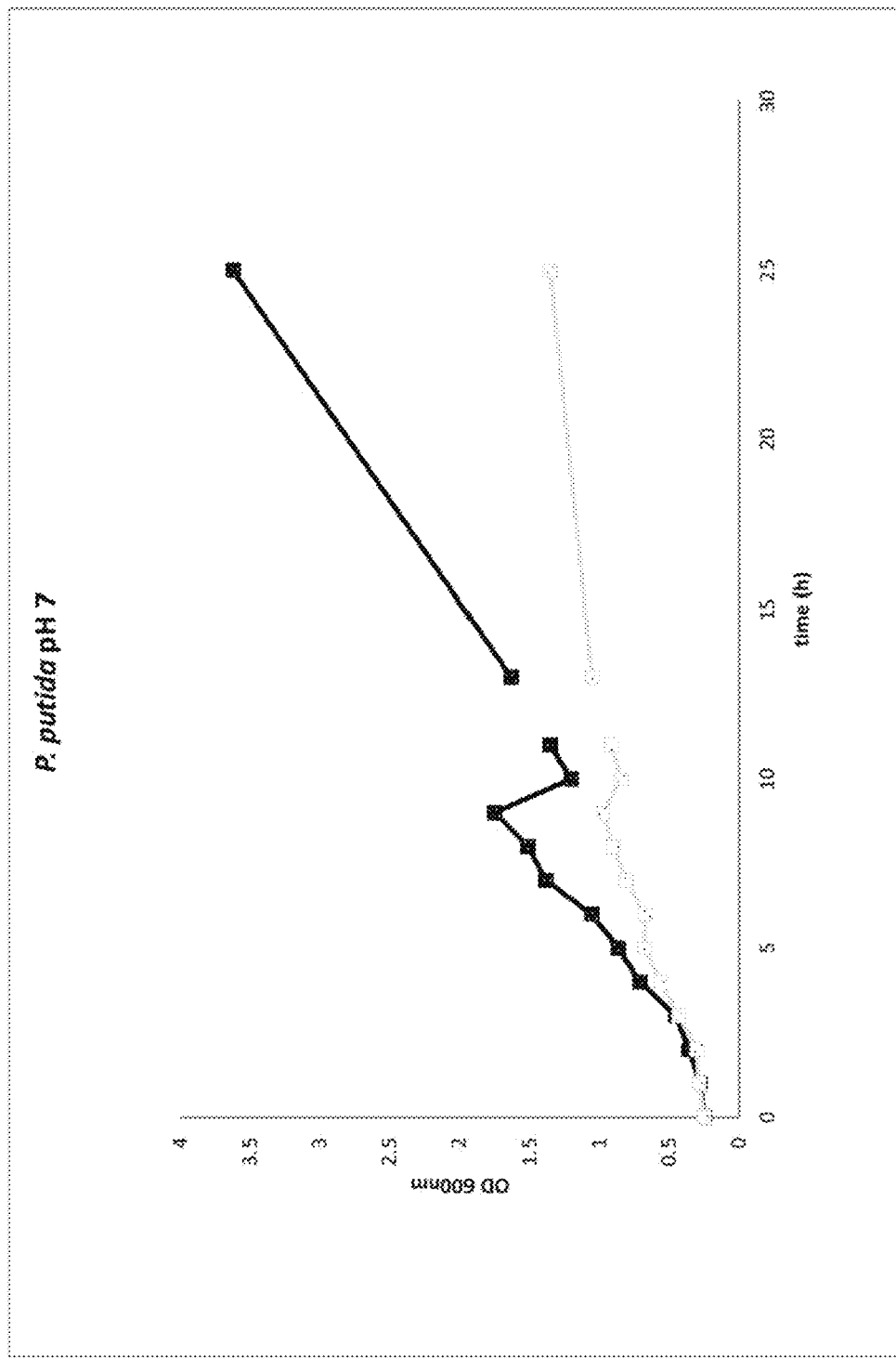
FIG. 15 shows the optical density at 600 nm ($OD_{600}$) followed over 25 h (double determination) of 100-mL-shake flask cultures at pH 7 (with MOPS buffer) not supplemented (black) or supplemented with 3 g/L oAB (grey) of the strain *Pseudomonas putida*.

The collected data showed that *C. glutamicum* exhibits the best growth at pH 5 of all investigated organisms. *E. coli, P. putida*, and *S. cerevisiae* did grow extremely weak at pH 5. Nevertheless, in some of the cultures, due to metabolic activity the pH dropped additionally below 4. To exclude growth effects due to metabolic activities the experiments were performed in fermenters with automatic pH regulation. Already visible was, as expected, that cultivation at low pH decreases the growth rate of all tested organisms. However, to compare the growth of all considered organisms under standard cultivation conditions at pH 7 the experiment was repeated with all minimal media supplemented with MOPS buffer. Additionally, the analogously cultures were supplemented with oAB (final concentration of 3 g/L, added in the beginning of the exponential growth phase in three portions (after 2, 3, 4 h incubation time)). 100-mL-shake flask cultures of the strains at pH 7 with or without supplementation with 3 g/L oAB were incubated for 25 h and the growth was followed by measurement of the optical density at 600 nm ($OD_{600}$) over the time (double determination) (FIG. 12 and FIG. 13). *C. glutamicum* reached the highest $OD_{600}$ values under the chosen cultivation conditions and furthermore its growth was not inhibited by the addition of 3 g/L oAB, whereas the growth of other organisms, like for example *B. subtilis* was at 3 g/L oAB already strongly decreased. From these results *C. glutamicum* was identified as the preferred candidate for an oAB production at pH 7 (FIG. 14 and FIG. 15).

Figure 16:
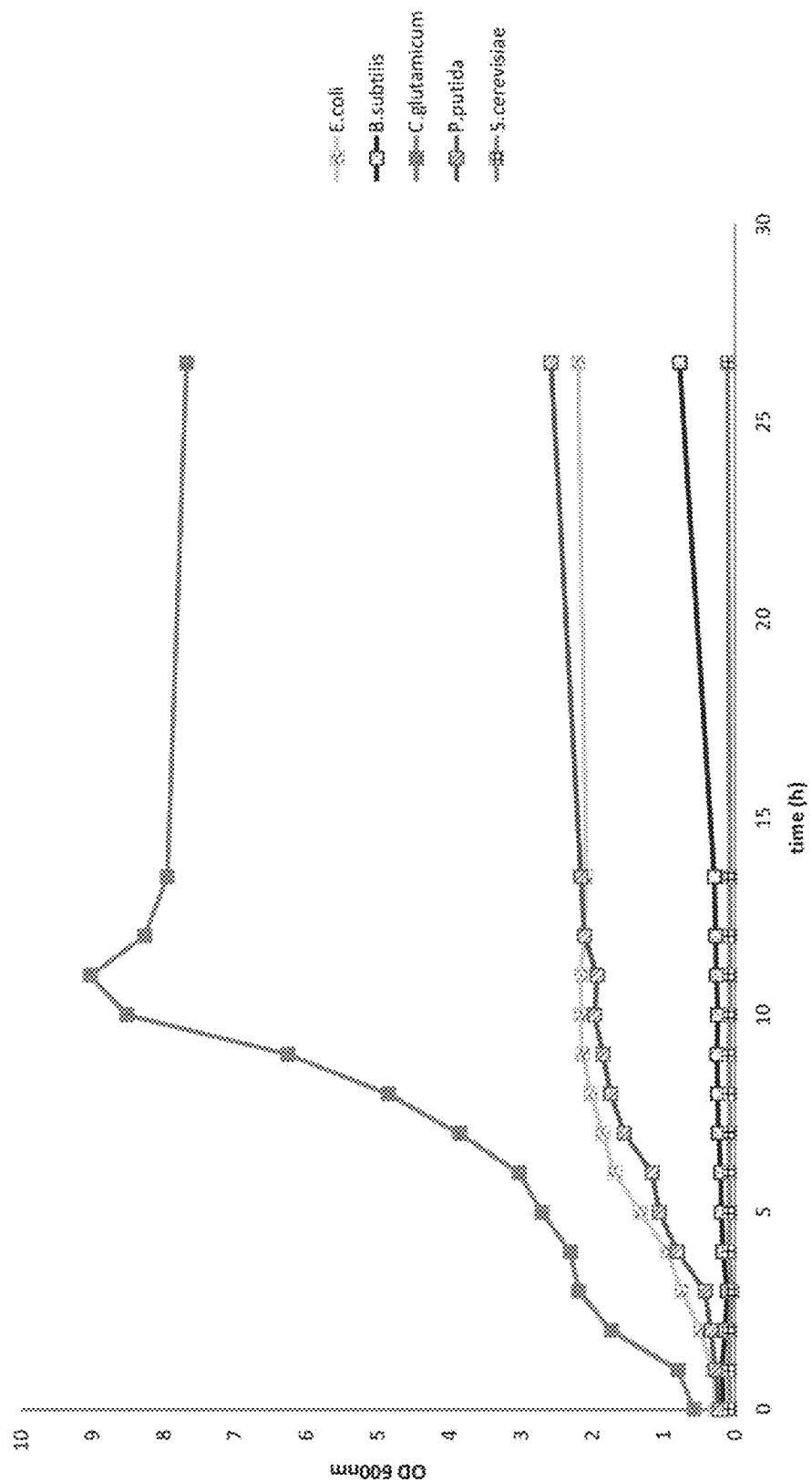
FIG. 16 shows the optical density at 600 nm ($OD_{600}$) followed over 27 h (double determination) of 100-mL-shake flask cultures at pH 7 (with MOPS buffer) supplemented with 3 g/L pAB of the strains *Escherichia coli, Bacillus subtilis, Corynebacterium glutamicum, Pseudomonas putida*, and *Saccharomyces cerevisiae*.
Figure 17:
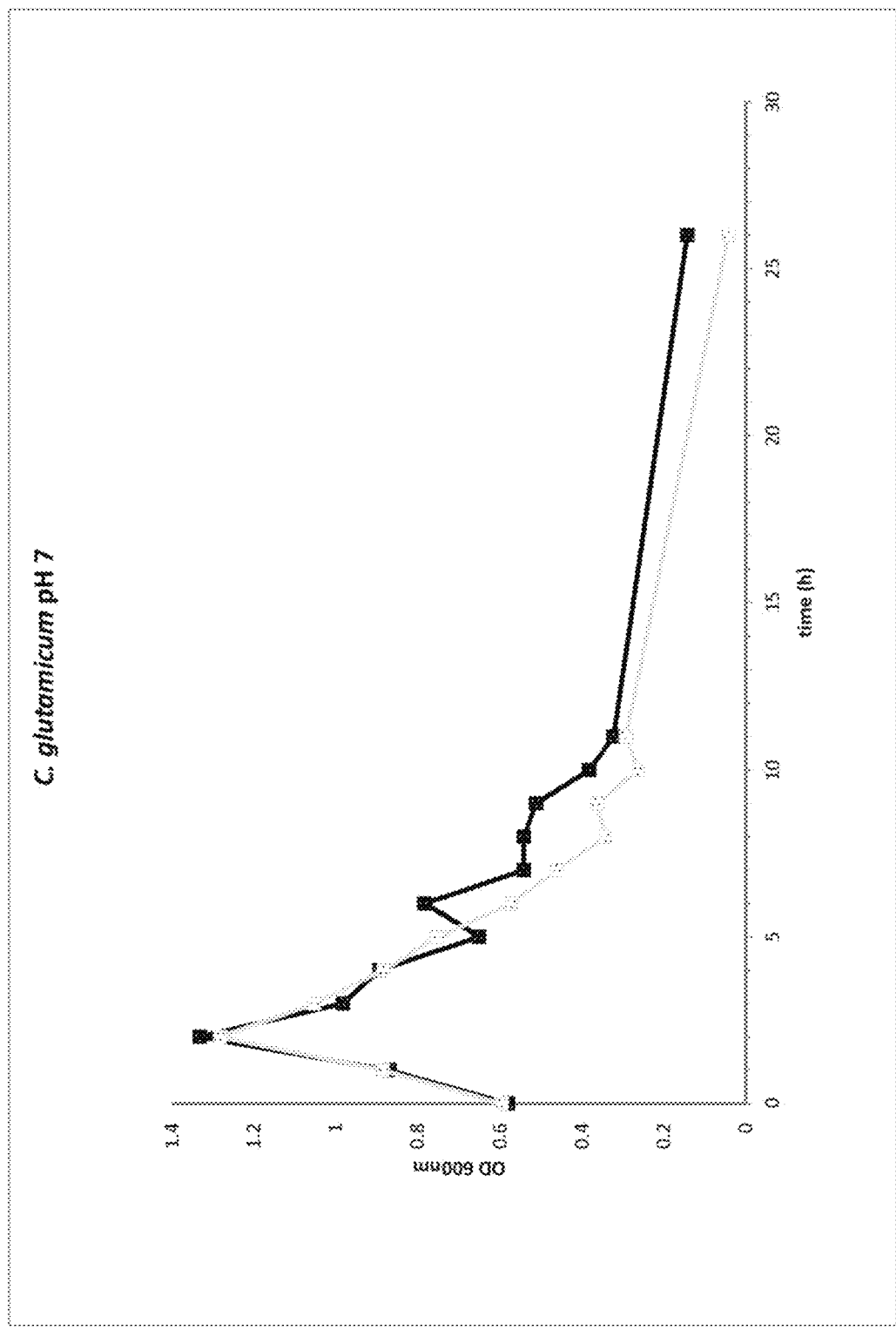
FIG. 17 shows the optical density at 600 nm ($OD_{600}$) followed over 25 h (double determination) of 100-mL-shake flask cultures at pH 7 (with MOPS buffer) supplemented with 0.1 g/L octanol (duplicates in black and grey) of the strain *Corynebacterium glutamicum*.
Figure 18:
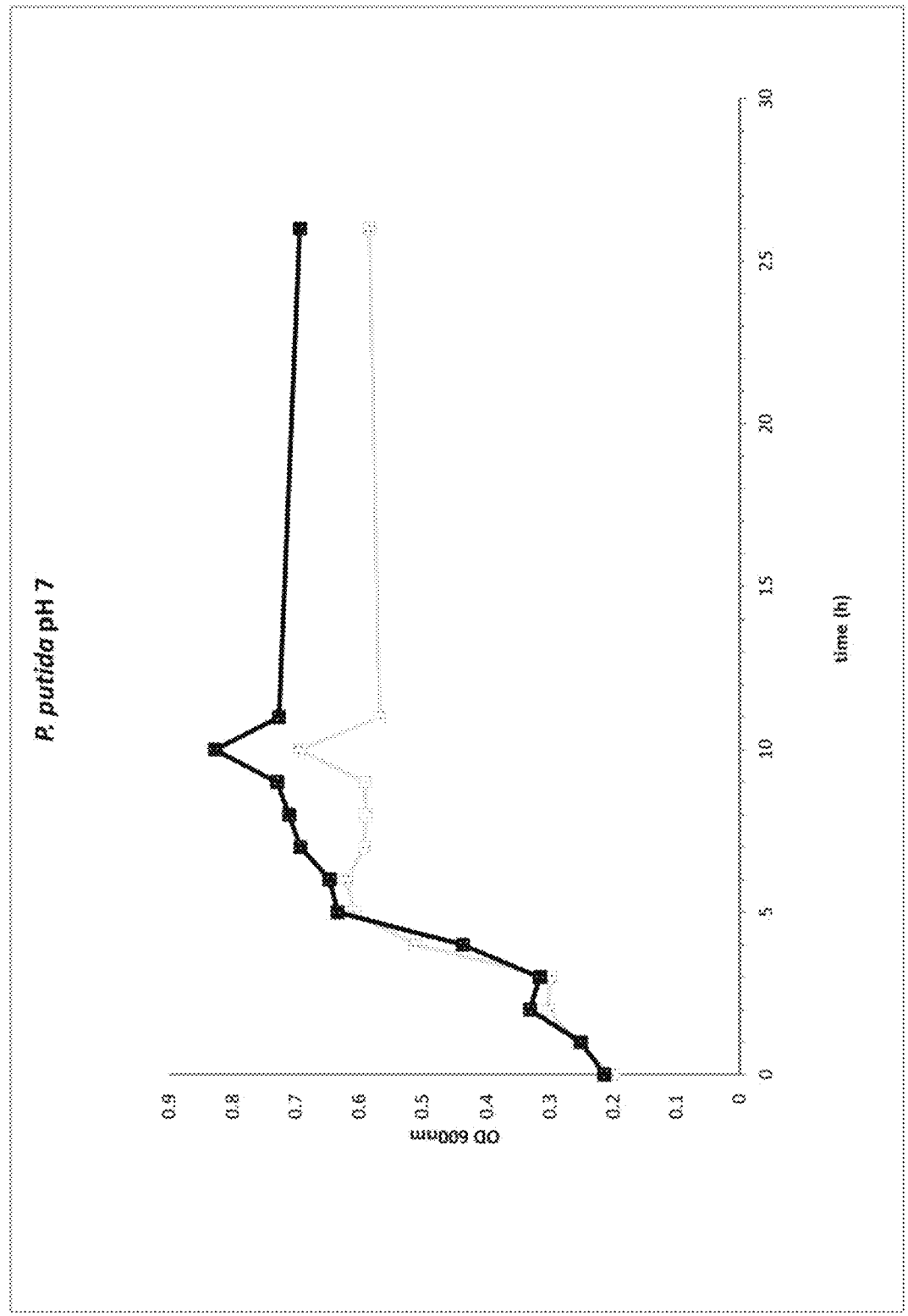
FIG. 18 shows the optical density at 600 nm ($OD_{600}$) followed over 25 h (double determination) of 100-mL-shake flask cultures at pH 7 (with MOPS buffer) supplemented with 0.1 g/L octanol (duplicates in black and grey) of the strain *Pseudomonas putida*.

In order to investigate the resistance of the considered strains against para-aminobenzoate (pAB) and solvents (octanol and 1-dodecanol), the strains were cultivated at pH 7 (*S. cerevisiae* at pH 5.5) as described before and supplemented with 3 g/L pAB (FIG. 16). The growth of *C. glutamicum, E. coli, P. putida*, and *P. pastoris* was not inhibited by pAB under these conditions, whereas the growth of *S. cerevisiae* and *B. subtilis* was severely reduced. The toxicity of the extraction solvent octanol was investigated. The solubility of octanol in water is about 0.1 g/L, therefore cultures were supplemented with such an octanol amount and in addition with 3 g/L. It was shown that already at 0.1 g/L but even clearer at 3 g/L octanol all organisms were unable to grow. Only *P. putida* has shown minor growth activity after octanol addition (FIG. 17 and FIG. 18).

Figure 19:
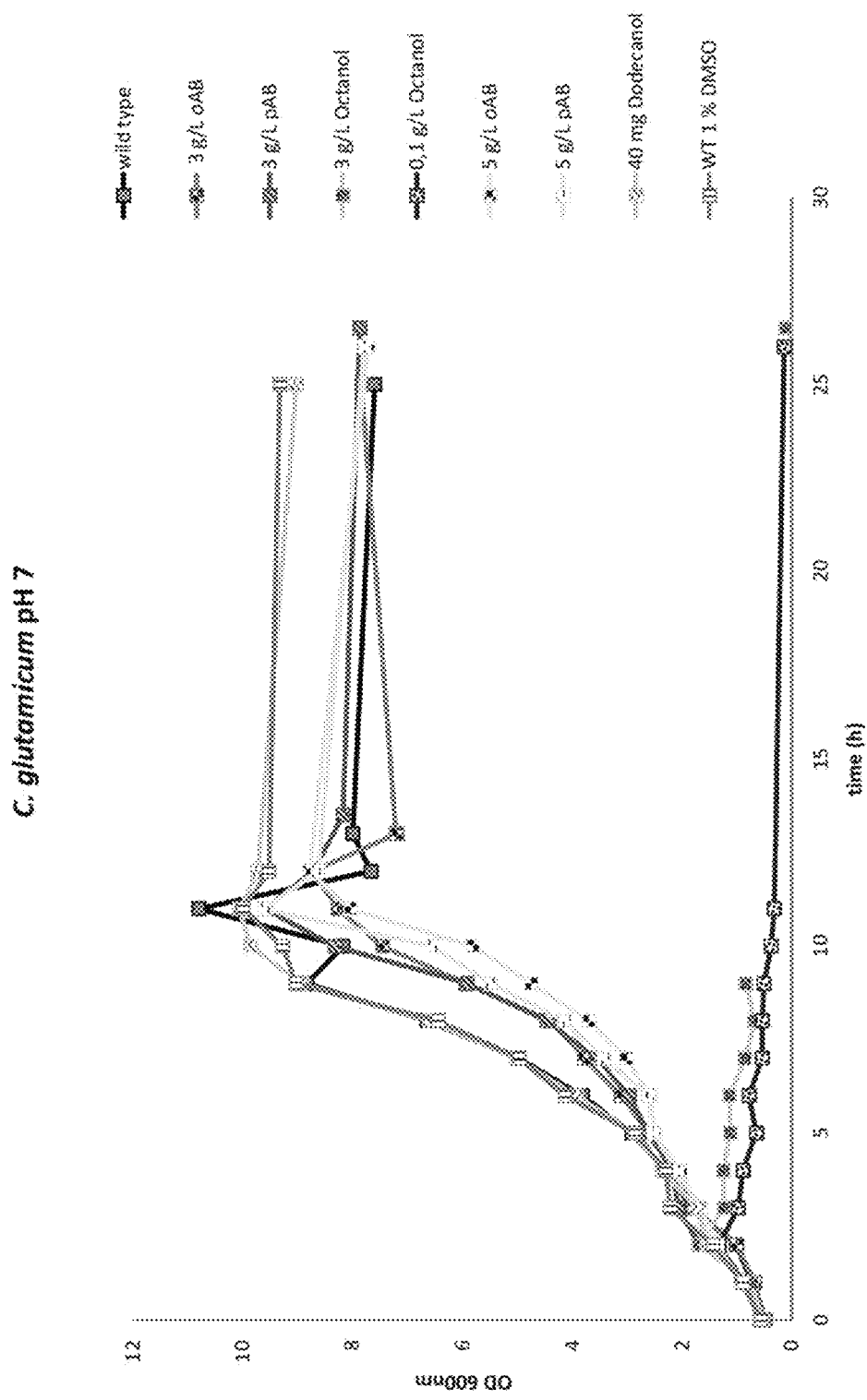
FIG. 19 shows the optical density at 600 nm ($OD_{600}$) followed over 25 h of 100-mL-shake flask cultures at pH 7 of *Corynebacterium glutamicum* (supplemented as denoted in the graph; duplicates).
Figure 20:
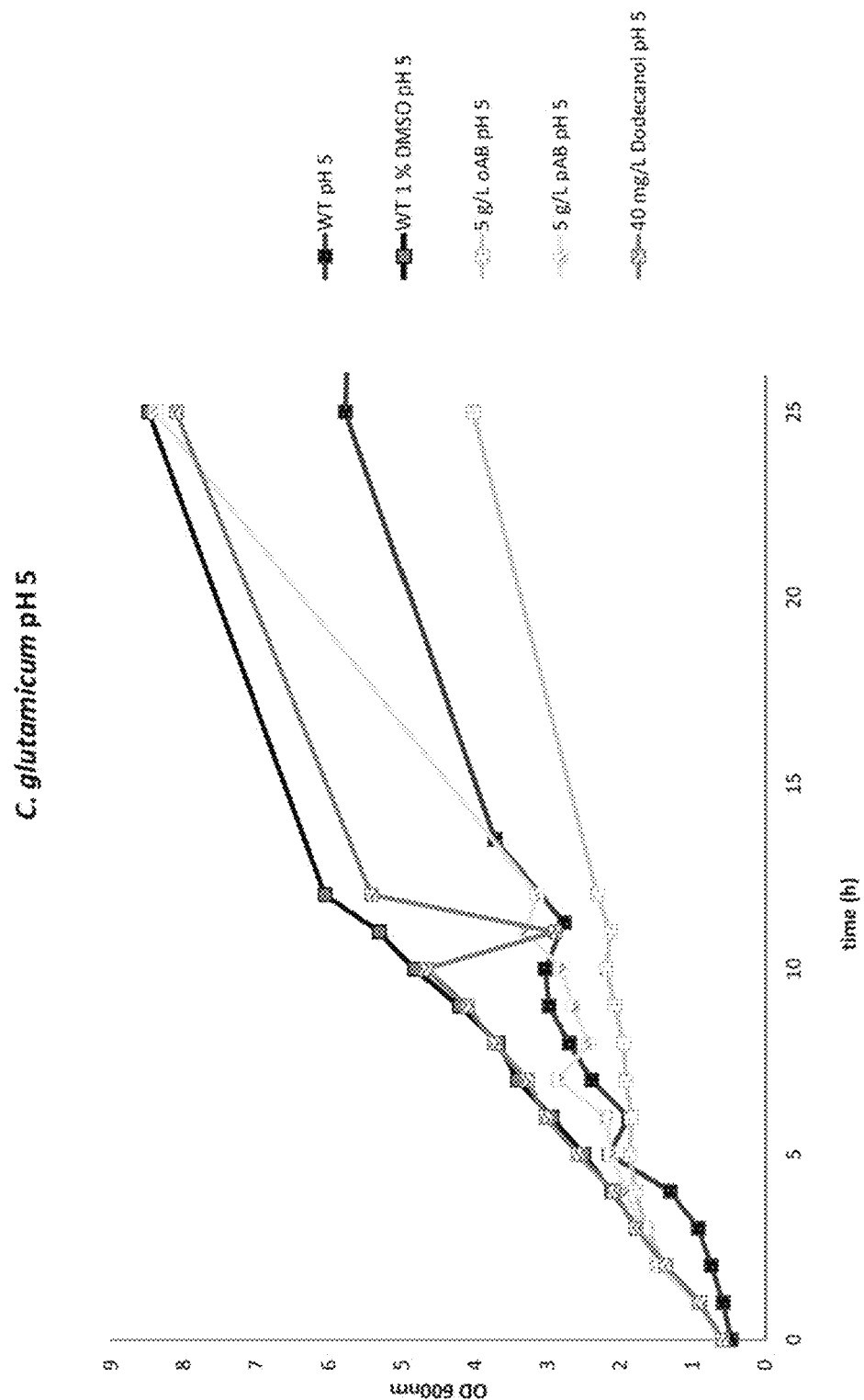
FIG. 20 shows the optical density at 600 nm ($OD_{600}$) followed over 25 h of 100-mL-shake flask cultures at pH 5 of *Corynebacterium glutamicum* (supplemented as denoted in the graph; duplicates).

As in all performed experiments *C. glutamicum* had shown the highest cell densities and best resistance capabilities, this strain was analogously cultivated with 5 g/L oAB and 5 g/L pAB at pH 5 and pH 7, respectively. No growth inhibition was detected under these conditions (FIG. 19 and FIG. 20). At pH 5, the cell density is halved, resulting in the conclusion that the fermentation should more preferably be performed at pH 7.

Dodecanol was investigated as an alternative extraction solvent. Dodecanol exhibits solubility in water of about 40 mg/L. *C. glutamicum* was cultivated as described above at pH 5 and 7 under supplementation with 40 mg/L 1-dodecanol. Dodecanol did not influence the growth of the strain under these conditions (see FIG. 19 and FIG. 20).

Figure 21:
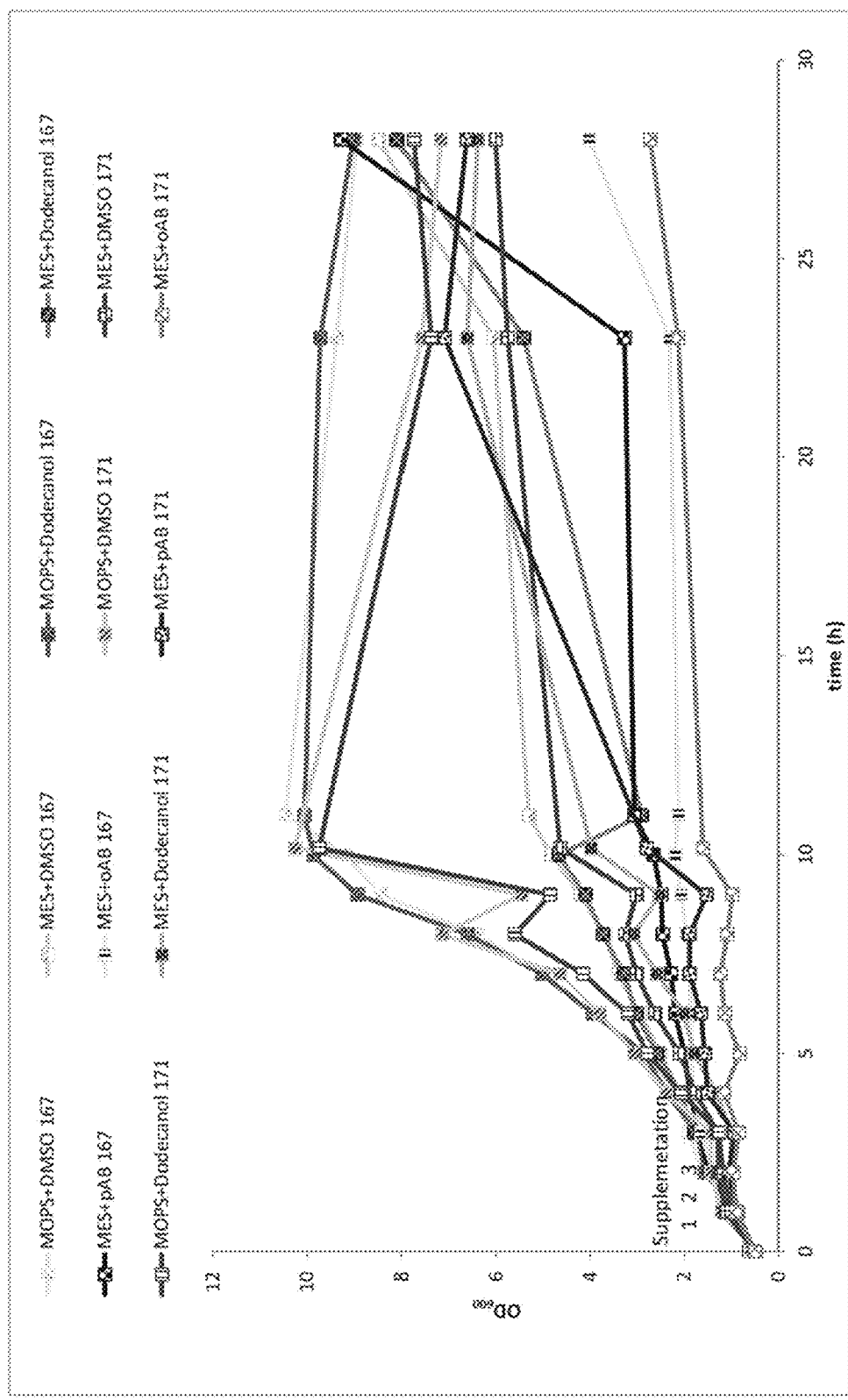
FIG. 21 shows the optical density at 600 nm ($OD_{600}$) followed over 28 h of 100-mL-shake flask cultures at pH 7 (MOPS) and pH 5 (MES) of *Corynebacterium glutamicum* (supplemented as denoted in the graph; duplicates).

The results obtained in the shake flask experiments with *C. glutamicum* were reproduced in small-scale fermenters (FIG. 21). To further characterize the resistance of *C. glutamicum* against aminobenzoates and 1-dodecanol stress at pH 7 small-scale fermentations of the organism were performed using a 1 L-4fold-fermentation unit (HiTecZang) with regulated pH, agitation, oxygen supply, temperature, and under glucose feeding. The glucose-fed allowed the strain to grow to higher cell densities.

Figure 22:
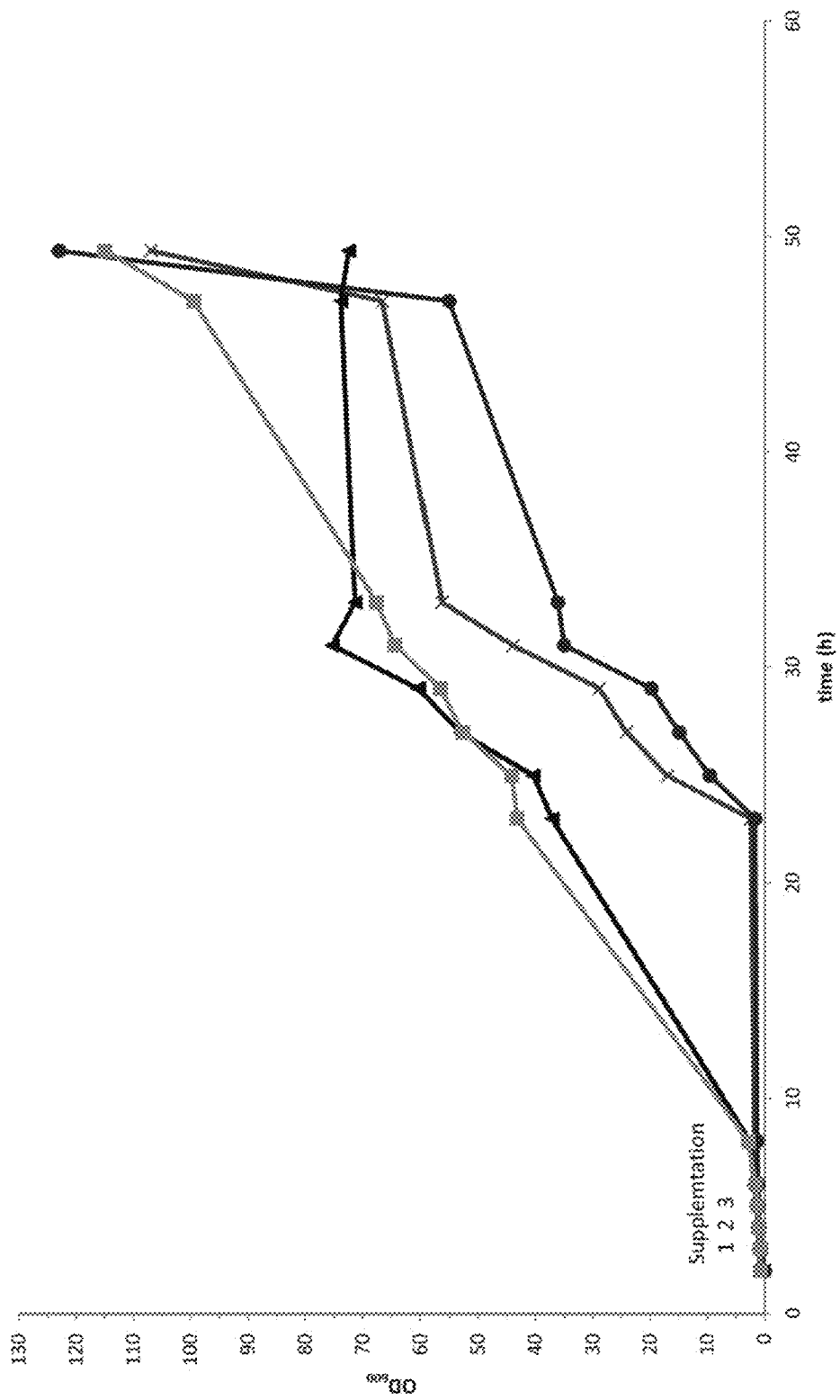
FIG. 22 shows the optical density at 600 nm ($OD_{600}$) followed over 50 h of fermentation cultures at pH 7 of *Corynebacterium glutamicum* supplemented after 3, 4, and 5 h to a final concentration of 0 g/L supplement (square), 7 g/L oAB (circle), 7 g/L pAB (cross), 40 mg/L dodecanol (triangle).

A fermentation experiment was performed with *C. glutamicum* in minimal medium pH 7 (as described above but without addition of MOPS, biotin, protocathecuat and urea) and supplementation of one fermenter with nothing (positive control), one fermenter with 7 g/L oAB, one fermenter with 7 g/L pAB and one fermenter with 40 mg/L 1-dodecanol. The resulting growth curves show that the growth of *C. glutamicum* is not influenced by the added 1-dodecanol. This confirmed the results obtained in shake flasks (see FIG. 22). Supplementation with oAB and pAB, respectively, resulted in a prolonged lag-phase but finally same cell densities were reached (see FIG. 22). It was concluded that 1-dodecanol is a suitable oAB extraction solvent.

Figure 23:
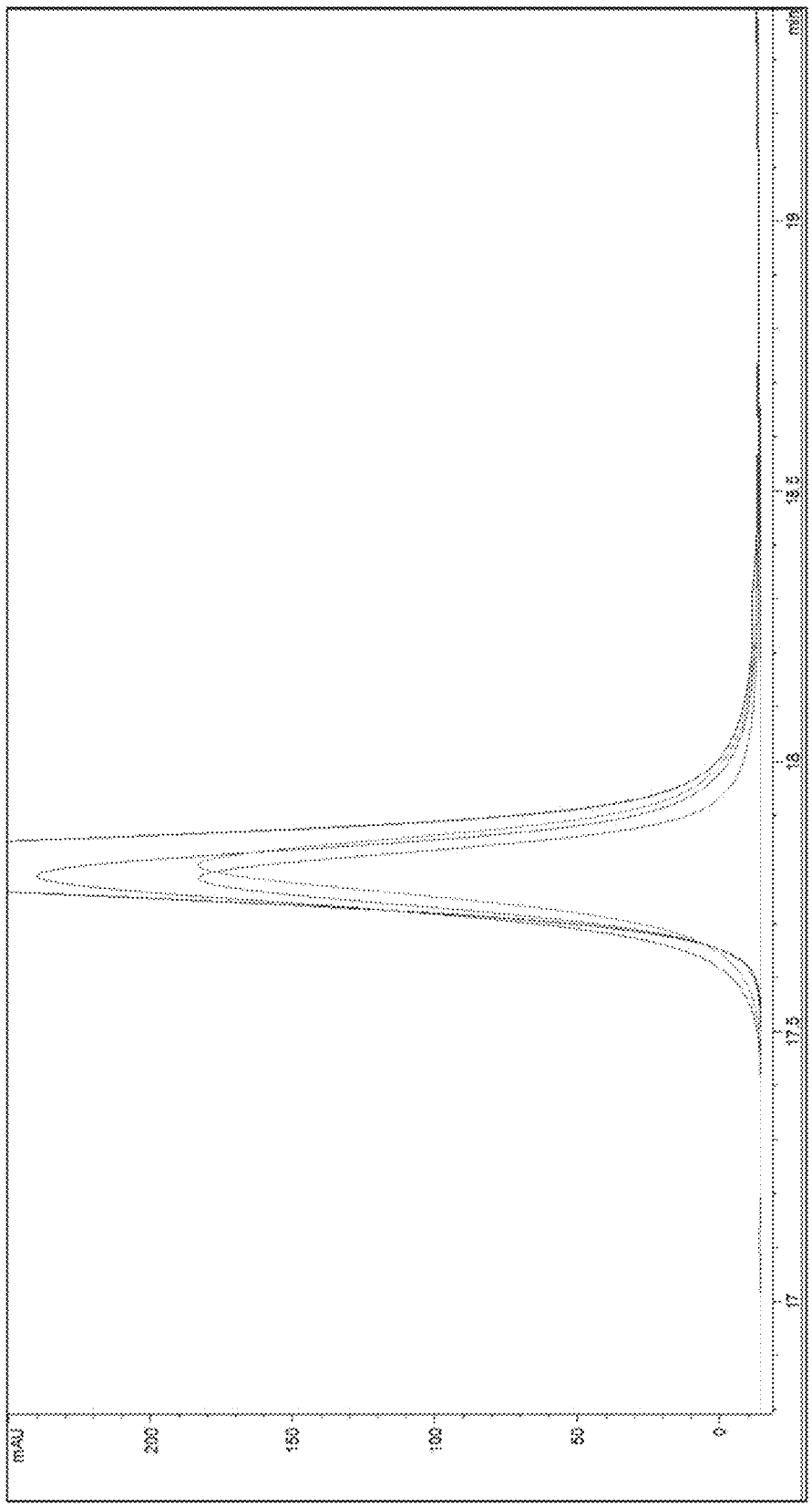
FIG. 23 shows the HPLC-chromatogram at 254 nm of culture supernatants of fermentation of *Corynebacterium glutamicum* with 7 g/L oAB after 2 h (before supplementation with oAB), 5 h (after supplementation with 7 g/L oAB), 25 h, and 49.5 h. Plus oAB standard.

The concentration of aminobenzoate was further increased to find the border at which it significantly inhibits the growth of *C. glutamicum*. It had to be excluded that the aminobenzoates were degraded by the organism and therefor the growth is restored after the prolonged lag-phase. To investigate the aminobenzoate stability in the fermenters culture supernatant samples were collected during the fermentation and analyzed by HPLC-DAD (254 nm) (see FIG. 23 and Example 3). The aminobenzoate was not significantly degraded during cultivation.

Figure 24:
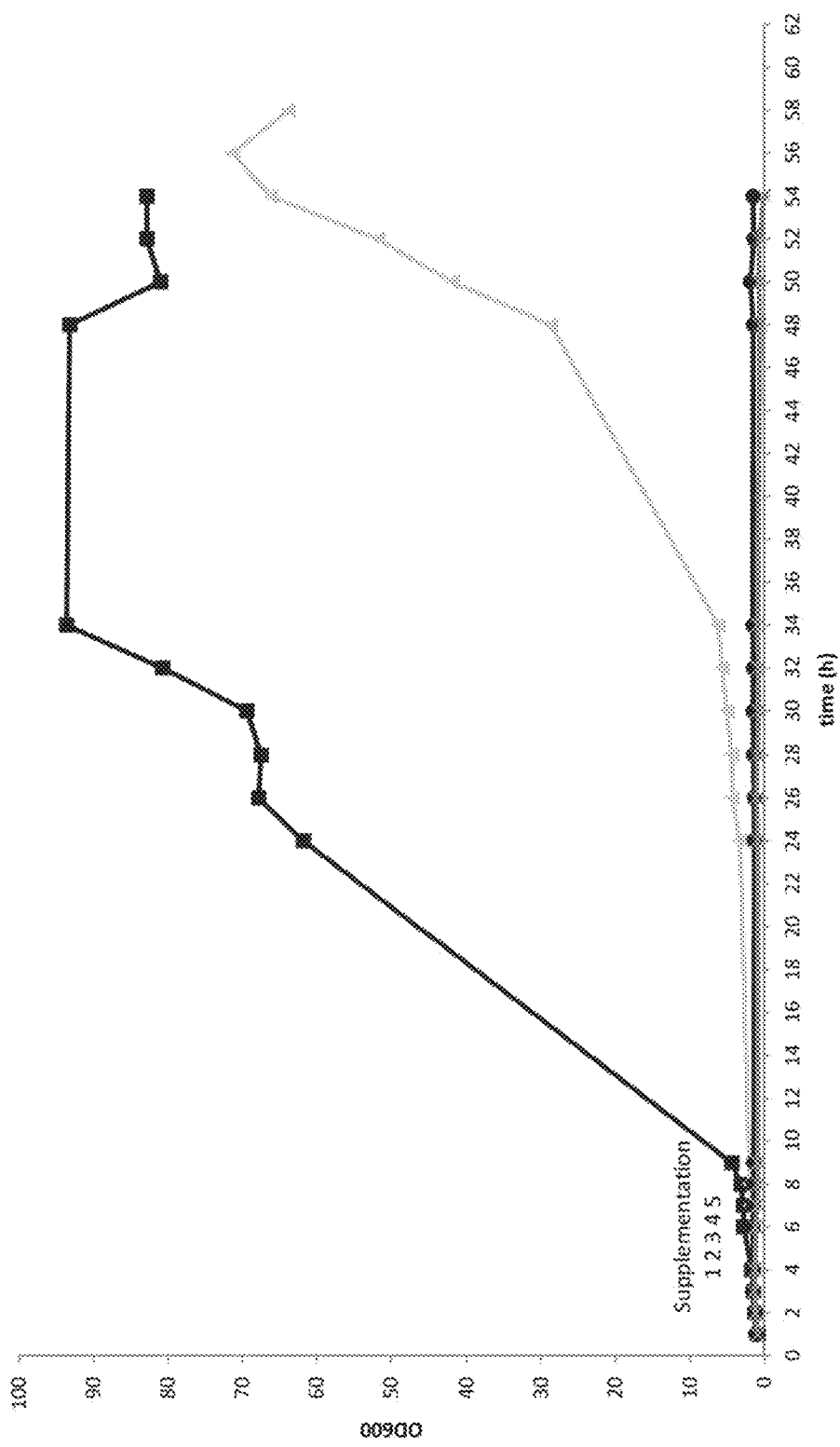
FIG. 24 shows the optical density at 600 nm ($OD_{600}$) followed over 58 h of fermentation cultures at pH 7 of *Corynebacterium glutamicum* supplemented after 3, 4, 5, 6, and 7 h to a final concentration of 0 g/L supplement (squares), 15 g/L oAB (triangles), 35 g/L oAB (crosses), and 80 g/L oAB (circles).
Figure 25:
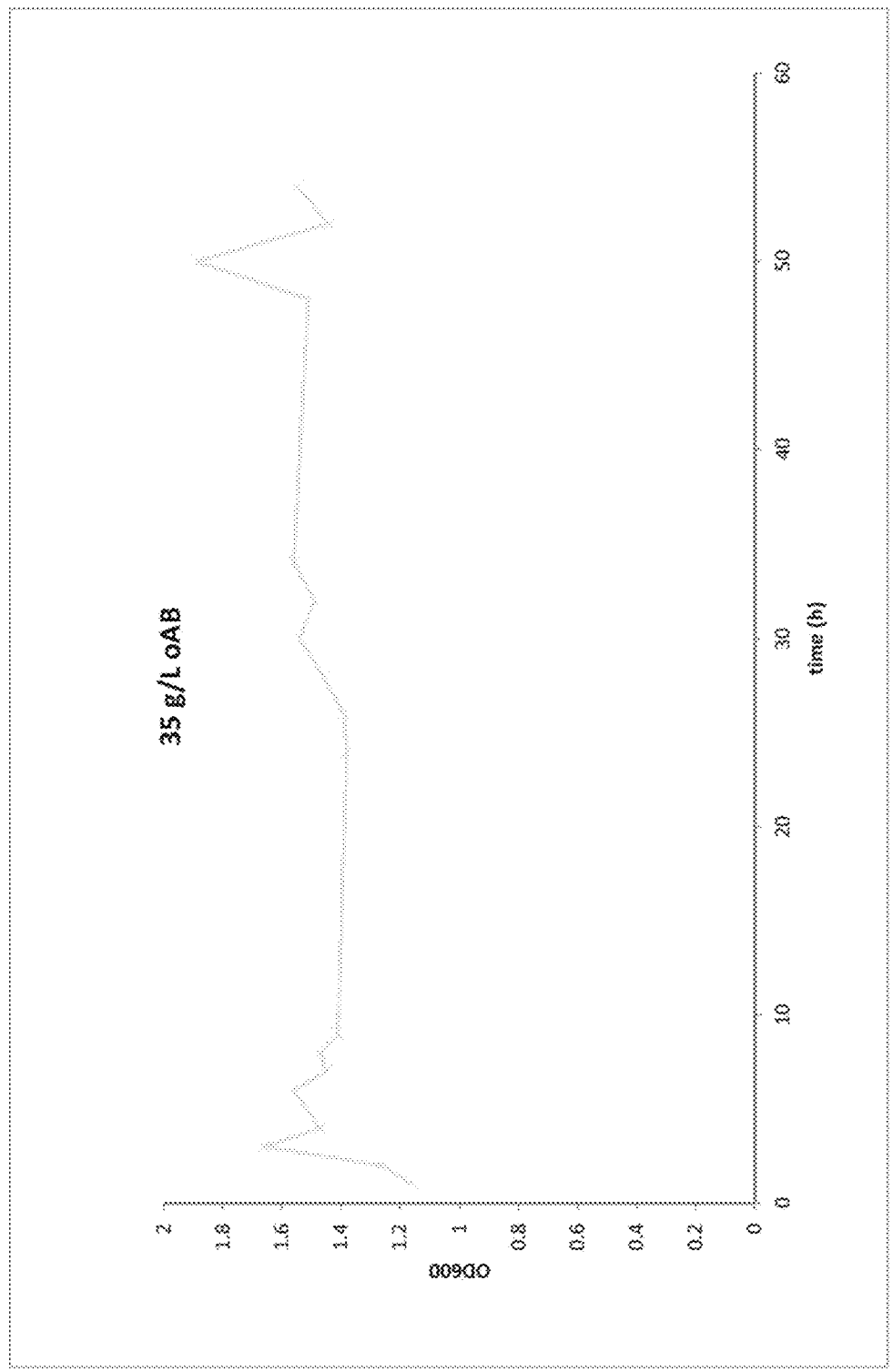
FIG. 25 shows the optical density at 600 nm ($OD_{600}$) followed over 58 h of fermentation cultures at pH 7 of *Corynebacterium glutamicum* supplemented after 3, 4, 5, 6, and 7 h to a final concentration of 35 g/L oAB.
Figure 26:
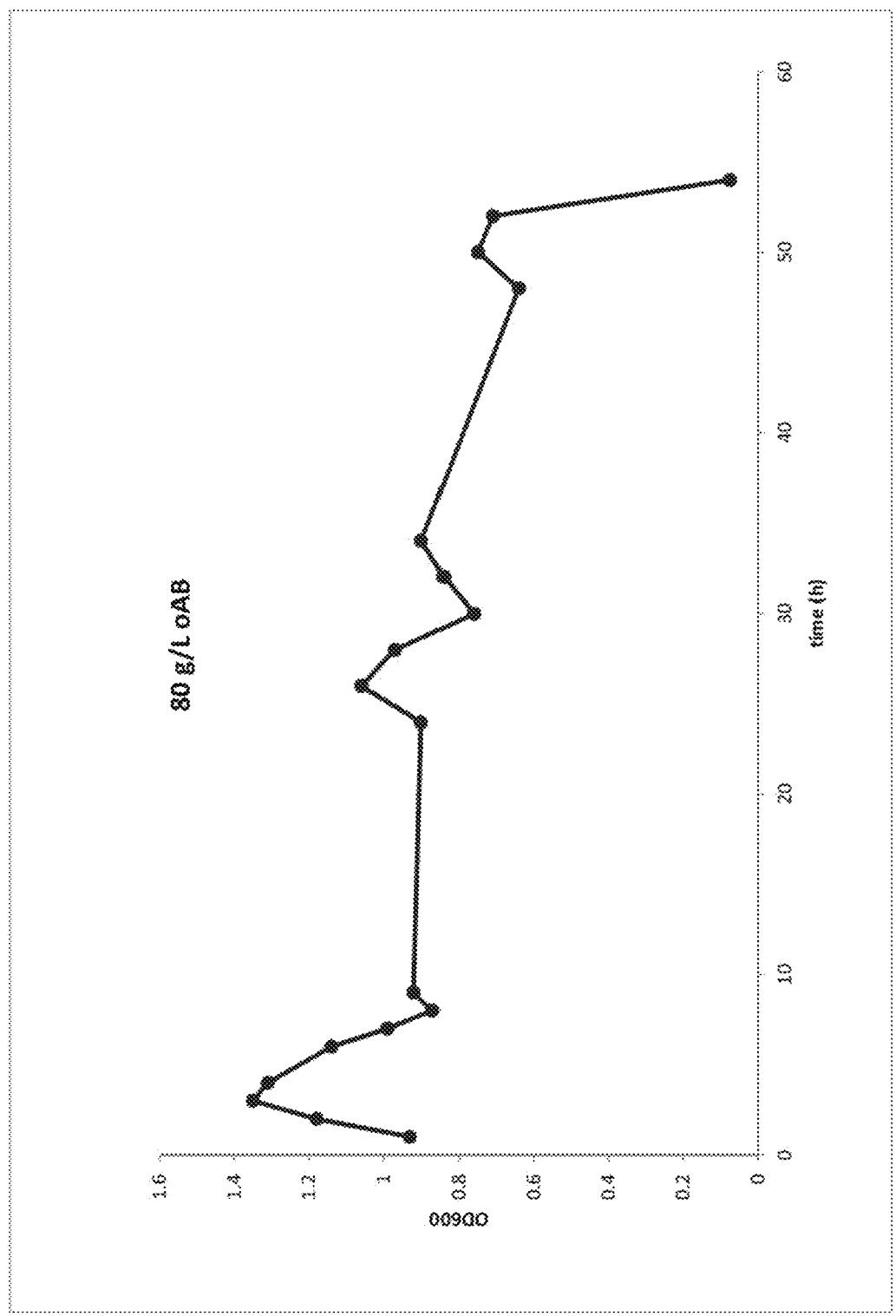
FIG. 26 shows the optical density at 600 nm ($OD_{600}$) followed over 58 h of fermentation cultures at pH 7 of *Corynebacterium glutamicum* supplemented after 3, 4, 5, 6, and 7 h to a final concentration of 80 g/L oAB.

In a further experiment the concentration of oAB was increased to investigate the effect on the *C. glutamicum* strain. The four fermenters were hereto supplemented with 0 g/L, 15 g/L, 35 g/L and 80 g/L of oAB. To achieve solubility of the acid in such high concentrations at pH 7 the acid was titrated with ammonium hydroxide to form the corresponding ammonium salt of oAB in stock solutions later added to the fermenters in five portions over 5 h (after cultivation of 3, 4, 5, 6, and 7 h). The rest of the cultivation conditions was kept as described above. The addition of 80 g/L oAB led to a dying (lysis) of the cells over 54 hours and 35 g/L oAB resulted in a growth inhibition (see FIG. 24, FIG. 25, and FIG. 26). Cultures supplemented with 15 g/L oAB have shown an extensive lag-phase over 34-48 h before growth was recovered and cells entered the exponential phase (see FIG. 24). An oAB degradation during fermentation was again excluded by HPLC measurements of culture supernatants (data not shown).

Taken together it was concluded that the production of oAB should most preferably be done with a *Corynebacterium glutamicum* ATCC 13032 strain. Furthermore it was concluded that the process fermentation should preferably be performed at pH 5-7, and more preferably at pH 7 and the extraction (if needed) should preferably be conducted with 1-dodecanol as extraction solvent. Octanol was not a suitable extraction solvent.

Example 3—Production of o-Aminobenzoate with *C. glutamicum*

A bacterial strain that produces anthranilate in a g/L scale was developed. This work was based on genetic manipulations of tryptophan producers (e.g. in *E. coli* and *C. glutamicum*) and included the development and implementation of a strategy to genetically manipulate central metabolism, common aromatic biosynthesis and the L-tryptophan branch pathway in order to gain an anthranilate (oAB) producer. Based on the above described results, the metabolic engineering was preferably based on *Corynebacterium glutamicum* ATCC 13032.

General Cultivation of *Escherichia coli* DH5α Based Strains

If not denoted differently all chemicals were acquired from Sigma-Aldrich (Sternheim) and all applied enzymes from New England Biolabs (Schwalbach). *E. coli* strains were cultivated under sterile conditions in LB medium (Luria-Bertani; Roth, Karlsruhe) or on LB-agar (Abcr GmbH & Co. Kg, Karlsruhe) plates at 37° C. Selective cultivation was achieved by adding antibiotics (100 mg/L ampicillin sodium salt; 50/25 mg/L kanamycin sulfate; 100 mg/L spectinomycin sulfate). For plasmid preparation the stains have been cultivated in 15 mL-tubes for 14 h-16 h with constant shaking at 200 rpm in 3 mL LB medium and a selecting antibiotic at 37° C. (Kuhner Shaker ISF-4-W; Adolf Kühner AG, Basel (Switzerland)).

General Molecular Biology Methods

PCR reactions were generally performed using Platinum® Taq DNA Polymerase (5 U/µL; Life technologies, Darmstadt) with ca. 50 ng PCR template and 10 pmol of the responding primer pair (see Table 3). PCR conditions: 98° C. 5 min, 98° C. 30 sec, 56° C. 30 sec, 72° C. 1 min/kb, 30×, 16° C. hold (Mastercycler® nexus Cycler; Eppendorf, Hamburg). Plasmid DNA purification was done using the NucleoSpin® Plasmid Pure kit (Macherey & Nagel, Düren) following the manufacturer's instructions. Plasmid DNA digestion was done in a 20 µL scales with 5 U of the related restriction enzyme(s) and ca. 1 µg plasmid DNA in buffer, recommend by the enzyme supplier, and incubated for about 2 h at 37° C. and after that analyzed by agarose gel electrophoresis. Agarose gels were made with 1% agarose (Abcr GmbH & Co. Kg, Karlsruhe) dissolved in 1×TAE electrophoresis buffer (Promega, Fitchburg USA). The supplied electric field was 90 V-120 V (EPS300; Pharmacia Biotech; VWR International GmbH, Darmstadt) and the DNA was detected via ethidium bromide (0.3-0.5 mg/L) or Midori Green (Midori Green Advance DNA Strain; NIPPON Genetics EUROPE GmbH, Düren). Gel documentation: Gene Genius®; VWR; Darmstadt. For the agarose gel DNA extraction the NucleoSpin® Gel and PCR Clean-up (Macherey & Nagel, Düren) kit was used as specified by the manufacturer. For DNA ligation a T4-DNA ligase (20 U) was used in the buffer supplied by the manufacturer. The used insert to plasmid mass ratio was 4:1. The mixture was incubated for ca. 15 h at 16° C. and afterwards incubated at 65° C. for 10 min. Plasmids and ligation reactions were introduced into electro-competent *Escherichia coli* DH5α cells (ElectroMAX™ DH5α-E™ Competent Cells; Life Technologies, Darmstadt). After electro-transformation (conditions: ~20 ms exponentially decaying pulse, 2.5 kV/cm, 25 F, 200Ω) in 0.2 cm gap electroporation cuvettes (BioRad, Hercules, Calif.) using a Gene Pulser Xcell System (BioRad, Hercules, Calif.), 800 µL LB recovery medium was immediately added and the suspension was transferred into 1.5 mL microcentrifuge tube. After 1 h at 37° C., a cell suspension were spread onto LB agar plates, supplemented with appropriate antibiotics, and incubated at 37° C. over night. Clones were collected and correct transformation confirmed via restriction analysis, colony PCR and/or sequencing. For colony PCR analysis of colonies a colony was picked with a sterile toothpick, transferred to a separate plate (master plate), dissolved in 1 μL DMSO and boiled for 10 min at 98° C., before being added into a standard PCR mixture. The correct cloning of all plasmids and generation of the related mutants was proven by PCR and/or DNA sequencing.

General Cultivation of *Corynebacterium glutamicum* ATCC13032 Based Strains

*C. glutamicum* strains were cultivated under sterile conditions in BHI medium (37 g/L; Brain-Heart-Infusion; Becton Dickenson and Company, Heidelberg) tubes, shake flasks or on agar plates at 30° C. Selective cultivation was achieved by adding antibiotics (15 mg/L kanamycin sulfate; 100 mg/L spectinomycin sulfate).

For strain characterizations the first pre-culture was started from an isolated colony and cultivated for 10 h with constant shaking at 400 rpm in 4 mL BHI medium and, depending on the strain, supplemented with a suiting antibiotic or aromatic amino acids. The second pre-culture was grown in 50 mL CGXII-MOPS medium (42 g/L MOPS buffer, 20 g/L $(NH_4)_2SO_4$, 5 g/L urea (Fisher Scientific, Schwerte), 3.7 g/L Brain-Heart-Infusion, 1 g/L $KH_2PO_4$, 1 g/L $K_2HPO_4$, 0.25 g/L $MgSO_4.7H_2O$ (Merck, Darmstadt), 0.01 g/L $CaCl_2$, and 10 g/L glucose (autoclaved separately). The pH was adjusted to 7 with 5 mol/L sodium hydroxide solution. The following components were added after sterile filtration: 2 mg/L biotin, 0.01 g/L $MnSO_4.H_2O$ (Merck, Darmstadt), 0.01 g/L $FeSO_4.7H_2O$ (Merck, Darmstadt), 1 mg/L $ZnSO_4.7H_2O$, 0.2 mg/L $CuSO_4.5H_2O$ (Merck, Darmstadt), 0.02 mg/L $NiCl_2.6H_2O$ (Merck, Darmstadt), and 0.03 g/L 3.4-dihydroxybenzoic acid (Acros Organics, Nidderau)) in a 250 mL shake flask after inoculation with 1 mL of the first pre-culture and cultivated 16 h-18 h with constant shaking at 400 rpm. The fermentation culture was grown in 100 mL CGXII medium (20 g/L $(NH_4)_2SO_4$, 5 g/L urea, 1 g/L $KH_2PO_4$, 1 g/L $K_2HPO_4$, 0.25 g/L $MgSO_4.7H_2O$, 0.01 g/L $CaCl_2$, 100 μL/L polypropylenglycol (autoclaved separately), and 18 g/L glucose (autoclaved separately). The pH was adjusted to 7 with 5 mol/L sodium hydroxide solution. The following components were added after sterile filtration: 2 mg/L biotin, 0.01 g/L $MnSO_4.H_2O$, 0.01 g/L $FeSO_4.7H_2O$, 1 mg/L $ZnSO_4.7H_2O$, 0.2 mg/L $CuSO_4.5H_2O$, 0.02 mg/L $NiCl_2.6H_2O$, and 0.03 g/L 3.4-dihydroxybenzoic acid). Each bioreactor (DasBox, Eppendorf, Hamburg) was inoculated with the second pre-culture to a final $OD_{600}$ of 0.5. The initial stirring speed was set to 100 rpm and air was supplied at 2.2 L/h (0.37 V/(V*min). Dissolved oxygen was continuously monitored (OxyFermFDA 120; Hamilton, Bonaduz (Switzerland)) and maintained at 30% air saturation by automatic adjustment of the stirring speed. The pH was measured (EasyFermPlus K8 120; Hamilton, Bonaduz (Switzerland)) and maintained at 7 by automatic addition of 1 M NaOH and the temperature was kept at 30° C. To prevent foam formation the addition of 10% polypropylene glycol solution was automatically added by a conductivity sensor measuring the conductivity above the fermentation broth. The fermentation was performed as a repeated batch process. Three times an additional feeding with 18 g/L glucose (autoclaved separately) was performed. During the fermentation cell dry weight (BDW), glucose concentration, and the anthranilate concentrations were measured offline from 1.5 mL fermenter samples. A 1 mL aliquot of each sample was centrifuged for 5 min at 16000×g (5415R; Eppendorf, Hamburg) in a weighted reaction tube. To determine the cell dry weight the pellet was dried for at least 72 h at 60° C. (Hybridisation oven; Appligene Oncor Lifescreen, Watford (UK)). Afterwards an analytical balance (La 230 S; Satorius AG, Göttingen) was used for determining the exact pellet weight. The supernatant was analyzed via HPLC-DAD (1100; Agilent Technologies, Santa Clara (USA)) and YSI (YSI-Select 2700; Kreienbaum Neoscience GmBH, Langenfeld). The collected data is shown in Table 4.

General Manipulation of *Corynebacterium glutamicum* ATCC13032

Plasmid DNA was transferred into *Corynebacterium glutamicum* ATCC13032 by electroporation. For transformation cells were harvested from a 200 mL culture grown in BHI medium and in the exponential growth phase ($OD_{600}$=1.75-2.0) by centrifugation (4000 g, 10 min, 4° C. (5810R; Eppendorf, Hamburg)) and washed three times with 20 mL ice-cold TG buffer (1 mM Tris-HCl, 10% glycerin, pH 7.0). The pellet was resuspended in 2 mL 10% glycerin solution and directly used for transformation or stored until use at −80° C. For transformation plasmid DNA (ca. 1 μg) was first pipetted in an ice-cold 0.2 cm gap electroporation cuvette followed by 150 μL cell suspension. After incubation on ice for 5 min electroporation was performed (conditions: 20 ms exponentially decaying pulse, 2.5 kV/cm, 25 F, 200Ω). The suspension was transferred into a reaction tube with 500 μL preheated (46° C.) BHI-medium and incubated at 30° C. for 1 h with constant shaking at 400 rpm. The cells were spread on BHI medium agar plates containing the corresponding antibiotics.

For the expression of designated target genes the *E. coli-C. glutamicum* shuttle vector pEKEx2 was employed (Eikmanns B J, Kleinertz E, Liebl W, Sahm H, Gene, 1991, 102:93). The 8.16 kb vector derives from vector pU18 and encodes a kanamycin-resistance-cassette, a pBL1 point of origin V (oriV) for proliferation in *C. glutamicum*, a pU18 oriV for proliferation in *E. coli*, a strong tac-promotor (isopropyl β-D-1-thiogalactopyranoside (IPTG)-inducible), and a lacIQ gene. Alternatively, the *E. coli-C. glutamicum* shuttle vector pCRB210 was employed (Yukawa H, Inui M, US20130302860(A1), 2013), which is compatible for co-transformation with pEKEx2. The 4.96 kb vector encodes a spectinomycin-resistance-cassette, a pCASE1 point of origin V (oriV) for proliferation in *C. glutamicum*, an oriV for proliferation in *E. coli*, and a gapA-promotor for constitutive gene expression. Gene-fragments selected for overexpression in *C. glutamicum* or mutants thereof were synthesized by MWG Operon GmbH under removal of all naturally occurring SbfI, BamHI, BglII, NcoI, and NdeI restriction sites by single nucleotide exchanges (silent mutations) and insertion of a ribosomal binding site upstream of the corresponding ORF (apart from the gene sequences of aroG, aroK, glnA, and aroL, which were amplified from their natural loci by PCR, see primers (Table 3)). In case of the trpEG and aroG genes single nucleotide exchanges were included into gene to access feedback-resistant version of the related enzymes. The resulting sequences were cloned into the multiple cloning site of the pEKEx2 vector via SbfI and BamHI restriction and re-ligation. Apart from glnA gene sequence, this was cloned into the pCRB210 vector via NcoI restriction and re-ligation yielding pCRB-gklnA (Table 1). The synthesized gene fragments basically have the structure: "SbfI-BglII-RBS-gene-BamHI". This allows the iterative ligation of target genes (as BglII-BamHI-fragments) into the vector via singular BamHI restriction sites. The plasmids were sequenced to confirm correct cloning and sequence. *C. glutamicum* (and mutants thereof) transformants were screened for antibiotics resistance and the correct generation of the related mutants was proven by PCR.

For the deletion of target genes, as well as for the insertion of genes or other sequences fragments into the genome of *C. glutamicum* the *E. coli-C. glutamicum* shuttle vector pK19mobsacB was employed (Schäfer A, Tauch A, Jäger W, Kalinowski J, Thierbach G, Pühler A, Gene, 1994, 145:69). The 5.72 kb vector derives from vector pU18 and encodes a kanamycin-resistance-cassette, no point of origin for proliferation in *C. glutamicum*, a pU18 oriV for proliferation in *E. coli*, a lacZα gene, and a sacB gene. The target sequences were synthesized by MWG Operon GmbH (apart from trpD and csm, which were PCR amplified from the *C. glutamicum* ATCC13032 genome with specific primers (Table 3) with removal of all naturally occurring HindIII and EcoRI restriction sites by single nucleotide exchanges (silent mutations) and cloned into the multiple cloning site of the vector via HindIII and EcoRI restriction and re-ligation. For gene deletions (or integrations) the cloned DNA sequences consist of 300-500 bp of 5'-flanking region of the target gene (including the first 6 codons of the gene), 21 bp of foreign missense-sequence (or a sequence to be integrated into the genome), and 300-500 bp of 3'-flanking region of the target gene (including the last 6 codons of the gene of interest). *C. glutamicum* transformants were screened for single cross-over events integrating the plasmids into the genome by kanamycin-selection, as the resulting plasmids cannot proliferate in *C. glutamicum* by themself. The BHI medium agar plates (containing 15 mg/L kanamycin) carrying transformants were cultivated at 30° C. for 1-7 days. Afterwards isolated clones were screened for double-cross-over events, resulting into the in frame deletion of the target genes, leaving behind only the 21 bp of foreign missense sequence (or instead sequences to be integrated into the genome), by selection with sucrose (Colonies were cultivated for 4 h-6 h in 5 mL BHI medium and then plated in two different dilutions (1:100 and 1:10000) on BHI medium agar plates containing 10% (w/v) sucrose. The sacB gene on the vector encodes a levansucrase, which transforms sucrose into a lethal product and, as a result, prevents the growth of all clones still carrying the plasmid sequences in their genome. All colonies that grew on the sucrose containing plates were analyzed by co-transfer on BHI medium agar plates supplemented with 15 mg/L kanamycin as well as BHI medium agar plates and cultivated at 30° C. for 1-7 days. Colonies that grew only on the plates without kanamycin supplementation were analyzed by colony PCR to confirm the correct recombination. The correct cloning of all plasmids and generation of the related mutants was proven by PCR and/or DNA-sequencing.

High Performance Liquid Chromatography

An Agilent 1100 series HPLC-DAD system (with diode array detector; Agilent Technologies, Santa Clara (USA)) was used to quantify oAB concentrations in culture supernatants. As stationary phase a C18 column Luna® HPLC-column (4.6×250 mm; 3 μm; Phenomenex) was used at 20° C. with a binary solvent system consisting of methanol (solvent B) and water containing 0.1% formic acid (solvent A) was used. 10 μL of diluted culture supernatants were injected. The following gradient with a flow rate of 0.5 mL/min was applied: 0-1 min, 2% B; 1-2 min, 2-10% B; 2-12 min, 10-70% B; 12-23 min, 70-90% B; 23-25 min, 90-98% B, 25-27 min, 98% B; 27-27.5 min, 98%-2% B; 27.5-30 min, 2% B. The oAB concentration was determined from the signal integration at 254 nm (retention time: 18.9 min) using an external calibration curve.

Engineering of the trpD Gene in *C. glutamicum* Strains

The strain *Corynebacterium glutamicum* ΔtrpD (see Table 2) was created by in-frame deletion of the trpD gene (encoding anthranilate phosphoribosyl transferase; Cgl3032; SEQ ID NO: 1) using the *E. coli-C. glutamicum* shuttle vector pK19mobsacB. The 5'-flanking region of the trpD open reading frame (including the first 7 codons of the gene) and the 3'-flanking region of the target gene (including the last 8 codons of trpD open reading frame) were amplified from genomic DNA, isolated from *Corynebacterium glutamicum* ATCC 13032, by PCR using the primer pairs Del-trpD-1 and Del-trpD-2, and Del-trpD-3 and Del-trpD-4, respectively (Table 3, SEQ ID NO: 66-69). The resulting two fragments were combined by crossover PCR using the primer pair Del-trpD-1 and Del-trpD-4. The resulting fragment was cloned into the multiple cloning site of the pK19mobsacB vector via SmaI restriction and re-ligation. The resulting vector was applied for in-frame deletion of trpD from the genome of *Corynebacterium glutamicum* ATCC 13032 and introduced in-frame a 24 bp foreign missense-sequence into the genome, which was employed for the crossover PCR (resulting sequences in trpD locus: SEQ ID No. 2). Correct mutants were isolated as described above and correct gene deletion proven by PCR. This yielded an L-tryptophan auxotroph strain with oAB accumulation. The strain was characterized towards its properties as an oAB producer as described above with addition of 0.1 mM L-tryptophan or 0.1 mM indole (see Table 4).

Six versions of the trpD gene were cloned into vector pEKEx2 via SbfI and BamHI restriction and re-ligation as described above. The six different versions of the trpD gene were generated with different start codons, and spacer lengths between ribosomal binding site and start codon of trpD (SEQ ID No. 3-8) by PCR using *C. glutamicum* genomic DNA as a template. The applied primers for the six fragments generation were forward primers (Ex-trpD-1 to -6, Table 2, SEQ ID No. 70-75), which included the changed start codon and spacer between ribosomal binding site and start codon, together with the for each version unchanged reverse primer (Ex-trpD-rev, Table 2, SEQ ID No. 76). This method was chosen in order to achieve a reduction of TrpD protein translation in the produced strains. The strain *Corynebacterium glutamicum* ΔtrpD (Table 2) was transformed with the resulting plasmids (Table 1) and the resulting strains *Corynebacterium glutamicum* ΔtrpD1pEKEx2-trpD1-6 (Table 2) grew without the addition of L-tryptophan and were, accordingly, characterized towards their properties as an oAB producer as described above with supplementation of 25 mg/L kanamycin and 1 μM IPTG (isopropyl-(3-D-thiogalactopyranosid) to the medium (see Table 4). Also the strains *Corynebacterium glutamicum* ΔtrpD/pEKEx2-trpD5-6 produced enough L-tryptophan to enable biomass formation; they accumulated significant amounts of oAB (Table 4). The versions of the trpD gene trpD1-3, trpD5, and trpD6 were furthermore each integrated into the genome of the strain *Corynebacterium glutamicum* ΔtrpD (Table 2) by homologous recombination using the pK19mobsacB vector as described above. The 5'-flanking region of the trpD gene versions and the 3'-flanking region of the target gene were amplified from genomic DNA, isolated from *Corynebacterium glutamicum* ATCC 13032, by PCR using the primer pairs Del-trpD-1 and Ko-trpD-1, as well as Del-trpD-3 and Del-trpD-4, respectively (Table 3, SEQ ID No. 66, 77, 68, and 69). The resulting two fragments were combined with the different trpD variants by crossover PCR using the primer pairs Ex-trpD-1-3, -5 or -6 and Ko-trpD-2 (Table 3, SEQ ID No. 70-72, 74, 75, and 78). The resulting five fragments were cloned into the multiple cloning site of the pK19mobsacB vector via SmaI restriction and re-ligation. The resulting plasmids (Table 1) were applied for introduction of the six trpD versions into the genome of strain *Corynebacterium glutamicum* ΔtrpD. Additionally, 10 foreign nucleotides (GCCCTGCAGG, SEQ ID NO: 92)

were integrated into the genomes, as a result of the cloning procedure, upstream of the ribosomal binding site of the trpD gene, that were employed for the crossover PCR. Correct mutants were isolated as described above and the integrations were verified by sequencing of the trpD region. The resulting strains *Corynebacterium glutamicum* ΔtrpD:: trpD1-3, trpD5, or trpD6 (Table 2) grow without the addition of L-tryptophan or kanamycin and were accordingly characterized towards their properties as an oAB producer as described above without further medium supplements (see Table 4).

The described method for gene expression reduction can be applied for other genes instead of performing gene deletions.

Engineering of the csm Gene in *C. glutamicum* Strains

The strains *Corynebacterium glutamicum* Δcsm, *Corynebacterium glutamicum* ΔtrpDΔcsm, and *Corynebacterium glutamicum* ΔtrpD::trpD5Δcsm (Table 2) were created by in-frame deletion of the csm gene (encoding chorismate mutase; Cgl0853) using the *E. coli-C. glutamicum* shuttle vector pK19mobsacB. The 5'-flanking region of the csm open reading frame (including the first 6 codons of the gene) and the 3'-flanking region of the target gene (including the last 6 codons of csm open reading frame) were amplified from genomic DNA, isolated from *Corynebacterium glutamicum* ATCC 13032, by PCR using the primer pairs Del-csm-1 and Del-csm-2, and Del-csm-3 and Del-csm-4, respectively (Table 3, SEQ ID NO: 79-82). The resulting two fragments were combined by crossover PCR using the primer pair Del-csm-1 and Del-csm-4. The resulting fragment was cloned into the multiple cloning site of the pK19mobsacB vector via SmaI restriction and re-ligation, as described above. The resulting vector was applied for in-frame deletion of csm from the genome of *Corynebacterium glutamicum* ATCC 13032, *C. glutamicum* ΔtrpD::trpD5, and from the strain *Corynebacterium glutamicum* ΔtrpD, respectively, and introduced in-frame a 24 bp foreign missense-sequence into the genome, which was employed for the crossover PCR (resulting sequence in csm locus: SEQ ID No. 10). Correct mutants were isolated as described above and correct gene deletion proven by PCR. This yielded the L-tyrosin and L-phenylalanin auxotroph strains *C. glutamicum* Δcsm and *C. glutamicum* ΔtrpD::trpD5Δcsm, as well as the L-tyrosin, L-phenylalanin, and L-tryptophan auxotroph strain *C. glutamicum* ΔtrpDΔcsm. Strains were characterized towards their properties as an oAB producer strains as described above with supplementation of the medium with 0.1 mM L-tyrosin and 0.1 mM L-phenylalanin for the *C. glutamicum* Δcsm strain and with supplementation of the medium with 0.1 mM L-tyrosin, 0.1 mM L-phenylalanin, and 0.1 mM L-tryptophan for the *C. glutamicum* ΔtrpDΔcsm strain (Table 2). The generated strains had an impaired growth rate, compared to the wild type strain as well as strain *C. glutamicum* ΔtrpD, and under standard cultivation conditions they did not accumulate significant amounts of oAB (Table 4).

Six versions of the csm gene were cloned into vector pEKEx2 via SbfI and BamHI restriction and re-ligation as described above. The six different versions of the csm gene were generated with different start codons, and spacer lengths between ribosomal binding site and start codon of csm (SEQ ID No. 11-16) by PCR using *C. glutamicum* genomic DNA as a template. The applied primers for the six fragments generation were forward primers (Ex-csm-1 to -6), which included the changed start codon and spacer between ribosomal binding site and start codon, together with the for each version unchanged reverse primer (Ex-csm-rev, Table 3, SEQ ID No. 89). This method was chosen in order to achieve a reduction of Csm protein translation in the produced strains. The strain *C. glutamicum* Δcsm (Table 2) was transformed with the resulting plasmids (Table 1) and the resulting strains *C. glutamicum* Δcsm/pEKEx2-csm1-6 (Table 2) grew without the addition of L-tyrosin, L-phenylalanin, and L-tryptophan and were, accordingly, characterized towards their properties as an oAB producer as described above with supplementation of 25 mg/L kanamycin and 1 μM IPTG to the medium (see Table 4). The strain *C. glutamicum* ΔtrpD::trpD5Δcsm (Table 2) was transformed with the empty vector control pEKEx2 (Table 1) and the resulting strain *C. glutamicum* ΔtrpD::trpD5Δcsm/ pEKEx2 (Table 2) grew without the addition of L-tryptophan and was, accordingly, characterized towards its properties as an oAB producer as described above with supplementation of 25 mg/L kanamycin and 0.1 mM IPTG to the medium (Table 4). The generated strains produced enough aromatic amino acids to enable biomass formation, but under standard cultivation conditions they did not accumulate significant amounts of oAB (Table 4).

Engineering of the Common Aromatic Pathway and the L-Tryptophan Branch of *C. glutamicum* Strains Engineering of the trpEG Gene in *C. glutamicum* Strains The aromatic biosynthesis pathway of *C. glutamicum* has been elucidated and the genes related to the encoding the enzymes for the biosynthesis of oAB are known (Ikeda M, Appl Microbiol Biotechnol, 2006, 69:615). oAB is an intermediate of the L-tryptophan biosynthesis pathway and is derived from chorismate (CHO) by an anthranilate synthase, consisting of an amidotransferase (TrpE; donor: L-glutamine) and an anthranilate synthase unit (TrpEG), which releases a pyruvate molecule under formation of oAB and L-glutamate. The increased expression of TrpEG-encoding genes has been shown to lead to an accumulation of L-tryptophan in *Escherichis coli* strains (Ikeda M, Appl Microbiol Biotechnol, 2006, 69:615). Nevertheless, the enzyme has been reported to be strongly feedback-inhibited by L-tryptophan (Ikeda M, Appl Microbiol Biotechnol, 2006, 69:615), resulting in the application of feedback-resistant versions of the TrpEG proteins. Feedback-resistant versions of TrpEG protein have been reported based on trpEG sequences from *Brevibacterium lactofermentum* (*C. glutamicum*), *E. coli* and *Salmonella typhimurium* (Calguri et al., J Bio Chem, 1991, 8328-8335; Kwak et al., J Biochem Mol Bio, 1999, 20-24, Ikeda M, Appl Microbiol Biotechnol, 2006, 69:615 and Matsui et al., J Bac, 1987, 5330-5332). The most favorable trpEG versions based on the *E. coli* genes were expressed in *C. glutamicum* strains, as well as selected amino acid exchanges on the trpEG sequence of the natural TrpEG protein of *C. glutamicum* ATCC13032 were implemented and expressed in *C. glutamicum* strains. Taken together four feedback-resistant TrpEG proteins (based on *E. coli* TrpEG: TrpEGS40R and TrpEGS40F (SEQ ID No. 50-51); and based on *C. glutamicum* TrpEG: TrpEGS38R and TrpEGS38F) (SEQ ID No. 52-53) were characterized, in comparison to the natural TrpEG protein of *C. glutamicum*. The five versions of the trpEG genes were synthesized by Eurofins MWG Operon GmbH and cloned into vector pEKEx2 via SbfI and BamHI restriction and re-ligation as described above and correct cloning was verified by sequencing. The strains *C. glutamicum* ATCC13032 and *C. glutamicum* ΔtrpD::trpD5 (Table 2) were transformed with the resulting plasmids (Table 3) (*C. glutamicum* ΔtrpD:: trpD5 only with plasmid pEKEx2-trpEG$^{S40F}$) and the resulting strains *C. glutamicum*/pEKEx2-trpEG, *C. glutamicum*/ pEKEx-trpEG$^{S38F}$, *C. glutamicum*/pEKEx2-trpEG$^{S38R}$, *C.* glutamicum/pEKEx2-trpEG$^{S40F}$, C. glutamicum/pEKEx2-trpEG$^{S40R}$, C. glutamicum ΔtrpD::trpD5/pEKEx2-trpEG$^{S40F}$ (Table 2) were characterized towards their properties as an oAB producer, as described above, with supplementation of 25 mg/L kanamycin and 0.1 mM IPTG to the medium (see Table 4). Additionally the cell lysates of the five C. glutamicum ΔtrpD-based strains carrying the pEKEx2-trpEG variants were analyzed towards the anthranilate synthase activity, according to Caliguri and Bauerle (1991). Cell lysates were produced from cell pellets generated from 30 mL cultures of C. glutamicum ΔtrpD-based strains carrying the pEKEx2-trpEG variants in 300 mL-shake flask with 30 mL BHI medium supplemented with 25 mg/L kanamycin and 1 mM IPTG and grown at 30° C. with shaking at 150 rpm (final OD$_{600}$ 4). The cell pellets were lysed using 0.1 mm zirconia beads (Zymo Research Cooperation, Irvine, Calif.) and resuspended in assay buffer (50 mM KH$_2$PO$_4$/K$_2$HPO$_4$, 20 mM L-glutamine, 10 mM MgCl$_2$, and 25 μM chorimate) according to Caliguri and Bauerle (1991) at 25° C. The emission was measured at 390 nm using a spectrofluorometer (excitation: 390 nm). All tested variants showed a higher specific activity for anthranilate synthase activity compared to the cell lysate with the natural C. glutamicum TrpEG protein. Three biological replicates were used for measurements. Both E. coli TrpEG protein variants had a higher activity and a lower K$_M$ compared the C. glutamicum TrpEG protein variants (determination of K$_M$ and v$_{max}$ values was performed with Graphpad Prism (La Jolla, Calif.). The cell lysate of strain C. glutamicum ΔtrpD/pEKEx2-trpEG$^{S40F}$ has shown the best performance (see Table 5).

TABLE 5

Biochemical characteristics of C. glutamicum ΔtrpD raw extracts producing different variants of TrpEG towards TrpEG activity.

| Strain | K$_M$ (μmol) | V$_{max}$ (mU/mg) |
| --- | --- | --- |
| C. glutamicum ΔtrpD/pEKEx2-trpEG | 11.4 | 12.7 |
| C. glutamicum ΔtrpD/pEKEx2-trpEG$^{S38F}$ | 16.2 | 68.8 |
| C. glutamicum ΔtrpD/pEKEx2-trpEG$^{S38R}$ | 21.6 | 231.2 |
| C. glutamicum ΔtrpD/pEKEx2-trpEG$^{S40F}$ | 1.9 | 427.5 |
| C. glutamicum ΔtrpD/pEKEx2-trpEG$^{S40R}$ | 1.9 | 317.9 |

Engineering of the aroG Gene in C. glutamicum Strains

In both C. glutamicum and E. coli it has been reported, that carbon flux through the common aromatic pathway up to chorismate is primarily controlled at the first reaction of 3-deoxy-D-arabino-heptulosonate 7-phosphate synthase (Ikeda M, Appl Microbiol Biotechnol, 2006, 69:615). In C. glutamicum, two types of DSs with different subunit sizes exist. One is an L-tyrosine-sensitive DS with a predicted molecular mass of 39 kDa (type I-DS; the aro product; Cgl0950) and an L-phenylalanine- and L-tyrosine-sensitive DS with a predicted molecular mass of 51 kDa (type II-DS; the aroII product; Cgl2098). The type II-DS forms a polypeptide complex with chorismate mutase, which converts chorismate to prephenate. The type II-DS exhibits its activity by itself, while CM activity requires the presence of the type II-DS protein (Ikeda M, Appl Microbiol Biotechnol, 2006, 69:615). A feedback-resistant AroI DS has been described (AroIS187C) (Ikeda M, Appl Microbiol Biotechnol, 2006, 69:615). The feedback-resistant equivalent DS of AroII, AroG$^{fbr}$ (aroG$^{D146N}$; SEQ ID No. 55) from E. coli, which is not inhibited by the aromatic amino acids, was expressed in C. glutamicum strains to enhance the carbon flux through the common aromatic pathway towards CHO and oAB. The aroG$^{D146N}$ gene was amplified by PCR using the primers Ex-aroG-1 and Ex-aroG-2 (Table 3, SEQ ID No. 109-110), which included the restrictions sites and ribosomal binding site, as described above. The resulting DNA fragment was and cloned into vector pEKEx2 via SbfI and BamHI restriction and re-ligation, as described above, and correct cloning was verified by sequencing. The strain C. glutamicum ΔtrpD::trpD5 (Table 2) was transformed with the resulting plasmid (Table 1) and the resulting strain C. glutamicum ΔtrpD::trpD5/pEKEx2-aroG$^{D146N}$ (Table 2) was characterized towards its properties as an oAB producer, as described above, with supplementation of 25 mg/L kanamycin and 0.1 mM IPTG to the medium (see Table 4).

Engineering of the trpEG and aroG Gene in C. glutamicum Strains

To allow investigation of the influence of combined expression of aroG$^{D146N}$ and TrpEGS40F in C. glutamicum strains the DNA sequences encoding these proteins were fused onto the pEKEx2 vector. The aroG$^{D146N}$ sequence was fused to pEKEx2-trpEG$^{S40F}$ to gain pEKEx2-trpEG$^{S40F}$ aroG$^{D146N}$ (Table 1) and the gene trpEG$^{S40F}$ was fused to the plasmid pEKEx2-aroG$^{D146N}$ to gain pEKEx2-aroG$^{D146N}$-trpEG$^{S40F}$ (Table 1), both via BglII and BamHI restriction and re-ligation, as described above, and correct cloning was verified by sequencing. The strain C. glutamicum ΔtrpD::trpD5 (Table 2) was transformed with each of the resulting plasmids and the resulting strains C. glutamicum ΔtrpD::trpD5/pEKEx2-aroG$^{D146N}$-trpEG$^{S40F}$ and C. glutamicum ΔtrpD::trpD5/pEKEx2-trpEG$^{S40F}$-aroG$^{D146N}$ (Table 2) were characterized towards their properties as oAB producers, as described above, with supplementation of 25 mg/L kanamycin and 0.1 mM IPTG to the medium (see Table 4). Additionally, the strain C. glutamicum ΔtrpD::trpD5Δcsm (Table 2) was transformed with plasmid pEKEx2-aroG$^{D146N}$-trpEG$^{S40F}$ and the resulting strain C. glutamicum ΔtrpD::trpD5Δcsm/pEKEx2-aroG$^{D146N}$-trpEG$^{S40F}$ (Table 2) was characterized towards its properties as an oAB producer, as described above, with supplementation of 25 mg/L kanamycin, 0.1 mM L-tyrosin, 0.1 mM L-phenylalanin, and 0.1 mM IPTG to the medium (see Table 4).

Engineering of the aroK and aroL Gene in C. glutamicum Strains

To prevent an accumulation of intermediates in the common aromatic amino acid biosynthesis pathway of C. glutamicum strains the gene aroK (encodes shikimate kinase; Cgl1622; SEQ ID No. 94) from C. glutamicum and the gene aroL (encodes shikimate kinase; CP000948; SEQ ID No. 93) from E. coli were investigated. The aroK and the aroL genes were separately amplified by PCR using the primers Ex-aroK-1 and Ex-aroK-2 (Table 3, SEQ ID No. 101-102) and Ex-aroL-1 and Ex-aroL-2 (Table 3, SEQ ID No. 99-100), respectively. The primers included the restrictions sites and ribosomal binding site, as described above. The resulting DNA fragments were separately integrated into vector pEKEx2 via SbfI and BamHI restriction and re-ligation, as described above, to yield the plasmids pEKEx2-aroK and pEKEx2-aroL and correct cloning was verified by sequencing. The strain C. glutamicum ΔtrpD::trpD5 (Table 2) was transformed with the resulting plasmids (Table 3) and the resulting strains C. glutamicum ΔtrpD::trpD5/pEKEx2-aroL and C. glutamicum ΔtrpD::trpD5/pEKEx2-aroK (Table 2) were characterized towards their properties as oAB producers, as described above, with supplementation of 25 mg/L kanamycin and 0.1 mM IPTG to the medium (see Table 4). In strain C. glutamicum ΔtrpD::trpD5/pEKEx2-aroL no significant accumulation of shikimate and 3-dehydroshikimat was detectable by HPLC-DAD analyses of culture supernatants.

Engineering of the glnA Gene in *C. glutamicum* Strains To analyze the impact of the L-glutamine synthetase (GlnA; Cgl2214, SEQ ID No. 95) activity on the production of oAB by *C. glutamicum* strains the L-glutamine synthetase gene, glnA, was expressed in strain *C. glutamicum strains*. The glnA gene was amplified by PCR using the primers Ex-glnA-1 and Ex-glnA-2 (Table 3, SEQ ID No. 97-98), which included the restrictions sites and ribosomal binding site, as described above. The resulting DNA fragment was and cloned into vector pCRB210 via NcoI restriction and re-ligation, as described above, and correct cloning was verified by sequencing. The strain *C. glutamicum* ΔtrpD::trpD5 was transformed with the resulting plasmid (Table 3) and the resulting strain *C. glutamicum* ΔtrpD::trpD5/pCRB-glnA (Table 2) was characterized towards its properties as an oAB producer, as described above, with supplementation of 25 mg/L kanamycin and 0.1 mM IPTG to the medium (see Table 4). As a control the strain *C. glutamicum* ΔtrpD::trpD was transformed with the empty vector control pCRB210 (Table 1) and the resulting strain *C. glutamicum* ΔtrpD::trpD5/pCRB210 (Table 2) was characterized towards its properties as an oAB producer, as described above, with supplementation of 25 mg/L kanamycin and 0.1 mM IPTG to the medium (see Table 4). Although the growth of the strain was reduced a beneficial effect on the anthranilate accumulation of *C. glutamicum* ΔtrpD::trpD5 could not be observed. It cannot be ruled out that the increased activity of GlnA will increase the accumulation of anthranilate in a more advanced oAB producer strain as it has been observed in *E. coli* (Sun et al., Appl Environ Microbiol, 2013, 4024-4030).

Engineering of the Central Metabolism of *C. glutamicum* Strains

Engineering of the pyk Gene in *C. glutamicum* Strains

A pyruvate kinase (Pyk) consumes phosphoenolpyruvate by production of pyruvate and ATP. The effect of an in-frame deletion of the pyk gene (SEQ ID NO: 23) in *C. glutamicum* strains was investigated. The strain *C. glutamicum* ΔtrpD::trpD5Δpyk (Table 2) was created by in-frame deletion of the pyk gene (encoding pyruvate kinase; Cgl2089) using the *E. coli*-*C. glutamicum* shuttle vector pK19mobsacB, as described above. The resulting plasmid pSB082 (Table 1) was applied for in-frame deletion of pyk gene from the genome of *C. glutamicum* ΔtrpD::trpD5, and introduced in-frame a 24 bp foreign missense-sequence into the genome (resulting sequence in pyk locus: SEQ ID No. 24). Correct mutants were isolated as described above and correct gene deletion proven by PCR. This yielded strain *C. glutamicum* ΔtrpD::trpD5Δpyk, which was characterized towards its properties as an oAB producer strain, as described above (Table 4).

Engineering of the gpi Gene in *C. glutamicum* Strains

In order to direct the carbon flux towards the pentose phosphate pathway the effect of an in-frame deletion of the glucose-6-phosphate isomerase (Gpi) encoding gene (SEQ ID NO: 27) in *C. glutamicum* strains was investigated. The strain *C. glutamicum* ΔtrpD::trpD5Δgpi (Table 2) was created by in-frame deletion of the gpi gene (encoding glucose-6-phosphate isomerase; Cgl0851) using the *E. coli*-*C. glutamicum* shuttle vector pK19mobsacB, as described above. The resulting plasmid pSB064 (Table 1) was applied for in-frame deletion of gpi gene from the genome of *C. glutamicum* ΔtrpD::trpD5, and introduced in-frame a 24 bp foreign missense-sequence into the genome (resulting sequence in gpi locus: SEQ ID No. 28). Correct mutants were isolated as described above and correct gene deletion proven by PCR. This yielded strain *C. glutamicum* ΔtrpD::trpD5Δgpi, which was characterized towards its properties as an oAB producer strain, as described above (Table 4).

Engineering of the Pepco Gene in *C. glutamicum* Strains

The phosphoenolpyruvate carboxylase (Pepco) consumes PEP by transforming it into oxaloacetate. In order to access an increased PEP pool an in-frame deletion of the phosphoenolpyruvate carboxylase encoding gene (SEQ ID NO: 21) in *C. glutamicum* strains was investigated. The strain *C. glutamicum* ΔtrpD::trpD5Δpepco (Table 2) was created by in-frame deletion of the pepco gene (encoding phosphoenolpyruvate carboxylase; Cgl1585) using the *E. coli*-*C. glutamicum* shuttle vector pK19mobsacB, as described above. The resulting plasmid pSB061 (Table 1) was applied for in-frame deletion of pepco gene from the genome of *C. glutamicum* ΔtrpD::trpD5, and introduced in-frame a 24 bp foreign missense-sequence into the genome (resulting sequence in pepco locus: SEQ ID No. 22). Correct mutants were isolated as described above (with additional supplementation of 1% acetate to BHI medium agar plates) and correct gene deletion proven by PCR. This yielded strain *C. glutamicum* ΔtrpD::trpD5Δpepco, which was characterized towards its properties as an oAB producer strain, as described above (Table 4).

Engineering of the ptsG and the hpr Gene in *C. glutamicum* Strains

Glucose and fructose uptake of *C. glutamicum* is mainly utilized by the phosphotransferase system (PTS). This multi-enzyme complex performs a translocation of glucose via a phosphorylation cascade mediated by phosphoenolpyruvate with concomitant glucose phosphorylation to glucose-6-phosphate across the cytoplasmic membrane (Siebold et al. 2001). The system consists of two soluble components enzyme I and histidine rich protein (Hpr) and a membrane bound/associated enzyme complex (Tanaka et al. 2008). The strains *C. glutamicum* ΔtrpD::trpD5Δhpr and *C. glutamicum* ΔtrpD::trpD5ΔptsG (Table 2) were created by in-frame deletion of the hpr gene (encoding histidine rich protein; Cgl1937, SEQ ID NO: 17) and the ptsG gene (encoding phosphotransferase system unit G; Cgl1360, SEQ ID NO: 19), respectively, using the *E. coli*-*C. glutamicum* shuttle vector pK19mobsacB, as described above. The resulting plasmids pSB060 and pSB079 (Table 1) were applied for in-frame deletion of hpr gene and ptsG gene, respectively, from the genome of *C. glutamicum* ΔtrpD::trpD5, and introduced in-frame a 24 bp foreign missense-sequence into the genome (resulting sequence in hpr/ptsG locus: SEQ ID No. 18; ptsG locus: 20). Correct mutants were isolated as described above (with additional supplementation of 5 g/L ribose to BHI medium agar plates) and correct gene deletion proven by PCR. This yielded strain *C. glutamicum* ΔtrpD::trpD5Δhpr and *C. glutamicum* ΔtrpD::trpD5ΔptsG, which were characterized towards its properties as an oAB producer strain, as described above (Table 4). Both strains did not show significant growth under standard fermentation conditions, as described above, and as a result did not accumulate oAB.

Engineering of the ppk Gene in *C. glutamicum* Strains

The phosphoenolpyruvate carboxykinase (Ppk) can, as a part of the glyoxylate pathway, recycle oxaloacetate into PEP. In order to access an increased PEP pool a plasmid-based expression of the phosphoenolpyruvate carboxykinase encoding gene (Cgl2862; SEQ ID NO: 36) in *C. glutamicum* strains was investigated. The ppk gene was synthesized by Eurofins MWG Operon GmbH and cloned into vector pEKEx2 via SbfI and BamHI restriction and re-ligation, as described above, resulting in the plasmid pSB072 (Table 1), and correct cloning was verified by sequencing. The strain C. glutamicum ΔtrpD::trpD5/pSB072 (Table 2) was created by transformation of strain C. glutamicum ΔtrpD::trpD5 with plasmid pSB072, as described above. Correct mutants were isolated as described above and successful transformation with the target gene proven by colony PCR. This yielded strain C. glutamicum ΔtrpD::trpD5/pSB072, which was characterized towards its properties as an oAB producer strain, as described above (Table 4).

Engineering of the pps Gene in C. glutamicum Strains

The phosphoenolpyruvate synthase (Pps) catalysis, as part of the gluconeogenesis, the formation of PEP by pyruvate recycling and consumption of ATP to AMP. In order to access an increased PEP pool a plasmid-based expression of the phosphoenolpyruvate synthase encoding gene together with the PEP synthase binding domain encoding gene (Cgl0551 and Cgl0552; SEQ ID NO: 33-35) in C. glutamicum strains was investigated. The pps genes were together synthesized by Eurofins MWG Operon GmbH and cloned into vector pEKEx2 via SbfI and BamHI restriction and re-ligation, as described above, resulting in the plasmid pSB073, and correct cloning was verified by sequencing. The strain C. glutamicum ΔtrpD::trpD5/pSB073 (Table 2) was created by transformation of strain C. glutamicum ΔtrpD::trpD5 with plasmid pSB073, as described above. Correct mutants were isolated as described above and successful transformation with the target gene proven by colony PCR. This yielded strain C. glutamicum ΔtrpD::trpD5/pSB073, which was characterized towards its properties as an oAB producer strain, as described above (Table 4).

Engineering of the zwf1 Together with the opcA Gene in C. glutamicum Strains

In Zymomonas mobilis and E. coli the enhanced production of the enzyme catalyzing the first reaction of the pentose phosphate pathway (PPP) (formation of ribulose-5-phosphate from glucose-6-phosphate by glucose-6-phosphat dehydrogenase (Zwf1 and OpcA)) was reported to result in an increased carbon flux into the PPP and as a result an increase of the erythrose-4-phosphate (E4P) pool. In order to access an increased E4P pool a plasmid-based expression of the glucose-6-phosphat dehydrogenase encoding genes (zwf1 (Cgl1576) and opcA (Cgl1577; SEQ ID NO: 37-39) in C. glutamicum strains was investigated. The genes were together synthesized by Eurofins MWG Operon GmbH and cloned into vector pEKEx2 via SbfI and BamHI restriction and re-ligation, as described above, resulting in the plasmid pSB078 (Table 1), and correct cloning was verified by sequencing. The strain C. glutamicum ΔtrpD::trpD5/pSB078 (Table 2) was created by transformation of strain C. glutamicum ΔtrpD::trpD5 with plasmid pSB078, as described above. Correct mutants were isolated as described above and successful transformation with the target gene proven by colony PCR.

This yielded strain C. glutamicum ΔtrpD::trpD5/pSB078, which was characterized towards its properties as an oAB producer strain, as described above (Table 4).

Engineering of tal and tkt Genes in C. glutamicum Strains

An enhanced carbon flux through the PPP and an increased E4P pool has been described by the enhanced expression of transketolase and transaldolase in E. coli. Transketolase (Tkt) and transaldose (Tal) encoding genes of E. coli (tktEC (ECDH10B_3110) and talEC (ECDH10B_2629); SEQ ID NO: 41 and 43) as well as the equivalent genes of C. glutamicum (tktCG (Cgl1574) and talCG (Cgl1575); SEQ ID NO: 40 and 42) were plasmid-based expressed in C. glutamicum strains. The four sequences were synthesized by Eurofins MWG Operon GmbH and separately integrated into vector pEKEx2 via SbfI and BamHI restriction and re-ligation, as described above, resulting in the plasmids pSB074-pSB077 (Table 1), and correct cloning was verified by sequencing. The strains C. glutamicum ΔtrpD::trpD5/pSB074-pSB077 (Table 2) were created by transformation of strain C. glutamicum ΔtrpD::trpD5 with each of the plasmids, as described above. Correct mutants were isolated as described above and successful transformation with the target gene proven by colony PCR. This yielded strains C. glutamicum ΔtrpD::trpD5/pSB074—pSB077, which were characterized towards their properties as an oAB producer strains, as described above (Table 4).

To allow investigation of the effect of combined expression of transketolase and transaldolase in C. glutamicum strains the DNA sequences encoding these proteins were fused onto the pEKEx2 vector. The talCG sequence was fused to pSB075 to gain pSB085 (Table 1) and the gene talEC was fused to the plasmid pSB077 to gain pSB086 (Table 1), both via BglII and BamHI restriction and re-ligation, as described above, and correct cloning was verified by sequencing. The strain C. glutamicum ΔtrpD::trpD5 was transformed with each of the resulting plasmids and the resulting strains C. glutamicum ΔtrpD::trpD5/pSB085 and C. glutamicum ΔtrpD::trpD5/pSB086 (Table 2) were characterized towards their properties as oAB producers, as described above, with supplementation of 25 mg/L kanamycin and 0.1 mM IPTG to the medium (Table 4).

Engineering of the galP, the iolT2 and the ppgk Gene in C. glutamicum Strains

In order to restore efficient glucose uptake in Pts-deficient C. glutamicum strains a plasmid-based expression of galactopermease encoding gene (galP, Cgl2409; SEQ ID NO: 30) in combination with a polyphosphoglucokinase (a glucose phosphorylating enzyme) encoding gene (ppgk (Cgl910; SEQ ID NO: 32) in C. glutamicum strains was investigated. Furthermore, the inositolpermease T2 unit (of the inositolpermease) encoding gene (iolT2, Cgl3058; SEQ ID NO: 31) in combination with a polyphosphoglucokinase encoding gene (ppgk (Cgl910; SEQ ID NO: 32) in C. glutamicum strains was investigated. The four genes were synthesized by Eurofins MWG Operon GmbH and each integrated into vector pEKEx2 via SbfI and BamHI restriction and re-ligation, as described above, resulting in the plasmid pSB068, pSB070, and pSB071 (Table 1) and correct integration was verified by sequencing. The ppgk sequence was fused to galP sequence and iolT2, respectively, onto the pEKEx2 vector. The galP sequence was fused to pSB071 to gain pSB083 (Table 1) and the gene iolT2 was fused to the plasmid pSB071 to gain pSB084 (Table 1), both via BglII and BamHI restriction and re-ligation, as described above, and correct cloning was verified by sequencing. The strains C. glutamicum ΔtrpD::trpD5ΔptsG and C. glutamicum ΔtrpD::trpD5Δhpr (Table 2) were each transformed with the plasmids pSB083 and pSB084, respectively, and the resulting strains C. glutamicum ΔtrpD::trpD5ΔptsG/pSB083, C. glutamicum ΔtrpD::trpD5ΔptsG/pSB084, C. glutamicum ΔtrpD::trpD5ΔptsG/pSB083, and C. glutamicum ΔtrpD::trpD5Δhpr/pSB084 (Table 2) were characterized towards their properties as oAB producers, as described above, with supplementation of 25 mg/L kanamycin and 0.1 mM IPTG to the medium (Table 4). The strain ΔtrpD::trpD5Δhpr/pSB083 did not show significant growth under standard fermentation conditions, as described above, and as a result did not accumulate oAB.

Engineering of the oAB Export from *C. glutamicum* Strains

With increasing production rates of oAB the export of the product from producing cells can easily become a production limiting step. Furthermore, intracellular accumulation of oAB very likely can have a significant toxic effect on cells. No oAB exporter has been described so far. Recently, a shikimate permease (QsuA), belonging to the family of major facilitator systems, was described by Kubota et al., which facilitates the import of shikimate and quinate (Kubota et al., Molecular Microbiol, 2014, 92(2), 356) in *C. glutamicum*. In order to test the effect of the shikimate permease on intra- and extracellular concentrations of oAB in *C. glutamicum* strains, the related gene (qsuA, Cgl0492; SEQ ID NO: 96) was synthesized by Eurofins MWG Operon GmbH and integrated into vector pEKEx2 via SbfI and BamHI restriction and re-ligation, as described above, resulting in the plasmid pSB096 (Table 1), and correct cloning was verified by sequencing. The strain *C. glutamicum* ΔtrpD::trpD5/pSB096 (Table 2) was created by transformation of strain *C. glutamicum* ΔtrpD::trpD5 with plasmid pSB096, as described above. Correct mutants were isolated as described above and successful transformation with the target gene proven by colony PCR. This yielded strain *C. glutamicum* ΔtrpD::trpD5/pSB096, which was characterized towards its properties as an oAB producer strain, as described above (Table 4).

Example 4—Production of o-Aminobenzoate with *P. putida*

Figure 27:
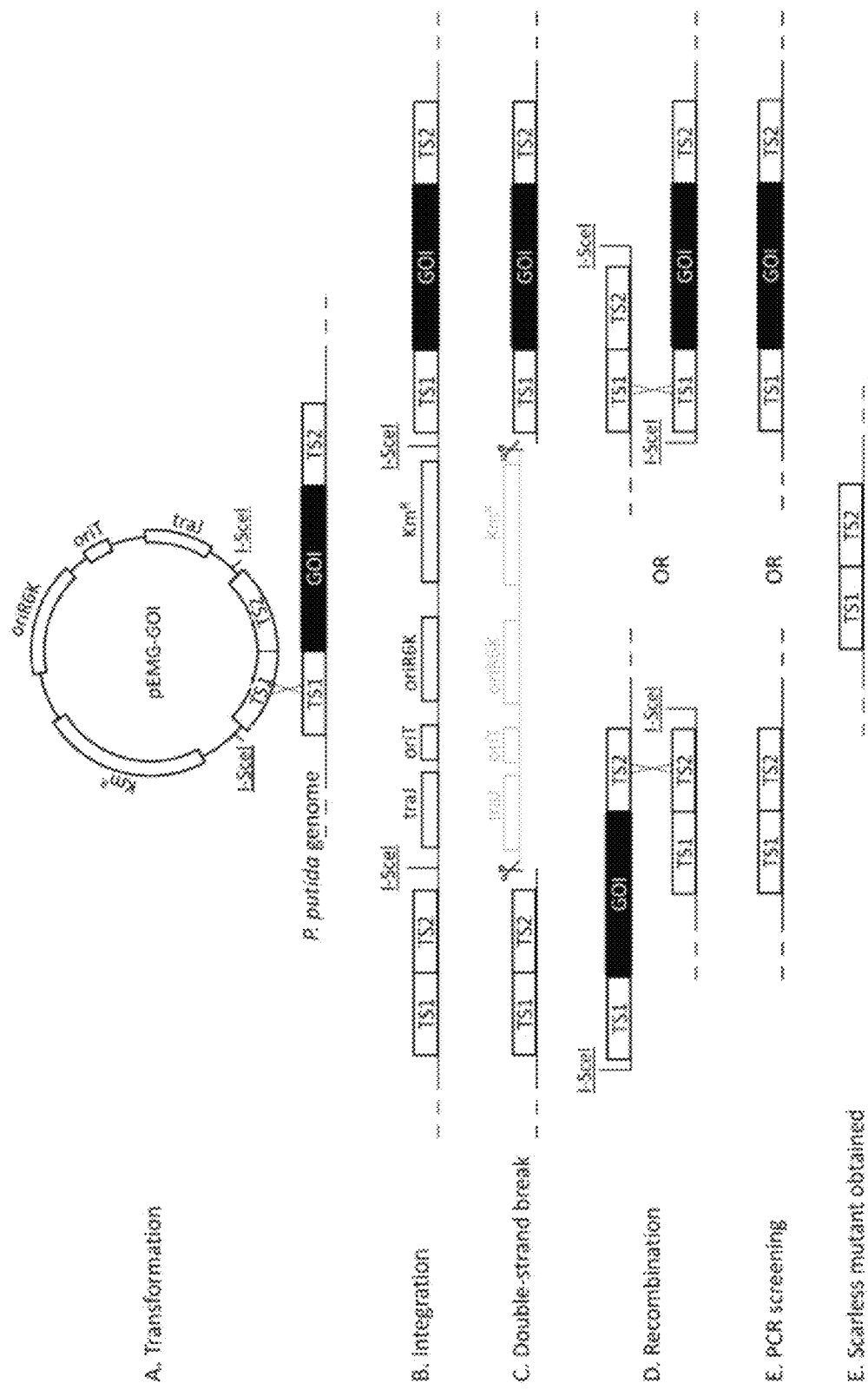
FIG. 27 shows a scheme of the knockout procedure based on vector system pEMG.
Figure 28:
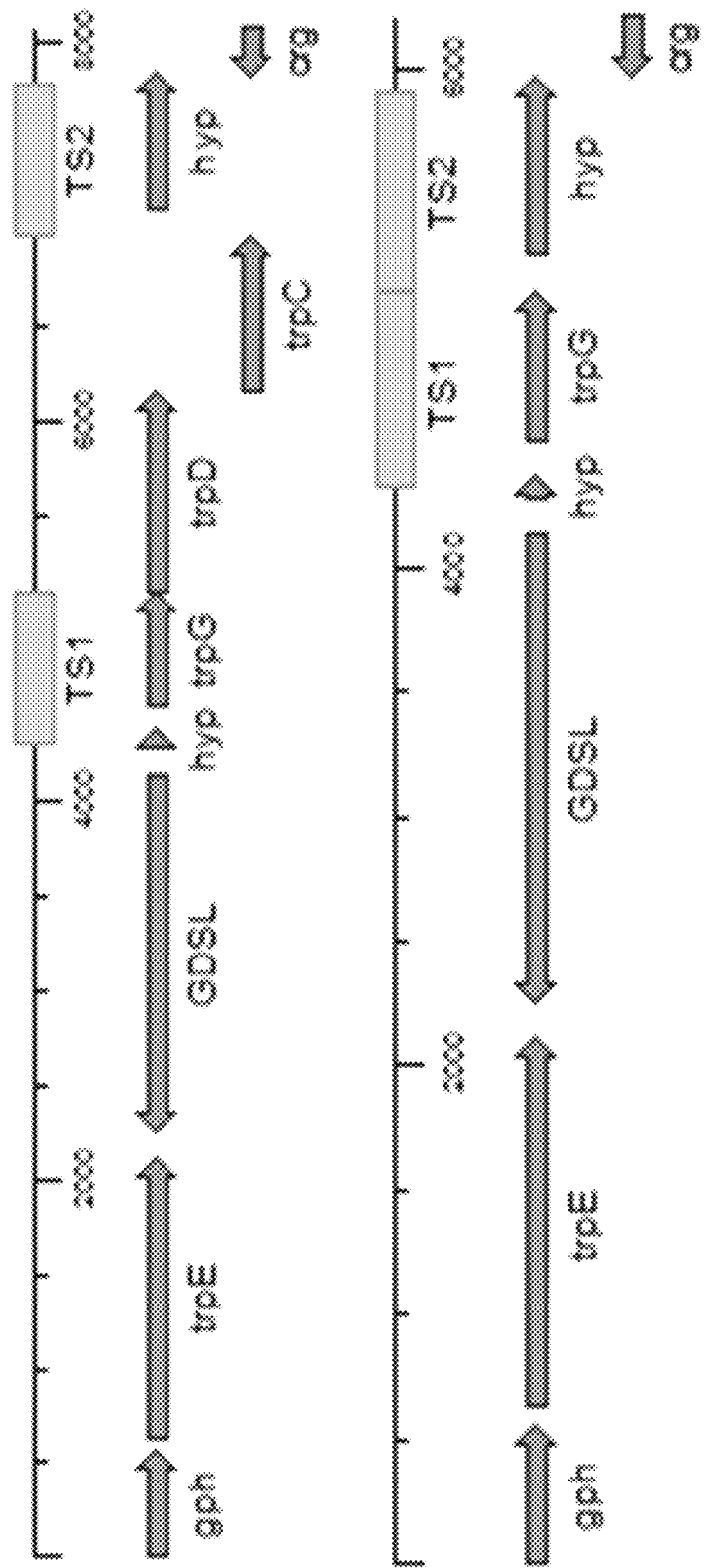
FIG. 28 shows the genetic map of the *P. putida* KT2440 trpEGDC cluster (above) and genetic map of the *P. putida* KT2440 trpDC deletion (below) (gph: phosphoglycolate phosphatase (partial); trpE: anthranilate synthase component I; GDSL: GDSL family lipase (unrelated to L-tryptophane biosynthesis); hyp: hypothetical protein; trpG: anthranilate synthase component II; crg: cAMP-regulatory protein (partial); TS1: deletion flank 1; TS2: deletion flank 2).

Strains derived from *Pseudomonas putida* KT2440 were developed, that produce oAB. In order to achieve an oAB accumulation by *P. putida* strains, the trpDC genes (PP_0421 and PP_0422; SEQ ID NO: 63), encoding anthranilate phosphoribosyltransferase and indole-3-glycerol phosphate synthase, were chosen to be disrupted in *Pseudomonas putida* KT2440. The construction of the deletion mutant *P. putida* ΔtrpDC, based on a knockout plasmid pEMG-Del-trpDC (Table 1), was approached by the method describe in Martinez-Garcia et al (Martinez-Garcia et al, Environ Microbiol, 2011, 13(10), 2702) using the vector pEMG. This approach results in the removal of the gene sequences (gen of interest, GOI) without residual cloning scars or markers. The concept of the method is shown in the FIG. 27. In Step A-B the designed knockout vector pEMG, bearing the disruption flanks TS1 and TS2, a kanamycin marker and the I-SceI sites, is integrated into the genome of *P. putida*. In step C the double strand break is induced by the transformation of a second plasmid @SW-2), bearing the meganuclease I-SceI genes. The break is repaired in vivo, by homologous recombination of either the TS1 or the TS2 region, resulting in either *P. putida* wild type or *P. putida* ΔtrpDC (step D). Step E shows the PCR screening which is required to distinguish and isolate the different strains. Deletion flanks were chosen such that the open reading frame of the genes is removed while keeping neighbouring genes intact (FIG. 28). This strategy can lead to greater strain stability in long-term continuous cultivation. The 800 bp disruption flanks TS1 and TS2 were amplified using a Phusion® High-Fidelity DNA Polymerase (New England Biolabs). The Phusion PCR was performed according to the manufacturer's manual (25 cycles, 61.8° C. (TS1), 70.2° C. (TS2) 1:30 minutes). The PCR fragment TS1 was digested with BamHI and XhoI and the PCR fragment TS2 was digested with XhoI and SbfI. The plasmid pEMG and the fused TS1-TS2 PCR product were digested with BamHI and SbfI. All restriction mixtures were purified using a High Pure PCR Product Purification Kit (Roche). The ligation of pEMG-Del-trpDC, using the individual flanks TS1 and TS2, was performed with a T4 DNA ligase (Thermo Fisher Scientific) according to the manufacturer's instructions. The ligation mixture was transformed to the chemically competent *E. coli* DH5α λpir strain. Positive plasmids from the three point ligation mixture consisting of the two individual flanks and the digested vector pEMG were identified by restriction analysis and verified by sequencing, which confirmed the successful construction of pEMG-Del-trpDC (Table 1). The knockout vector pEMG-Del-trpDC was integrated into the genome of *P. putida* (FIG. 27, step A-B) by tri-parental mating using the acceptor strain *P. putida*, the donor strain *E. coli* DH5α λpir/pEMG-Del-trpDC and a helper strain *E. coli* HB101 pRK2013 (Martinez-Garcia et al, Environ Microbiol, 2011, 13(10), 2702). *P. putida*/pEMG-Del-trpDC was isolated from the cell mixture by using cetrimide agar plates with 50 mg/L kanamycin and single colonies were re-streaked on LB-kanamycin plates. Genome integration of the knockout vector was confirmed in single colonies via colony PCR. To introduce the double strand breakage in the genome (FIG. 27, step C), a second plasmid (pSW-2) bearing the 1-SceI meganuclease gene, was transformed into the newly constructed strain. Therefore electro-competent *P. putida*/pEMG-Del-trpDC cells were obtained according to Choi et al (Choi et al, J Microbiol Methods, 2005, 64(3), 391). The electroporation was performed using a Biorad Gene Pulser Xcell Electroporator (2.5 kV, 200 ohm, 25 μF) and the cell suspension was plated out on LB-gentamycin (30 mg/L) and LB-kanamycin-gentamycin plates (30 mg/L and 50 mg/L, respectively). Following the protocol of the knockout procedure described in Martinez-Garcia et al an induction of the 1-SceI meganuclease is necessary. However, this step was omitted due to practical experience implying a leaky expression of the I-SceI meganuclease. To distinguish the desired *P. putida* ΔtrpDC knockout strain from the *P. putida* and the *P. putida*/pEMG-Del-trpDC strain, single colonies were streaked out on LB and LB-kanamycin plates. Kanamycin sensitive colonies were checked via colony PCR as described above. In addition kanamycin sensitive colonies were checked for L-phenylalanine auxotrophy on minimal medium plates with 20 mM glucose and with and without 0.1 mM L-tryptophane. Gene deletions were verified by PCR analysis and sequencing. The resulting strain *P. putida* ΔtrpDC (Table 2) was not able to grow on minimal medium without L-tryptophane supplementation.

Figure 29:
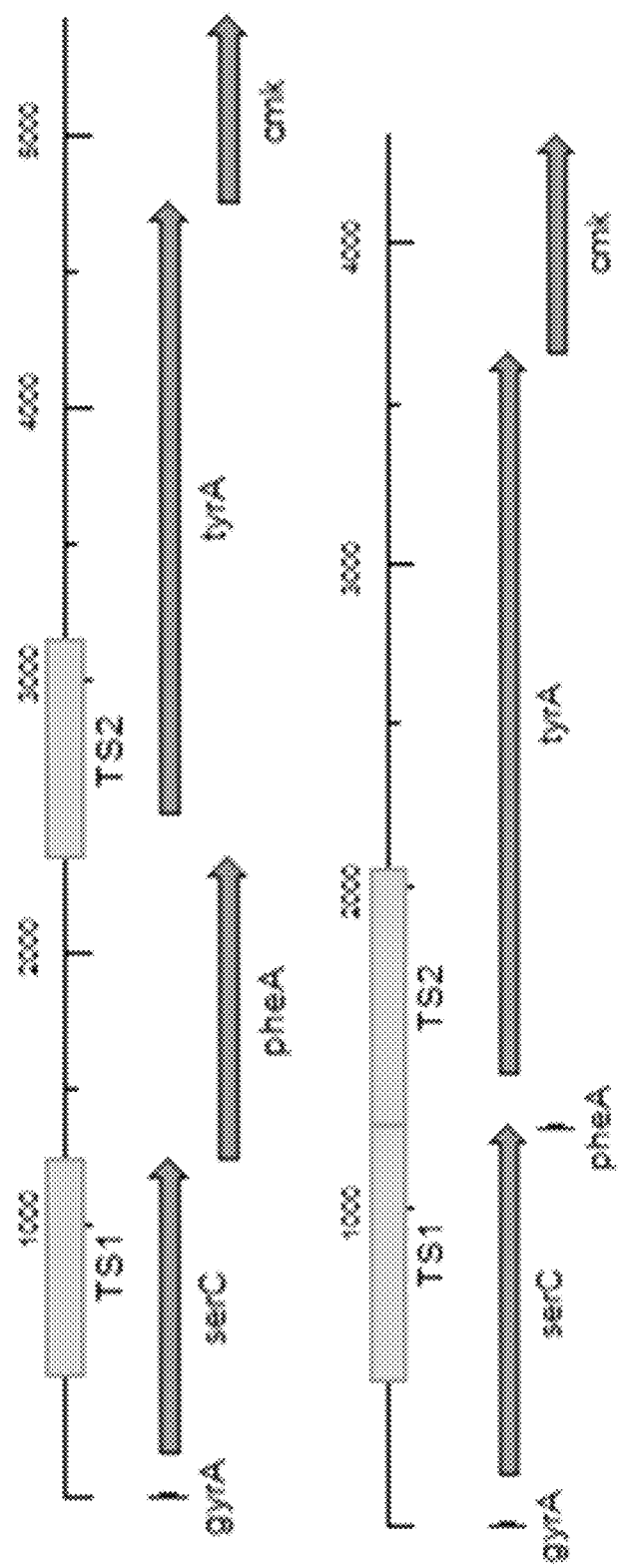
FIG. 29 shows the genetic map of the *P. putida* KT2440 serCpheAtyrA cluster (above) and genetic map of the indented *P. putida* KT2440 pheA deletion (below) (gyrA: DNA gyrase subunit A(partial); serC: phosphoserine aminotransferase; pheA: chorismate mutase/prephenate dehydratase; tyrA: prephenate dehydrogenase/3-phosphoshikimate carboxyvinyltransferase; cmk: cytidylate kinase; TS1: deletion flank 1; TS2: deletion flank 2).

In addition, the pheA gene (PP_1769, SEQ ID NO: 64), encoding chorismate mutase, was disrupted in the *Pseudomonas putida* ΔtrpDC strain. The pheA gene encodes the first step of L-phenylalanine and L-tyrosine biosynthesis, which likely competes with anthranilate production. The construction of the deletion mutant *P. putida* ΔtrpDCΔpheA, based on a knockout plasmid pEMG-Del-pheA, was approached by the method describe in Martinez-Garcia et al (Martinez-Garcia et al, Environ Microbiol, 2011, 13(10), 2702) using the vector pEMG, as described above. Deletion flanks were chosen such that the open reading frame of the gene is removed while keeping neighbouring genes intact (FIG. 29). This strategy can lead to greater strain stability in long-term continuous cultivation. In case of pheA this meant that the eight 5' nucleotides of the gene remained due to an overlap with the serC gene. To construct the 800 bp disruption flanks TS1 and TS2 the following primers were used JK038f, JK039r, JK040f, and JK041r (Table 3, SEQ ID NO: 103-106). The PCR fragment TS1 was digested with BamHI and XhoI and the PCR fragment TS2 was digested with XhoI and SbfI. The plasmid pEMG and the fused TS1-TS2 PCR product were digested with BamHI and SbfI. All restriction mixtures were purified using a High Pure PCR Product Purification Kit (Roche). The ligation of pEMG-Del-pheA, using the individual flanks TS1 and TS2, was performed with a T4 DNA ligase (Thermo Fisher Scientific) according to the manufacturer's instructions. The ligation mixture was transformed to the chemically competent E. coli DH5α kpir strain. Positive plasmids from the three point ligation mixture consisting of the two individual flanks and the digested vector pEMG were identified by restriction analysis and verified by sequencing, which confirmed the successful construction of pEMG-Del-pheA (Table 1). The knockout vector pEMG-Del-pheA was integrated into the genome of P. putida ΔtrpDC (FIG. 27, step A-B) by triparental mating using the acceptor strain P. putida ΔtrpDC, the donor strain E. coli DH5α λpir/pEMG-Del-pheA and a helper strain E. coli HB101 pRK2013 (Martinez-Garcia et al, Environ Microbiol, 2011, 13(10), 2702). P. putida ΔtrpDC/pEMG-Del-pheA was isolated from the cell mixture by using cetrimide agar plates with 50 mg/L kanamycin and single colonies were re-streaked on LB-kanamycin plates. Genome integration of the knockout vector was confirmed in single colonies via colony PCR. To introduce the double strand breakage in the genome (FIG. 27, step C), a second plasmid (pSW-2) bearing the I-SceI meganuclease gene, was transformed into the newly constructed strain. Therefore electro-competent P. putida ΔtrpDC/pEMG-Del-pheA cells were obtained according to Choi et al (Choi et al, J Microbiol Methods, 2005, 64(3), 391). The electroporation was performed using a Biorad Gene Pulser Xcell Electroporator (2.5 kV, 200 ohm, 25 µF) and the cell suspension Was plated out on LB-gentamycin (30 mg/L) and LB-kanamycin-gentamycin plates (30 mg/L and 50 mg/L, respectively). Following the protocol of the knockout procedure described in Martinez-Garcia et al an induction of the I-SceI meganuclease is necessary. However this step was omitted due to practical experience implying a leaky expression of the I-SceI meganuclease. To distinguish the desired P. putida ΔtrpDCΔpheA (Table 2) knockout strain from the P. putida ΔtrpDC and the P. putida ΔtrpDC/pEMG-Del-pheA strain, single colonies were streaked out on LB and LB-kanamycin plates. Kanamycin sensitive colonies were checked via colony PCR as described above. In addition kanamycin sensitive colonies were checked for L-phenylalanine auxotrophy on minimal medium plates with 20 mM glucose, 0.1 mM L-tryptophane, and with and without 1 mM L-phenylalanine. Gene deletions were verified by PCR analysis and sequencing. Since P. putida KT2440 possesses a L-phenylalanine-4-hydroxylase (PheA) which converts L-phenylalanine to L-tyrosine, L-tyrosine-auxotrophies were rescued by the addition of L-phenylalanine. Since both L-tryptophane, and L-phenylalanine auxotrophs were obtained by single gene disruptions, it was assumed that no redundant genes encoding alternative enzymes were present in P. putida KT2440.

The first dedicated reaction of the aromatic amino acid biosynthesis pathway is catalysed by DAHP synthase isoenzymes. It has been shown in several organisms that overexpression of a feedback-insensitive mutant of this enzyme leads to an increased flux through the aromatics biosynthesis pathway (Ikeda M, Appl Microbiol Biotechnol, 2006, 69:615). Therefore, in order to increase anthranilate production, a feedback-insensitive 3-deoxy-D-arabino-heptulosonate 7-phosphate (DAHP) synthase, encoded by the aroG$^{D146N}$ gene (SEQ ID NO: 55), was expressed in the strains P. putida KT2440, P. putida ΔtrpDC and P. putida ΔtrpDCΔpheA via vector pSEVA234 (under control of the lacP-Ptrc system; encoding a kanamycin resistance and a pBBR1 origin of replication) (Silva-Rocha et al, Nucleic Acids Research, 2013, D666-75). The aroG$^{D146N}$ gene was restricted from a donor plasmid (pCAS-2JF-aroG$^{D146N}$) using EcoRI and BamHI restriction enzymes and standard conditions, as described above (Example 3), resulting in a 1117 bp fragment. The vector pSEVA234 was restricted with the same enzymes. The fragments were purified using a High Pure PCR Product Purification Kit (Roche). The ligation of the fragment to gain pSEVA234-aroG$^{D146N}$ (Table 1) was performed with a T4 DNA ligase (Thermo Fisher Scientific) according to the manufacturer's instructions. The ligation mixture was introduced into electro-competent Escherichia coli DH5a cells (ElectroMAX™ DH5α-E™ Competent Cells; Life Technologies, Darmstadt). After electro-transformation (conditions: 20 ms exponentially decaying pulse, 2.5 kV/cm, 25 F, 200Ω) in 0.2 cm gap electroporation cuvettes (BioRad, Hercules, Calif.) using a Gene Pulser Xcell System (BioRad, Hercules, Calif.), 800 µL LB recovery medium (Luria-Bertani; Roth, Karlsruhe) was immediately added and the suspension was transferred into 1.5 mL microcentrifuge tube. After 1 h at 37° C., a cell suspension were spread onto LB agar plates (Abcr GmbH & Co. Kg, Karlsruhe), supplemented with 50 mg/L kanamycin, and incubated at 37° C. over night. Clones were collected and correct transformation confirmed via restriction analysis and sequencing. For plasmid preparation the stains were cultivated in 15 mL-tubes for 14 h-16 h with constant shaking at 200 rpm in 3 mL LB medium and 50 mg/L kanamycin at 37° C. (Kuhner. Shaker ISF-4-W; Adolf Kiihner AG, Basel (Switzerland)). Plasmid DNA purification was done using the NucleoSpin® Plasmid Pure kit (Macherey & Nagel, Düren) following the manufacturer's instructions. Electro-competent P. putida KT2440, P. putida ΔtrpDC, and P. putida ΔtrpDCΔpheA cells were obtained according to Choi et al (Choi et al, J Microbiol Methods, 2005, 64(3):391). The electroporation was performed using a Biorad Gene Pulser Xcell Electroporator (2.5 kV, 200 ohm, 25 µF) and the cell suspension was plated out on LB-agar plates supplemented with 50 m/L kanamycin. This resulted in the generation of the strains P. putida KT2440/pSEVA234-aroG$^{D46N}$, P. putida ΔtrpDC/pSEVA234-aroG$^{D46N}$, and P. putida ΔtrpDCΔpheA/pSEVA234-aroG$^{D46N}$ (Table 2). Additionally, the empty vector pSEVA234 was transformed into to the strains P. putida ΔtrpDC and P. putida ΔtrpDCΔpheA to gain the strains P. putida ΔtrpDC/pSEVA234, and P. putida ΔtrpDCΔpheA/pSEVA234 (Table 2).

oAB is an intermediate of the L-tryptophan biosynthesis pathway and is derived from chorismate by an anthranilate synthase, consisting of an amidotransferase (TrpE; donor: L-glutamine) and an anthranilate synthase unit (TrpEG), which releases a pyruvate molecule under formation of oAB and L-glutamate. The increased expression of TrpEG-encoding genes has been shown to lead to an accumulation of L-tryptophan in Escherichia coli strains (Ikeda M, Appl Microbiol Biotechnol, 2006, 69:615). Nevertheless, the enzyme has been reported to be strongly feedback-inhibited by L-tryptophan, resulting in the application of feedback-resistant versions of the TrpEG proteins. Feedback-resistant versions of TrpEG protein have been reported based on trpEG sequences from Salmonella typhimurium (Ikeda M, Appl Microbiol Biotechnol, 2006, 69:615). The most favorable trpEG version, based on the S. typhimurium genes, trpEG$^{S40F}$ (SEQ ID No. 53) was expressed in P. putida strains. The feedback-inhibition-resistant version of the trpEG gene was cloned into *P. putida* vector pSEVA234 to enable plasmid-based expression in the strains *P. putida* KT2440, *P. putida* ΔtrpDC, and *P. putida* ΔtrpDCΔpheA (under control of the lacF-Ptrc system; encoding a kanamycin resistance and a pBBR1 origin of replication) (Silva-Rocha et al, Nucleic Acids Research, 2013, D666-75). The trpEG$^{S40F}$ gene was restricted from a donor plasmid using BglII and BamHI restriction enzymes and standard conditions, as described above (Example 3), resulting in a 2200 bp fragment. The vector pSEVA234 was restricted with BamHI, resulting in a 4550 bp fragment. The fragments were purified using a High Pure PCR Product Purification Kit (Roche). The ligation of the fragments to gain pSEVA234-trpEG$^{S40F}$ (Table 1) was performed with a T4 DNA ligase (Thermo Fisher Scientific) according to the manufacturer's instructions. The ligation mixture was introduced into electro-competent *Escherichia coli* DH5α cells (ElectroMAX™ DH5α-E™ Competent Cells; Life Technologies, Darmstadt). After electro-transformation (conditions: ~20 ms exponentially decaying pulse, 2.5 kV/cm, 25 F, 200Ω) in 0.2 cm gap electroporation cuvettes (BioRad, Hercules, Calif.) using a Gene Pulser Xcell System (BioRad, Hercules, Calif.), 800 µL LB recovery medium (Luria-Bertani; Roth, Karlsruhe) was immediately added and the suspension was transferred into 1.5 mL microcentrifuge tube. After 1 h at 37° C., a cell suspension were spread onto LB agar plates (Abcr GmbH & Co. Kg, Karlsruhe), supplemented with 50 mg/L kanamycin, and incubated at 37° C. over night. Clones were collected and correct transformation confirmed via restriction analysis and sequencing. For plasmid preparation the stains were cultivated in 15 mL-tubes for 14 h-16 h with constant shaking at 200 rpm in 3 mL LB medium and 50 mg/L kanamycin at 37° C. (Kuhner Shaker ISF-4-W; Adolf Kühner AG, Basel (Switzerland)). Plasmid DNA purification was done using the NucleoSpin® Plasmid Pure kit (Macherey & Nagel, Düren) following the manufacturer's instructions. Electro-competent *P. putida* KT2440, *P. putida* ΔtrpDC, and *P. putida* ΔtrpDCΔpheA cells were obtained according to Choi et al (Choi et al, J Microbiol Methods, 2005, 64(3), 391). The electroporation was performed using a Biorad Gene Pulser Xcell Electroporator (2.5 kV, 200 ohm, 25 µF) and the cell suspension was plated out on LB-agar plates supplemented with 50 m/L kanamycin.

This resulted in the generation of the strains *P. putida* KT2440/pSEVA234-trpEG$^{S40F}$, *P. putida* ΔtrpDC/pSEVA234-trpEG$^{S40F}$ and *P. putida* ΔtrpDCΔpheA/pSEVA234-trpEG$^{S40F}$ (Table 2).

All resulting *P. putida* strains (*P. putida* KT2440, *P. putida* ΔtrpDC/pSEVA234, *P. putida* ΔtrpDCΔpheA/pSEVA234, *P. putida*/pSEVA234-aroG$^{D146N}$, *P. putida*/pSEVA234-trpEG$^{S40F}$, *P. putida* ΔtrpDC/pSEVA234-aroG$^{D146N}$, *P. putida* ΔtrpDC/pSEVA234-trpEG$^{S40F}$, *P. putida* ΔtrpDCΔpheA/pSEVA234-aroG$^{D146N}$, and *P. putida* ΔtrpDCΔpheA/pSEVA234-trpEG$^{S40F}$ (Table 2) were characterized towards their properties as oAB producers in shake-flask cultures. Strains were grown in minimal medium according to Wierckx et al. (Wierckx et al., AEM, 2005, 71:8221) at 30° C. and shaking at 250 rpm. The composition of the minimal medium was: 2 g/L $(NH_4)_2SO_4$, 1.63 g/L $NaH_2PO_4$, 3.88 g/L $K_2HPO_4$, 0.1 g/L $MgSO_4.7H_2O$, 1.0 mg/L $CaCl_2$, 10 mg/L EDTA, 5.0 mg/L $FeSO_4.7H_2O$, 1.0 mg/L $MnCl.H_2O$, 2.0 mg/L $ZnSO_4.7H_2O$, 0.2 mg/L $CuSO_4.5H_2O$, 0.4 mg/L $CoCl_2.6H_2O$, 0.2 mg/L $Na_2MoO_4.2H_2O$, and 5 g/L glucose. The pH was adjusted to 7 with 5 mol/L sodium hydroxide solution. The strains were pre-cultured in the minimal medium and inoculated into the main cultures of 50 mL in 500 mL-shake flasks with $OD_{600}$ of approximately 0.1. Cultures of plasmid-carrying strains were supplemented with 50 mg/L kanamycin. Cultures of strains with a disruption of the trpDC gene were additionally supplemented with 0.1 mM L-tryptophan and cultures of strains with a disruption of the pheA gene were additionally supplemented with 1 mM L-phenylalanine. The lacy system was induced at the beginning of the midexponential phase by addition of 1 mM IPTG to enable oAB production. The characteristics of the strains as oAB producers were measured as described in example 3. During the cultivation $OD_{600}$, glucose concentration, and the anthranilate concentrations were measured offline from 1.5 mL culture samples. A 1 mL aliquot of each sample was centrifuged for 5 min at 16000×g (5415R; Eppendorf, Hamburg) in reaction tube, after $OD_{600}$ measurement using a photometer. The supernatant was analyzed via HPLC-DAD (1100; Agilent Technologies, Santa Clara (USA)) and YSI (YSI-Select 2700; Kreienbaum Neoscience GmBH, Langenfeld). The collected data of Example 3 and Example 4 are shown in Table 4.

TABLE 1

Vectors and plasmids used and/or generated in the invention

| Designation | Description and relevant genotype | Source/reference |
|---|---|---|
| pEKEx2 | Shuttle vector *C. glutamicum* and *E. coli* for regulated gene expression; $P_{tac}$ lacI$^q$ pBL1oriV$_{C.g.}$ pUC18oriV$_{E.c.}$; Kan$^R$ | Eikmannis et al., 1991 |
| pK19mobsacB | *E. coli/C. glutamicum* shuttle vector for construction of insertion and deletion mutants in *C. glutamicum* (pK18oriV$_{Ec}$ sacB lacZα) Kan$^r$ | Schäfer et al., 1994 |
| pCRB210 | Shuttle vector *C. glutamicum* and *E. coli* for gene overexpression; $P_{gapA}$ pCASE1oriV$_{C.g.}$ oriV$_{E.c.}$; Spec$^r$ | Yukawa et al., 2013 |
| pEMG | *E. coli/P. putida* shuttle vector for construction of insertion and deletion mutants in *P. putida* (with two flanking I-SceI sites, R6KoriV lacZα) Kan$^r$ | Martinez-Garcia et al., 2011 |
| pSEVA234 | Shuttle vector *P. putida* and *E. coli* for regulated gene expression; $P_{trc}$ lacI$^q$ pBBR1oriV; Kan$^R$ | Silva-Rocha et al., 2013 |
| pEKEx2-trpD1 | Kan$^R$, pEKEx2 derivative for IPTG-inducible expression of trpD1 | This study |
| pEKEx2-trpD2 | Kan$^R$, pEKEx2 derivative for IPTG-inducible expression of trpD2 | This study |

TABLE 1-continued

Vectors and plasmids used and/or generated in the invention

| Designation | Description and relevant genotype | Source/reference |
|---|---|---|
| pEKEx2-trpD3 | Kan$^R$, pEKEx2 derivative for IPTG-inducible expression of trpD3 | This study |
| pEKEx2-trpD4 | Kan$^R$, pEKEx2 derivative for IPTG-inducible expression of trpD4 | This study |
| pEKEx2-trpD5 | Kan$^R$, pEKEx2 derivative for IPTG-inducible expression of trpD5 | This study |
| pEKEx2-trpD6 | Kan$^R$, pEKEx2 derivative for IPTG-inducible expression of trpD6 | This study |
| pEKEx2-trpEG | Kan$^R$, pEKEx2 derivative for IPTG-inducible expression of trpEG$^{CgWT}$ | This study |
| pEKEx2-trpEG$^{S38F}$ | Kan$^R$, pEKEx2 derivative for IPTG-inducible expression of trpEG$^{S38F}$ | This study |
| pEKEx2-trpEG$^{S38R}$ | Kan$^R$, pEKEx2 derivative for IPTG-inducible expression of trpEG$^{S38R}$ | This study |
| pEKEx2-trpEG$^{S40F}$ | Kan$^R$, pEKEx2 derivative for IPTG-inducible expression of trpEG$^{S40F}$ | This study |
| pEKEx2-trpEG$^{S40R}$ | Kan$^R$, pEKEx2 derivative for IPTG-inducible expression of trpEG$^{S40R}$ | This study |
| pEKEX2-aroG$^{D146N}$ | Kan$^R$, pEKEx2 derivative for IPTG-inducible expression of aroG$^{D146N}$ | This study |
| pEKEx2-aroG$^{D146N}$-trpEG$^{S40F}$ | Kan$^R$, pEKEx2 derivative for IPTG-inducible expression of aroG$^{D146N}$-trpEG$^{S40F}$ | This study |
| pEKEx2-trpEG$^{S40F}$-aroG$^{D146N}$ | Kan$^R$, pEKEx2 derivative for IPTG-inducible expression of trpEG$^{S40F}$-aroG$^{D146N}$ | This study |
| pEKEx2-csm1 | Kan$^R$, pEKEx2 derivative for IPTG-inducible expression of csm1 | This study |
| pEKEx2-csm2 | Kan$^R$, pEKEx2 derivative for IPTG-inducible expression of csm2 | This study |
| pEKEx2-csm3 | Kan$^R$, pEKEx2 derivative for IPTG-inducible expression of csm3 | This study |
| pEKEx2-csm4 | Kan$^R$, pEKEx2 derivative for IPTG-inducible expression of csm4 | This study |
| pEKEx2-csm5 | Kan$^R$, pEKEx2 derivative for IPTG-inducible expression of csm5 | This study |
| pEKEx2-csm6 | Kan$^R$, pEKEx2 derivative for IPTG-inducible expression of csm6 | This study |
| pEKEx2-aroK | Kan$^R$, pEKEx2 derivative for IPTG-inducible expression of aroK | This study |
| pEKEx2-aroL | Kan$^R$, pEKEx2 derivative for IPTG-inducible expression of aroL | This study |
| pSB068 | Kan$^R$, pEKEx2 derivative for IPTG-inducible expression of galP | This study |
| pSB070 | Kan$^R$, pEKEx2 derivative for IPTG-inducible expression of iolT2 | This study |
| pSB071 | Kan$^R$, pEKEx2 derivative for IPTG-inducible expression of ppgk | This study |
| pSB072 | Kan$^R$, pEKEx2 derivative for IPTG-inducible expression of ppk | This study |
| pSB073 | Kan$^R$, pEKEx2 derivative for IPTG-inducible expression of pps | This study |
| pSB074 | Kan$^R$, pEKEx2 derivative for IPTG-inducible expression of talCG | This study |
| pSB075 | Kan$^R$, pEKEx2 derivative for IPTG-inducible expression of tktCG | This study |
| pSB076 | Kan$^R$, pEKEx2 derivative for IPTG-inducible expression of talEC | This study |
| pSB077 | Kan$^R$, pEKEx2 derivative for IPTG-inducible expression of tktEC | This study |
| pSB078 | Kan$^R$, pEKEx2 derivative for IPTG-inducible expression of zwf1 and opcA | This study |
| pSB083 | Kan$^R$, pEKEx2 derivative for IPTG-inducible expression of ppgk and galP | This study |
| pSB084 | Kan$^R$, pEKEx2 derivative for IPTG-inducible expression of ppgk and iolT2 | This study |
| pSB085 | Kan$^R$, pEKEx2 derivative for IPTG-inducible expression of tktCG and talCG | This study |
| pSB086 | Kan$^R$, pEKEx2 derivative for IPTG-inducible expression of tktEC and talEC | This study |
| pSB096 | Kan$^R$, pEKEx2 derivative for IPTG-inducible expression of qsuA | This study |
| pCRB-glnA | pCRB210 derivative for constitutive expression of gln4 | This study |
| pK19mobsacB-Del-trpD | Kan$^R$, pK19mobsacB with trpD deletion construct | This study |

TABLE 1-continued

Vectors and plasmids used and/or generated in the invention

| Designation | Description and relevant genotype | Source/reference |
| --- | --- | --- |
| pK19mobsacB-inte-trpD1 | $Kan^R$, pK19mobsacB with trpD1 integration construct | This study |
| pK19mobsacB-inte-trpD2 | $Kan^R$, pK19mobsacB with trpD2 integration construct | This study |
| pK19mobsacB-inte-trpD3 | $Kan^R$, pK19mobsacB with trpD3 integration construct | This study |
| pK19mobsacB-inte-trpD4 | $Kan^R$, pK19mobsacB with trpD4 integration construct | This study |
| pK19mobsacB-inte-trpD5 | $Kan^R$, pK19mobsacB with trpD5 integration construct | This study |
| pK19mobsacB-inte-trpD6 | $Kan^R$, pK19mobsacB with trpD6 integration construct | This study |
| pK19mobsacB-Del-csm | $Kan^R$, pK19mobsacB with csm deletion construct | This study |
| pK19mobsacB-inte-csm1 | $Kan^R$, pK19mobsacB with csm1 integration construct | This study |
| pK19mobsacB-inte-csm2 | $Kan^R$, pK19mobsacB with csm2 integration construct | This study |
| pK19mobsacB-inte-csm3 | $Kan^R$, pK19mobsacB with csm3 integration construct | This study |
| pK19mobsacB-inte-csm4 | $Kan^R$, pK19mobsacB with csm4 integration construct | This study |
| pK19mobsacB-inte-csm5 | $Kan^R$, pK19mobsacB with csm5 integration construct | This study |
| pK19mobsacB-inte-csm6 | $Kan^R$, pK19mobsacB with csm6 integration construct | This study |
| pSB060 | $Kan^R$, pK19mobsacB with hpr deletion construct | This study |
| pSB061 | $Kan^R$, pK19mobsacB with pepco deletion construct | This study |
| pSB082 | $Kan^R$, pK19mobsacB with pyk deletion construct | This study |
| pSB064 | $Kan^R$, pK19mobsacB with gpi deletion construct | This study |
| pSB079 | $Kan^R$, pK19mobsacB with ptsG deletion construct | This study |
| pEMG-Del-trpDC | $Kan^R$, pEMG with trpDC deletion construct | This study |
| pEMG-Del-pheA | $Kan^R$, pEMG with pheA deletion construct | This study |
| pSEVA234-aroG$^{D146N}$ | $Kan^R$, pSEVA234 derivative for IPTG-inducible expression of aroG$^{D146N}$ | This study |
| pSEVA234-trpE$^{S40F}$ | $Kan^R$, pSEVA234 derivative for IPTG-inducible expression of trpEG$^{S40F}$ | This study |

TABLE 2

Bacterial strains used and/or generated in the invention

| Designation | Description and relevant genotype | Source/reference |
| --- | --- | --- |
| *Escherichia coli* | Strain DH5α; supE44, DlacU169 (f80 lacZDM15), hsdR17 (rk-mk+), recA1, endA1, thi1, gyrA, relA | Hanahan and Meselson, 1983 |
| *Escherichia coli*::trpD9923 | Strain W3110 with trpD9923 mutation | *E. coli* Genetic Resource Center (Yale University) |
| *Escherichia coli*::trpD9923Δhpr | In frame deletion of hpr in trpD9923 strain | Balderas-Hernandez et al., 2009 |
| *Corynebacterium glutamicum* | Strain ATCC 13032 | DSMZ |
| *Corynebacterium glutamicum*/pEKEx2 | Strain ATCC 13032 with empty expression vector pEKEx2 | This study |
| *Corynebacterium glutamicum* ΔtrpD | In frame deletion of trpD (Cgl3032) | This study |
| *Corynebacterium glutamicum* Δcsm | In frame deletion of csm (Cgl0853) | This study |
| *Corynebacterium glutamicum* ΔtrpDΔcsm | In frame deletion of trpD and csm | This study |
| *Corynebacterium glutamicum* ΔtrpD::trpD1 | Integration of trpD1 into *C. glutamicum* ΔtrpD | This study |

TABLE 2-continued

Bacterial strains used and/or generated in the invention

| Designation | Description and relevant genotype | Source/reference |
|---|---|---|
| Corynebacterium glutamicum ΔtrpD::trpD2 | Integration of trpD2 into C. glutamicum ΔtrpD | This study |
| Corynebacterium glutamicum ΔtrpD::trpD3 | Integration of trpD3 into C. glutamicum ΔtrpD | This study |
| Corynebacterium glutamicum ΔtrpD::trpD5 | Integration of trpD5 into C. glutamicum ΔtrpD | This study |
| Corynebacterium glutamicum ΔtrpD::trpD6 | Integration of trpD6 into C. glutamicum ΔtrpD | This study |
| Corynebacterium glutamicum ΔtrpD::trpD5/pEKEx2 | ΔtrpD::trpD5 strain with empty expression vector pEKEx2 | This study |
| Corynebacterium glutamicum ΔtrpD::trpD5Δcsm | ΔtrpD::trpD5Δcsm strain with empty expression vector pEKEx2 | This study |
| Corynebacterium glutamicum ΔtrpD::trpD5ΔptsG | In frame deletion of ptsG (Cgl1360) in ΔtrpD::trpD5 strain | This study |
| Corynebacterium glutamicum ΔtrpD::trpD5Δhpr | In frame deletion of hpr (Cgl1937) in ΔtrpD::trpD5 strain | This study |
| Corynebacterium glutamicum ΔtrpD::trpD5Δpepco | In frame deletion of pepco (Cgl1585) in ΔtrpD::trpD5 strain | This study |
| Corynebacterium glutamicum ΔtrpD::trpD5Δgpi | In frame deletion of gpi (Cgl0851) in ΔtrpD::trpD5 strain | This study |
| Corynebacterium glutamicum ΔtrpD::trpD5Δpyk | In frame deletion of pyk (Cgl2089) in ΔtrpD::trpD5 strain | This study |
| Corynebacterium glutamicum ΔtrpD/pEKEx2-trpD1 | Expression of trpD1 in ΔtrpD strain | This study |
| Corynebacterium glutamicum ΔtrpD/pEKEx2-trpD2 | Expression of trpD2 in ΔtrpD strain | This study |
| Corynebacterium glutamicum ΔtrpD/pEKEx2-trpD3 | Expression of trpD3 in ΔtrpD strain | This study |
| Corynebacterium glutamicum ΔtrpD/pEKEx2-trpD4 | Expression of trpD4 in ΔtrpD strain | This study |
| Corynebacterium glutamicum ΔtrpD/pEKEx2-trpD5 | Expression of trpD5 in ΔtrpD strain | This study |
| Corynebacterium glutamicum ΔtrpD/pEKEx2-trpD6 | Expression of trpD6 in ΔtrpD strain | This study |
| Corynebacterium glutamicum Δcsm/pEKEx2-csm1 | Expression of csm1 in Δcsm strain | This study |
| Corynebacterium glutamicum Δcsm/pEKEx2-csm2 | Expression of csm2 in Δcsm strain | This study |
| Corynebacterium glutamicum Δcsm/pEKEx2-csm3 | Expression of csm3 in Δcsm strain | This study |
| Corynebacterium glutamicum Δcsm/pEKEx2-csm4 | Expression of csm4 in Δcsm strain | This study |
| Corynebacterium glutamicum Δcsm/pEKEx2-csm5 | Expression of csm5 in Δcsm strain | This study |
| Corynebacterium glutamicum Δcsm/pEKEx2-csm6 | Expression of csm6 in Δcsm strain | This study |
| Corynebacterium glutamicum/ pEKEx2-trpEG | Expression of trpEG (Cgl3029/31) in ATCC 13032 strain | This study |
| Corynebacterium glutamicum/ pEKEx2-trpEG$^{S38F}$ | Expression of trpEG$^{S38F}$ in ATCC 13032 strain | This study |
| Corynebacterium glutamicum/ pEKEx2-trpEG$^{S38R}$ | Expression of trpEG$^{S38R}$ in ATCC 13032 strain | This study |
| Corynebacterium glutamicum/ pEKEx2-trpEG$^{S40F}$ | Expression of trpEG$^{S40F}$ in ATCC 13032 strain | This study |
| Corynebacterium glutamicum/ pEKEx2-trpEG$^{S40R}$ | Expression of trpEG$^{S40R}$ in ATCC 13032 strain | This study |
| Corynebacterium glutamicum ΔtrpD::trpD5/pEKEx2-trpEG$^{S40F}$ | Expression of trpEG$^{S40F}$ in ΔtrpD::trpD5 strain | This study |
| Corynebacterium glutamicum ΔtrpD::trpD5/pEKEx2-aroG$^{D146N}$ | Expression of aroG$^{D146N}$ (CP000948) in ΔtrpD::trpD5 strain | This study |
| Corynebacterium glutamicum ΔtrpD::trpD5/pEKEx2-aroG$^{D146N}$-trpEG$^{S40F}$ | Expression of aroG$^{D146N}$ and trpEG$^{S40F}$ in ΔtrpD::trpD5 strain | This study |
| Corynebacterium glutamicum ΔtrpD::trpD5/pEKEx2-trpEG$^{S40F}$-aroG$^{D146N}$ | Expression of trpEG$^{S40F}$ and aroG$^{D146N}$ in ΔtrpD::trpD5 strain | This study |

TABLE 2-continued

Bacterial strains used and/or generated in the invention

| Designation | Description and relevant genotype | Source/reference |
|---|---|---|
| *C. glutamicum* ΔtrpD::trpD5Δcsm pEKEx2-aroG$^{D146N}$-trpEG$^{S40F}$ | Expression of aroGD$^{D146N}$ and trpEG$^{S40F}$ in ΔtrpD::trpD5Δcsm strain | This study |
| *Corynebacterium glutamicum* ΔtrpD::trpD5/pEKEx2-aroK | Expression of aroK (Cgl1622) in ΔtrpD::trpD5 strain | This study |
| *Corynebacterium glutamicum* ΔtrpD::trpD5/pEKEx2-aroL | Expression of aroL (CP000948) in ΔtrpD::trpD5 strain | This study |
| *Corynebacterium glutamicum* ΔtrpD::trpD5/pCRB210 | Strain ΔtrpD::trpD5 with empty expression vector pCRB210 | This study |
| *Corynebacterium glutamicum* ΔtrpD::trpD5/pCRB-glnA | Expression of glnA (Cgl2214) in ΔtrpD::trpD5 strain | This study |
| *Corynebacterium glutamicum* ΔtrpD::trpD5ΔptsG/pSB084 | Expression of ppgk (Cgl1910) and iolT2 in ΔtrpD::trpD5ΔptsG strain | This study |
| *Corynebacterium glutamicum* ΔtrpD::trpD5ΔptsG/pSB083 | Expression of ppgk and galP (Cgl2409) in ΔtrpD::trpD5ΔptsG strain | This study |
| *Corynebacterium glutamicum* ΔtrpD::trpD5Δhpr/pSB084 | Expression of ppgk and iolT2 (Cgl3058) in ΔtrpD::trpD5Δhpr strain | This study |
| *Corynebacterium glutamicum* ΔtrpD::trpD5Δhpr/pSB083 | Expression of ppgk and galP in ΔtrpD::trpD5Δhpr strain | This study |
| *Corynebacterium glutamicum* ΔtrpD::trpD5/pSB072 | Expression of ppk (Cgl2862) in ΔtrpD::trpD5 strain | This study |
| *Corynebacterium glutamicum* ΔtrpD::trpD5/pSB073 | Expression of pps (Cgl0552/1) in ΔtrpD::trpD5 strain | This study |
| *Corynebacterium glutamicum* ΔtrpD::trpD5/pSB074 | Expression of talCG (Cgl1575) in ΔtrpD::trpD5 strain | This study |
| *Corynebacterium glutamicum* ΔtrpD::trpD5/pSB075 | Expression of tktCG (Cgl1574) in ΔtrpD::trpD5 strain | This study |
| *Corynebacterium glutamicum* ΔtrpD::trpD5/pSB076 | Expression of talEC (ECDH10B_2629) in ΔtrpD::trpD5 strain | This study |
| *Corynebacterium glutamicum* ΔtrpD::trpD5/pSB077 | Expression of tktEC (ECDH10B_3110) in ΔtrpD::trpD5 strain | This study |
| *Corynebacterium glutamicum* ΔtrpD::trpD5/pSB078 | Expression of zwf1 (Cgl1576) and opcA (Cgl1577) in ΔtrpD::trpD5 strain | This study |
| *Corynebacterium glutamicum* ΔtrpD::trpD5/pSB085 | Expression of tktCG and talCG in ΔtrpD::trpD5 strain | This study |
| *Corynebacterium glutamicum* ΔtrpD::trpD5/pSB086 | Expression of tktEC and talEC in ΔtrpD::trpD5 strain | This study |
| *Corynebacterium glutamicum* ΔtrpD::trpD5/pSB096 | Expression of qsuA (CgR0492) in ΔtrpD::trpD5 strain | This study |
| *Pseudomonas putida* | Strain KT2440 mt-2 derivative cured of TOL plasmid pWW0 | Bagdasarian et al., 1981 |
| *Pseudomonas putida* ΔtrpDC/pSEVA234 | In frame deletion of trpDC (PP_0422) with empty expression vector pSEVA234 | This study |
| *Pseudomonas putida* ΔtrpDCΔpheA/pSEVA234 | In frame deletion of pheA (PP_1769) with empty expression vector pSEVA234 | This study |
| *Pseudomonas putida*/pSEVA234-aroG$^{D46N}$ | Expression of aroG$^{D46N}$ in KT2440 strain | This study |
| *Pseudomonas putida*/pSEVA234-trpEG$^{S40F}$ | Expression of trpEG$^{S40F}$ in KT2440 strain | This study |
| *Pseudomonas putida* ΔtrpDC/pSEVA234-aroG$^{D46N}$ | Expression of aroG$^{D46N}$ in ΔtrpDC strain | This study |
| *Pseudomonas putida* ΔtrpDC/pSEVA234-trpEG$^{S40F}$ | Expression of trpEG$^{S40F}$ in ΔtrpDC strain | This study |
| *Pseudomonas putida* ΔtrpDCΔpheA/pSEVA234-aroG$^{D46N}$ | Expression of aroG$^{D146N}$ in ΔtrpDCΔpheA strain | This study |
| *Pseudomonas putida* ΔtrpDCΔpheA/pSEVA234-trpEG$^{S40F}$ | Expression of trpEG$^{S40F}$ in ΔtrpDCΔpheA strain | This study |

TABLE 3

Primers used in the invention

| Designation | Sequence (5'->3') | SEQ ID NO. |
|---|---|---|
| Del-trpD-1 | TAT GCC GTG TTG AAT GCC ATT | 66 |
| Del-trpD-2 | CCC GGG ATC CAC TAA ACT TAA CAC AGT GTT GCT GGA GAA GTC AT | 67 |
| Del-trpD-3 | TGT TTA AGT TTA GTG GAT CCC GGG GAA AAG GAG TCT TCC AAT GAC TAG | 68 |
| Del-trpD-4 | CCA GAT CGACGT TTT CCT GGC | 69 |
| Ko-trpD-1 | AAT CCT TTT TTT ACC TGC AGG GCT TAG TTC GCG AGA AGC TGT TCG | 77 |
| Ko-trpD-2 | AAG GAG TCT TCC AAT GAC TAG | 78 |
| Del-csm-1 | GTC TCC CCA ATC AAA TCA TCA | 79 |
| Del-csm-2 | CCC GGG ATC CAC TAA ACT TAA ACA GTC ACC TGC ATT AGT CAT | 80 |
| Del-csm-3 | TGT TTA AGT TTA GTG GAT CCC GGG CGC GGA AAA CTC GGA TAA | 81 |
| Del-csm-4 | TGA TGA TGT GCC CGT CCA CA | 82 |
| Ko-csm-1 | CTT GCC GAC GAG CGT AGA AAT | 107 |
| Ko-csm-2 | GTT GAG GAC TAC CTT GAC TTG | 108 |
| Ex-csm1 | GCC CTG CAG GAC GTG GCA GAA TAG TGT GCA TGA CTA ATG CAG GTG AC | 83 |
| Ex-csm2 | GCC CTG CAG GAC GTG GCA GAA TAG TGT GCG TGA CTA ATG CAG GTG AC | 84 |
| Ex-csm3 | GCC CTG CAG GAC GTG GCA GAA TAG TGT GCT TGA CTA ATG CAG GTG AC | 85 |
| Ex-csm4 | GCC CTG CAG GAC GTG GCA GAA TAG ATG ACT AAT GCA GGT GAC | 86 |
| Ex-csm5 | GCC CTG CAG GAC GTG GCA GAA TAG GTG ACT AAT GCA GGT GAC | 87 |
| Ex-csm6 | GCC CTG CAG GAC GTG GCA GAA TAG TTG ACT AAT GCA GGT GAC | 88 |
| Ex-csm-rev | CCC GGG ATC CTT ATC CGA GTT TTC CGC GTC C | 89 |
| Ex-trpD1 | GCC CTG CAG GTA AAA AAA GGA TTT GAT TCA TGA CTT CTC CAG CAA CAC TG | 70 |
| Ex-trpD2 | GCC CTG CAG GTA AAA AAA GGA TTT GAT TCG TGA CTT CTC CAG CAA CAC TG | 71 |
| Ex-trpD3 | GCC CTG CAG GTA AAA AAA GGA TTT GAT TCT TGA CTT CTC CAG CAA CAC TG | 72 |
| Ex-trpD4 | GCC CTG CAG GTA AAA AAA GGA TTA TGA CTT CTC CAG CAA CAC TG | 73 |
| Ex-trpD5 | GCC CTG CAG GTA AAA AAA GGA TTG TGA CTT CTC CAG CAA CAC TG | 74 |
| Ex-trpD6 | GCC CTG CAG GTA AAA AAA GGA TTT TGA CTT CTC CAG CAA CAC TG | 75 |
| Ex-trpD-rev | CCC GGG ATC CTT AGT CAT TGG AAG ACT CCT T | 76 |
| Ex-aroG-1 | GC CCT GCA GGA GAT CTG AAA GGA GGC CCT TCA GAT GAA TTA TCA GAA CGA CGA T | 109 |
| Ex-aroG-2 | CCC GGG ATC CTT ACC CGC GAC GCG CTT TTA C | 110 |

TABLE 3-continued

Primers used in the invention

| Designation | Sequence (5'->3') | SEQ ID NO. |
|---|---|---|
| Ex-glnA-1 | TTA GAG GAG ACA CCA TAT GGC GTT TGA AAC CCC GGA AGA | 97 |
| Ex-glnA-2 | GAA CCA TGG GCT AGC CTC GAG TTA GCA GTC GAA GTA CAA TTC | 98 |
| Ex-aroL-1 | GGC CCT GCA GGG AAA GGA GGC CCT TCA GAT GAC ACA ACC TCT TTT TCT GA | 99 |
| Ex-aroL-2 | CCC GGG ATC CTC AAC AAT TGA TCG TCT GTG C | 100 |
| Ex-aroK-1 | GGC CCT GCA GGG AAA GGA GGC CCT TCA GAT GAA TGA TCA AAT CA CTT AG | 101 |
| Ex-aroK-2 | CCC GGG ATC CTT AAT CGA TTT CTA GAT GAT GC | 102 |
| JK038f | ATT CGA GCT CGG TAC CCG GGG ATC CAC TAC ATC GAA ACC GGC ATC | 103 |
| JK039r | CTG AAC TCG AGT CAG CCA TGC TCC TTC TC | 104 |
| JK040f | GCA TGG CTG ACT CGA GTT CAG GGG CCT TGG GGC T | 105 |
| JK041r | TAG AAG CTT GCA TGC CTG CAG GCA GTG AGT CGA CCA GGC CAA AG | 106 |

TABLE 4

Characteristics towards oAB production of bacterial strains used and/or generated in the invention (CDW: cell dry weight; Y: yield; $\mu_{max}$: maximal growth rate; STY: space time yield).

| Strain | oAB Titer$_{final}$ (g/L) | CDW$_{final}$ (g/L) | Y$_{oAB/Glc}$ (g/g) | Y$_{oAB/CDW}$ (g/g) | $\mu_{max}$ (h$^{-1}$) | oAB STY (g/(L*h)) | Process time (h) |
|---|---|---|---|---|---|---|---|
| E. coli::trpD9923 | 0.06 | n.a. | 0.01 | n.a. | n.a. | 0.002 | 26 |
| E. coli::trpD9923Δhpr | 0.07 | n.a. | 0.01 | n.a. | n.a. | 0.003 | 25 |
| C. glutamicum | 0.00 | 14.5 | 0.00 | 0.00 | 0.16 | 0.00 | 26 |
| C. glutamicum ΔtrpD | 1.07 | 8.78 | 0.02 | 0.12 | 0.19 | 0.02 | 47 |
| C. glutamicum Δcsm | 0.00 | 2.26 | 0.00 | 0.00 | 0.02 | 0.00 | 72 |
| C. glutamicum ΔtrpDΔcsm | 0.00 | 2.41 | 0.00 | 0.00 | 0.03 | 0.00 | 72 |
| C. glutamicum ΔtrpD::trpD1 | 0.00 | 7.3 | 0.00 | 0.00 | 0.27 | 0.00 | 24 |
| C. glutamicum ΔtrpD::trpD2 | 0.00 | 7.0 | 0.00 | 0.00 | 0.28 | 0.00 | 24 |
| C. glutamicum ΔtrpD::trpD3 | 0.00 | 7.4 | 0.00 | 0.00 | 0.25 | 0.00 | 24 |
| C. glutamicum ΔtrpD::trpD5 | 4.50 | 18.9 | 0.08 | 0.24 | 0.12 | 0.10 | 45 |
| C. glutamicum ΔtrpD::trpD6 | 0.36 | 7.20 | 0.01 | 0.05 | 0.09 | 0.005 | 76 |
| C. glutamicum ΔtrpD::trpD5/pEKEx2 | 3.51 | 15.1 | 0.06 | 0.23 | 0.12 | 0.05 | 68 |
| C. glutamicum ΔtrpD::trpD5Δcsm | 0.26 | 7.3 | 0.01 | 0.04 | 0.21 | 0.04 | 44 |
| C. glutamicum ΔtrpD::trpD5ΔptsG | No growth under standard fermentation conditions | | | | | | |
| C. glutamicum ΔtrpD::trpD5Δhpr | No growth under standard fermentation conditions | | | | | | |
| C. glutamicum ΔtrpD::trpD5Δpepco | 8.6 | 14.2 | 0.11 | 0.61 | 0.06 | 0.18 | 48 |
| C. glutamicum ΔtrpD::trpD5Δgpi | 4.42 | 14.3 | 0.06 | 0.31 | 0.02 | 0.04 | 125 |
| C. glutamicum ΔtrpD::trpD5Δpyk | 5.34 | 19.4 | 0.07 | 0.30 | 0.05 | 0.10 | 55 |
| C. glutamicum ΔtrpD/pEKEx2-trpD1 | 0.00 | 8.3 | 0.00 | 0.00 | 0.19 | 0.00 | 51 |
| C. glutamicum ΔtrpD/pEKEx2-trpD2 | 0.00 | 7.9 | 0.00 | 0.00 | 0.21 | 0.00 | 51 |

TABLE 4-continued

Characteristics towards oAB production of bacterial strains used
and/or generated in the invention (CDW: cell dry weight; Y: yield;
$\mu_{max}$: maximal growth rate; STY: space time yield).

| Strain | oAB Titer$_{final}$ (g/L) | CDW$_{final}$ (g/L) | Y$_{oAB/Glc}$ (g/g) | Y$_{oAB/CDW}$ (g/g) | $\mu_{max}$ (h$^{-1}$) | oAB STY (g/(L*h)) | Process time (h) |
|---|---|---|---|---|---|---|---|
| C. glutamicum ΔtrpD/pEKEx2-trpD3 | 0.00 | 8.4 | 0.00 | 0.00 | 0.15 | 0.00 | 51 |
| C. glutamicum ΔtrpD/pEKEx2-trpD4 | 0.00 | 8.5 | 0.00 | 0.00 | 0.13 | 0.00 | 51 |
| C. glutamicum ΔtrpD/pEKEx2-trpD5 | 1.04 | 8.35 | 0.01 | 0.12 | 0.18 | 0.01 | 76 |
| C. glutamicum ΔtrpD/pEKEx2-trpD6 | 1.02 | 8.90 | 0.02 | 0.11 | 0.15 | 0.02 | 54 |
| C. glutamicum Δcsm/pEKEx2-csm1 | 0.00 | 5.9 | 0.00 | 0.00 | 0.21 | 0.00 | 48 |
| C. glutamicum Δcsm/pEKEx2-csm2 | 0.00 | 6.5 | 0.00 | 0.00 | 0.22 | 0.00 | 48 |
| C. glutamicum Δcsm/pEKEx2-csm3 | 0.00 | 6.3 | 0.00 | 0.00 | 0.16 | 0.00 | 48 |
| C. glutamicum Δcsm/pEKEx2-csm4 | 0.00 | 7.1 | 0.00 | 0.00 | 0.20 | 0.00 | 48 |
| C. glutamicum Δcsm/pEKEx2-csm5 | 0.00 | 6.6 | 0.00 | 0.00 | 0.15 | 0.00 | 48 |
| C. glutamicum Δcsm/pEKEx2-csm6 | 0.00 | 6.5 | 0.00 | 0.00 | 0.12 | 0.00 | 48 |
| C. glutamicum/ pEKEx2-trpEG | 0.00 | 7.7 | 0.00 | 0.00 | 0.25 | 0.00 | 26 |
| C. glutamicum/ pEKEx2-trpEG$^{S38F}$ | 0.03 | 8.1 | 0.002 | 0.003 | 0.26 | 0.008 | 26 |
| C. glutamicum/ pEKEx2-trpEG$^{S38R}$ | 0.01 | 8.5 | 0.001 | 0.002 | 0.26 | 0.004 | 26 |
| C. glutamicum/ pEKEx2-trpEG$^{S40F}$ | 0.01 | 7.9 | 0.0001 | 0.002 | 0.24 | 0.004 | 26 |
| C. glutamicum/ pEKEx2-trpEG$^{S40R}$ | 0.01 | 8.2 | 0.001 | 0.002 | 0.25 | 0.004 | 26 |
| C. glutamicum ΔtrpD::trpD5/pEKEx2-trpEG$^{S40F}$ | 1.44 | 6.7 | 0.08 | 0.22 | 0.09 | 0.21 | 50 |
| C. glutamicum ΔtrpD::trpD5/pEKEx2-aroG$^{D146N}$ | 1.36 | 7.1 | 0.08 | 0.19 | 0.09 | 0.19 | 50 |
| C. glutamicum ΔtrpD::trpD5/pEKEx2-aroG$^{D146N}$-trpEG$^{S40F}$ | 1.71 | 6.3 | 0.10 | 0.27 | 0.08 | 0.25 | 50 |
| C. glutamicum ΔtrpD::trpD5Δcsm pEKEx2-aroG$^{D146N}$-trpEG$^{S40F}$ | 1.56 | 6.8 | 0.09 | 0.23 | 0.15 | 0.26 | 44 |
| C. glutamicum ΔtrpD::trpD5/pEKEx2-trpEG$^{S40F}$-aroG$^{D146N}$ | 1.58 | 6.7 | 0.09 | 0.24 | 0.08 | 0.23 | 50 |
| C. glutamicum ΔtrpD::trpD5/pEKEx2-aroK | 1.03 | 7.5 | 0.06 | 0.18 | 0.08 | 0.19 | 52 |
| C. glutamicum ΔtrpD::trpD5/pEKEx2-aroL | 1.36 | 6.7 | 0.07 | 0.15 | 0.18 | 0.14 | 52 |
| C. glutamicum ΔtrpD::trpD5/pCRB210 | 0.80 | 6.7 | 0.04 | 0.12 | 0.12 | 0.07 | 78 |
| C. glutamicum ΔtrpD::trpD5/pCRB-glnA | 0.82 | 6.2 | 0.05 | 0.13 | 0.06 | 0.08 | 78 |
| C. glutamicum ΔtrpD::trpD5ΔptsG/pSB084 | 0.10 | 10.2 | 0.03 | 0.01 | 0.01 | 0.0004 | 240 |
| C. glutamicum ΔtrpD::trpD5ΔptsG/pSB083 | 1.10 | 8.20 | 0.06 | 0.13 | 0.01 | 0.006 | 192 |
| C. glutamicum ΔtrpD::trpD5Δhpr/pSB084 | 0.12 | 9.60 | 0.06 | 0.01 | 0.01 | 0.001187 | 71 |
| C. glutamicum ΔtrpD::trpD5Δhpr/pSB083 | No growth under standard cultivation conditions | | | | | | |
| C. glutamicum ΔtrpD::trpD5/pSB072 | 3.48 | 15.8 | 0.05 | 0.22 | 0.04 | 0.05 | 75 |
| C. glutamicum ΔtrpD::trpD5/pSB073 | 4.13 | 16.4 | 0.06 | 0.25 | 0.02 | 0.05 | 77 |
| C. glutamicum ΔtrpD::trpD5/pSB074 | 4.99 | 16.2 | 0.07 | 0.31 | 0.07 | 0.10 | 50 |
| C. glutamicum ΔtrpD::trpD5/pSB075 | 4.77 | 14.6 | 0.08 | 0.33 | 0.04 | 0.07 | 47 |

TABLE 4-continued

Characteristics towards oAB production of bacterial strains used and/or generated in the invention (CDW: cell dry weight; Y: yield; $\mu_{max}$: maximal growth rate; STY: space time yield).

| Strain | oAB Titer$_{final}$ (g/L) | CDW$_{final}$ (g/L) | Y$_{oAB/Glc}$ (g/g) | Y$_{oAB/CDW}$ (g/g) | $\mu_{max}$ (h$^{-1}$) | oAB STY (g/(L*h)) | Process time (h) |
|---|---|---|---|---|---|---|---|
| C. glutamicum ΔtrpD::trpD5/pSB076 | 5.56 | 14.2 | 0.09 | 0.39 | 0.03 | 0.11 | 50 |
| C. glutamicum ΔtrpD::trpD5/pSB077 | 4.85 | 16.8 | 0.07 | 0.29 | 0.04 | 0.09 | 53 |
| C. glutamicum ΔtrpD::trpD5/pSB078 | 3.21 | 5.50 | 0.06 | 0.58 | 0.07 | 0.05 | 66 |
| C. glutamicum ΔtrpD::trpD5/pSB085 | 4.18 | 15.2 | 0.06 | 0.30 | 0.03 | 0.05 | 72 |
| C. glutamicum ΔtrpD::trpD5/pSB086 | 0.97 | 12.2 | 0.06 | 0.40 | 0.05 | 0.01 | 68 |
| C. glutamicum ΔtrpD::trpD5/pSB096 | 3.23 | 7.20 | 0.05 | 0.45 | 0.03 | 0.05 | 66 |
| Pseudomonas putida | 0.00 | n.a. | 0.00 | n.a. | 0.50 | 0.00 | 24 |
| P. putida ΔtrpDC/pSEVA234 | 0.14 | n.a. | 0.01 | 0.11 | n.a. | n.a. | 32 |
| P. putida ΔtrpDCΔpheA/pSEVA234 | 0.04 | n.a. | 0.005 | 0.09 | 0.19 | 0.006 | 49 |
| P. putida/ pSEVA234- aroG$^{fbr}$ | n.a. | n.a. | n.a. | n.a. | n.a. | n.a. | n.a. |
| P. putida/ pSEVA234- trpEG$^{S40F}$ | 0.00 | n.a. | 0.00 | n.a. | 0.44 | 0.00 | 32 |
| P. putida ΔtrpDC/ pSEVA234-aroG$^{fbr}$ | 0.12 | n.a. | 0.01 | 0.09 | n.a. | 0.004 | 32 |
| P. putida ΔtrpDC/ pSEVA234-trpEG$^{S40F}$ | 0.25 | n.a. | 0.02 | 0.11 | 0.40 | 0.005 | 47 |
| P. putida ΔtrpDCΔpheA/ pSEVA234-aroG$^{fbr}$ | 0.09 | n.a. | 0.01 | 0.05 | n.a. | 0.002 | 38 |
| P. putida ΔtrpDCΔpheA/ pSEVA234-trpEG$^{S40f}$ | 0.12 | n.a. | 0.01 | 0.22 | 0.28 | 0.002 | 47 |

Figure 30:
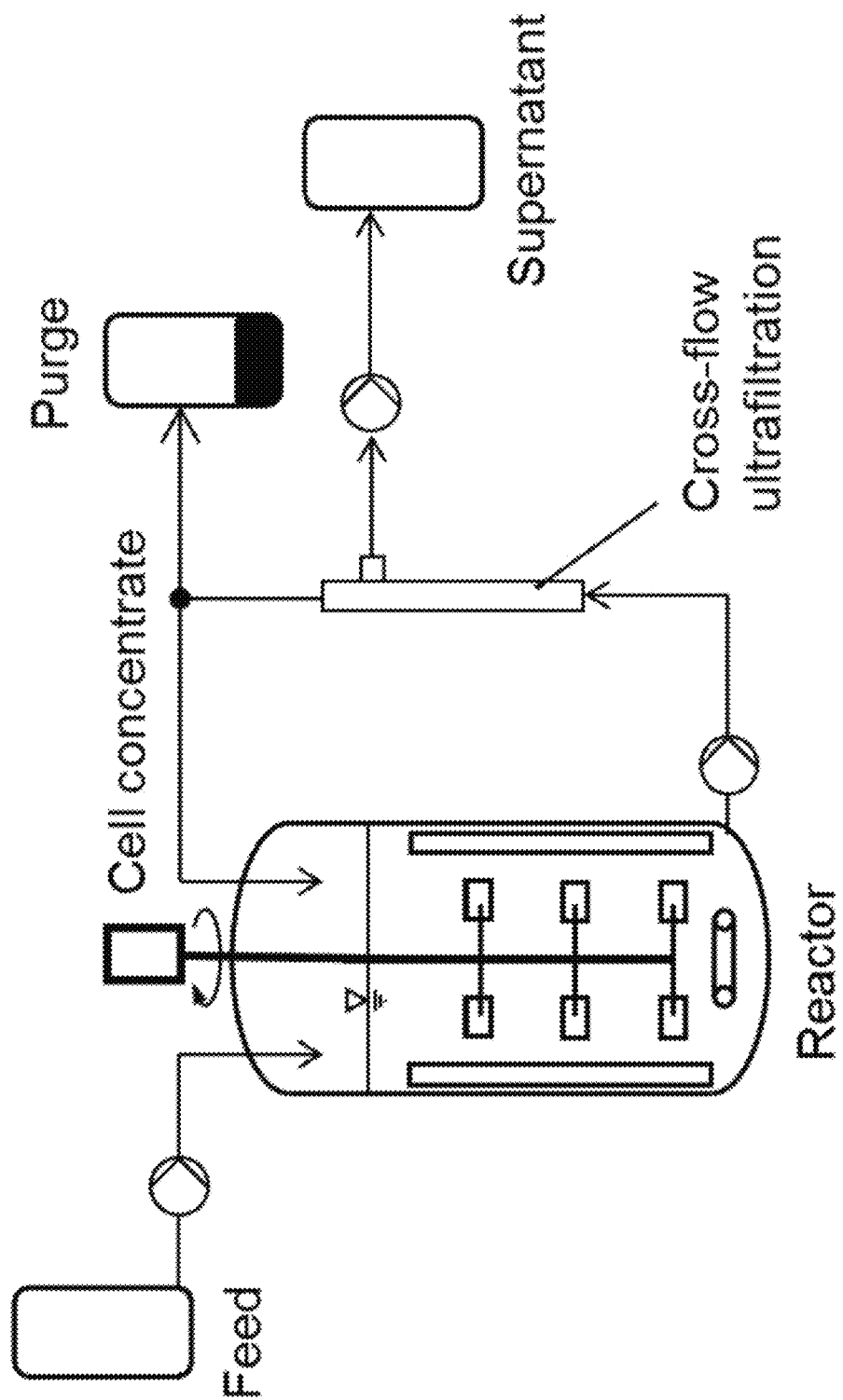
FIG. 30 shows the integration of a cross-flow ultrafiltration module (cut of value of 750 kDa) for continuous fermentations with cell retention in a 1 L lab scale bioreactor.
Figure 31:
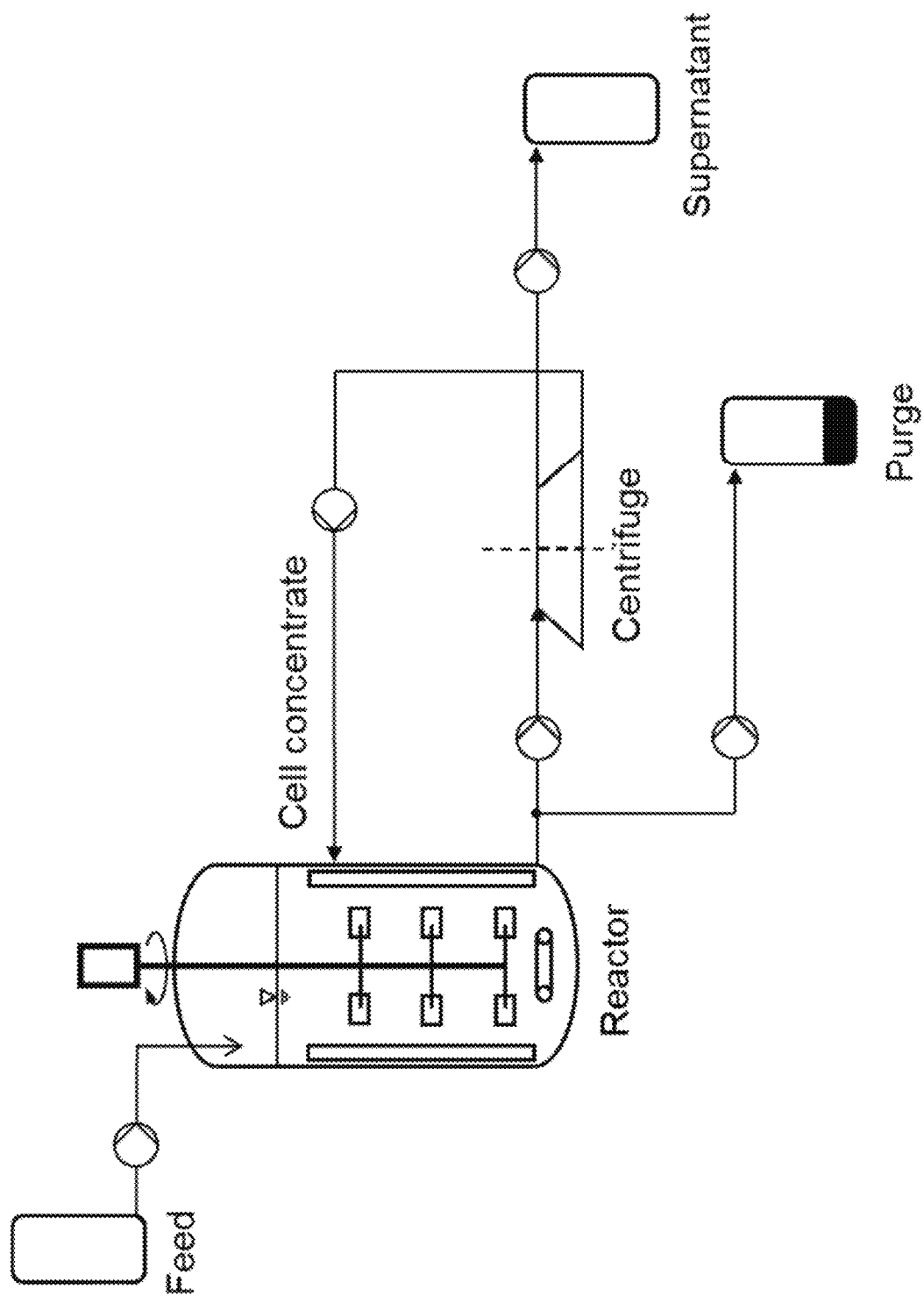
FIG. 31 shows the integration of a centrifuge (Centritech Lab III) for continuous fermentations with cell retention in a 1 L lab scale bioreactor.

Example 5—Cultivation of C. glutamicum Strains in Continuous Fermenters with Cell Retention Continuous fermentations were used for the production of anthranilate to achieve an optimized space-time yield. A cell retention system was applied during continuous fermentation to increase the biomass concentration without increasing the glucose concentration of the feed solution. Two different systems were used for cell retention experiments in lab scale: a hollow fibre filtration module from JM Water Separations (WaterSep Technology Corporation, Marlborough, Mass., USA) with a cut of value of 750 kDa and a disposable centrifuge (Centritech Lab III) from Pneumatic Scale Angelus (Allen Road, Stow, Ohio, USA). Both systems are connected to 1 L lab-scale bioreactors (OmniFenn, HiTec Zang, Herzogenrath, Germany). The integration of the filtration module is shown in FIG. 30 and the integration of the centrifuge is shown in FIG. 31.

Continuous Fermentation of Strain C. glutamicum ΔtrpD

Figure 32:
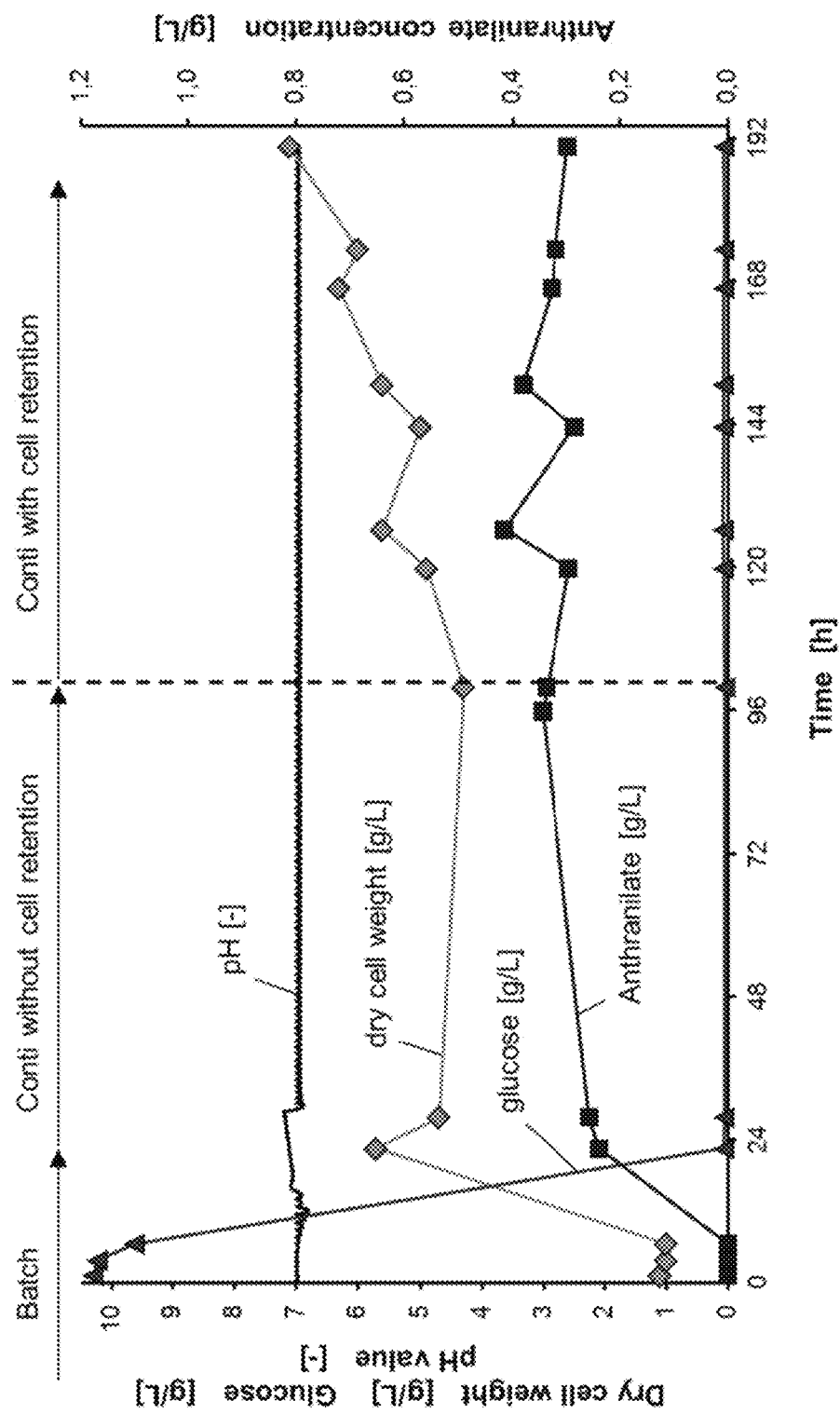
FIG. 32 shows the fermentation of *C. glutamicum* ΔtrpD for the production of oAB during batch- and continuous mode using a culture volume of 1 L, a dilution rate 0.05 L/h, cultivation temperature 30° C. at pH 7 controlled with 1 M $NH_4OH$, air flow rate of 0.2 L/min for aeration, $pO_2$ controlled at 30% air saturation by adjusting the stirrer speed between 200 and 1200 rpm. Cell retention achieved by cross-flow ultrafiltration.

A preculture of C. glutamicum ΔtrpD (see Table 2) was prepared using a sterile 250 mL Erlenmeyer flask filled with 50 mL sterile BHIS medium containing 37 g/L Brain-Heart-Infusion (BHI) and 91 g/L sorbitol. Incubation for 24 h at 28° C. with a shaking frequency of 140 rpm resulted in an OD$_{600}$ of 6.0. A culture volume of 9 mL was transferred into 91 mL fresh CGXII-MOPS derived medium containing 42 g/L MOPS buffer, 20 g/L (NH$_4$)$_2$SO$_4$, 5 g/L urea, 3.7 g/L Brain-Heart-Infusion, 9.1 g/L sorbitol, 1 g/L KH$_2$PO$_4$, 1 g/L K2HPO$_4$, 0.25 g/L MgSO$_4$.7H$_2$O, 0.01 g/L CaCl$_2$ and 10 g/L glucose (autoclaved separately). The following components were added after sterile filtration: 2 mg/L biotin, 0.1 mM L-tryptophan, 0.01 g/L MnSO$_4$.H$_2$O, 0.01 g/L FeSO$_4$.7H$_2$O, 1 mg/L ZnSO$_4$.7H$_2$O, 0.2 mg/L CuSO$_4$5.H$_2$O, 0.02 mg/L NiCl$_2$.6H$_2$O and 0.03 g/L 3.4-dihydroxybenzoic acid. Incubation of the 100 mL culture volume in a 500 mL Erlenmeyer flask for 24 h at 28° C. with a shaking frequency of 140 rpm resulted in an OD$_{600}$ of 18.7. A culture volume of 27 mL was centrifuged, the supernatant was discarded and the pellet resuspended in 25 mL sterile isotonic PBS buffer, The suspension was injected into a fermenter with 1 L sterile CGXII derived medium containing 20 g/L (NH$_4$)$_2$SO$_4$, 1 g/L KH$_2$PO$_4$, 1 g/L K$_2$HPO$_4$, 0.25 g/L MgSO$_4$.7H$_2$O, 0.01 g/L CaCl$_2$, 100 μL/L polypropylenglycol and 10 g/L glucose (autoclaved separately). The following components were added after sterile filtration: 2 mg/L biotin, 0.1 mM L-tryptophan, 0.01 g/L MnSO$_4$.H$_2$O, 0.01 g/L FeSO$_4$.7H$_2$O, 1 mg/L ZnSO$_4$.7H$_2$O, 0.2 mg/L CuSO$_4$.5H$_2$O, 0.02 mg/L NiCl$_2$.6H$_2$O and 0.03 g/L 3.4-dihydroxybenzoic acid. The same medium was used for feeding during continuous operation. The dissolved oxygen concentration was controlled at 30% by adjusting the stirrer speed between 200 and 1200 rpm. A constant gas flow rate of 0.2 l/h air was adjusted for aeration and the pH was controlled at pH 7 with 1 M NH$_4$OH. The fermentation results are shown in FIG. 32. During the batch phase within the first 24 h glucose was consumed and biomass and oAB where produced. The fermenter was switched to continuous operation after a cultivation time of 24 h by feeding 50 mL/h sterile medium and purging 50 mL/h fermentation broth including biomass and oAB. A constant production of oAB was achieved during continuous cultivation. After a cultivation time of 100 h the cell retention was started using a cross-flow ultrafiltration as specified in FIG. 30. An increase of dry cell weight was achieved by cell-retention as shown in FIG. 32.

Continuous Fermentation of Strain C. glutamicum ΔtrpD:: trpD5Δgpi

Figure 33:
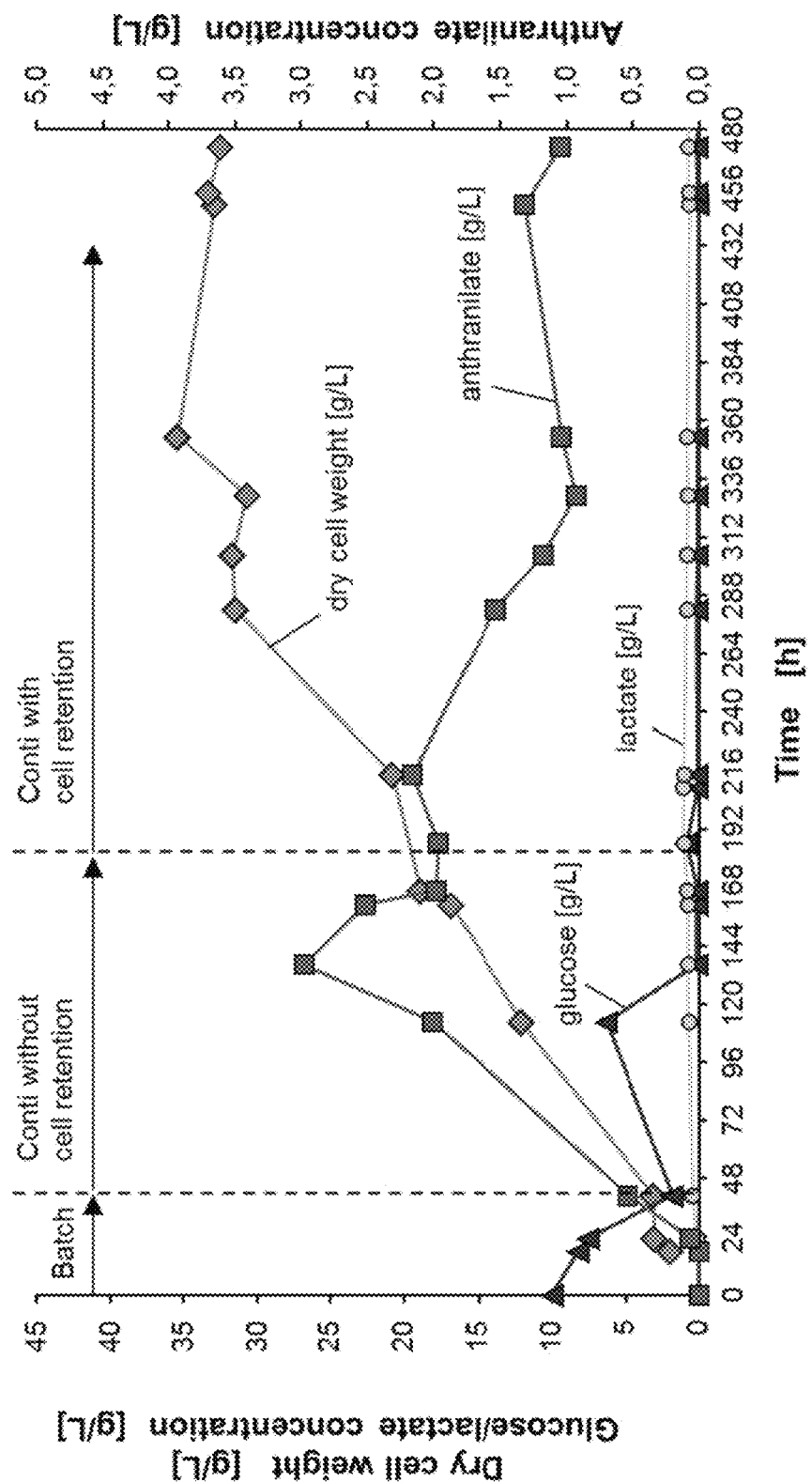
FIG. 33 shows the fermentation of *C. glutamicum* ΔtrpD:: trpD5Δgpi for the production of oAB during batch- and continuous mode using a culture volume of 1 L, a dilution rate 0.01 L/h, cultivation temperature 30° C. at pH 7 controlled with 1 M $NH_4OH$ and 1 M HCl, air flow rate of 0.2 L/min for aeration, $pO_2$ controlled at 30% air saturation by adjusting the stirrer speed between 200 and 1400 rpm. Cell retention achieved by centrifugation.

A preculture of *C. glutamicum* ΔtrpD::trpD5Δgpi (Table 2) was prepared using a sterile 250 mL Erlenmeyer flask filled with 50 mL sterile BHIS medium containing 37 g/L Brain-Heart-Infusion (BHI) and 91 g/L sorbitol. Incubation for 24 h at 28° C. with a shaking frequency of 140 rpm resulted in an Moo of 8.2. A culture volume of 10 mL was transferred into 90 mL CGXII-MOPS derived medium containing 42 g/L MOPS buffer, 20 g/L $(NH_4)_2SO_4$, 5 g/L urea, 3.7 g/L Brain-Heart-Infusion, 9.1 g/L sorbitol, 1 g/L $KH_2PO_4$, 1 g/L $K_2HPO_4$, 0.25 g/L $MgSO_4.7H_2O$, 0.01 g/L $CaCl_2$ and 10 g/L glucose (autoclaved separately). The following components were added after sterile filtration: 2 mg/L biotin, 0.01 g/L $MnSO_4.H_2O$, 0.01 g/L $FeSO_4.7H_2O$, 1 mg/L $ZnSO_4.7H_2O$, 0.2 mg/L $CuSO_4.5H_2O$, 0.02 mg/L $NiCl_2.6H_2O$ and 0.03 g/L 3.4-dihydroxybenzoic acid. Incubation of the 100 mL culture volume in two 250 mL Erlenmeyer flask for 24 h at 30° C. with a shaking frequency of 300 rpm resulted in an $OD_{600}$ of 20.5. A volume of 55 mL culture broth was injected into a fermenter with 1 L CGXII derived medium containing 20 g/L $(NH_4)_2SO_4$, 1 g/L $KH_2PO_4$, 1 g/L $K_2HPO_4$, 0.25 g/L $MgSO_4.7H_2O$, 0.01 g/L $CaCl_2$, 100 µL/L polypropylenglycol and 10 g/L glucose (autoclaved separately). The following components were added after sterile filtration: 2 mg/L biotin, 0.01 g/L $MnSO_4.H_2O$, 0.01 g/L $FeSO_4.7H_2O$, 1 mg/L $ZnSO_4.7H_2O$, 0.2 mg/L $CuSO_4.5H_2O$, 0.02 mg/L $NiCl_2.6H_2O$ and 0.03 g/L 3.4-dihydroxybenzoic acid. A high concentrated medium was used for feeding containing 20 g/L $(NH_4)_2SO_4$, 10 g/L $KH_2PO_4$, 10 g/L $K_2HPO_4$, 2.5 g/L $MgSO_4.7H_2O$, 0.1 g/L $CaCl_2$, 2 mL/L polypropylenglycol and 100 g/L glucose (autoclaved separately). The following components were added after sterile filtration: 20 mg/L biotin, 0.1 g/L $MnSO_4.H_2O$, 0.1 g/L $FeSO_4.7H_2O$, 10 mg/L $ZnSO_4.7H_2O$, 2 mg/L $CuSO_4.5H_2O$, 0.2 mg/L $NiCl_2.6H_2O$ and 0.3 g/L 3.4-dihydroxybenzoic acid. The dissolved oxygen concentration was controlled at 30% by adjusting the stirrer speed between 200 and 1400 rpm. A constant gas flow rate of 0.2 l/h air was adjusted for aeration and the pH was controlled at pH 7 with 1 M $NH_4OH$ and 1 M HCl. The fermentation results are shown in FIG. 33. During the batch phase within the first 40 h glucose was consumed and biomass and oAB where produced. The fermenter was switched to continuous operation after a cultivation time of 40 h by feeding 10 mL/h medium and purging 10 mL/h fermentation broth including biomass and oAB. At the beginning of the continuous operation the biomass concentration was not high enough to completely consume the added glucose in the feed solution resulting in an accumulation of glucose in the reactor as shown in FIG. 33. After 136 h the cell concentration was high enough to completely consume the added glucose. Cell retention was started after 184 h using a centrifuge, as shown in FIG. 31. An increase of dry cell weight was achieved by cell recycling as pictured in FIG. 33. A continuous production of oAB was achieved during 400 h continuous fermentation.

Figure 34:
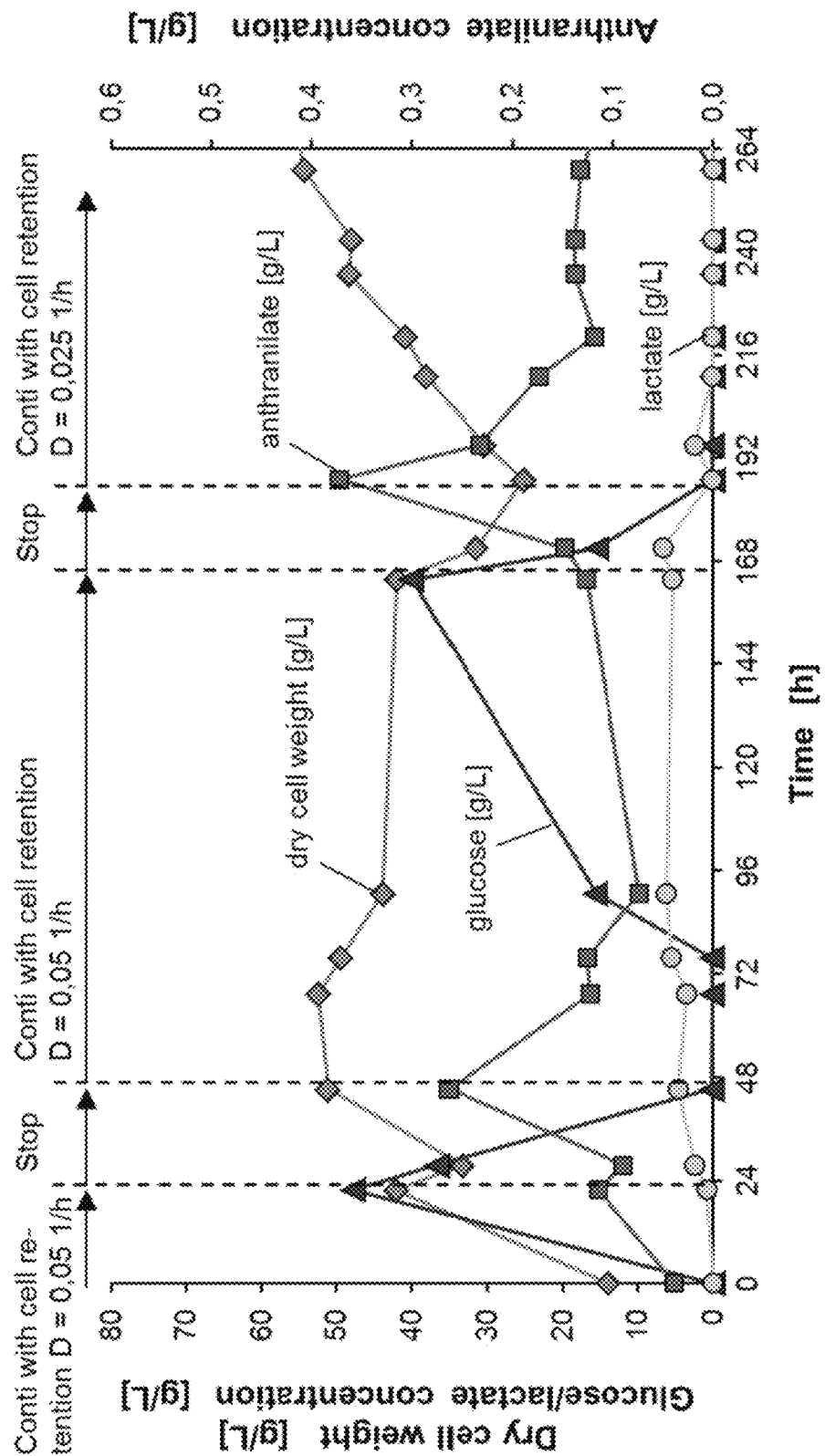
FIG. 34 shows the fermentation of *C. glutamicum* ΔtrpD for the continuous production of oAB using a culture volume of 1 L, a dilution rate of 0.025 L/h or 0.05 L/h as stated in the diagram, cultivation temperature 30° C. pH 7 controlled with 1 M $NH_4OH$, air flow rate of 0.2 L/min for aeration, $pO_2$ controlled at 30% air saturation by adjusting the stirrer speed between 200 and 1200 rpm. Cell retention achieved by cross-flow ultrafiltration.

Continuous Fermentation of Strain *C. glutamicum* ΔtrpD with Complex Carbon Sources A preculture of *C. glutamicum* ΔtrpD (Table 2) was prepared using a sterile 250 mL Erlenmeyer flask filled with 50 mL sterile BHIS medium containing 37 g/L Brain-Heart-Infusion and 91 g/L sorbitol. Incubation for 24 h at 28° C. with a shaking frequency of 140 rpm resulted in an $OD_{600}$ of 7.53. A culture volume of 7 mL was transferred into 93 mL fresh CGXII-MOPS derived medium containing 42 g/L MOPS buffer, 20 g/L $(NH_4)_2SO_4$, 5 g/L urea, 3.7 g/L Brain-Heart-Infusion, 9.1 g/L sorbitol, 1 g/L $KH_2PO_4$, 1 g/L $K_2HPO_4$, 0.25 g/L $MgSO_4.7H_2O$, 0.01 g/L $CaCl_2$ and 10 g/L glucose (autoclaved separately). The following components were added after sterile filtration: 2 mg/L biotin, 0.1 mM L-tryptophan, 0.01 g/L $MnSO_4.H_2O$, 0.01 g/L $FeSO_4.7H_2O$, 1 mg/L $ZnSO_4.7H_2O$, 0.2 mg/L $CuSO_4.5H_2O$, 0.02 mg/L $NiCl_2.6H_2O$ and 0.03 g/L 3.4-dihydroxybenzoic acid. Incubation of the 100 mL culture volume in a 500 mL Erlenmeyer flask for 24 h at 28° C. with a shaking frequency of 140 rpm resulted in an $OD_{600}$ of 21.3. A culture volume of 25 mL was centrifuged, the supernatant was discarded and the pellet resuspended in 25 mL sterile isotonic PBS buffer. The suspension was injected into a fermenter with 1 L sterile CGXII derived medium containing 20 g/L $(NH_4)_2SO_4$, 1 g/L $KH_2PO_4$, 1 g/L $K_2HPO_4$, 0.25 g/L $MgSO_4.7H_2O$, 0.01 g/L $CaCl_2$, 100 µL/L polypropylenglycol 2000 and 10 g/L glucose (autoclaved separately). The following components were added after sterile filtration: 2 mg/L biotin, 0.1 mM L-tryptophan, 0.01 g/L $MnSO_4.H_2O$, 0.01 g/L $FeSO_4.7H_2O$, 1 mg/L $ZnSO_4.7H_2O$, 0.2 mg/L $CuSO_4.5H_2O$, 0.02 mg/L $NiCl_2.6H_2O$ and 0.03 g/L 3.4-dihydroxybenzoic acid. The same medium was used for feeding during the first 772 hours of continuous operation (feed medium 1). After 772 hours, the feed composition was changed to feed medium 2 containing 40 g/L $(NH_4)_2SO_4$, 0.5 g/L $KH_2PO_4$, 5 mL/L corn steep liquor (Sigma Aldrich, C4648, lot number: MKBP5720V), 1 mL/L polypropylenglycol, 267 g/L glucose syrup (Cargill C*Sweet D02767, lot number: 03285882), autoclaved separately, to achieve a final glucose concentration in the feed solution of 200 g/L and 0.1 mM L-tryptophan (sterile filtered and added after autoclaving). The dissolved oxygen concentration was controlled at 30% by adjusting the stirrer speed between 200 and 1200 rpm. A constant gas flow rate of 0.2 l/h air was adjusted for aeration and the pH was controlled at pH 7 with 1 M $NH_4OH$. The results of the continuous fermentation with feed media 2 are shown in FIG. 34. The preceded 772 h of continuous fermentation with feed medium 1 are not shown. Continuous cell retention was achieved by cross-flow ultrafiltration as specified in FIG. 30 and a continuous production of anthranilate was achieved during the cultivation as shown in FIG. 34. The continuous operation was temporarily interrupted as indicated by a stop phase in FIG. 34 due to an accumulation of glucose. Feed and harvest were restarted after the glucose level decreased.

Example 6—Adsorption/Desorption of Anthranilic Acid (AA)

In order to get the anthranilic acid (AA), a solution with higher concentration, AA was transferred from the aqueous solution into an organic solvent by performing an adsorption-desorption operation. To do so, the adsorption capacity of AA on different types of adsorbents was tested.

Zeolite Y (Zeolyst International, catalog no. CBV600) and ZSM5 (Süd-Chemie/Clariant catalog no. H-MFI-27) were selected as zeolites, which function as molecular sieves for different molecules. Hydroxyapatite $(Ca_{10}(PO_4)_6(OH)_2)$ (Sigma-Aldrich catalog no. 289396) was tested due to its ability in the adsorption of AA and some other similar compounds in different solvents.

Adsorption test: Adsorbents were already calcined at 300° C. for 3 h to release any remained moisture. A solution of AA (0.5 wt %) in water was prepared. 20 mL of this solution was transferred to a 50 mL flask containing 0.2 g adsorbent. After a certain period of time under stirring, the concentration of AA in water was analysed by HPLC. The decrease of AA concentration in water was considered as the adsorbed AA.

Synthesis of metal-exchanged zeolite: given the improved adsorption capacity of Ca-incorporated zeolite (following W. H. Goodman, U.S. Pat. No. 4,910,336, 1990), Ca-exchanged zeolites were prepared by ion exchange to be tested in the adsorption of AA (S. M. Seo, S. Y. Coi, J. M. Suh, K. J. Jung, N. H. Heo and W. T. Lim, Bull. Korean Chem. Soc. 2009, 30:1703). 3 g of zeolite as powder was added to a solution of $Ca(NO_3)_2 \cdot 4H_2O$ (0.5 M). The slurry was stirred for 4 h and then the solution was replaced by a fresh one and this procedure was repeated two more times. Finally, the solids were separated by centrifuge and dried at 80° C. and calcined at 300° C. for 3 h. Four other metal-exchanged zeolite Y samples using K, Na, Mg and Fe were prepared with same method as explained above. The samples were then labelled K—Y, Na—Y, Ca—Y, Mg—Y and Fe—Y. The pore size of zeolite H—ZSM5 can be in the range of 0.4-0.6 nm, preferably 0.5 nm. The pore size of zeolite H—Y can be in the range of 0.6 nm-0.9 nm, preferably 0.7-0.9 nm (e.g. as obtained from Zeolyst International, catalog number CBV600).

The adsorption test of AA was performed using the adsorbents mentioned above. The results of these tests are shown in Table 6.

TABLE 6

| Absorbent | HAP | H-ZSM5 | H—Y | Na—Y | K—Y | Mg—Y | Ca—Y | Fe—Y |
|---|---|---|---|---|---|---|---|---|
| Adsorption of AA 0.5% | | | | | | | | |
| Absorption capacity (gAA/kg absorbent) | 10.8 g/kg | 11.6 g/kg | 24.8 g/kg | 25.0 g/kg | 27.4 g/kg | 27.6 g/kg | 36.8 g/kg | 51.2 g/kg |

Zeolite Y showed the highest ability in adsorption of AA from aqueous solution. Ca exchanged Zeolite Y could improve the adsorption of AA to nearly 50%. Fe exchanged Zeolite Y could improve the adsorption of AA to nearly double. The tests were performed with the AA solution in distilled water and also in buffer solution containing $(NH_4)_2SO_4$ (20 g/L), $Na_2HPO_4$ (1 g/L), $KH_2PO_4$ (1 g/L) and $MgSO_4$ (0.25 g/L). Later, $MgSO_4$ was eliminated from the buffer solution, because it caused the formation of insoluble magnesium anthranilate salt. Among the above metal-exchanged zeolites, Fe—Y showed highest AA adsorption capacity (higher than 50 g AA/kg Fe—Y). Fortunately, the buffer solution contents did not influence the adsorption of AA and the adsorption capacities were similar to those in distilled water. The IR spectra of the Fe—Y sample after adsorption test showed some characteristic peaks of AA which can be an evidence for the existence of AA on the surface of Fe—Y most probably chelating with Fe.

TABLE 7

AA adsorption capacities[a] of metal-exchanged zeolite Y in distilled water and buffered aqueous solution after 10 and 60 minutes of contacting.

| | Adsorbent | | | | |
|---|---|---|---|---|---|
| | Na—Y | K—Y | Mg—Y | Ca—Y | Fe—Y |
| distilled water (10 min) | 24.2 | 29.6 | 29.2 | 36.2 | 50.6 |
| distilled water (60 min) | 22.6 | 31.6 | 34 | 42.2 | 54.2 |
| buffer solution (10 min) | 25 | 27.4 | 27.6 | 36.8 | 51.2 |
| buffer solution (60 min) | 25.9 | 22.3 | 22.8 | 25.6 | 45.3 |

[a] g AA/kg adsorbent

The Fe—Y after adsorption test and the fresh Fe—Y sample were analysed by ICP-MS. This analysis showed that the Fe/Al ratio in both samples were 1.25 and 1.3 respectively which are very close to each other. Therefore, the amount of Fe leaching was negligible. In case of Ca-Y, 64% Ca leaching was detected after the adsorption test.

Decomposition of AA desorbed on Fe—Y was studied at the temperatures up to 550° C. using thermal gravimetric analyser equipped with a mass analyser (TGA-MS). As can be seen in FIG. 7, no ANL was formed at the temperatures less than 400° C. At higher than 400° C., AA was decomposed directly to polyaniline which was observed as dark materials on the sample holder. A small amount of ANL was detected at higher than 400° C. Therefore, direct thermal conversion of AA adsorbed on the adsorbent to ANL was not successful.

Desorption of AA from Adsorbent into Liquid Phase

The desorption test of AA from Fe—Y into water showed that the adsorption of AA by metal-exchanged zeolite in aqueous solution is reversible. Subsequently, the desorption of AA into an organic solvent was tested. 1-dodecanol was selected as organic solvent due to the high solubility of AA in it and also its very low miscibility in water (0.004 g/L). Besides, its boiling point (259° C.) is much higher than aniline (183° C.) and water so that its separation from the final mixture was more convenient. Desorption of AA from Fe—Y into 1-dodecanol was performed by suspending 0.2 g Fe—Y containing 10.8 mg AA in 2 mL 1-dodecanol. The slurry was stirred for 0.5 h at the temperature range of 25-120° C. The desorption results are shown in FIG. 8 in which maximum 27.8% AA could be desorbed into 1-dodecanol phase at 120° C.

Example 7—Reaction Kinetics of the Decarboxylation of Anthranilic Acid to Aniline by Thermal Decarboxylation in an Organic Solvent Decarboxylation of AA Dissolved in 1-Dodecanol The decarboxylation of AA 3 wt % dissolved in 1-dodecanol at 160° C. was tested. Catalysts with different characters were screened. The results can be seen in FIG. 9. The blank test without any catalyst showed only 1.4% conversion, while in the presence of zeolite Y (CBV600, "G0257") resulted in more than 70% conversion to ANL in 1 h.

High AA conversion over zeolite Y (CBV600, "G0257") can be due to its highly acidic character and also the pore size (0.7-0.8 nm). ZSM5 (MFI-27) despite of possessing acidic character, has smaller pore size (0.5 nm) so that AA molecules cannot penetrate into them and consequently do not have access to active sites. Hydrotalcite (HTC, $Mg_6Al_2(CO_3)(OH)_{16} \cdot 4H_2O$) has basic character and the low conversion of AA indicates that basic sites are not as active as acidic sites in the decarboxylation of AA. The addition of Na to the zeolite H—Y ("G0257") decreases its acidic character and thus a low conversion of AA was achieved. The ammonia form (CBV500, "G055") also has a lower number of acidic sites than H—Y (CBV600, "G0257").

Figure 10:
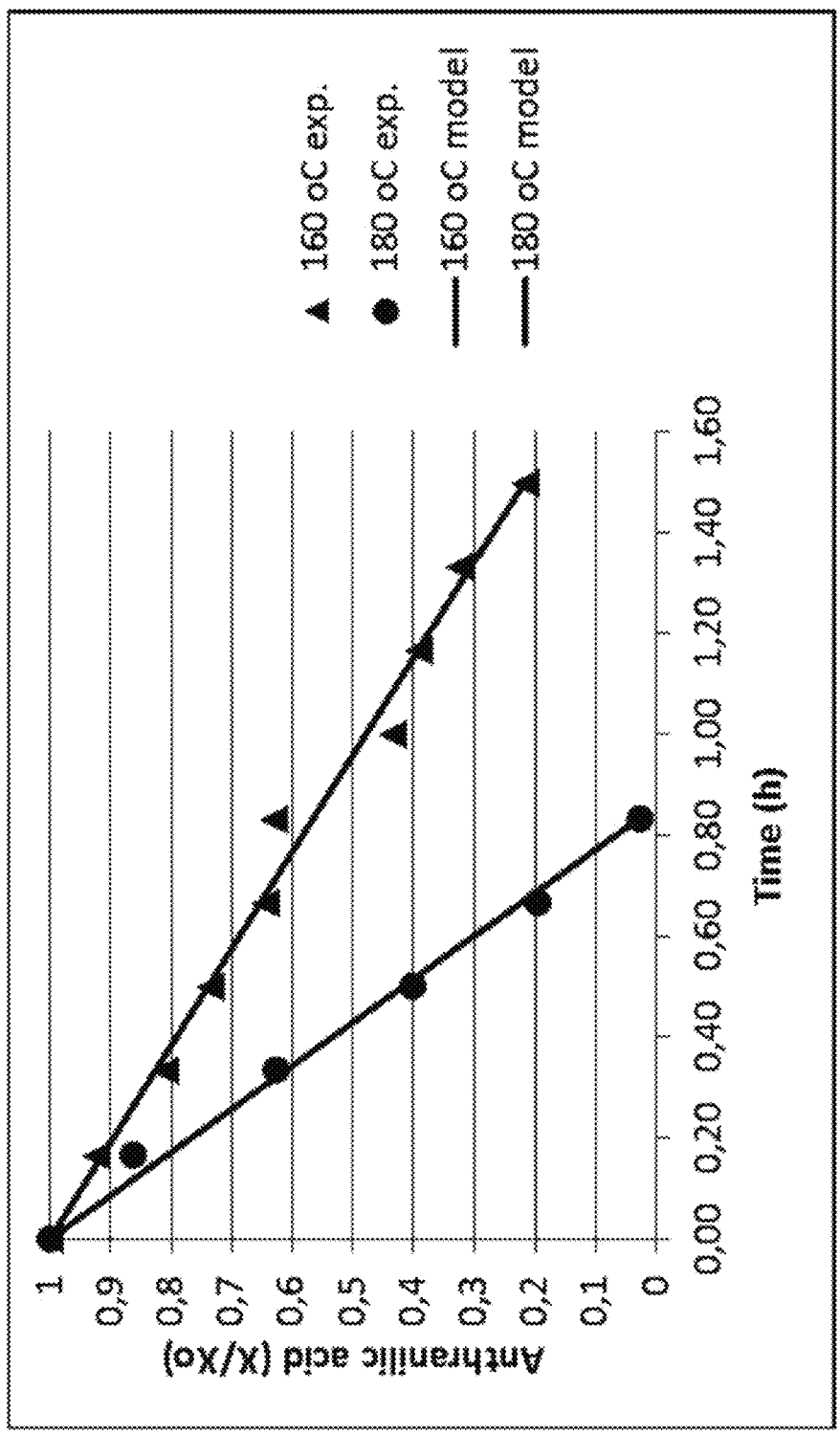
FIG. 10 shows the decomposition of anthranilic acid in organic media with a catalyst. The kinetics of decarboxylation of anthranilic acid dissolved 3 wt % in 1-dodecanol in the presence of zeolite Y at 160° C. and 180° C. is shown. Anthranilic Acid (3 wt %) was dissolved in 1-dodecanol. At this concentration the acid was perfectly soluble in the organic solvent even at room temperature. 80 mL of the above solutions are then transferred into an autoclave of 160 mL, 1.5 g of zeolite catalyst are added and heated to 160° C. or 180° C. For comparison a blank test without catalyst (Blank) and with an alkaline hydrotalcite (HTC), H-ZSM5, sodium doped zeolite Y (NaY), zeolite Y ammonium form ($NH_4$-Y) are also tested. Samples were taken at different time intervals and analyzed by HPLC methods to determine the rate of aniline formation.

As can be seen in FIG. 10, the decarboxylation of AA profile in 1-dodecanol at 160° C. and 180° C. showed that the AA conversion and the ANL formation follow zero order kinetics. The simulated models for the reaction at 160° C. and 180° C. could calculate rate coefficients (k) as 0.235 mol $L^{-1} \cdot h^{-1}$ and 0.522 $mol \cdot L^{-1} \cdot h^{-1}$ respectively. The selectivity of these reactions to ANL was 100% and a mass balance of 95-110% (with an average of 100.4%) was observed.

Decarboxylation of AA Dissolved in Aniline

Aniline is a much better solvent for AA than dodecanol and, being also the product of the decarboxylation, its use presented great advantages compared to 1-dodecanol. We found that up to 30% AA could be dissolved in aniline at room temperature (20° C.), up to 40% AA could be dissolved in aniline at 50° C. and that up to 50% AA could be dissolved at 90° C.

Figure 35:
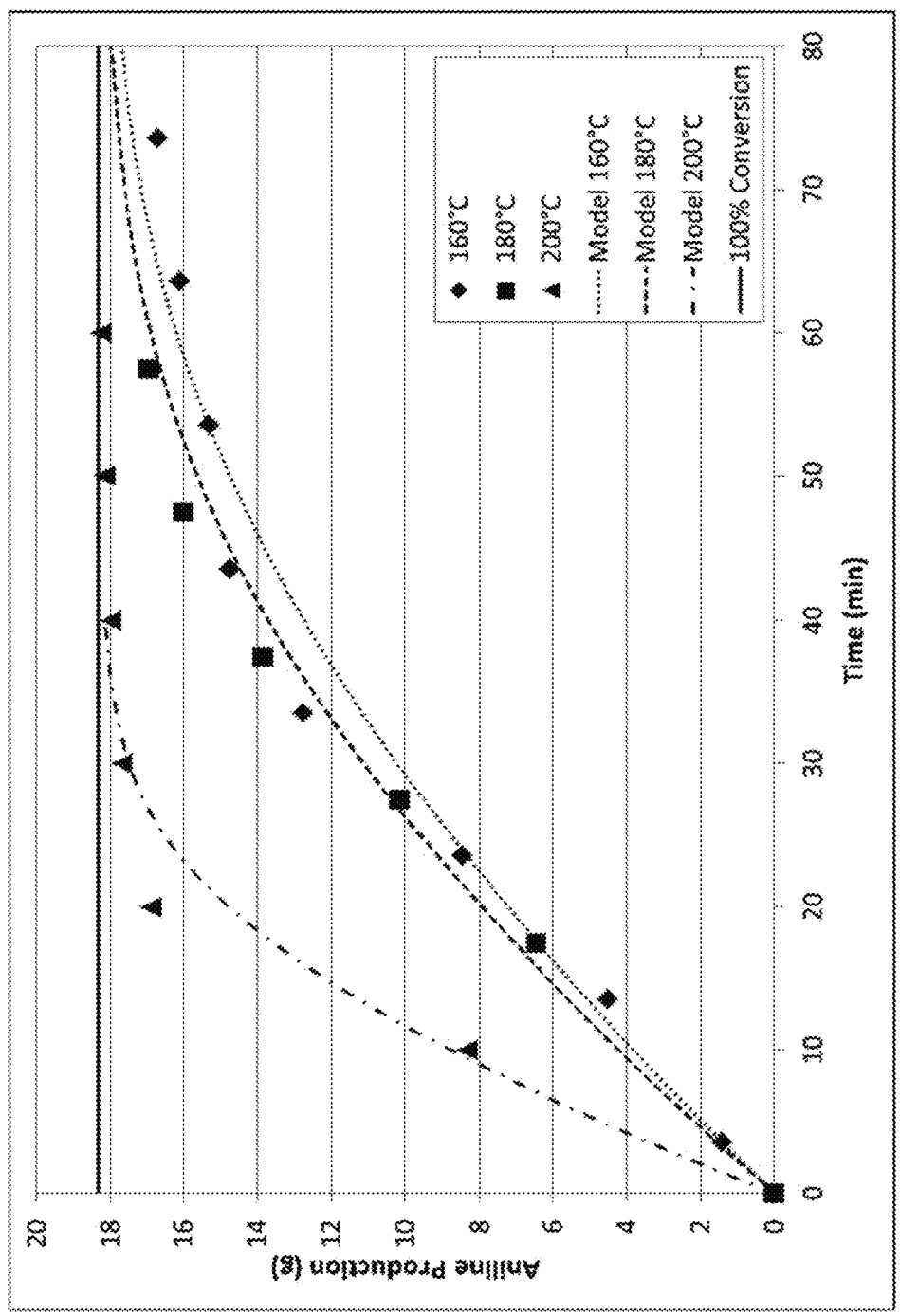
FIG. 35 shows the decomposition of 2-aminobenzoic acid (anthranilic acid, AA) in aniline with a catalyst. The kinetics of decarboxylation of anthranilic acid (AA) dissolved 40 wt % in aniline in the presence of zeolite Y at 160° C., 180° C. and 200° C. is shown.

The decarboxylation of AA 40 wt % dissolved in aniline at 160, 180 and 200° C. was tested. The blank test without any catalyst showed, as before, negligible conversion, while in the presence of zeolite Y (CBV600, "G0257") resulted in more than 99% conversion to ANL in 2 h. The results are shown in FIG. 35. We were also able to fit the data according to a simple kinetic model:

$$r\left(\frac{g_{ANL}}{g_{CAT}h}\right) = k^0 \exp\left(-\frac{E_a}{RT}\right) AA^n$$

Where "r" is the reaction rate in g aniline per g catalyst per hour, "$k^0$" is the kinetic constant also in g aniline per g catalyst per hour, "$E_a$" is the reaction activation energy in kJ/mol, "R" is the ideal gas constant of 8.31 J/K mol, "T" is the temperature in K, "AA" is the concentration of AA and "n" is the reaction order. FIG. 35 also shows the fittings of this reaction model at the different temperatures. The results of the fittings can be summarized as follows:

$k^0$=55492 g $AN$/g CAT h $E_a$=37.4 kJ/mol $n$=0.16

FIG. 35 shows the decomposition of 2-aminobenzoic acid (anthranilic acid, AA) in aniline with a catalyst. The kinetics of decarboxylation of anthranilic acid (AA) dissolved 40 wt % in aniline in the presence of zeolite Y at 160° C., 180° C. and 200° C. is shown.

Anthranilic Acid (40 wt %) was dissolved in aniline. At this concentration the acid was perfectly soluble in the organic solvent once heated to about 50° C. 80 mL of the above solutions are then transferred into an autoclave of 160 mL, 1.5 g of zeolite catalyst are added and heated to 160° C., 180° C. or 200° C. Samples were taken at different time intervals and analysed by HPLC methods to determine the rate of aniline formation.

Decarboxylation of AA Dissolved in Aniline in Presence of Water

As the anthranilic acid separated from the crystallization process could present some residual moisture (approximately 10%), we decided to look at the kinetic of the reaction in presence of water. Experiments analog to the previous one were conducted, except that 10 wt % water was added on purpose to the reaction mixture. We found that the overall kinetic and reaction profile remains unchanged. Results for the reaction temperature 200° C. are presented in FIG. 36.

Figure 36:
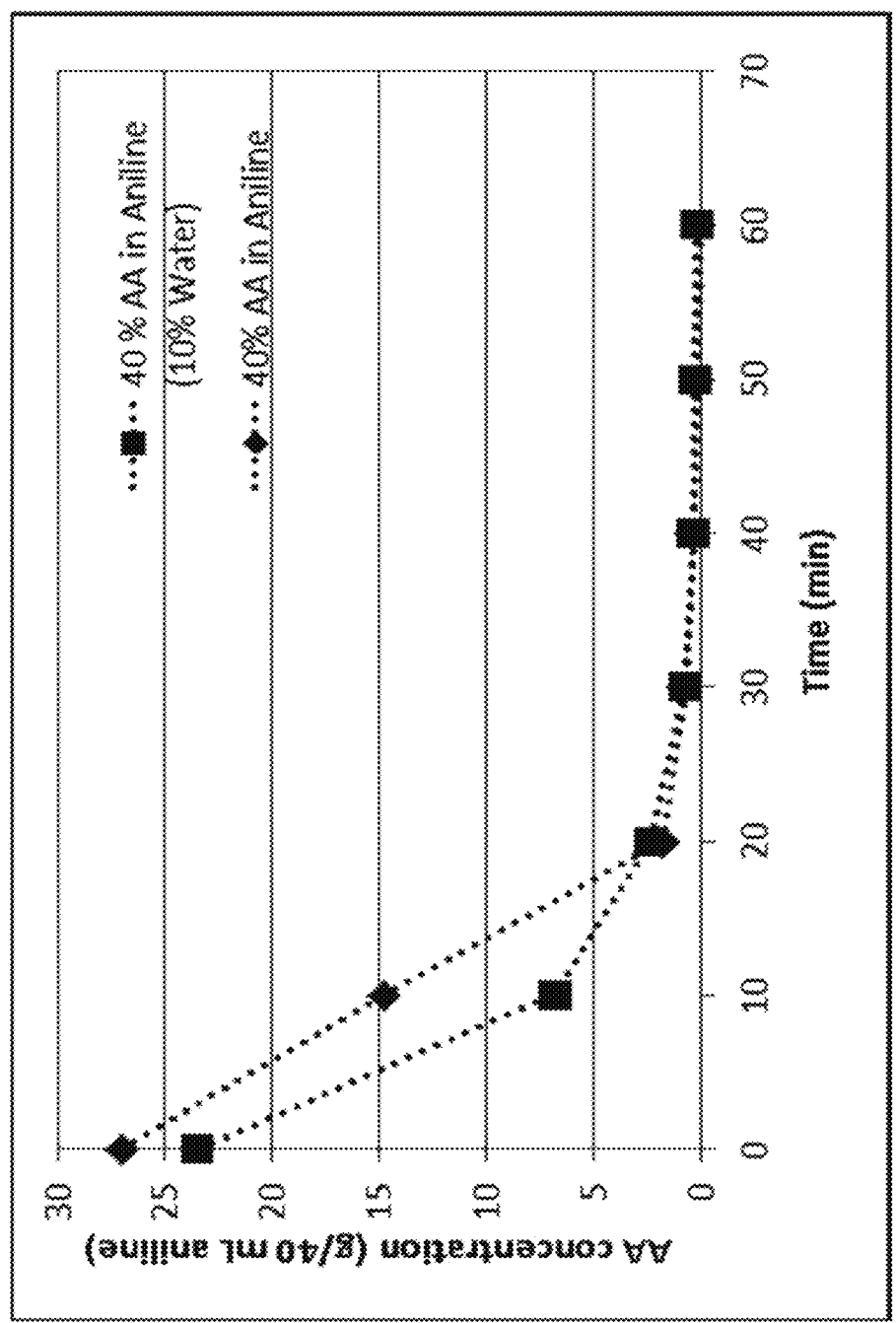
FIG. 36 shows the decomposition of 2-aminobenzoic acid (anthranilic acid, AA) in aniline with a catalyst. The kinetics of decarboxylation of anthranilic acid (AA) dissolved 40 wt % in aniline and in 10% Water-90% Aniline in the presence of zeolite Y at 200° C. is shown.

FIG. 36 shows the decomposition of 2-aminobenzoic acid (anthranilic acid, AA) in aniline with a catalyst. The kinetics of decarboxylation of anthranilic acid (AA) dissolved 40 wt % in aniline and in 10% Water-90% Aniline in the presence of zeolite Y at 200° C. is shown.

Anthranilic Acid (40 wt %) was dissolved in aniline. At this concentration the acid was perfectly soluble in the organic solvent once heated to about 50° C. 80 mL of the above solutions are then transferred into an autoclave of 160 mL, then 10% (8 g) of water was added, 1.5 g of zeolite catalyst are added and heated to 160° C., 180° C. or 200° C. Samples were taken at different time intervals and analysed by HPLC methods to determine the rate of aniline formation.

Decarboxylation of AA Dissolved in Aniline from Different Organic Sources

According to the present invention, anthranilic acid could be produced biologically by fermentation of different sugar mediums. It is expectable that the differences in trace elements present in the different media (i.e. hydrolyzed corn starch, sugar cane juice, or glucose) could affect the anthranilic acid that should be further decarboxylated to aniline. To verify if these differences could interfere with the catalyst and the decarboxylation reaction, different anthranilic acid, separated by crystallization from different growth media were tested. The comparison was always done against the chemically pure anthranilic acid purchased by the laboratory supplier Sigma Aldrich.

The different AA was tested in the same conditions as the previous tests starting from a 40% solution of AA in Aniline at 180° C. Results are summarized in FIG. 47. All the AA sources were fully converted to aniline in less than 90 minutes. The fastest conversion is shown by the pure chemical material (Aldrich). This is comparable with the material produce by fermentation of chemically pure glucose (VN35). Slightly slower is the material isolated from hydrolyzed corn starch (VN32 and 33) followed by the material isolated from sugar cane juice (VN 34). This sequence follows the degree of refining of the media used. The purest sugar source resulted in faster decomposition of the AA isolated from it. This could be explained by the presence of trace elements, like ions or minerals, which could interfere with the zeolite catalyst. However the effect is so limited that would not interfere with the decarboxylation reaction, which proceed very quickly to completion independently from the source of the AA.

Figure 37:
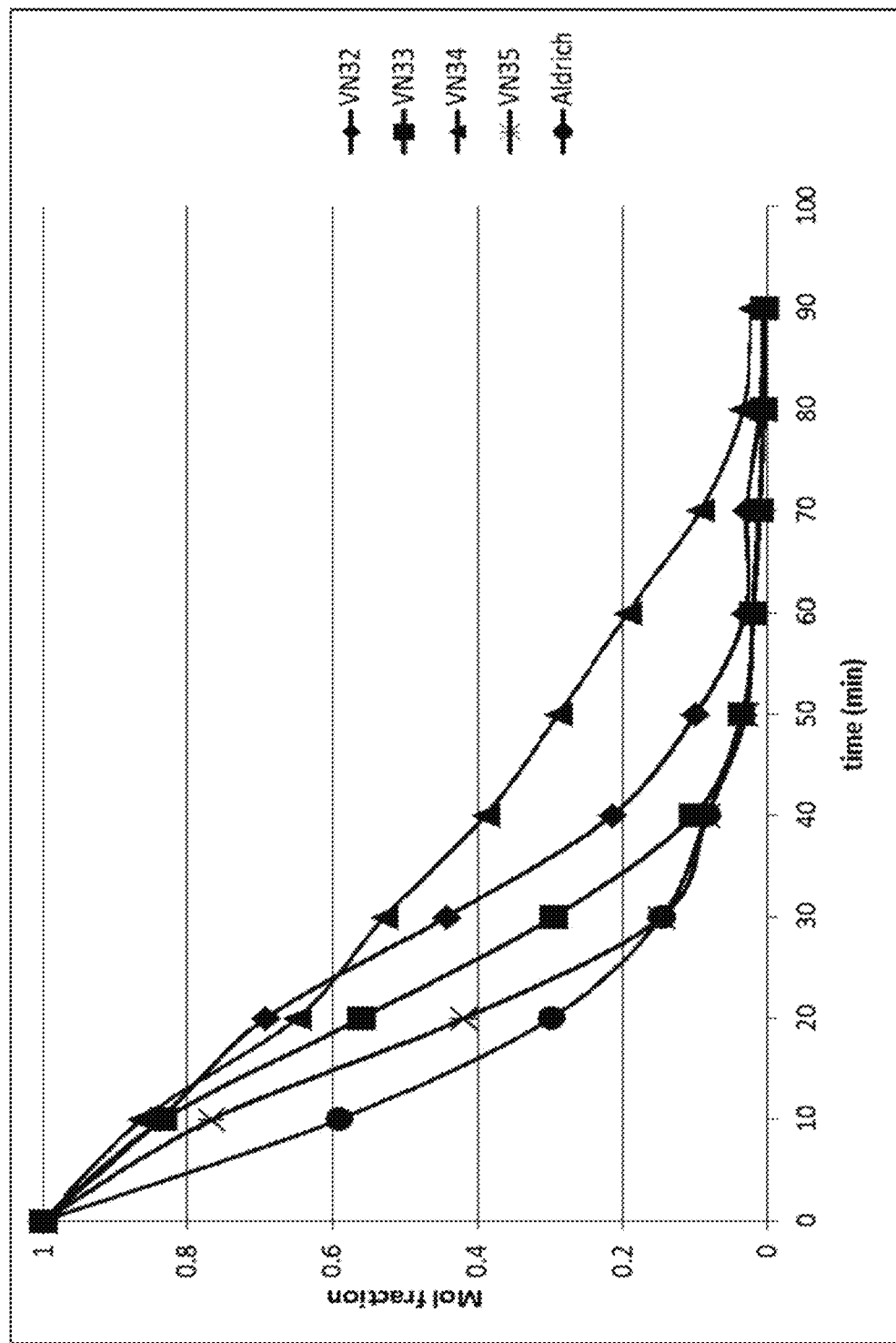
FIG. 37 shows the decomposition of 2-aminobenzoic acid (anthranilic acid, AA) in aniline with a catalyst. The kinetics of decarboxylation of anthranilic acid (AA) dissolved 40 wt % in aniline in the presence of zeolite Y at 180° C. is shown.

FIG. 37 shows the decomposition of 2-aminobenzoic acid (anthranilic acid, AA) in aniline with a catalyst. The kinetics of decarboxylation of anthranilic acid (AA) dissolved 40 wt % in aniline in the presence of zeolite Y at 180° C. is shown.

Anthranilic Acid was obtained by crystallization from different sugar media like chemically pure glucose, hydrolysed corn starch and sugar cane juice. The resulting isolated Anthranilic Acid (40 wt %) was dissolved in aniline. At this concentration the acid was perfectly soluble in the organic solvent once heated to about 50° C. 80 mL of the above solutions are then transferred into an autoclave of 160 mL, 1.5 g of zeolite catalyst are added and heated to 180° C. Samples were taken at different time intervals and analysed by HPLC methods to determine the rate of aniline formation.

Catalyst Stability for the Decarboxylation of AA Dissolved in Aniline from Hydrolyzed Corn Starch Considering the effect of the trace elements observed before, we tested the catalyst stability over several runs. We performed this by recycling the catalyst and by using it in the following reaction without any washing step, following the reaction procedure described before. The results are presented in FIG. 38. The difference in activity between the freshly prepared catalyst and the reused one is minimal. The reused seems to be even faster or better than the fresh system. This showed that there is no poisoning or inhibition effect of the trace elements on the catalyst, which remains active in the decarboxylation reaction. To further confirm that we analysed post mortem the catalyst and compared it with the freshly prepared one. The IR spectrum of the 2 catalyst is shown in FIG. 39. Beside some absorbed aniline species, only a small decrease in OH signal is present. This OH could be quenched after exchange with other ions (trace elements), however they are probably not the active site for the catalysis, as the strong acidity of the zeolites comes from the Al—O—Si bridge.

Figure 38:
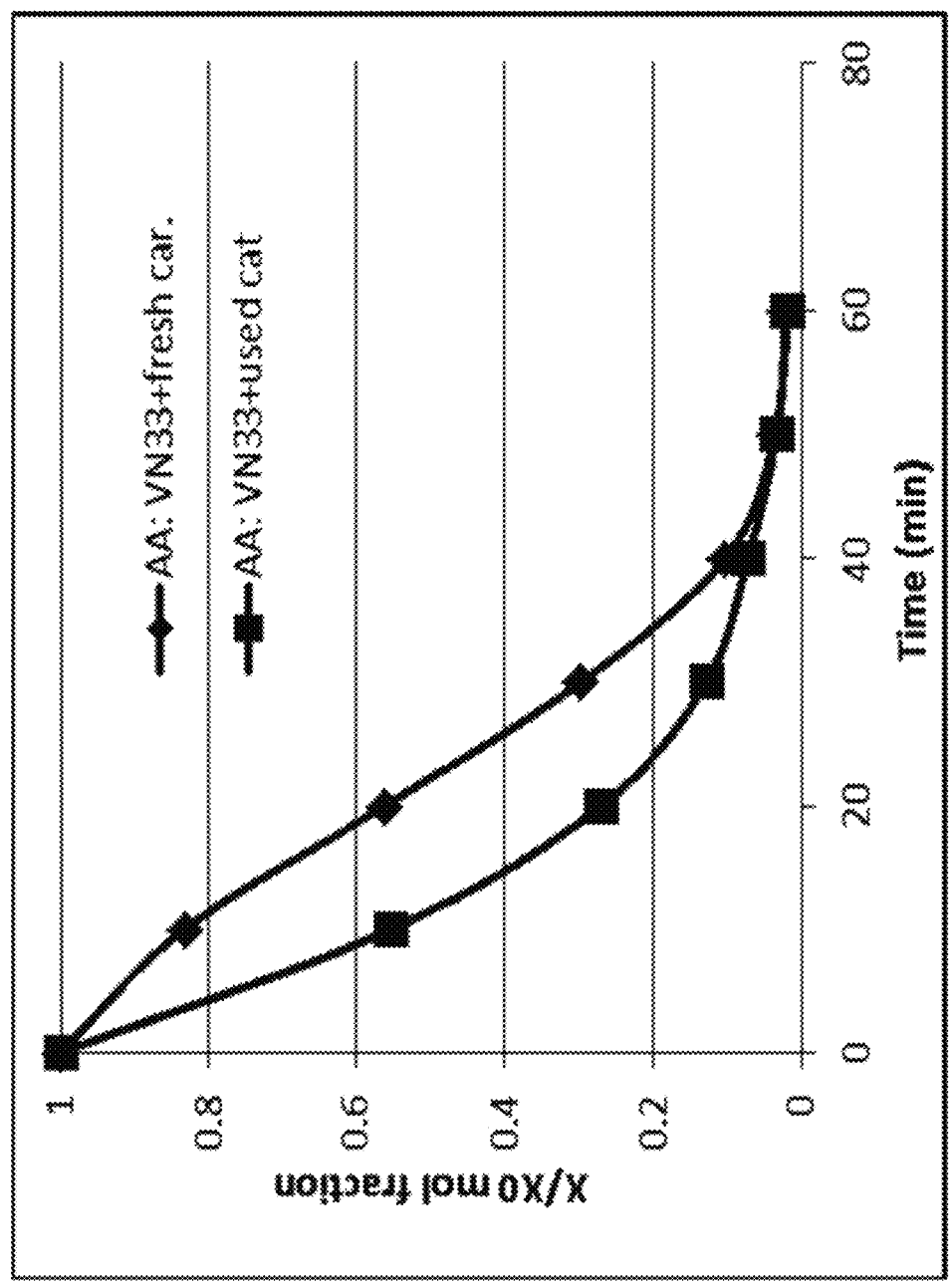
FIG. 38 shows the decomposition of 2-aminobenzoic acid (anthranilic acid, AA) in aniline with a catalyst. The kinetics of decarboxylation of anthranilic acid (AA) dissolved 40 wt % in aniline in the presence of zeolite Y at 180° C. is shown.
Figure 39:
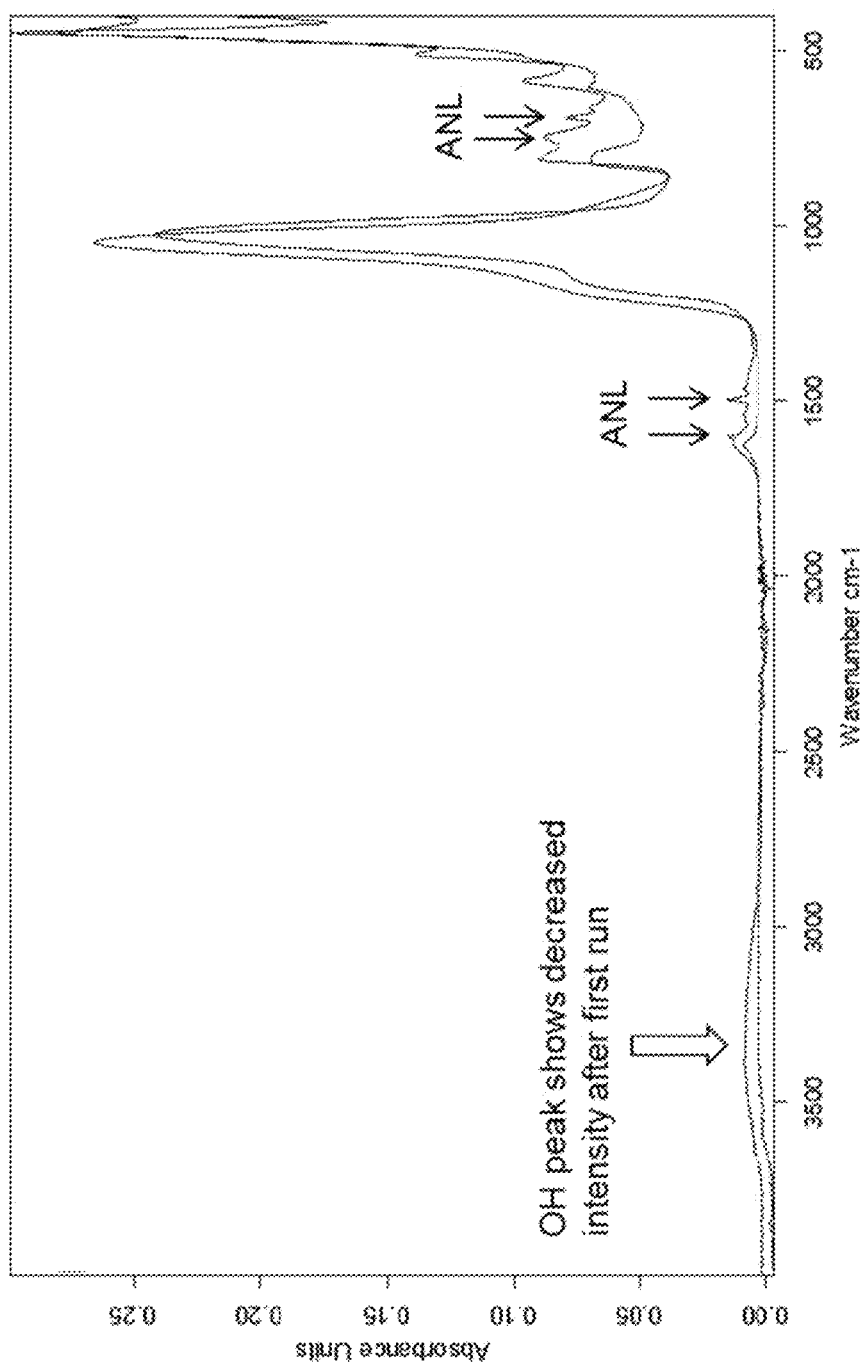
FIG. 39 shows the IR Spectrum of a freshly prepared H—Y catalyst and one after reaction as above using AA isolated from hydrolyzed corn starch. The typical bands for aniline are marked. Absorption of this highly basic species takes place. The OH region is also highlighted. A reduction of OH signal is compatible with some partial ion exchange that could take place with trace elements present, however the OH groups seam not be active in the catalysis, but is probably the Al—O—Si bridge the responsible.

FIG. 38 shows the decomposition of 2-aminobenzoic acid (anthranilic acid, AA) in aniline with a catalyst. The kinetics of decarboxylation of anthranilic acid (AA) dissolved 40 wt % in aniline in the presence of zeolite Y at 180° C. is shown.

Anthranilic Acid was obtained by crystallization from hydrolysed corn starch. The resulting isolated Anthranilic Acid (40 wt %) was dissolved in aniline. At this concentration the acid was perfectly soluble in the organic solvent once heated to about 50° C. 80 mL of the above solutions are then transferred into an autoclave of 160 mL, 1.5 g of zeolite catalyst are added and heated to 180° C. The catalyst was isolated and recycled for a subsequent reaction without further treatment or washing. Samples were taken at different time intervals and analysed by HPLC methods to determine the rate of aniline formation.

FIG. 39 shows the IR Spectrum of a freshly prepared H-Y catalyst and one after reaction as above using AA isolated from hydrolyzed corn starch. The typical bands for aniline are marked. Absorption of this highly basic species takes place indeed. The OH region is also highlighted. A reduction of OH signal is compatible with some partial ion exchange that could take place with trace elements present, however the OH groups seams not be active in the catalysis, but is probably the Al—O—Si bridge the responsible.

Example 8—Dissolution and Crystallization of oAB from Fermentation Broth

An industrial sugar source was used for fermentation of *Corynebacterium glutamicum*. 100 ml of the broth with a content of 21.5 g/L glucose, 3.7 g/L lactate was mixed with 10 g anthranilic acid in a 250 ml laboratory reactor. The slurry had a pH-value of 4.7. The solubility of oAB was about 4.5 g/L at room temperature at pH 4.5. Afterwards 9.12 g NaOH (32%) were added in 4 portions until a solution was present. The solution had a pH-value of 8.3. Following 7, g HCl (37%) were added within 1 hour. By dosing of HCl first nucleation took place as from a pH-value of 5.8. The number of crystals increased during dosing. At the end of dosing the suspension had a pH-value of 3.6. Afterwards the slurry was stirred for 1 hour. Finally the slurry was filtered.

Filtration:

The filtration was performed according to the VDI guideline "VDI 2762" at 0.2 bar and a filter area of 12.6 cm$^2$. 125 g suspension was filtered and washed with 25 g water. 91 g mother liquor and 23.1 g wet solid were measured. The resistance of the filter cake being determined according to "VDI 2762" accounted to $5\times10^{10}$ l/m$^2$. The filter cake was dried in a drying furnace. After drying 9.1 g of dry solid were measured, corresponding to a yield of 91%.

The fraction of anthranilic acid being in the mother liquor was 0.72%. The ash content of the solid was determined as an indication for the salt content of anthranilic acid. The ash content was determined to be at 0.55%.

Example 9—Solubility of oAB in 1-Dodecanol

The solubility of oAB in dodecanol was tested with increasing temperature.

| SLE oAB/1-dodecanol | | | | | | |
|---|---|---|---|---|---|---|
| input 1-dodecanol | | | | | | |
| full = | | | 270.74 | | g | |
| empty = | | | 170.67 | | g | |
| clean = | | | 100.07 | | g | |
| Input oAB: | | | | | | |
| No. | target g | full g | empty g | clean g | sum g | concentration wt % | temperature ° C. |
| 1 | 5 | 25.49 | 20.36 | 5.13 | 5.13 | 4.88 | 40 |
| 2 | 10 | 30.36 | 20.41 | 9.95 | 15.08 | 13.10 | 68 |
| 3 | 15 | 35.22 | 20.32 | 14.90 | 29.98 | 23.05 | 93 |
| 4 | 25 | 53.81 | 29.10 | 24.71 | 54.69 | 35.34 | 111 |
| 5 | 25 | 53.51 | 28.87 | 24.64 | 79.33 | 44.22 | 119 |
| 6 | 25 | 53.72 | 29.19 | 24.53 | 103.86 | 50.93 | 123 |

SLE = solid liquid equilibrium

The solubility of oAB in 1-dodecanol was increasing with rising temperature.

---

The invention claimed is:

1. A recombinant microbial host cell capable of converting a raw material comprising a fermentable carbon substrate to o-aminobenzoate biologically,
   wherein the microbial host cell is a *Corynebacterium* strain,
   wherein said *Corynebacterium* strain is *Corynebacterium glutamicum*,
   wherein said fermentable carbon substrate is selected from the group consisting of C-5 monosaccharides, C-6 monosaccharides, disaccharides, and tri-saccharides, and
   wherein said *Corynebacterium glutamicum* has decreased expression of anthranilate phosphoribosyl transferase caused by reduced expression of trpD gene encoding anthranilate phosphoribosyl transferase, wherein said reduced expression is caused by a genetic modification of the trpD gene, and wherein said genetic modification is selected from the group consisting of SEQ ID NO: 2, SEQ ID NO: 3, SEQ ID NO: 4, SEQ ID NO: 5, SEQ ID NO: 6, SEQ ID NO: 7, and SEQ ID NO: 8.

2. A recombinant microbial host cell capable of converting a raw material comprising a fermentable carbon substrate to o-aminobenzoate biologically,
  wherein the microbial host cell is a *Corynebacterium* strain,
  wherein said *Corynebacterium* strain is *Corynebacterium glutamicum*,
  wherein said fermentable carbon substrate is selected from the group consisting of C-5 monosaccharides, C-6 monosaccharides, disaccharides, and tri-saccharides, and
  wherein said *Corynebacterium glutamicum* has decreased expression of chorismate mutase caused by reduced expression of csm gene encoding chorismate mutase, wherein said reduced expression is caused by a genetic modification of the csm gene, wherein said genetic modification is selected from the group consisting of SEQ ID NO: 10, SEQ ID NO: 11, SEQ ID NO: 12, SEQ ID NO: 13, SEQ ID NO: 14, SEQ ID NO: 15, and SEQ ID NO: 16.

3. The recombinant microbial host cell of claim 1, wherein said *Corynebacterium glutamicum* further comprises a deletion in hpr gene or ptsG gene expressing phosphoenolpyruvate-phosphotransferase.

4. The recombinant microbial host cell of claim 1, wherein said raw material is selected from the group consisting of sugar beet, sugar cane, starch-containing plants, lignocellulose, glycerol, and C1-compounds.

5. A method for producing aniline, the method comprising:
  a) producing o-aminobenzoate by fermentation of a raw material comprising at least one fermentable carbon substrate using the recombinant microbial host cell of claim 1, wherein said o-aminobenzoate comprises an anthranilate anion,
  b) converting said o-aminobenzoate from said anthranilate anion to anthranilic acid by acid protonation,
  c) recovering said anthranilic acid by precipitation or by dissolving in an organic solvent, and
  d) converting said anthranilic acid to aniline by thermal decarboxylation in an organic solvent.

6. The method of claim 5, wherein said fermentation of step a) is a batch fermentation, a fed-batch fermentation, or a continuous fermentation.

7. The method of claim 5, wherein at least step a) and step b) are run continuously.

8. The method of claim 5, wherein said recombinant microbial host is removed prior to performing step b) of converting said o-aminobenzoate from said anthranilate anion to anthranilic acid.

9. The method of claim 5, wherein said acid protonation of step b) is done by adding HCl.

10. The method of claim 5, wherein in step c) said recovering of said anthranilic acid by precipitation comprises filtration, thereby generating a slurry comprising said recovered anthranilic acid.

11. The method of claim 5, wherein in step c) said recovering of said anthranilic acid by dissolving in an organic solvent comprises adding said organic solvent to said anthranilic acid such that said anthranilic acid is recovered as a solute in said organic solvent.

12. The method of claim 5, wherein step c) is followed by washing and drying the recovered anthranilic acid precipitate in advance of performing the thermal decarboxylation of step d).

13. The method of claim 5, wherein step d) is performed in the presence of a catalyst.

14. The method of claim 5, wherein following step c) residual anthranilate anion is recovered by adsorption to an ion exchange resin or an active carbon material or a zeolite, followed by desorption of the recovered anthranilate anion.

15. The method according to claim 14, wherein subsequent to the recovery of the residual anthranilate anion by adsorption following step c), a water stream devoid of the adsorbed anthranilate anion is at least partially re-fed to the fermentation of step a).

16. The recombinant microbial host cell of claim 4, wherein said raw material comprises a starch-containing plant comprising corn, wheat, rye, or a combination thereof.

17. The recombinant microbial host cell of claim 4, wherein said raw material comprises a lignocellulose comprising straw, wood, bagasse, or a combination thereof.

18. The recombinant microbial host cell of claim 4, wherein said raw material comprises a C1 compound comprising CO.

19. The recombinant microbial host cell of claim 1, wherein said fermentable carbon substrate comprises a C-5 monosaccharide comprising xylose arabinose, or a combination thereof.

20. The recombinant microbial host cell of claim 1, wherein said fermentable carbon substrate comprises a C-6 monosaccharide comprising glucose, fructose mannose, or a combination thereof.

21. The recombinant microbial host cell of claim 1, wherein said fermentable carbon substrate comprises a disaccharide comprising saccharose.

22. The recombinant microbial host cell of claim 1, wherein said fermentable carbon substrate comprises a tri-saccharide comprising kestose.

23. The method of claim 8, wherein said removed recombinant microbial host is re-fed to the fermentation of step a).

24. The method of claim 9, wherein said HCl is added to a pH of 2.5 to 4.5.

25. The method of claim 24, wherein said HCl is added to a pH of 3 to 4.

26. The method of claim 10, wherein said slurry comprising said recovered anthranilic acid is dissolved in an organic solvent.

27. The method of claim 26, wherein said organic solvent is aniline or 1-dodecanol or a mixture thereof.

28. The method of claim 11, wherein said organic solvent comprises aniline or 1-dodecanol or a mixture thereof.

29. The method of claim 13, wherein said catalyst is a zeolite catalyst and wherein the thermal decarboxylation step d) is followed by a further step e) of purifying the aniline.

30. The method of claim 29, wherein said zeolite catalyst is zeolite H-Y.

31. The method of claim 29, wherein purifying the aniline comprises distillation.

32. The method of claim 14, wherein following step c) residual anthranilate anion is recovered by adsorption to a zeolite modified with $Fe^{3+}$ or $Ca^{2+}$.

33. The method of claim 14, further comprising at least partially refeeding said anthranilate anion to step b) for converting said anthranilate anion to anthranilic acid by acid protonation.

34. The method of claim 33, wherein the zeolite modified with $Fe^{3+}$ or $Ca^{2+}$ is Fe—Y zeolite.

35. The recombinant microbial host cell of claim 1, wherein said *Corynebacterium glutamicum* further comprises a deletion in pepco gene expressing phosphoenolpyruvate carboxylase.

36. The recombinant microbial host cell of claim 1, wherein said *Corynebacterium glutamicum* further comprises a deletion in pyk-pyk gene expressing pyruvate kinase.

37. The recombinant microbial host cell of claim 1, wherein said *Corynebacterium glutamicum* further comprises a deletion in gpi gene expressing glucose-6-phosphate isomerase.

38. The recombinant microbial host cell of claim 2, wherein said raw material is selected from the group consisting of sugar beet, sugar cane, starch-containing plants, lignocellulose, glycerol, and C1-compounds.

39. A method for producing aniline, the method comprising:
   a) producing o-aminobenzoate by fermentation of a raw material comprising at least one fermentable carbon substrate using the recombinant microbial host cell of claim 2, wherein said o-aminobenzoate comprises an anthranilate anion,
   b) converting said o-aminobenzoate from said anthranilate anion to anthranilic acid by acid protonation,
   c) recovering said anthranilic acid by precipitation or by dissolving in an organic solvent, and
   d) converting said anthranilic acid to aniline by thermal decarboxylation in an organic solvent.

40. The recombinant microbial host cell of claim 2, wherein said fermentable carbon substrate comprises a C-5 monosaccharide comprising xylose arabinose, or a combination thereof.

41. The recombinant microbial host cell of claim 2, wherein said fermentable carbon substrate comprises a C-6 monosaccharide comprising glucose, fructose mannose, or a combination thereof.

42. The recombinant microbial host cell of claim 2, wherein said fermentable carbon substrate comprises a disaccharide comprising saccharose.

43. The recombinant microbial host cell of claim 2, wherein said fermentable carbon substrate comprises a trisaccharide comprising kestose.

44. The recombinant microbial host cell of claim 1, wherein the microbial host cell is a tryptophan auxotrophic cell.

45. The recombinant microbial host cell of claim 2, wherein the microbial host cell is a tryptophan auxotrophic cell.

* * * * *

SEQUENCE LISTING

<160> NUMBER OF SEQ ID NOS: 110

<210> SEQ ID NO 1
<211> LENGTH: 1047
<212> TYPE: DNA
<213> ORGANISM: Corynebacterium glutamicum

<400> SEQUENCE: 1

```
atgacttctc cagcaacact gaaagttctc aacgcctact tggataaccc cactccaacc      60
ctggaggagg caattgaggt gttcaccccg ctgaccgtgg gtgaatacga tgacgtgcac     120
atcgcagcgc tgcttgccac catccgtact cgcggtgagc agttcgctga tattgccggc     180
gctgccaagg cgttcctcgc ggcggctcgt ccgttcccga ttactggcgc aggttttgcta    240 gattccgctg gtactggtgg cgacggtgcc aacaccatca acatcaccac cggcgcatcc    300
ctgatcgcag catccggtgg agtgaagctg gttaagcacg gcaaccgttc ggtgagctcc    360
aagtccggct ccgccgatgt gctggaagcg ctgaatattc ctttgggcct tgatgtggat    420
cgtgctgtga gtggttcga agcgtccaac ttcaccttcc tgttcgcacc tgcgtacaac     480
cctgcgattg cgcatgtgca gccggttcgc caggcgctga aattccccac catcttcaac    540
acgcttggac cattgctgtc cccggcgcgc ccggagcgtc agatcatggg cgtgccaat     600 gccaatcatg gacagctcat cgccgaggtc ttccgcgagt gggccgtac acgcgcgctt    660 gttgtgcatg gcgcaggcac cgatgagatc gcagtccacg gcaccacctt ggtgtgggag    720
cttaaagaag acggcaccat cgagcattac accatcgagc ctgaggacct tggccttggc    780
cgctacaccc ttgaggatct cgtaggtggc ctcggcactg agaacgccga agctatgcgc    840
gctactttcg cgggcaccgg ccctgatgca caccgtgatg cgttggctgc gtccgcaggt    900
gcgatgttct acctcaacgg cgatgtcgac tccttgaaag atggtgcaca aaaggcgctt    960
tccttgcttg ccgacggcac cacccaggca tggttggcca agcacgaaga gatcgattac   1020
tcagaaaagg agtcttccaa tgactag                                       1047

<210> SEQ ID NO 2
<211> LENGTH: 69
<212> TYPE: DNA
<213> ORGANISM: Artificial Sequence
<220> FEATURE:
<223> OTHER INFORMATION: Artificial construct

<400> SEQUENCE: 2
atgacttctc cagcaacact gtgtttaagt ttagtggatc ccggggaaaa ggagtcttcc     60
aatgactag                                                            69

<210> SEQ ID NO 3
<211> LENGTH: 32
<212> TYPE: DNA
<213> ORGANISM: Artificial Sequence
<220> FEATURE:
<223> OTHER INFORMATION: Artificial construct

<400> SEQUENCE: 3
gccctgcagg taaaaaaagg atttgattca tg                                   32

<210> SEQ ID NO 4
<211> LENGTH: 32
<212> TYPE: DNA
<213> ORGANISM: Artificial Sequence
<220> FEATURE:
<223> OTHER INFORMATION: Artificial construct

<400> SEQUENCE: 4
gccctgcagg taaaaaaagg atttgattcg tg                                   32

<210> SEQ ID NO 5
<211> LENGTH: 32
<212> TYPE: DNA
<213> ORGANISM: Artificial Sequence
```

<220> FEATURE:
<223> OTHER INFORMATION: Artificial construct

<400> SEQUENCE: 5
gccctgcagg taaaaaaagg atttgattct tg                                32

<210> SEQ ID NO 6
<211> LENGTH: 26
<212> TYPE: DNA
<213> ORGANISM: Artificial Sequence
<220> FEATURE:
<223> OTHER INFORMATION: Artificial construct

<400> SEQUENCE: 6
gccctgcagg taaaaaaagg attatg                                       26

<210> SEQ ID NO 7
<211> LENGTH: 26
<212> TYPE: DNA
<213> ORGANISM: Artificial Sequence
<220> FEATURE:
<223> OTHER INFORMATION: Artificial construct

<400> SEQUENCE: 7
gccctgcagg taaaaaaagg attgtg                                       26

<210> SEQ ID NO 8
<211> LENGTH: 26
<212> TYPE: DNA
<213> ORGANISM: Artificial Sequence
<220> FEATURE:
<223> OTHER INFORMATION: Artificial construct

<400> SEQUENCE: 8
gccctgcagg taaaaaaagg attttg                                       26

<210> SEQ ID NO 9
<211> LENGTH: 312
<212> TYPE: DNA
<213> ORGANISM: Corynebacterium glutamicum

<400> SEQUENCE: 9
gtgtgcatga ctaatgcagg tgacaacttc gagatcagga tgccttctgg cacggatgac    60
ccattgtccg atgcggagat ccaaaagtat cgcgaggaga tcaaccgctt ggaccgcgaa   120
atcctcgatg cggtgaaacg ccgcacgaag atttcccaaa ccatcggaaa aacacgcatg   180
agctcgggcg aacacgtctc cgtgcacacc cgagaagtag caatcatcaa ccaattccgt   240
gaagagatcg cgaggaaggg ccctgccctc gctggaattt tgctgcgcat gggacgcgga   300
aaactcggat aa                                                      312

<210> SEQ ID NO 10
<211> LENGTH: 60
<212> TYPE: DNA
<213> ORGANISM: Artificial Sequence
<220> FEATURE:
<223> OTHER INFORMATION: Artificial construct

<400> SEQUENCE: 10
atgactaatg caggtgactg tttaagttta gtggatcccg ggcgcggaaa actcggataa    60

<210> SEQ ID NO 11
<211> LENGTH: 32
<212> TYPE: DNA

```
<213> ORGANISM: Artificial Sequence
<220> FEATURE:
<223> OTHER INFORMATION: Artificial construct

<400> SEQUENCE: 11
gccctgcagg acgtggcaga atagtgtgca tg                                     32

<210> SEQ ID NO 12
<211> LENGTH: 32
<212> TYPE: DNA
<213> ORGANISM: Artificial Sequence
<220> FEATURE:
<223> OTHER INFORMATION: Artificial construct

<400> SEQUENCE: 12
gccctgcagg acgtggcaga atagtgtgcg tg                                     32

<210> SEQ ID NO 13
<211> LENGTH: 32
<212> TYPE: DNA
<213> ORGANISM: Artificial Sequence
<220> FEATURE:
<223> OTHER INFORMATION: Artificial construct

<400> SEQUENCE: 13
gccctgcagg acgtggcaga atagtgtgct tg                                     32

<210> SEQ ID NO 14
<211> LENGTH: 27
<212> TYPE: DNA
<213> ORGANISM: Artificial Sequence
<220> FEATURE:
<223> OTHER INFORMATION: Artificial construct

<400> SEQUENCE: 14
gccctgcagg acgtggcaga atagatg                                           27

<210> SEQ ID NO 15
<211> LENGTH: 27
<212> TYPE: DNA
<213> ORGANISM: Artificial Sequence
<220> FEATURE:
<223> OTHER INFORMATION: Artificial construct

<400> SEQUENCE: 15
gccctgcagg acgtggcaga ataggtg                                           27

<210> SEQ ID NO 16
<211> LENGTH: 27
<212> TYPE: DNA
<213> ORGANISM: Artificial Sequence
<220> FEATURE:
<223> OTHER INFORMATION: Artificial construct

<400> SEQUENCE: 16
gccctgcagg acgtggcaga atagttg                                           27

<210> SEQ ID NO 17
<211> LENGTH: 270
<212> TYPE: DNA
<213> ORGANISM: Corynebacterium glutamicum

<400> SEQUENCE: 17
atggcttcca agactgtaac cgtcggttcc tccgttggcc tgcacgcacg tccagcatcc       60
atcatcgctg aagcggctgc tgagtacgac gacgaaatct tgctgaccct ggttggctcc      120
```

```
gatgatgacg aagagaccga cgcgtcctct tccctcatga tcatggcgct gggcgcagag    180
cacggcaacg aagttaccgt cacctccgac aacgctgaag ctgttgagaa gatcgctgcg    240
cttatcgcac aggaccttga cgctgagtaa                                     270

<210> SEQ ID NO 18
<211> LENGTH: 63
<212> TYPE: DNA
<213> ORGANISM: Artificial Sequence
<220> FEATURE:
<223> OTHER INFORMATION: Artificial construct

<400> SEQUENCE: 18
atggcttcca agactgtaac ctgtttaagt ttagtggatg ggcaggacct tgacgctgag    60
taa                                                                  63

<210> SEQ ID NO 19
<211> LENGTH: 2052
<212> TYPE: DNA
<213> ORGANISM: Corynebacterium glutamicum

<400> SEQUENCE: 19
atggcgtcca aactgacgac gacatcgcaa catattctgg aaaaccttgg tggaccagac    60
aatattactt cgatgactca ctgtgcgact cgccttcgct tccaagtgaa ggatcaatcc    120
attgttgatc aacaagaaat tgactccgac ccatcagttc ttggcgtagt accccaagga    180
tccaccggta tgcaggtggt gatgggtgga tctgttgcaa actattacca agaaatcctc    240
aaacttgatg gaatgaagca cttcgccgac ggtgaagcta cagagagttc atccaagaag    300
gaatacggcg gagtccgtgg caagtactcg tggattgact acgccttcga gttcttgtct    360
gatactttcc gaccaatcct gtgggccctg cttggtgcct cactgattat taccttgttg    420
gttcttgcgg atactttcgg tttgcaagac ttccgcgctc caatggatga gcagcctgat    480
acttatgtat tcctgcactc catgtggcgc tcggtcttct acttcctgcc aattatggtt    540
ggtgccaccg cagctcgaaa gctcggcgca aacgagtgga ttggtgcagc tattccagcc    600
gcacttctta ctccagaatt cttggcactg ggttctgccg cgataccgt cacagtcttt    660 ggcctgccaa tggttctgaa tgactactcc ggacaggtat tcccaccgct gattgcagca    720
attggtctgt actgggtgga aaagggactg aagaagatca tccctgaagc agtccaaatg    780
gtgttcgtcc cattcttctc cctgctgatt atgatcccag cgaccgcatt cctgcttgga    840
cctttcggca tcggtgttgg taacggaatt tccaacctgc ttgaagcgat taacaacttc    900
agcccattta ttctttccat cgttatccca ttgctctacc cattcttggt tccacttgga    960
ttgcactggc cactaaacgc catcatgatc cagaacatca cacccctggg ttacgacttc    1020
attcagggac caatgggtgc ctggaacttc gcctgcttcg gcctggtcac cggcgtgttc    1080
ttgctctcca ttaaggaacg aaacaaggcc atgcgtcagg tttccctggg tggcatgttg    1140
gctggtttgc tcggcggcat ttccgagcct tccctctacg tgttctgct ccgattcaag    1200 aagacctact tccgcctcct gccgggttgt ttggcaggcg gtatcgtgat gggcatcttc    1260
gacatcaagg cgtacgcttt cgtgttcacc tccttgctta ccatcccagc aatggaccca    1320 tggtttgggct acaccattgg tatcgcagtt gcattcttcg tttccatgtt ccttgttctc    1380 gcactgact accgttccaa cgaagagcgc gatgaggcac gtgcaaaggt tgctgctgac    1440
aagcaggcag aagaagatct gaaggcagaa gctaatgcaa ctcctgcagc tccagtagct    1500
```

```
gctgcaggtg cgggagccgg tgcaggtgca ggagccgctg ctggcgctgc aaccgccgtg   1560
gcagctaagc cgaagctggc cgctggggaa gtagtggaca ttgtttcccc actcgaaggc   1620
aaggcaattc cactttctga agtacctgac ccaatctttg cagcaggcaa gcttggacca   1680
ggcattgcaa tccaaccaac tggaaacacc gttgttgctc cagcagacgc tactgtcatc   1740
cttgtccaga atctggaca cgcagtggca ttgcgcttag atagcggagt tgaaatcctt   1800
gtccacgttg gattggacac cgtgcaattg ggcggcgaag gcttcaccgt tcacgttgag   1860
cgcaggcagc aagtcaaggc gggggatcca ctgatcactt ttgacgctga cttcattcga   1920
tccaaggatc tacctttgat cacccccagtt gtggtgtcta acgccgcgaa attcggtgaa   1980
attgaaggta ttcctgcaga tcaggcaaat tcttccacga ctgtgatcaa ggtcaacggc   2040
aagaacgagt aa                                                       2052

<210> SEQ ID NO 20
<211> LENGTH: 63
<212> TYPE: DNA
<213> ORGANISM: Artificial Sequence
<220> FEATURE:
<223> OTHER INFORMATION: Artificial construct

<400> SEQUENCE: 20
atggcgtcca aactgacgac gtgtttaagt ttagtggatg gggtcaacgg caagaacgag    60
taa                                                                  63

<210> SEQ ID NO 21
<211> LENGTH: 2760
<212> TYPE: DNA
<213> ORGANISM: Corynebacterium glutamicum

<400> SEQUENCE: 21
atgactgatt ttttacgcga tgacatcagg ttcctcggtc aaatcctcgg tgaggtaatt    60
gcggaacaag aaggccagga ggtttatgaa ctggtcgaac aagcgcgcct gacttctttt   120
gatatcgcca agggcaacgc cgaaatggat agcctggttc aggttttcga cggcattact   180
ccagccaagg caacaccgat tgctcgcgca ttttccccact cgctctgct ggctaacctg   240 gcggaagacc tctacgatga agagcttcgt gaacaggctc tcgatgcagg cgacacccct   300
ccggacagca ctcttgatgc cacctggctg aaactcaatg agggcaatgt tggcgcagaa   360
gctgtggccg atgtgctgcg caatgctgag gtggcgccgg ttctgactgc gcacccaact   420
gagactcgcc gccgcactgt ttttgatgcg caaaagtgga tcaccaccca catgcgtgaa   480
cgccacgctt tgcagtctgc ggagcctacc gctcgtacgc aaagcaagtt ggatgagatc   540
gagaagaaca tccgccgtcg catcaccatt ttgtggcaga ccgcgttgat tcgtgtggcc   600
cgcccacgta tcgaggacga gatcgaagta gggctgcgct actacaagct gagccttttg   660
gaagagattc cacgtatcaa ccgtgatgtg ctgttgagc ttcgtgagcg tttcggcgag   720
ggtgttcctt tgaagcccgt ggtcaagcca ggttcctgga ttggtggaga ccacgacggt   780
aacccttatg tcaccgcgga aacagttgag tattccactc accgcgctgc ggaaaccgtg   840
ctcaagtact atgcacgcca gctgcattcc ctcgagcatg agctcagcct gtcggaccgc   900
atgaataagg tcaccccgca gctgcttgcg ctggcagatg cagggcacaa cgacgtgcca   960
agccgcgtgg atgagcctta cgacgcgcc gtccatggcg ttcgcggacg tatcctcgcg   1020
acgacggccg agctgatcgg cgaggacgcc gttgagggcg tgtggttcaa ggtctttact   1080
ccatacgcat ctccggaaga attcttaaac gatgcgttga ccattgatca ttctctgcgt   1140
```

```
gaatccaagg acgttctcat tgccgatgat cgtttgtctg tgctgatttc tgccatcgag    1200
agctttggat tcaaccttta cgcactggat ctgcgccaaa actccgaaag ctacgaggac    1260
gtcctcaccg agcttttcga acgcgcccaa gtcaccgcaa actaccgcga gctgtctgaa    1320
gcagagaagc ttgaggtgct gctgaaggaa ctgcgcagcc ctcgtccgct gatcccgcac    1380
ggttcagatg aatacagcga ggtcaccgac cgcgagctcg gcatcttccg caccgcgtcg    1440
gaggctgtta agaaattcgg ccacggatg gtgcctcact gcatcatctc catggcatca    1500
tcggtcaccg atgtgctcga gccgatggtg ttgctcaagg aattcggact catcgcagcc    1560 aacgcgaca acccacgcgg caccgtcgat gtcatcccac tgttcgaaac catcgaagat    1620
ctccaggccg cgccggaat cctcgacgaa ctgtggaaaa ttgatctcta ccgcaactac    1680
ctcctgcagc gcgacaacgt ccaggaagtc atgctcggtt actccgattc caacaaggat    1740
ggcggatatt tctccgcaaa ctgggcgctt tacgacgcgg aactgcagct cgtcgaacta    1800
tgccgatcag ccggggtcaa gcttcgcctg ttccacggcc gtggtggcac cgtcggccgc    1860
ggtggcggac cttcctacga cgcgattctt gcccagccca gggggctgt ccaaggttcc    1920 gtgcgcatca ccgagcaggg cgagatcatc tccgctaagt acggcaaccc cgaaaccgcg    1980
cgccgaaacc tcgaagccct ggtctcagcc acgcttgagg catcgcttct cgacgtctcc    2040
gaactcaccg atcaccaacg cgcgtacgac atcatgagtg agatctctga gctcagcttg    2100
aagaagtacg cctccttggt gcacgaggat caaggcttca tcgattactt cacccagtcc    2160
acgccgctgc aggagattgg atccctcaac atcggatcca ggccttcctc acgcaagcag    2220
acctcctcgg tggaagattt gcgagccatc ccatgggtgc tcagctggtc acagtctcgt    2280
gtcatgctgc caggctggtt tggtgtcgga accgcattag agcagtggat ggcgaaggg    2340 gagcaggcca cccaacgcat tgccgagctg caaacactca atgagtcctg gccatttttc    2400
acctcagtgt tggataacat ggctcaggtg atgtccaagg cagagctgcg tttggcaaag    2460
ctctacgcag acctgatccc agatacggaa gtagccgagc gagtctattc cgtcatccgc    2520
gaggagtact tcctgaccaa gaagatgttc tgcgtaatca ccggctctga tgatctgctt    2580
gatgacaacc cacttctcgc acgctctgtc cagcgccgat accctacct gcttccactc    2640 aacgtgatcc aggtagagat gatgcgacgc taccgaaaag gcgaccaaag cgagcaagtg    2700
tcccgcaaca ttcagctgac catgaacggt ctttccactg cgctgcgcaa ctccggctag    2760
```

<210> SEQ ID NO 22
<211> LENGTH: 63
<212> TYPE: DNA
<213> ORGANISM: Artificial Sequence
<220> FEATURE:
<223> OTHER INFORMATION: Artificial construct

<400> SEQUENCE: 22

```
atgactgatt ttttacgcga ttgtttaagt ttagtggatg gggcgctgcg caactccggc    60
tag                                                                  63
```

<210> SEQ ID NO 23
<211> LENGTH: 1414
<212> TYPE: DNA
<213> ORGANISM: Corynebacterium glutamicum

<400> SEQUENCE: 23

```
atgggcgtgg ataagacgaac taagattgta tgtaccctag gcccagcggt ggctagtgca    60
```

```
gatggaattc tgcgtttggt agaagacggc atggatgttg ctcgcctcaa cttctcccat    120
ggtgaccacc cagatcatga gcaaaactac aagtgggtcc gcgaggcggc ggagaagact    180
ggccgtgcag tcggtattct cgcagacctc caaggaccga agatccgtct tggccgtttc    240
actgacggcg caaccgtgtg ggaaaacggc gagaccattc ggatcaccgt tgacgatgta    300
gagggaacgc acgatcgtgt gtccaccacc tacaagaatc tggcaaaaga cgcgaagcca    360
ggcgaccgcc tgctcgttga tgacggcaag gttggcctcg tctgcgtttc cgtcgaaggt    420
aacgacgtca tctgtgaggt tgttgagggc ggaccagtct ccaacaacaa gggtgtttcc    480
ctgccaggta tggatatttc cgtacctgca ctgtccgaaa aggatatccg tgacctgcgc    540
ttcgccctga agctcggcgt ggactttatt gcactgtcct tcgtacgttc cccagcagat    600
gctgaactcg ttcacaagat catggacgaa gaaggtcgtc gtgttcctgt gatcgccaag    660
ctggaaaagc cagaggctgt cacctccctc gagccaatcg tgttggcatt cgacgccgtc    720
atggttgctc gtggtgacct cggcgttgag gttcctctgg aggaggttcc actggttcag    780
aagcgcgcaa tccagattgc ccgtgagaac gcaaagccag ttatcgtggc aacccagatg    840
ctggattcca tgattgagaa ctcccgccca acccgtgcgg aagcttctga cgtggcaaac    900
gctgtgctcg atggcgcaga tgctgtcatg ctttctggtg aaacttcagt gggcaaagat    960
ccgcacaacg ttgtgcgcac catgtctcgc attgttcgct tcgctgaaac cgacggtcgc   1020
gtcccagacc tgacccacat ccctcgcact aagcgtggcg ttatttccta ctctgcacgt   1080
gatatcgccg agcgcctcaa cgctcgtgca ttggttgcgt tcaccacctc tggtgatacc   1140
gcaaagcgtg tggctcgtct gcacagccac ctgccactgc tcgtgttcac tccaaatgag   1200
gcagttcgct ctgagctggc gctgacctgg ggtgcaacca ccttcctgtg tccacctgtc   1260
agcgataccg atgacatgat gcgcgaagtc gaccgtgctc ttttagcaat gcctgagtac   1320
aacaagggtg acatgatggt tgttgttgca ggttcccctc ctggtgttac cggtaacacc   1380
aacatgattc acgtccacct tcttggtgat ctaa                              1414

<210> SEQ ID NO 24
<211> LENGTH: 63
<212> TYPE: DNA
<213> ORGANISM: Artificial Sequence
<220> FEATURE:
<223> OTHER INFORMATION: Artificial construct

<400> SEQUENCE: 24
atgggcgtgg atagacgaac ttgtttaagt ttagtggatg ggacaaggat tgcaaagctc     60
taa                                                                  63

<210> SEQ ID NO 25
<211> LENGTH: 1860
<212> TYPE: DNA
<213> ORGANISM: Corynebacterium glutamicum

<400> SEQUENCE: 25
atgaatgagt ttgaccagga cattctccag gagatcaaga ctgaactcga cgagttaatt     60
ctagaacttg atgaggtgac acaaactcac agcgaggcca tcgggcaggt ctccccaacc    120
cattacgttg gtgcccgcaa cctcatgcat tacgcgcatc ttcgcaccaa agacctccgt    180
ggcctgcagc aacgcctctc ctctgtggga gctacccgct tgactaccac cgaaccagca    240
gtgcaggccc gcctcaaggc cgcccgcaat gttatcggag ctttcgcagg tgaaggccca    300 cttatccac cctcagatgt cgtcgatgcc ttcgaagatg ccgatgagat tctcgacgag    360
```

```
cacgccgaaa ttctccttgg cgaacccta ccggatactc catcctgcat catggtcacc      420
ctgcccaccg aagccgccac cgacattgaa cttgtccgtg gcttcgccaa aagcggcatg      480
aatctagctc gcatcaactg tgcacacgac gatgaaaccg tctggaagca gatgatcgac      540
aacgtccaca ccgttgcaga agaagttggc cgggaaatcc gcgtcagcat ggacctcgcc      600
ggaccaaaag tacgcaccgg cgaaatcgcc ccaggcgcag aagtaggtcg cgcacgagta      660
acccgcgacg aaaccggaaa agtactgacg cccgcaaaac tgtggatcac cgcccacggc      720
tccgaaccag tcccagcccc cgaaagcctg cccggtcgcc ccgctctgcc gattgaagtc      780
accccagaat ggttcgacaa actagaaatc ggcagcgtca tcaacgtccc agacacccgc      840
ggatcccgcc gagcattcac cgtgaccagg ttttttgatg gcgcggtcct cgccgaaggc      900
ccacaaaaag cctacatctc caacggcacc ctcctggaac acaactacga ccgctcccgg      960
gtctacggca tccccgccgt agttcagcgc atcaacctca aagtcggcga ccgcctcatc     1020
cttaccgacg aagaactcac ctacgatcca tccctcggat ccggccgcac accacgcatc     1080
agctgcaccc ttccacaagc agtcgatgca attaaagtcg ggcaccgcgt gcttttcgac     1140
gacggagcca tcgccgcagt ctgcatcgac aagacctcca ctgccgacgg ccacaacgac     1200
gtagaattgg aagtcaccca cgcccgccca aaggcgtaa acctggccgc atacaaggga     1260
atcaacctcc cagactccga acttccactc ccaagcctca ctgaagaaga cctccaacac     1320
ctgcgctttg tcgtcaaata cgccgacatc gcagccatct ccttcatccg aaacgtcgcc     1380
gacgtggaat acctcctcca agcactcgcc gacatcggag atccagtagc cgtcgaacgc     1440
cttggcctcg tccttaaaat cgagaccatc ccaggctacg aaggcctcgc ccaaatcctc     1500
ctgaccggca tgcgccacga aaacttcggc atcatgatcg cccgcggaga cctcgccgtc     1560
gaactcggct tcgaccgcat ggcagaagtc ccccaactga tcatggccct tgccgaagcc     1620
gcccacgtcc caaccatctt ggccacccaa gtcctggaaa acatggccaa aaacggactc     1680
ccatctcgcg cagaaatcac cgacgcagca atggcacttc gcgctgaatg cgtcatgctg     1740
aacaagggac cacacatcaa cgacgccatc aaggtcctca ccgaaatgag ccgcaaactt     1800
ggtgcatccc aacgaaagag taggctgctg ctgcgcaagg tgaagagctg ggaagagtaa     1860
```

<210> SEQ ID NO 26
<211> LENGTH: 63
<212> TYPE: DNA
<213> ORGANISM: Artificial Sequence
<220> FEATURE:
<223> OTHER INFORMATION: Artificial construct

<400> SEQUENCE: 26

```
atgaatgagt ttgaccagga ctgtttaagt ttagtggatg gggtgaagag ctgggaagag      60
taa                                                                     63
```

<210> SEQ ID NO 27
<211> LENGTH: 1603
<212> TYPE: DNA
<213> ORGANISM: Corynebacterium glutamicum

<400> SEQUENCE: 27

```
atggcggaca tttcgaccac ccaggtttgg caagacctga ccgatcatta ctcaaacttc      60
caggcaacca ctctgcgtga acttttcaag gaagaaaacc gcgccgagaa gtacaccttc     120
tccgcggctg gcctccacgt cgacctgtcg aagaatctgc ttgacgacgc caccctcacc     180
```

```
aagctccttg cactgaccga agaatctggc cttcgcgaac gcattgacgc gatgtttgcc    240
ggtgaacacc tcaacaacac cgaagaccgc gctgtcctcc acaccgcgct gcgccttcct    300
gccgaagctg atctgtcagt agatggccaa gatgttgctg ctgatgtcca cgaagttttg    360
ggacgcatgc gtgacttcgc tactgcgctg cgctcaggca actggttggg acacaccggc    420
cacacgatca agaagatcgt caacattggt atcggtggct ctgacctcgg accagccatg    480
gctacgaagg ctctgcgtgc atacgcgacc gctggtatct cagcagaatt cgtctccaac    540
gtcgacccag cagacctcgt ttctgtgttg aagacctcg atgcagaatc cacattgttc    600
gtgatcgctt cgaaaacttt caccacccag gagacgctgt ccaacgctcg tgcagctcgt    660
gcttggctgg tagagaagct cggtgaagag gctgtcgcga agcacttcgt cgcagtgtcc    720
accaatgctg aaaaggtcgc agagttcggt atcgacacgg acaacatgtt cggcttctgg    780
gactgggtcg gaggtcgtta ctccgtggac tccgcagttg gtctttccct catggcagtg    840
atcggccctc gcgacttcat gcgtttcctc ggtggattcc acgcgatgga tgaacacttc    900
cgcaccacca agttcgaaga aacgttcca atcttgatgg ctctgctcgg tgtctggtac    960
tccgatttct atggtgcaga aacccacgct gtcctacctt attccgagga tctcagccgt    1020
tttgctgctt acctccagca gctgaccatg gaatcaaatg gcaagtcagt ccaccgcgac    1080
ggctcccctg tttccactgg cactggcgaa atttactggg gtgagcctgg cacaaatggc    1140
cagcacgctt tcttccagct gatccaccag ggcactcgcc ttgttccagc tgatttcatt    1200
ggtttcgctc gtccaaagca ggatcttcct gccggtgagc gcaccatgca tgacctttg    1260 atgagcaact tcttcgcaca gaccaaggtt ttggcttcg gtaagaacgc tgaagagatc    1320
gctgcggaag gtgtcgcacc tgagctggtc aaccacaagg tcatgccagg taatcgccca    1380
accaccacca ttttggcgga ggaacttacc ccttctattc tcggtgcgtt gatcgctttg    1440
tacgaacaca tcgtgatggt tcagggcgtg atttgggaca tcaactcctt cgaccaatgg    1500
ggtgttgaac tgggcaaaca gcaggcaaat gacctcgctc cggctgtctc tggtgaagag    1560
gatgttgact cgggagattc ttccactgat tcaaaatagg tag    1603
```

<210> SEQ ID NO 28
<211> LENGTH: 63
<212> TYPE: DNA
<213> ORGANISM: Artificial Sequence
<220> FEATURE:
<223> OTHER INFORMATION: Artificial construct

<400> SEQUENCE: 28

```
atggcggaca tttcgaccac ctgtttaagt ttagtggatg ggtggtaccg cgcaaatagg    60
tag                                                                  63
```

<210> SEQ ID NO 29
<211> LENGTH: 975
<212> TYPE: DNA
<213> ORGANISM: Corynebacterium glutamicum

<400> SEQUENCE: 29

```
atgagcaccg ccgtagtttc acagaagaag tccacaacgg catccaaaat tggacattgg    60
atgctcaata acggtgcgtt ggtggggctg attgcactgt gtgttggact ttttattgca    120
acaccccact ttctcaccat tcctaacctg atcaacatcg gtatccaatc ggcgacggtg    180
gcgatcctgg cgttcggcat gaccttcgtc atcgttaccg caggcattga tttgtctgtg    240
ggatcagtgg ctgcgttggg tgcgatgacc tcggcgtatt tcttcgcgga agttggtttg    300
```

```
ccgggctgga tcacgctgct gattggcctg ttcatcggat tgttggcggg tgcgatctct    360
ggcatttcta ttgcttatgg caagttgcct gcgtttattg ccaccttggc catgatgtcg    420
atcgccaggg gaatcacctt ggtcatttcc caaggctcac caattcccag tgcaccagct    480
gtgaacgctt tggggcgcac ctactttggc atcccgatgc cgattctgat gatggcactg    540
gctggcattg tgtgttggtt tattttgagc cgcaccgtgc tgggacggtc catgtacgcc    600
attggcggaa acatggaagc agcccgacta tctggtctgc cagtgaagaa aatcctggtc    660
atggtctatg cactggctgg tgtgtatgca gcacttgcgg gtctggtcat gacgggacgc    720
ttgtcgtccg cgcagccgca ggcaggcgtg ggatacgaac tcgatgcgat tgccgccgtg    780
gtcattggtg gtgcgtcact tgctggcgga accggaaaag caacgggcac tttgattggt    840
gccatcttgt tggccgtgat ccgcaatggc ttgaacattt tgaacgtgtc ctcgttctgg    900
cagcagattg tcatcggttg tgtcatcgcg cttgcggtgg gcttcgatgt catccgaaac    960
aaaacctcta agtaa                                                    975

<210> SEQ ID NO 30
<211> LENGTH: 1383
<212> TYPE: DNA
<213> ORGANISM: Corynebacterium glutamicum

<400> SEQUENCE: 30
atgacaatgt gcgattactt cacaagctca aggagaattt ctgtggcttc ccaaatttct     60
ggcggctggc aaagtgccaa acaccgcacc actgtttaca tggtcctcgt agttgtgggc    120
atttctattc tttttgacgg ctacgatcta gtgatctacg gcgccgtgct gtcaacacta    180
cttgaagatc caacccagat cggtgcgctc agcccagcag tcgccggcac ccttggttcc    240
tacgccatga tcggcgtgat gatcggtgct ctatctgcag gtgccgttgg tgaccgcctt    300
ggtcgtcgca aagttatgct caccgcaatc gtctggttct ctgtgggcat ggcgctgacc    360
gcgttcgcgt cctcgattgc gctgttcggt ttcttgcgct tcctcaccgg acttggcgtg    420
ggcatgatcg ttgcaaccgg cggcgcaatc atcgcggagt tcgctccagc gaataggcgc    480
aacttgttca acgcaatcgt gtactccggt gtcccagccg gtgccgtgct ggcttctatc    540
cttgcactgc tctttgaaga tgtcatcggc tggcgcggac tcttcctcat cggtggttcc    600
ccactactgt tcctcctgcc acttgcatac ttcttcctcc cagagtcccc cgcgctggct    660
acctcccgcg ccgtgctgc ggacgccaaa gccctctgcg cacgctatgg gctgccgacg    720
gaggaatttg tcgtcgaaaa gcagcaggaa acaaagggca ccggattcgc tggaatttt   780 tcctccaagt acctcatggg caccattctc atcggcgcaa tgagcttcat cgggctgctt    840
tcgacctacg gcctgaacac ctggttgcca agatcatgg aatccaacgg cgcaacctca    900
catgattccc tgtactccct gctgttcctc aacggcggcg cagtgttcgg tggcctcatc    960
gcatcctggt tcgctgaccg catcggcgcg aagaccgtga tcacctccac cttcgctctc   1020
gccgcgatct gcctcggagt cctgccaaac atctcctcct ggccaatgat gtacaccgca   1080
atcgcattcg caggcgtcgg cgtcctgggc acccaggttc tcacctacgg cctgacctcg   1140
aacttcttcg gaaccgaatg ccgcgcagcg ggagttgcat ggtgtgcagg attcggccga   1200
ctcggcggaa tcgtcggacc agcaatcggt ggcctgatca tcggcgcagg attcggacca   1260
agctccgcat tcctcatctt cgcagcagct gccgcaatcg gcgcggtctg caccttgctg   1320
atcccgcgct ccccagcaga agtagaggtc aaggtcgcgc aggaaccact tgcacgtgtc   1380
```

| | |
|---|---|
| taa | 1383 |

<210> SEQ ID NO 31
<211> LENGTH: 1527
<212> TYPE: DNA
<213> ORGANISM: Corynebacterium glutamicum

<400> SEQUENCE: 31

| | |
|---|---|
| atgacggaca tcaaggccac atcaagtaca tcggccacta cagcaccaac agcaggccga | 60 |
| ccagcgcgtc gacttggaca aatttccctc gtcgcctgtc tcggcggact tctcttcggc | 120 |
| tatgacaccg gtgtcgccaa cggcgccgaa ggccacatgg cacaagaact cggactcaac | 180 |
| gtgctgcagc tcggcgttgt catcagttca ctggttttcg ctgcagcctt tggcgcgctg | 240 |
| ttcgctgggc gtatctcgga cgaaatcggg cgtcgaaaag caattatcac tttgtccgtg | 300 |
| ctgttcttcc tcggatcaat cctcgtcgta ttctcccccg ccggtgagct ggggcagttc | 360 |
| tacggaccag gatttgccac cttggtcacc gggcgcatca tgttgggtct cgcggttggc | 420 |
| ggcgcctcca cagtagttcc ggtgtacctc gctgaactcg caccactaga aatccgcggc | 480 |
| tccctgaccg gccgaaacga gcttgctatc gtcaccggcc agctgcttgc cttcgtgatc | 540 |
| aacgcgctta tcgccgtcac cctacacgga gttattgatg aatctggcg catcatgttc | 600 |
| gccgtctgtg ccctccctgc cgtcgccctc ttcctcggca tgctgcggat gccggaatca | 660 |
| ccacgctggc tggtcaacca ggggcgttac gacgacgccc gccgcgtcat ggagaccgtc | 720 |
| cgtaccctg agcgtgcgaa agccgaaatg gatgaaatca tcgcggtgca ctctgaaaac | 780 |
| aatgcggcac ttcctggtgt taagcagtct tcgggccagg cttcaggcca ggtttctagc | 840 |
| aagcacaccc acatgtccat cggcgaagtc ctcagcaaca aatggctggt tcgtctgctc | 900 |
| atcgccggca tcggtgttgc agttgcccag cagctcaccg gcatcaacgc catcatgtac | 960 |
| tacggaaccc gcgtcctcga ggaatccggc atgagcgcag aaatggctgt ggttgccaac | 1020 |
| attgctttcg gtgccgttgc cgtcatcggt ggactgatcg cactgcgcaa catggaccgc | 1080 |
| ctggatcgcc gcaccacctt catcatcggc ctgtcactga ccaccaccctt ccaccttttg | 1140 |
| atcgcagctg ccggcactct ccttccagaa ggtaactcca ttcgaccatt cgccatcatg | 1200 |
| atccttgttg ttgggttcgt gctctccatg cagactttcc tcaacgttgc agtgtgggtg | 1260 |
| tggctggcgg aaatcttccc agtccgaatg aagggtatcg gcaccggtat ttcggtattc | 1320 |
| tgcggttggg gcatcaatgg cgtcctagcg ttgttcttcc cagcactggt ctccggcgtg | 1380 |
| ggtatcaccct tctccttcct tatcttcgca gtcgtcggag tcattgccct ggcgttcgtc | 1440 |
| accaagtttg ttcctgaaac ccgtggccgc tcacttgaag aactcgatca cgcagcattc | 1500 |
| accggccaga ttttcaagaa ggcttaa | 1527 |

<210> SEQ ID NO 32
<211> LENGTH: 753
<212> TYPE: DNA
<213> ORGANISM: Corynebacterium glutamicum

<400> SEQUENCE: 32

| | |
|---|---|
| atgactgaga ctggatttgg aattgatatt ggtggctccg gcatcaaagg cgcccgcgtt | 60 |
| aaccttaaga ccggtgagtt tattgatgaa cgcataaaaa tcgccacccc taagccagca | 120 |
| accccagagg ctgtcgccga agtagtcgga gagattattt ctcaagccga atgggagggt | 180 |
| ccggtcggaa ttaccctgcc gtcgtcgtt cgcgggcaga tcgcgctatc cgcagccaac | 240 |
| attgacaagt cctggatcgg caccgatgtg cacgaacttt ttgaccgcca cctaaatggc | 300 |

```
cgagagatca ccgttctcaa tgacgcagac gccgccggca tcgccgaagc aacctttggc    360
aaccctgccg cacgcgaagg cgcagtcatc ctgctgaccc ttggtacagg tattggttcc    420
gcattccttg tggatggcca actgttcccc aacacagaac tcggtcacat gatcgttgac    480
ggcgaggaag cagaacacct tgcagcagca tccgtcaaaa aaacgagga tctgtcatgg     540 aagaaatggg cgaagcacct gaacaaggtg ctgagcgaat cgagaaaact tttctcccca    600
tccgtcttca tcatcggtgg cggaatttcc agaaagcacg aaaagtggct tccattgatg    660
gagctagaca ctgacattgt cccagctgag ctgcgcaatc gagccggaat cgtaggagct    720
gctatggcag taaaccaaca cctcaccca taa                                 753

<210> SEQ ID NO 33
<211> LENGTH: 1083
<212> TYPE: DNA
<213> ORGANISM: Corynebacterium glutamicum

<400> SEQUENCE: 33
atgaacatcc cgtttgtcca gcgcttcgat gaaggcctgg accctgttct agaagtactc     60
ggtggcaagg gcgcttcact agtcaccatg acagatgctg aatgcccgt tccacctgga    120 tttgtggtca ctactgccag cttttgatgag ttcatccgtg aagcaggggt tgctgaacac    180
atcgataaat tcctaaacga tctcgatgca gaagatgtta aggaagtgga tcgagtttct    240
gcgatcatcc gcgatgagct gtgcagtctt gacgttccag agaatgctcg tttcgcagtg    300
caccaggctt atcgcgatct catggaacga tgccgtggcg acgtcccggt tgctgtccgg    360
tcatcggcca ctgccgaaga cctgcccgat gcttccttcg cagggcaaca ggacacctat    420
ctgtggcaag tcggtttgag cgctgtcact gaacacatcc gtaaatgctg gcttcgctg     480 ttcacttccc gtgccattat ctaccgtctg aaaaacaaca tccccaatga gggcctctcg    540
atggcggtag ttgttcaaaa aatggtcaac tctcgtgtcg caggcgtggc aatcactatg    600
aatccttcca acggcgaccg ctcgaagatc accatcgatt cctcatgggg tgttggtgaa    660
atggtggtct caggtgaagt gacaccgac aatatcttgc tggacaagat cacgctgcag     720
gttgtctccg aacacattgg aagcaaacac gctgaactca tccccgatgc caccagtgga    780
agcctcgtgg aaaagcccgt tgatgaagaa cgcgcaaacc gccgcagtct gactgatgag    840
gaaatgctcg ctgtggcaca aatggctaag cgtgcagaaa acactacaa gtgcccacaa     900 gatatcgaat gggcgctgga cgctgatctg ccagatggag aaaaccttct gttattgcaa    960
tcccgcccgg aaactatcca ctccaacggt gtgaagaagg aaaccccaac tccgcaggct    1020
gccaaaacca taggcacctt cgatttcagc tcaatcaccg tcgcaatgac cggcacgaag    1080
taa                                                                 1083

<210> SEQ ID NO 34
<211> LENGTH: 1743
<212> TYPE: DNA
<213> ORGANISM: Corynebacterium glutamicum

<400> SEQUENCE: 34
atgttcaagc cttttgaaac tatcggtggt gagttcgctg taaagtgcct cggccaatac      60
aacgctcggc atttgatgat cccgaatgcc aatggcatcg agttccgcgt gcatctggga    120
tacctctata tgtcccctat tccagtgcct gaagatcaga ttgcggaacg cgtccccatg    180
ttccaggaac gcatcacgca ctacttccaa aactgggagc aatgctggc aaattggaag     240
```

```
gagcgagtat taggaaccat caatgagctg aatctctag agttcaagcc actgcctgac    300
tacgtgccta tcgatgatat tgtctccgga aaagccaaag acggcaccga agtactcatg    360
gaaaacttcg atcggctcat tcagctcgcc taccaaaact ggcaatacca ctttgagttc    420
ctcaacttgg gttacatcgc ttacctagat ttcttcaatt tctgcaagga agtcttccca    480
gatatccctg atcaatcaat tcgatgatg gttcagggcg tggatatgga gctgttccgc    540
cccgatgatg aactaaagat tctggcacag ctagcggtcg accttggcct gcaaactcac    600
tttgccaacc cggatgatcc gcaagctacc ttggctgcta tcgcaaaggc agaaggcggc    660
gcgacatgga tagcgcgctg ggaagaagca caagatccgt ggttcaactt caccgtcggt    720
aatggcttct acggtcacga taaatactgg atcgagcacc tggaacttcc actggggtac    780
atcgcggatt acatccgccg cctagatgaa ggccaaacca tctcccgccc gaaagatgaa    840
ctcatcgcag aaaaggaacg cgtggtggaa gaataccgcg acctttttgga tggagaacaa    900
ctcgcgcagt tgatgctaa atgcggcctc gctgctactg catcccccta tgtggaaaac    960
cataacttct acatcgagca ctggaccatg tcagtatttt ggcgcaaagt acgcgaactt   1020
tcccgcactc tccagggcta cggttttctgg gagaacgagg atgacatgtt gtacctcaac   1080
cgcactgaag tccgcgatgt cctcttcgac ctggctactg cgtggggtgt cggcgcaccc   1140
ggtggtccaa ttggcacgat catttggccg gaagaaattg agcgaagaaa agcaattgtc   1200
accgctttga aaactgcccg accagcgcca gctcttaaca ctcctccaga gtccatcacc   1260
gaacctttca cccgcatgct ctggggaatc accaccgaac aggtgcaatc atggttgggc   1320
aatgacgagg atgccgaaga aggaaccctt aaaggcatgg ctgcatcccc tggtgtggtg   1380
gaaggctacg ctcgagtaat tctcagcgca gatgaccttt cagaaatcca gcaggatgaa   1440
atcctcgttg cccctgtaac agcaccttct tggggcccaa tctttggcaa aatcaaggca   1500
acagtcactg atattggtgg catgatgagc catgctgcga tcgtgtgccg cgaatacggc   1560
ttgccggctg ttactggaac tggcgctgca tccaccacca tcaaaaccgg cgattacctc   1620
aaggtcgatg gaaccaaggg caaggttgtc attgttgatc cagatgcgcc acgcatcgaa   1680
ggacccggcg cgcacagcca tgcgcactca gtagcagcac atggggtgga tacacatgcc   1740
tag                                                                 1743

<210> SEQ ID NO 35
<211> LENGTH: 24
<212> TYPE: DNA
<213> ORGANISM: Artificial Sequence
<220> FEATURE:
<223> OTHER INFORMATION: Artificial construct

<400> SEQUENCE: 35
aaccaccgaa aggaggccct tcag                                            24

<210> SEQ ID NO 36
<211> LENGTH: 1833
<212> TYPE: DNA
<213> ORGANISM: Corynebacterium glutamicum

<400> SEQUENCE: 36
atgactactg ctgcaatcag gggccttcag ggcgaggcgc cgaccaagaa taaggaactg     60
ctgaactgga tcgcagacgc cgtcgagctc ttccagcctg aggctgttgt gttcgttgat    120
ggttcccagc tgagtgggga tcgcatggcg gaggatcttt tgaagccggg taccctcatc    180
aagctcaacg aggaaaagcg tccgaacagc tacctagctc gttccaaccc atctgacgtt    240
```

```
gcgcgcgttg agtcccgcac cttcatctgc tccgagaagg aagaagatgc tggcccaacc      300
aacaactggg ctccaccaca ggcaatgaag gacgaaatgt ccaagcatta cgctggttcc      360
atgaaggggc gcaccatgta cgtcgtgcct ttctgcatgg gtccaatcag cgatccggac      420
cctaagctcg gtgtgcagct cactgactcc gagtacgttg tcatgtccat gcgcatcatg      480
acccgcatgg gtattgaagc gctggacaag atcggcgcga acggcagctt cgtcaggtgc      540
ctccactccg ttggtgctcc tttggagcca ggcaggaag acgttgcatg gccttgcaac       600
gacaccaagt acatcaccca gttcccagag accaaggaaa tttggtccta cggttccggc      660
tacggcggaa acgcaatcct ggcaaagaag tgctacgcac tgcgtatcgc atctgtcatg      720
gctcgcgaag aaggatggat ggctgagcac atgctcatcc tgaagctgat caacccagag      780
ggcaaggcgt accacatcgc agcagcattc ccatctgctt gtggcaagac caacctcgcc      840
atgatcactc caaccatccc aggctggacc gctcaggttg ttggcgacga catcgcttgg      900
ctgaagctgc gcgaggacgg cctctacgca gttaacccag aaaatggttt cttcggtgtt      960
gctccaggca ccaactacgc atccaaccca atcgcgatga agactatgga accaggcaac     1020
accctgttca ccaacgtggc actcaccgac gacggcgaca tctggtggga aggcatggac     1080
ggcgacgccc cagctcacct cattgactgg atgggcaacg actggacccc agagtccgac     1140
gaaaacgctg ctcaccctaa ctcccgttac tgcgtagcaa tcgaccagtc cccagcagca     1200
gcacctgagt tcaacgactg ggaaggcgtc aagatcgacg caatcctctt cggtggacgt     1260
cgcgcagaca ccgtcccact ggttacccag acctacgact gggagcacgg cactatggtt     1320
ggtgcactgc tcgcatccgg tcagaccgca gcttccgcag aagcaaaggt cggcacactc     1380
cgccacgacc caatggcaat gctcccattc attggctaca cgctggtgaa atacctgcag     1440
aactggattg acatgggtaa caagggtggc gacaagatgc catccatctt cctggtcaac     1500
tggttccgcc gtggcgaaga tggacgcttc ctgtggcctg gcttcggcga caactctcgc     1560
gttctgaagt gggtcatcga ccgcatcgaa ggccacgttg gcgcagacga gaccgttgtt     1620
ggacacaccg ctaaggccga agacctcgac ctcgacggcc tcgacacccc aattgaggat     1680
gtcaaggaag cactgaccgc tcctgcagag cagtgggcaa cgacgttga agacaacgcc      1740 gagtacctca ctttcctcgg accacgtgtt cctgcagagg ttcacagcca gttcgatgct      1800
ctgaaggccc gcatttcagc agctcacgct taa                                  1833
```

<210> SEQ ID NO 37  
<211> LENGTH: 1455  
<212> TYPE: DNA  
<213> ORGANISM: Corynebacterium glutamicum

<400> SEQUENCE: 37

```
atggtgatct tcggtgtcac tggcgacttg gctcgaaaga agctgctccc cgccatttat       60
gatctagcaa accgcggatt gctgccccca ggattctcgt tggtaggtta cggccgccgc      120
gaatggtcca agaagacttt gaaaaatac gtacgcgatg ccgcaagtgc tggtgctcgt       180
acggagttcc gtgaaaatgt ttgggagcgc ctcgccgagg gtatggaatt tgttcgcggc      240
aactttgatg atgatgcagc tttcgacaac ctcgctgcaa cactcaagcg catcgacaaa      300
acccgcggca ccgccggcaa ctgggcttac tacctgtcca ttccaccaga ttccttcaca      360
gcggtctgcc accagctgga gcgttccggc atggctgaat ccaccgaaga agcatggcgc      420
cgcgtgatca tcgagaagcc tttcggccac aacctcgaat ccgcacacga gctcaaccag      480
```

```
ctggtcaacg cagtcttccc agaatcttct gtgttccgca tcgaccacta tttgggcaag      540
gaaacagttc aaaacatcct ggctctgcgt tttgctaacc agctgtttga gccactgtgg      600
aactccaact acgttgacca cgtccagatc acaatggctg aagatattgg cttgggtgga      660
cgtgctggtt actacgacgg catcggcgca gcccgcgacg tcatccagaa ccacctgatc      720
cagctcttgg ctctggttgc tatggaagaa ccaatttctt tcgtgccagc gcagctgcag      780
gcagaaaaga tcaaggtgct ctctgcgaca aagccgtgct acccattgga taaaacctcc      840
gctcgtggtc agtacgctgc cggttggcag ggctctgagt tagtcaaggg acttcgcgaa      900
gaagatggct tcaaccctga gtccaccact gagactttg cggcttgtac cttagagatc       960
acgtctcgtc gctgggctgg tgtgccgttc tacctgcgca ccggtaagcg tcttggtcgc     1020
cgtgttactg agattgccgt ggtgtttaaa gacgcaccac accagccttt cgacggcgac     1080
atgactgtat cccttggcca aaacgccatc gtgattcgcg tgcagcctga tgaaggtgtg     1140
ctcatccgct tcggttccaa ggttccaggt tctgctatgg aagtccgtga cgtcaacatg     1200
gacttctcct actcagaatc cttcactgaa gaatcacctg aagcatacga gcgcctcatt     1260
ttggatgcgc tgttagatga atccagcctc ttccctacca cgaggaagt ggaactgagc      1320 tggaagattc tggacccaat tcttgaagca tgggatgccg atggagaacc agaggattac     1380
ccagcgggta cgtggggtcc aaagagcgct gatgaaatgc tttcccgcaa cggtcacacc     1440
tggcgcaggc cataa                                                      1455

<210> SEQ ID NO 38
<211> LENGTH: 960
<212> TYPE: DNA
<213> ORGANISM: Corynebacterium glutamicum

<400> SEQUENCE: 38
atgatctttg aacttccgga taccaccacc cagcaaattt ccaagaccct aactcgactg       60
cgtgaatcgg gcacccaggt caccaccggc cgagtgctca ccctcatcgt ggtcactgac      120
tccgaaagcg atgtcgctgc agttaccgag tccaccaatg aagcctcgcg cgagcaccca      180
tctcgcgtga tcattttggt ggttggcgat aaaactgcag aaaacaaagt tgacgcagaa      240
gtccgtatcg gtggcgacgc tggtgcttcc gagatgatca tcatgcatct caacggacct      300
gtcgctgaca agctccagta tgtcgtcaca ccactgttgc ttcctgacac ccccatcgtt      360
gcttggtggc caggtgaatc accaaagaat ccttcccagg acccaattgg acgcatcgca      420
caacgacgca tcactgatgc tttgtacgac cgtgatgacg cactagaaga tcgtgttgag      480
aactatcacc caggtgatac cgacatgacg tgggcgcgcc ttacccagtg gcggggactt      540
gttgcctcct cattggatca cccaccacac agcgaaatca cttccgtgag gctgaccggt      600
gcaagcggca gtacctcggt ggatttggct gcaggctggt tggcgcggag gctgaaagtg      660
cctgtgatcc gcgaggtgac agatgctccc accgtgccaa ccgatgagtt tggtactcca      720
ctgctggcta tccagcgcct ggagatcgtt cgcaccaccg gctcgatcat catcaccatc      780
tatgacgctc ataccttca ggtagagatg ccggaatccg gcaatgcccc atcgctggtg      840
gctattggtc gtcgaagtga gtccgactgc ttgtctgagg agcttcgcca catgacccca      900
gatttgggct accagcacgc actatccggc ttgtccagcg tcaagctgga aaccgtctaa      960

<210> SEQ ID NO 39
<211> LENGTH: 14
<212> TYPE: DNA
<213> ORGANISM: Artificial Sequence
```

```
<220> FEATURE:
<223> OTHER INFORMATION: Artificial construct

<400> SEQUENCE: 39
tttaggggca aaaa                                                            14

<210> SEQ ID NO 40
<211> LENGTH: 2031
<212> TYPE: DNA
<213> ORGANISM: Corynebacterium glutamicum

<400> SEQUENCE: 40
atggacacca aggctgtaga cactgttcgt gtcctcgctg cagacgctgt agaaaactgt      60
ggctccggcc acccaggcac cgcaatgagc ctggctcccc ttgcatacac cttgtaccag     120
cgggttatga acgtagatcc acaggacacc aactgggcag gccgtgaccg cttcgttctt     180
tcttgtggcc actcctcttt gacccagtac atccagcttt acttgggtgg attcggcctt     240
gagatggatg acctgaaggc tctgcgcacc tgggattcct tgaccccagg acaccctgag     300
taccgccaca ccaagggcgt tgagatcacc actggccctc ttggccaggg tcttgcatct     360
gcagttggta tggctatggc tgctcgtcgt gagcgtggcc tattcgaccc aaccgctgct     420
gagggcgaat ccccattcga ccaccacatc tacgtcattg cttctgatgg tgaccttcag     480
gaaggtgtca cctctgaggc atcctccatc gctggcaccc agcagctggg caacctcatc     540
gtgttctggg atgacaaccg catctccatc gaagacaaca ctgagatcgc tttcaacgag     600
gacgttgttg ctcgttacaa ggcttacggc tggcagacca ttgaggttga ggctggcgag     660
gacgttgcag caatcgaagc tgcagtggct gaggctaaga aggacaccaa gcgacctacc     720
ttcatccgcg ttcgcaccat catcggcttc ccagctccaa ctatgatgaa caccggtgct     780
gtgcacggtg ctgctcttgg cgcagctgag gttgcagcaa ccaagactga gcttggattc     840
gatcctgagg ctcacttcgc gatcgacgat gaggttatcg ctcacacccg ctccctcgca     900
gagcgcgctg cacagaagaa ggctgcatgg caggtcaagt cgatgagtg ggcagctgcc     960 aaccctgaga caaggctct gttcgatcgc ctgaactccc gtgagcttcc agcgggctac    1020
gctgacgagc tcccaacatg ggatgcagat gagaagggcg tcgcaactcg taaggcttcc    1080
gaggctgcac ttcaggcact gggcaagacc cttcctgagc tgtgggggcgg ttccgctgac    1140 ctcgcaggtt ccaacaacac cgtgatcaag ggctcccctt ccttcggccc tgagtccatc    1200
tccaccgaga cctggtctgc tgagccttac ggccgtaacc tgcacttcgg tatccgtgag    1260
cacgctatgg gctccatcct caacggcatt tccctccacg gtggcacccg cccatacggc    1320
ggaaccttcc tcatcttctc cgactacatg cgtcctgcag ttcgtcttgc agctctcatg    1380
gagaccgacg cttactacgt ctggacccac gactccatcg gtctgggcga agatggccca    1440
acccaccagc tgttgaaaac cttggctgca ctgcgcgcca tcccaggtct gtccgtcctg    1500
cgtcctgcag atgcgaacga gaccgcccag gcttgggctg cagcacttga gtacaaggaa    1560
ggccctaagg gtcttgcact gacccgccag aacgttcctg ttctggaagg caccaaggag    1620
aaggctgctg aaggcgttcg ccgcggtggc tacgtcctgg ttgagggttc caaggaaacc    1680
ccagatgtga tcctcatggg ctccggctcc gaggttcagc ttgcagttaa cgctgcgaag    1740
gctctggaag ctgagggcgt tgcagctcgc gttgtttccg ttccttgcat ggattggttc    1800
caggagcagg acgcagagta catcgagtcc gttctgcctg cagctgtgac cgctcgtgtg    1860
tctgttgaag ctggcatcgc aatgccttgg taccgcttct gggcacccca gggccgtgct    1920
```

```
gtctcccttg agcacttcgg tgcttctgcg gattaccaga ccctgtttga gaagttcggc   1980
atcaccaccg atgcagtcgt ggcagcggcc aaggactcca ttaacggtta a            2031
```

<210> SEQ ID NO 41
<211> LENGTH: 1992
<212> TYPE: DNA
<213> ORGANISM: Corynebacterium glutamicum

<400> SEQUENCE: 41

```
atgtcctcac gtaaagagct tgccaatgct attcgtgcgc tgagcatgga cgcagtacag     60
aaagccaaat ccggtcaccc gggtgcccct atgggtatgg ctgacattgc cgaagtcctg    120
tggcgtgatt tcctgaaaca caacccgcag aatccgtcct gggctgaccg tgaccgcttc    180
gtgctgtcca acggccacgg ctccatgctg atctacagcc tgctgcacct caccggttac    240
gatctgccga tggaagaact gaaaaacttc cgtcagctgc actctaaaac tccgggtcac    300
ccggaagtgg gttacaccgc tgtgtgtgaa accaccaccg tccgctgggt cagggtatt    360 gccaacgcag tcggtatggc gattgcagaa aaaacgctgg cggcgcagtt taaccgtccg    420
ggccacgaca ttgtcgacca ctacacctac gccttcatgg cgacggctg catgatggaa    480 ggcatctccc acgaagtttg ctctctggcg gtacgctga agctgggtaa actgattgca    540
ttctacgatg acaacggtat ttctatcgat ggtcacgttg aaggctggtt caccgacgac    600
accgcaatgc gtttcgaagc ataccggctgg cacgttattc gcgacatcga cggtcatgac    660
gcggcatcta tcaaacgcgc agtagaagaa gcgcgcgcag tgactgacaa accttccctg    720
ctgatgtgca aaaccatcat cggtttcggt tccccgaaca aagccggtac ccacgactcc    780
cacggtgcgc cgctgggcga cgctgaaatt gccctgaccc gcgaacaact gggctggaaa    840
tatgcgccgt tcgaaatccc gtctgaaatc tatgctcagt gggatgcgaa agaagcaggc    900
caggcgaaag aatccgcatg gaacgagaaa ttcgctgctt acgcgaaagc atatccgcag    960
gaagccgctg aatttacccg ccgtatgaaa ggcgaaatgc cgtctgactt cgacgctaaa   1020
gcgaaagagt tcatcgctaa actgcaggct aatccggcga aaatcgccag ccgtaaagcg   1080
tctcagaatg ctatcgaagc gttcggtccg ctgttgccgg agttcctcgg cggttctgct   1140
gacctggcgc cgtctaacct gaccctgtgg tctggttcta agcaatcaa cgaagatgct   1200 gcgggtaact acatccacta cggtgttcgc gagttcggta tgaccgcgat gctaacggt   1260 atctccctgc acggtggctt cctgccgtac acctccacct tcctgatgtt cgtggaatac   1320
gcacgtaacg ccgtacgtat ggctgcgctg atgaaacagc gtcaggtgat ggtttacacc   1380
cacgactcca tcggtctggg cgaagacggc ccgactcacc agccggttga gcaggtcgct   1440
tctctgcgcg taaccccgaa catgtctaca tggcgtccgt gtgaccaggt tgaatccgcg   1500
gtcgcgtgga aatacggtgt tgagcgtcag gacggcccga ccgcactgat cctctcccgt   1560
cagaacctgg cgcagcagga acgaactgaa gagcaactgg caaacatcgc gcgcggtggt   1620
tatgtgctga aagactgcgc cggtcagccg gaactgattt tcatcgctac cggttcagaa   1680
gttgaactgg ctgttgctgc ctacgaaaaa ctgactgccg aaggcgtgaa agcgcgcgtg   1740
gtgtccatgc cgtctaccga cgcatttgac aagcaggatg ctgcttaccg tgaatccgta   1800
ctgccgaaag cggttactgc acgcgttgct gtagaagcgg gtattgctga ctactggtac   1860
aagtatgttg gcctgaacgg tgctatcgtc ggtatgacca ccttcggtga atctgctccg   1920
gcagagctgc tgtttgaaga gttcggcttc actgttgata cgttgttgc gaaagcaaaa   1980 gaactgctgt aa                                                        1992
```

<210> SEQ ID NO 42
<211> LENGTH: 1083
<212> TYPE: DNA
<213> ORGANISM: Corynebacterium glutamicum

<400> SEQUENCE: 42

```
atgtctcaca ttgatgatct tgcacagctc ggcacttcca cttggctcga cgacctctcc      60
cgcgagcgca ttacttccgg caatctcagc caggttattg aggaaaagtc tgtagtcggt     120
gtcaccacca acccagctat tttcgcagca gcaatgtcca agggcgattc ctacgacgct     180
cagatcgcag agctcaaggc cgctggcgca tctgttgacc aggctgttta cgccatgagc     240
atcgacgacg ttcgcaatgc ttgtgatctg ttcaccggca tcttcgagtc ctccaacggc     300
tacgacggcc gcgtgtccat cgaggttgac ccacgtatct tgctgaccg cgacgcaacc     360
ctggctcagg ccaaggagct gtgggcaaag gttgatcgtc caaacgtcat gatcaagatc     420
cctgcaaccc caggttcttt gccagcaatc accgacgctt ggctgaggg catcagcgtt     480
aacgtcacct tgatcttctc cgttgctcgc taccgcgagg tcatcgctgc gttcatcgag     540
ggcatcaagc aggctgctgc aaacggccac gacgtctcca agatccactc tgtggcttcc     600
ttcttcgtct cccgcgtcga cgttgagatc gacaagcgcc tcgaggcaat cggctccgat     660
gaggctttgg ctctgcgcgg caaggcaggc gttgccaacg ctcagcgcgc ttacgctgtg     720
tacaaggagc ttttcgacgc cgccgagctg cctgaaggtg ccaacactca gcgcccactg     780
tgggcatcca ccggcgtgaa gaaccctgcg tacgctgcaa ctctttacgt ttccgagctg     840
gctggtccaa acaccgtcaa caccatgcca gaaggcacca tcgacgcggt tctggagcag     900
ggcaacctgc acggtgacac cctgtccaac tccgcggcag aagctgacgc tgtgttctcc     960
cagcttgagg ctctgggcgt tgacttggca gatgtcttcc aggtcctgga gaccgagggt    1020
gtggacaagt tcgttgcttc ttggagcgaa ctgcttgagt ctatggaagc tcgcctgaag    1080
tag                                                                  1083
```

<210> SEQ ID NO 43
<211> LENGTH: 951
<212> TYPE: DNA
<213> ORGANISM: Corynebacterium glutamicum

<400> SEQUENCE: 43

```
atgaacgagt tagacggcat caaacagttc accactgtcg tggcagacag cggcgatatt      60
gagtccattc gccattatca tccccaggat gccaccacca atccttcgct gttactcaaa     120
gctgccggat tatcacaata tgagcattta atagacgatg ctatcgcctg gggtaaaaaa     180
aatggcaaga cccaggaaca acaggtggtc gcagcgtgtg acaaactggc ggtcaatttc     240
ggtgctgaaa tcctcaaaat cgtacccggt cgcgtgtcaa cagaagttga tgcacgcctc     300
tcttttgata agaaaagag tattgagaag gcgcgccatc tggtggactt gtatcagcaa     360
caaggcgttg agaaatcacg cattctgatc aagctggctt cgacctggga aggtattcgc     420
gcggcagaag agctggaaaa agaaggtatt aactgcaacc tgacgctgct gttttctttt     480
gcacaggcac gggcctgtgc ggaagcaggc gttttctga tttcgccgtt tgtcgggcgt      540
atttatgact ggtatcaggc acgcaagccg atggaccgt atgtggtgga agaagatccg     600
ggcgttaaat cggtgcgcaa tatctacgac tactataagc aacaccacta tgaaaccatt     660
gtgatgggcg cgagcttccg tcgcaccgaa caaatcctcg ccttaaccgg ctgcgatcga     720
```

```
ctgactatcg caccgaattt actgaaggag ctgcaggaaa agtttcgcc agtggtacgt      780 aaattaatcc caccttctca gacgttccca cgcccagctc ccatgagcga agcggagttc     840
cgttgggagc acaatcagga tgcgatggcg gtagaaaaac tgtctgaagg cattcgtctg    900
ttcgccgttg atcaacgcaa actggaagac cttcttgccg ccaaactata a              951

<210> SEQ ID NO 44
<211> LENGTH: 1452
<212> TYPE: DNA
<213> ORGANISM: Corynebacterium glutamicum

<400> SEQUENCE: 44
atgtcttaca catcttttaa aggcgatgat aaagccctca tcggcatagt tttatcagtt     60
ctcacatttt ggcttttttgc tcagtcaacc ctaaatatcg cccagatat ggcaactgat    120 ttagggatga gcgatggcac catgaacata gctgtcgtgg ccgccgcgtt attctgtgga    180
acatttatcg tcgcagccgg cggcatcgca gatgtctttg gccgagtacg aatcatgatg    240
attggcaaca tccttaacat cctgggatct ctcctcatcg ccacggcaac gacttcttta    300
gccacccaaa tggtgatcac cggccgagtt ctccaaggac tggcagcagc ggccatcatg    360
tctgcatccc tagcattagt taagacatat tggttaggta ctgaccgcca acgagcagtc    420
tccatttggt ccattggttc atggggtggc accggattct gcgcgctttt cgcgggtctt    480
gttgtagcaa gccccctttgg ttggagagga atcttcgccc tctgcgcgat cgtctccatc    540
gttgctattg cccttacccg ccacatcccg gaatcccgtc cggctcaatc cattggcatg    600
catttggatt ggagtggcat catcgttctt gccctcagtg ttctatctct tgaattgttt    660
attacccaag gtgaatcact tggctggacg cactggatga cctggactct ccttgccgtt    720
tctttgacat ttcttgcagt tttcgtcttc attgaacgca tcgccagctg gccagttctc    780
gacttcaacc ttttcaaaga ccacgccttc agcggtgcga ccatcaccaa cttcattatg    840
agcgctactg gcggagtagt tgccgttgtc atgtgggttc agcaaatggg atggggtgtc    900
tccccaacaa tctcgggact caccagcatc ggcttcgcag cctttgtcat cctttttcatt    960 cgagttggag aaaaggccat gcagaaagtt ggcgcccgag cagtgatcat caccgctggc   1020
atcttggtag cgaccgcgac cgccctccta atgatcaccg cggtcagcga gtcaacgtac   1080
atcgtcatct ccctcgccgg cttctccctt tatggcttg gctcggact cttcgccacc     1140 ccagtcaccg atactgcgct tggaacactt cccaaagacc gtaccggcgc tggtgcaggt   1200
gtattcaaga tgtcctcttc cctcggcgca gcactcggca tcgcaatctc cacttcagtg   1260
ttcctcgcac ttcgcgacgg cacctccatc aactccgacg tcgcactcgc cggaacagtt   1320
tcacttggca tcaacgttgt attcgcagca acagccacca tcaccgcagc agtcccttatt   1380 ccaaaagccg ctggcaaagt ctcacaaacc agcatcaccc ttcctgagcc agctatcgct   1440
gtaaaaatct aa                                                       1452

<210> SEQ ID NO 45
<211> LENGTH: 174
<212> TYPE: DNA
<213> ORGANISM: Artificial Sequence
<220> FEATURE:
<223> OTHER INFORMATION: Artificial construct

<400> SEQUENCE: 45
atggatcttt cccttctcaa ggaaaccctc ggcaactacg agaccttcgg tggcaacatc      60
ggtaccgctc ttcagagcat cccaacccctg ctcgattcca tccttaactt cttcgacaac  120
```
ttcggagacc tcgctgacac caccggcgag aatctggata acttctcttc ctaa    174

<210> SEQ ID NO 46
<211> LENGTH: 27
<212> TYPE: DNA
<213> ORGANISM: Artificial Sequence
<220> FEATURE:
<223> OTHER INFORMATION: Artificial construct

<400> SEQUENCE: 46
gagaaatcct gaaaggaggc ccttcag    27

<210> SEQ ID NO 47
<211> LENGTH: 138
<212> TYPE: DNA
<213> ORGANISM: Artificial Sequence
<220> FEATURE:
<223> OTHER INFORMATION: Artificial construct

<400> SEQUENCE: 47
atggaaaacg tttacgagtt ccttggaaac cttgatgtcc tttccggctc cggcctcatc    60
ggctacgtct tcgacttcct cggcgcttcc agcaagtggg ctggcgcagt tgctgacctc    120
atcggtctgc ttggctaa    138

<210> SEQ ID NO 48
<211> LENGTH: 1209
<212> TYPE: DNA
<213> ORGANISM: Bacillus subtilis

<400> SEQUENCE: 48
atgaaaaata ttattgcatt gtcttctgtc ccgcttgtga tgacactcgg gaactccatg    60
ctgattcctg ttcttccgat gatggagaaa aagctgtctg tgacttcatt tcaagtatct    120
ttaatcatta ctgtatattc agtagtagca attatttgca ttccgattgc cggatatttg    180
tcggatcgtt tcgggagaaa aaaaatattg cttccatgcc tcctcattgc aggattgggg    240
ggagccgtag ctgcttttgc ctcgacctat atgaaaaatc cttatgctat gatcttggcg    300
gggcgggttc ttcaaggcat tggttctgca ggtgccgctc cgattgtcat gccgtttatc    360
ggcgacctgt ttaaaggaga cgatgaaaag gtcagcgcgg tcttggcga tattgaaacc    420
gccaacacgt cagggaaggt actgagtccc atacttggag ccttactggc ttcttggtat    480
tggtttgtac cgttttggtt tattccgttt ttctgtttga tcagcttttt gctcgtattg    540
tttttggtgg ccaagcctga agaagatgaa gatgcgcctg ctgtttctga gtttattaag    600
agtgtgaaga aaattttaa acaggatggt cgctggcttt ataccggtctt cattatcggg    660
tgtgtcatta tgttttttgtt atttggcgta ttattttatt tatcagatac gctggagaac    720
aagtatgcta ttgacggagt agctaaaggc ggattactgg caatcccact tttgtttttg    780
tcaaccagtt ctttatagc tggcaaaaag atcggtaaag ataaaggccg aatgaaattt    840
tgcgttgtta caggaatgat tctgttaacc ctttcgttta ttgccttgtg gtggaaccac    900
agttttatt ttttatttgt cttttttaagc tttggcggga ttgggattgg aatggctctt    960
cctgctttag atgcattgat aaccgaaggg attgaaagtg aacaatgcgg aaccatttcc    1020
tccttttaca atagcatgcg ctttatagga gtagctctcg gtccacctgt ttttgctgca    1080
ttaatgtcta atgcaaactg gattattttc atactctcgg cgtttttgcag catcgtttct    1140
ttattttttag tgctctttac tgtagatgct aaaaaaagtg aagaagaaaa aaacttaggg    1200
acggtctag                                                    1209

<210> SEQ ID NO 49
<211> LENGTH: 1209
<212> TYPE: DNA
<213> ORGANISM: Artificial Sequence
<220> FEATURE:
<223> OTHER INFORMATION: ymfD BSU16825 codon optimized for
      Corynebacterium glutamicum

<400> SEQUENCE: 49

```
atgaagaaca tcattgcgct gtcctctgtg ccactcgtta tgacccttgg caactctatg     60
ctgatccccg ttctccccat gatggagaag aaactctcag tcacttcgtt tcaggtgtcc    120
ctcatcatca ccgtgtattc tgtcgttgcc atcatctgca ttcccatcgc tggctacctt    180
tcagatcgct tcggtcgcaa gaagattctg ctcccttgct tgctgatcgc tggccttggc    240
ggagctgtcg cagcattcgc atctacgtac atgaagaacc cgtatgctat gatccttgcg    300
ggtcgtgtcc ttcaaggcat cggctctgct ggtgctgccc cgattgtaat gccgttcatt    360
ggtgacctct taagggcga tgatgagaaa gtatcagctg gcctgggaga tattgaaacc    420
gccaatacgt ccgggaaagt gcttagccca attctcggag ccttttggc tagctggtat     480
tggtttgtcc cgttttggtt catccctttc ttctgcctta tttccttcct tctggtgctc    540
tttctggtgg ccaaacctga agaggacgaa gatgccccag cagttagcga gttcatcaaa    600
tcggtcaaga aaatcttcaa gcaggatggc cgatggctgt acaccgtgtt catcatcggg    660
tgtgtcatta tgttccttct cttcggggta ctgtttttacc tgagcgacac cctggaaaac    720
aagtacgcaa tcgacggtgt tgcgaagggt ggtttgctgg caattccact gctcttcctg    780
tccacatcct cctttatcgc tggtaagaaa atcggtaaag acaagggccg catgaagttt    840
tgcgttgtga ccggaatgat cctgctcaca ttgtccttca tcgcactgtg gtggaatcac    900
agcttctact tcttgttcgt gttcctgtct tttggcggaa tcggcattgg catggcgttg    960
cctgcgttgg atgccctcat taccgaaggg atcgaatcgg agcagtgtgg aaccatttcc   1020
tccttctaca actcaatgcg gttcatcgga gtcgctctgg gtccaccagt ctttgcagcc   1080
ctgatgtcca atgcgaactg gatcatcttt atcctgtcgg cattctgctc cattgtttcc   1140
ctgttcttgg tgctgttcac tgttgacgca agaagtccg aagaggagaa gaacttgggc    1200
actgtttaa                                                           1209
```

<210> SEQ ID NO 50
<211> LENGTH: 2180
<212> TYPE: DNA
<213> ORGANISM: Artificial Sequence
<220> FEATURE:
<223> OTHER INFORMATION: Artificial construct for a gene encoding
      TrpEGS38F

<400> SEQUENCE: 50

```
atgagcacga tcccccatgt tttctcccta gatgtccgct atcacgagga tgcttctgca     60
ttgtttgccc acttgggtgg cacaaccgca gatgatgcag ccctgttgga attcgctgat    120
atcaccacca agaatggtat ttcttccctc gcggtgttga agagttcggt gcgcattacg    180
tgcacgggca acacggtggt aacgcagccg ctgacggact cgggtagggc agtggttgcg    240
cgcctaacgc agcagcttgg ccagtacaac accgcagaga acacctttag cttccccgcc    300
tcagatgcgt tgatgagcg cgagcgcctc accgcaccaa gcaccatcga agtgctgcgc    360
aagttgcagt tcgagtccgg ctacagcgac gcgtccctgc cactgctcat gggcggtttc    420
```

```
gcgtttgatt tcttagaaac ctttgaaacg ctccccgctg tcgaggagag cgtcaacact      480
taccccgatt accagttcgt cctcgcggaa atcgtcctgg acatcaatca ccaggaccag      540
accgccaaac tcgccggcgt ctccaacgcc ccaggcgagc tcgaggccga gctcaacaag      600
ctttcattgc ttatcgacgc cgccctcccc gcaaccgaac acgcctacca aaccacccct      660
cacgacggcg acactcttcg cgttgtggct gatattcccg atgctcagtt ccgcacccag      720
atcaatgagc tgaaagaaaa catttacaac ggtgacatct accaagttgt cccggcgcgc      780
actttcaccg caccatgtcc tgatgcattc gctgcttatc tgcagctgcg tgccaccaac      840
ccgtcgccgt acatgttcta tatccgtggc ctcaacgaag ccgctcccta tgaactttt       900 ggcgcatccc ctgagtccaa cctcaagttc accgctgcta accgtgagct gcagctgtac      960
ccaatcgcag gtaccgcc   ccgtggactc aacccagatg gctccatcaa cgatgagcta     1020
gatatccgca atgagttgga tatgcgcact gatgccaaag agatcgcgga gcacaccatg     1080
cttgtcgatc tcgcccgcaa cgacctggcc cgcgtctcgg tcccagcgtc gcgccgggtt     1140
gcggatcttt tgcaggtgga tcgctattcc cgcgtgatgc acttggtgtc ccgtgtgacg     1200
gcgacgttgg acccagagct tgatgctttg gacgcctatc gggcgtgcat gaatatgggc     1260
acgttgaccg gcgctccgaa gttgcgcgct atggagctgt tgcgcggcgt cgaaaagcgc     1320
aggcgtggtt cttatggtgg ggcagtgggg tacctgcgcg gcaatggcga tatggataat     1380
tgcattgtta ttcgttcggc gtttgtccag gatggtgtgg ctgctgtgca ggctggtgct     1440
ggtgtggtcc gcgattctaa tcctcaatct gaagccgatg agacgttgca caaggcgtat     1500
gccgtgttga atgccattgc gcttgctgct ggttccactt tggaggtcat ccgatgacac     1560
acgttgttct cattgataat cacgattctt ttgtctacaa cctggtggat gcgttcgccg     1620
tggccggtta taagtgcacg gtgttccgca atacggtgcc agtggaaacc attttggcag     1680
ccaacccgga cctgatctgc ctttcacctg gacctggtta ccctgccgat gcgggcaaca     1740
tgatggcgct gatcgagcgc acactcggcc agattccttt actgggtatt tgcctcggct     1800
accaggcact catcgaatac cacggcggca aggttgagcc ttgtggccct gtgcacggca     1860
ccaccgacaa catgatcctt actgatgcag gtgtgcagag ccctgttttt gcaggtcttg     1920
ccactgatgt tgagcctgat catccagaaa tcccaggccg caaggttcca attggccgtt     1980
atcactcact gggctgcgtg gttgcccag acggtattga atcactaggt acctgttcct      2040
cggagattgg tgatgtcatc atggcggcac gcaccaccga tggaaaggcc attggcctgc     2100
agtttcaccc tgagtcagtg ctaagcccaa cgggtcctgt catttttgtcc cgctgtgtcg     2160 aacagcttct cgcgaactaa                                                 2180
```

<210> SEQ ID NO 51
<211> LENGTH: 2180
<212> TYPE: DNA
<213> ORGANISM: Artificial Sequence
<220> FEATURE:
<223> OTHER INFORMATION: Artificial construct for a gene encoding
      TrpEGS38R

<400> SEQUENCE: 51

```
atgagcacga atccccatgt tttctcccta gatgtccgct atcacgagga tgcttctgca       60
ttgtttgccc acttgggtgg cacaaccgca gatgatgcag ccctgttgga acgcgctgat      120
atcaccacca agaatggtat ttcttccctc gcggtgttga agagttcggt gcgcattacg      180
tgcacgggca acacggtggt aacgcagccg ctgacggact cgggtagggc agtggttgcg      240
```

```
cgcctaacgc agcagcttgg ccagtacaac accgcagaga acacctttag cttccccgcc 300
tcagatgcgg ttgatgagcg cgagcgcctc accgcaccaa gcaccatcga agtgctgcgc 360
aagttgcagt tcgagtccgg ctacagcgac gcgtccctgc cactgctcat gggcggtttc 420
gcgtttgatt tcttagaaac ctttgaaacg ctccccgctg tcgaggagag cgtcaacact 480
```

```

taccccgatt accagttcgt cctcgcggaa atcgtcctgg acatcaatca ccaggaccag 540
accgccaaac tcgccggcgt ctccaacgcc ccaggcgagc tcgaggccga gctcaacaag 600
ctttcattgc ttatcgacgc cgccctcccc gcaaccgaac acgcctacca aaccacccct 660
cacgacggcg acactcttcg cgttgtggct gatattcccg atgctcagtt ccgcacccag 720
atcaatgagc tgaaagaaaa catttacaac ggtgacatct accaagttgt cccggcgcgc 780
actttcaccg caccatgtcc tgatgcattc gctgcttatc tgcagctgcg tgccaccaac 840
ccgtcgccgt acatgttcta tatccgtggc ctcaacgaag gccgctccta tgaacttttt 900
ggcgcatccc ctgagtccaa cctcaagttc accgctgcta accgtgagct gcagctgtac 960
ccaatcgcag gtacccgccc ccgtggactc aacccagatg gctccatcaa cgatgagcta 1020
gatatccgca atgagttgga tatgcgcact gatgccaaag agatcgcgga gcacaccatg 1080
cttgtcgatc tcgcccgcaa cgacctggcc cgcgtctcgg tcccagcgtc gcgccgggtt 1140
gcggatcttt tgcaggtgga tcgctattcc cgcgtgatgc acttggtgtc ccgtgtgacg 1200
gcgacgttgg acccagagct tgatgctttg gacgcctatc gggcgtgcat gaatatgggc 1260
acgttgaccg gcgctccgaa gttgcgcgct atggagctgt tgcgcggcgt cgaaaagcgc 1320
aggcgtggtt cttatggtgg ggcagtgggg tacctgcgcg gcaatggcga tatggataat 1380
tgcattgtta ttcgttcggc gtttgtccag gatggtgtgg ctgctgtgca ggctggtgct 1440
ggtgtggtcc gcgattctaa tcctcaatct gaagccgatg agacgttgca caaggcgtat 1500
gccgtgttga atgccattgc gcttgctgct ggttccactt tggaggtcat ccgatgacac 1560
acgttgttct cattgataat cacgattctt ttgtctacaa cctggtggat gcgttcgccg 1620
tggccggtta taagtgcacg gtgttccgca atacggtgcc agtggaaacc attttggcag 1680
ccaacccgga cctgatctgc ctttcacctg gacctggtta ccctgccgat gcgggcaaca 1740
tgatggcgct gatcgagcgc acactcggcc agattccttt actgggtatt tgcctcggct 1800
accaggcact catcgaatac cacggcggca aggttgagcc ttgtggccct gtgcacggca 1860
ccaccgacaa catgatcctt actgatgcag gtgtgcagag ccctgttttt gcaggtcttg 1920
ccactgatgt tgagcctgat catccagaaa tcccaggccg caaggttcca attggccgtt 1980
atcactcact gggctgcgtg gttgccccag acggtattga atcactaggt acctgttcct 2040
cggagattgg tgatgtcatc atggcggcac gcaccaccga tggaaaggcc attggcctgc 2100
agtttcaccc tgagtcagtg ctaagcccaa cgggtcctgt cattttgtcc cgctgtgtcg 2160
aacagcttct cgcgaactaa 2180
```

<210> SEQ ID NO 52
<211> LENGTH: 2177
<212> TYPE: DNA
<213> ORGANISM: Artificial Sequence
<220> FEATURE:
<223> OTHER INFORMATION: Artificial construct for a gene encoding TrpEGS40R

<400> SEQUENCE: 52

```
atgcaaacac aaaaaccgac tctcgaactg ctaacctgcg aaggcgctta tcgcgacaat 60
```

```
cccaccgcgc ttttcacca gttgtgtggg gatcgtccgg caacgctgct gctggaattc      120
gcagatatcg acagcaaaga tgatttaaaa agcctgctgc tggtagacag tgcgctgcgc      180
attacagctt taggtgacac tgtcacaatc caggcacttt ccggcaacgg cgaagccctc      240
ctggcactac tggataacgc cctgcctgcg ggtgtggaaa gtgaacaatc accaaactgc      300
cgtgtgctgc gcttccccc tgtcagtcca ctgctggatg aagacgcccg cttatgctcc      360
ctttcggttt ttgacgcttt ccgtttattg cagaatctgt tgaatgtacc gaaggaagaa      420
cgagaagcca tgttcttcgg cggcctgttc tcttatgacc ttgtggcggg atttgaagat      480
ttaccgcaac tgtcagcgga aaataactgc cctgatttct gttttatct cgctgaaacg      540 ctgatggtga ttgaccatca gaaaaaagc acccgtattc aggccagcct gtttgctccg      600
aatgaagaag aaaaacaacg tctcactgct cgcctgaacg aactacgtca gcaactgacc      660
gaagccgcgc cgccgctgcc agtggtttcc gtgccgcaca tgcgttgtga atgtaatcag      720
agcgatgaag agttcggtgg cgtagtgcgt ttgttgcaaa aagcgattcg cgctggagaa      780
attttccagg tggtgccatc tcgccgtttc tctctgccct gcccgtcacc gctggcggcc      840
tattacgtgt gaaaaagag taatcccagc ccgtacatgt tttttatgca ggataatgat      900
ttcaccctat ttggcgcgtc gccggaaagc tcgctcaagt atgatgccac cagccgccag      960
attgaaatct acccgattgc cggaacacgc ccacgcggtc gtcgcgccga tggttcactg     1020
gacagggatc tcgacagccg tattgaactg gaaatgcgta ccgatcataa agagctgtct     1080
gaacatctga tgctggttga tctcgcccgt aatgatctgg cacgcatttg cacccccggc     1140
agccgctacg tcgccgatct caccaaagtt gaccgttatt cctatgtgat gcacctcgtc     1200
tctcgcgtag tcgcgaact gcgtcacgat cttgacgccc tgcacgctta tcgcgcctgt     1260
atgaatatgg ggacgttaag cggtgcgccg aaagtacgcg ctatgcagtt aattgccgag     1320
gcggaaggtc gtcgccgcgg cagctacggc ggcgcggtag gttatttcac cgcgcatggc     1380
gatctcgaca cctgcattgt gatccgctcg gcgctggtgg aaaacggtat cgccaccgtg     1440
caagcgggtg ctggtgtagt ccttgattct gttccgcagt cggaagccga cgaaacccgt     1500
aacaaagccc gcgctgtact gcgcgctatt gccaccgcgc atcatgcaca ggagactttc     1560
tgatggctga cattctgctg ctcgataata tcgactcttt tacgtacaac ctggcagatc     1620
agttgcgcag caatgggcat aacgtggtga tttaccgcaa ccatattccg gcgcaaacct     1680
taattgaacg cctggcgacc atgagcaatc cggtgctgat gctttctcct ggccccggtg     1740
tgccgagcga agccggttgt atgccggaac tcctcacccg cttgcgtggc aagctgccca     1800
ttattggcat ttgcctcgga catcaggcga ttgtcgaagc ttacggggc tatgtcggtc     1860 aggcgggcga aattctccac ggtaaagcct ccagcattga acatgacggt caggcgatgt     1920
ttgccggatt aacaaacccg ctgccggtgg cgcgttatca ctcgctggtt ggcagtaaca     1980
ttccggccgg tttaaccatc aacgcccatt ttaatggcat ggtgatggca gtacgtcacg     2040
atgcggatcg cgtttgtgga ttccagttcc atccggaatc cattctcacc acccagggcg     2100
ctcgcctgct ggaacaaacg ctggcctggg cgcagcagaa actagagcca gccaacacgc     2160
tgcaaccgat tctgtaa                                                    2177

<210> SEQ ID NO 53
<211> LENGTH: 2177
<212> TYPE: DNA
<213> ORGANISM: Artificial Sequence
<220> FEATURE:
```

<223> OTHER INFORMATION: Artificial construct for a gene encoding TrpEGS40F

<400> SEQUENCE: 53

```
atgcaaacac aaaaaccgac tctcgaactg ctaacctgcg aaggcgctta tcgcgacaat    60
cccaccgcgc ttttcacca gttgtgtggg gatcgtccgg caacgctgct gctggaattc   120
gcagatatcg acagcaaaga tgatttaaaa agcctgctgc tggtagacag tgcgctgcgc   180
attacagctt taggtgacac tgtcacaatc caggcacttt ccggcaacgg cgaagccctc   240
ctggcactac tggataacgc cctgcctgcg ggtgtggaaa gtgaacaatc accaaactgc   300
cgtgtgctgc gcttccccc tgtcagtcca ctgctggatg aagacgcccg cttatgctcc   360
ctttcggttt ttgacgcttt ccgtttattg cagaatctgt tgaatgtacc gaaggaagaa   420
cgagaagcca tgttcttcgg cggcctgttc tcttatgacc ttgtggcggg atttgaagat   480
ttaccgcaac tgtcagcgga aaataactgc cctgatttct gttttatct cgctgaaacg   540
ctgatggtga ttgaccatca gaaaaaaagc accgtattc aggccagcct gtttgctccg   600
aatgaagaag aaaaacaacg tctcactgct cgcctgaacg aactacgtca gcaactgacc   660
gaagccgcgc gccgctgcc agtggtttcc gtgccgcaca tgcgttgtga atgtaatcag   720
agcgatgaag agttcggtgg cgtagtgcgt ttgttgcaaa aagcgattcg cgctggagaa   780
attttccagg tggtgccatc tcgccgtttc tctctgccct gcccgtcacc gctggcggcc   840
tattacgtgc tgaaaagag taatcccagc ccgtacatgt tttttatgca ggataatgat   900
ttcaccctat ttggcgcgtc gccggaaagc tcgctcaagt atgatgccac cagccgccag   960
attgaaatct acccgattgc cggaacacgc ccacgcggtc gtcgcgccga tggttcactg  1020
gacagggatc tcgacagccg tattgaactg gaaatgcgta ccgatcataa agagctgtct  1080
gaacatctga tgctggttga tctcgcccgt aatgatctgg cacgcatttg caccccggc  1140
agccgctacg tcgccgatct caccaaagtt gaccgttatt cctatgtgat gcacctcgtc  1200
tctcgcgtag tcggcgaact gcgtcacgat cttgacgccc tgcacgctta tcgcgcctgt  1260
atgaatatgg ggacgttaag cggtgcgccg aaagtacgcg ctatgcagtt aattgccgag  1320
gcggaaggtc gtcgccgcgg cagctacggc ggcgcggtag gttatttcac cgcgcatggc  1380
gatctcgaca cctgcattgt gatccgctcg gcgctggtgg aaaacggtat cgccaccgtg  1440
caagcgggtg ctggtgtagt ccttgattct gttccgcagt cggaagccga cgaaacccgt  1500
aacaaagccc gcgctgtact gcgcgctatt gccaccgcgc atcatgcaca ggagactttc  1560
tgatggctga cattgctg tcgataata tcgactcttt tacgtacaac ctggcagatc  1620
agttgcgcag caatgggcat aacgtggtga tttaccgcaa ccatattccg gcgcaaacct  1680
taattgaacg cctggcgacc atgagcaatc cggtgctgat gctttctcct ggccccggtg  1740
tgccgagcga agccggttgt atgccggaac tcctcacccg cttgcgtggc aagctgccca  1800
ttattggcat ttgcctcgga catcaggcga ttgtcgaagc ttacggggc tatgtcggtc  1860
aggcgggcga aattctccac ggtaaagcct ccagcattga acatgacggt caggcgatgt  1920
tgccggatt aacaaacccg ctgccggtgg cgcgttatca ctcgctggtt ggcagtaaca  1980
ttccggccgg tttaaccatc aacgcccatt ttaatggcat ggtgatggca gtacgtcacg  2040
atgcggatcg cgtttgtgga ttccagttcc atccggaatc cattctcacc acccagggcg  2100
ctcgcctgct ggaacaaacg ctggcctggg cgcagcagaa actagagcca gccaacacgc  2160
tgcaaccgat tctgtaa                                                 2177
```

<210> SEQ ID NO 54
<211> LENGTH: 2177
<212> TYPE: DNA
<213> ORGANISM: Artificial Sequence
<220> FEATURE:
<223> OTHER INFORMATION: Artificial construct

<400> SEQUENCE: 54

| | | | | | |
|---|---|---|---|---|---|
| atgcaaacac | aaaaaccgac | tctcgaactg | ctaacctgcg | aaggcgctta | tcgcgacaat | 60 |
| cccaccgcgc | ttttttcacca | gttgtgtggg | gatcgtccgg | caacgctgct | gctggaatcc | 120 |
| gcagatatcg | acagcaaaga | tgatttaaaa | agcctgctgc | tggtagacag | tgcgctgcgc | 180 |
| attacagctt | taggtgacac | tgtcacaatc | caggcacttt | ccggcaacgg | cgaagccctc | 240 |
| ctggcactac | tggataacgc | cctgcctgcg | ggtgtggaaa | gtgaacaatc | accaaactgc | 300 |
| cgtgtgctgc | gcttcccccc | tgtcagtcca | ctgctggatg | aagacgcccg | cttatgctcc | 360 |
| ctttcggttt | ttgacgcttt | ccgtttattg | cagaatctgt | tgaatgtacc | gaaggaagaa | 420 |
| cgagaagcca | tgttcttcgg | cggcctgttc | tcttatgacc | ttgtggcggg | atttgaagat | 480 |
| ttaccgcaac | tgtcagcgga | aaataactgc | cctgatttct | gtttttatct | cgctgaaacg | 540 |
| ctgatggtga | ttgaccatca | gaaaaaaagc | acccgtattc | aggccagcct | gtttgctccg | 600 |
| aatgaagaag | aaaaacaacg | tctcactgct | cgcctgaacg | aactacgtca | gcaactgacc | 660 |
| gaagccgcgc | cgccgctgcc | agtggtttcc | gtgccgcaca | tgcgttgtga | atgtaatcag | 720 |
| agcgatgaag | agttcggtgg | cgtagtgcgt | tgttgcaaa | aagcgattcg | cgctggagaa | 780 |
| attttccagg | tggtgccatc | tcgccgtttc | tctctgccct | gcccgtcacc | gctggcggcc | 840 |
| tattacgtgc | tgaaaaagag | taatcccagc | ccgtacatgt | tttttacgca | ggataatgat | 900 |
| ttcacccctat | ttggcgcgtc | gccggaaagc | tcgctcaagt | atgatgccac | cagccgccag | 960 |
| attgaaatct | acccgattgc | cggaacacgc | ccacgcggtc | gtcgcgccga | tggttcactg | 1020 |
| gacagggatc | tcgacagccg | tattgaactg | gaaatgcgta | ccgatcataa | agagctgtct | 1080 |
| gaacatctga | tgctggttga | tctcgcccgt | aatgatctgg | cacgcatttg | cacccccggc | 1140 |
| agccgctacg | tcgccgatct | caccaaagtt | gaccgttatt | cctatgtgat | gcacctcgtc | 1200 |
| tctcgcgtag | tcggcgaact | gcgtcacgat | cttgacgccc | tgcacgctta | tcgcgcctgt | 1260 |
| atgaatatgg | ggacgttaag | cggtgcgccg | aaagtacgcg | ctatgcagtt | aattgccgag | 1320 |
| gcggaaggtc | gtcgccgcgg | cagctacggc | ggcgcggtag | gttatttcac | cgcgcatggc | 1380 |
| gatctcgaca | cctgcattgt | gatccgctcg | gcgctggtgg | aaaacggtat | cgccaccgtg | 1440 |
| caagcgggtg | ctggtgtagt | ccttgattct | gttccgcagt | cggaagccga | cgaaacccgt | 1500 |
| aacaaagccc | gcgctgtact | gcgcgctatt | gccaccgcgc | atcatgcaca | ggagactttc | 1560 |
| tgatggctga | cattctgctg | ctcgataata | tcgactcttt | tacgtacaac | ctggcagatc | 1620 |
| agttgcgcag | caatgggcat | aacgtggtga | tttaccgcaa | ccatattccg | gcgcaaacct | 1680 |
| taattgaacg | cctggcgacc | atgagcaatc | cggtgctgat | gctttctcct | ggccccggtg | 1740 |
| tgccgagcga | agccggttgt | atgccggaac | tcctcacccg | cttgcgtggc | aagctgccca | 1800 |
| ttattggcat | ttgcctcgga | catcaggcga | ttgtcgaagc | ttacggggc | tatgtcggtc | 1860 |
| aggcgggcga | aattctccac | ggtaaagcct | ccagcattga | acatgacggt | caggcgatgt | 1920 |
| tgccggatt | aacaaacccg | ctgccggtgg | cgcgttatca | ctcgctggtt | ggcagtaaca | 1980 |
| ttccggccgg | tttaaccatc | aacgcccatt | ttaatggcat | ggtgatggca | gtacgtcacg | 2040 |
| atgcggatcg | cgtttgtgga | ttccagttcc | atccggaatc | cattctcacc | acccagggcg | 2100 |

```
ctcgcctgct ggaacaaacg ctggcctggg cgcagcagaa actagagcca gccaacacgc    2160
tgcaaccgat tctgtaa                                                   2177

<210> SEQ ID NO 55
<211> LENGTH: 1053
<212> TYPE: DNA
<213> ORGANISM: Artificial Sequence
<220> FEATURE:
<223> OTHER INFORMATION: Artificial construct for the gene encoding
      AroGD146N

<400> SEQUENCE: 55
atgaattatc agaacgacga tttacgcatc aaagaaatca aagagttact tcctcctgtc     60
gcattgctgg aaaaattccc cgctactgaa atgccgcga atacggttgc ccatgcccga    120
aaagcgatcc ataagatcct gaaaggtaat gatgatcgcc tgttggttgt gattggccca    180
tgctcaattc atgatcctgt cgcggcaaaa gagtatgcca ctcgcttgct ggcgctgcgt    240
gaagagctga aagatgagct ggaaatcgta atgcgcgtct attttgaaaa gccgcgtacc    300
acggtgggct ggaaagggct gattaacgat ccgcacatgg ataatagctt ccagatcaac    360
gacggtctgc gtatagcccg taaattgctg cttgatatta cgacagcgg tctgccagcg    420 gcaggtgagt ttctcaatat gatcacccca caatatctcg ctgacctgat gagctggggc    480
gcaattggcg cacgtaccac cgaatcgcag gtgcaccgcg aactggcatc agggctttct    540
tgtccggtcg gcttcaaaaa tggcaccgac ggtacgatta agtggctat cgatgccatt    600 aatgccgccg tgcgccgca ctgcttcctg tccgtaacga aatgggggca ttcggcgatt    660
gtgaatacca gcggtaacgg cgattgccat atcattctgc gcggcggtaa agagcctaac    720
tacagcgcga agcacgttgc tgaagtgaaa gaagggctga caaagcagg cctgccagca    780 caggtgatga tcgatttcag ccatgctaac tcgtccaaac aattcaaaaa gcagatggat    840
gtttgtgctg acgtttgcca gcagattgcc ggtggcgaaa aggccattat tggcgtgatg    900
gtggaaagcc atctggtgga aggcaatcag agcctcgaga gcggggagcc gctggcctac    960
ggtaagagca tcaccgatgc ctgcatcggc tgggaagata ccgatgctct gttacgtcaa   1020
ctggcgaatg cagtaaaagc gcgtcgcggg taa                                1053

<210> SEQ ID NO 56
<211> LENGTH: 1101
<212> TYPE: DNA
<213> ORGANISM: Artificial Sequence
<220> FEATURE:
<223> OTHER INFORMATION: Artificial construct

<400> SEQUENCE: 56
atgagttctc cagtctcact cgaaaacgcg gcgtcaacca gcaacaagcg cgtcgtggct     60
ttccacgagc tgcctagccc tacagacctc atcgccgcaa acccactgac accaaagcag    120
gcttccaagg tggagcagga tcgccaggac atcgctgata tcttcgctgg cgacgatgac    180
cgcctcgttg tcgttgtggg accttgctca gttcacgatc ctgaagcagc catcgattac    240
gcaaaccgcc tggctccgct ggcaaagcgc cttgatcagg acctcaagat tgtcatgcgc    300
gtgtacttcg agaagcctcg caccatcgtc ggatggaagg gattgatcaa tgatcctcac    360
ctcaacgaaa cctacgacat cccagagggc ttgcgcattg cgcgcaaagt gcttatcgac    420
gttgtgaacc ttgatctccc agtcggctgc gaattcctcg aaccaaacag ccctcagtac    480
tacgccgaca ctgtcgcatg gggagcaatc ggcgctcgta ccaccgaatc tcaggtgcac    540
```

| | |
|---|---|
| cgccagctgg cttctgggat gtgtatgcca attggtttca agaacggaac tgacggaaac | 600 |
| atccaggttg cagtcgacgc ggtacaggct gcccagaacc cacacttctt cttcggaacc | 660 |
| tccgacgacg gcgcgctgag cgtcgtggag accgcaggca acagcaactc ccacatcatt | 720 |
| ttgcgcggcg gtacctccgg cccgaatcat gatgcagctt cggtggaggc cgtcgtcgag | 780 |
| aagcttggtg aaaacgctcg tctcatgatc gatgcttccc atgctaactc cggcaaggat | 840 |
| catatccgac aggttgaggt tgttcgtgaa atcgcagagc agatttctgg cggttctgaa | 900 |
| gctgtggctg gaatcatgat tgagtccttc ctcgttggtg gcgcacagaa ccttgatcct | 960 |
| gcgaaattgc gcatcaatgg cggtgaaggc ctggtgtacg gacagtctgt gaccgataag | 1020 |
| tgcatcgata ttgacaccac catcgatttg ctcgctgagc tggccgcagc agtaagggaa | 1080 |
| cgccgagcag cagccaagta a | 1101 |

<210> SEQ ID NO 57
<211> LENGTH: 1089
<212> TYPE: DNA
<213> ORGANISM: Corynebacterium glutamicum

<400> SEQUENCE: 57

| | |
|---|---|
| atggagagga ttgtcgttac tctcggggaa cgtagttacc caattaccat cgcatctggt | 60 |
| ttgtttaatg aaccagcttc attcttaccg ctgaaatcgg gcgagcaggt catgttggtc | 120 |
| accaacgaaa ccctggctcc tctgtatctc gataaggtcc gcggcgtact tgaacaggcg | 180 |
| ggtgttaacg tcgatagcgt tatcctccct gacggcgagc agtataaaag cctggctgta | 240 |
| ctcgataccg tctttacggc gttgttacaa aaccgcatg gtcgcgatac tacgctggtg | 300 |
| gcgcttggcg gcggcgtagt gggcgatctg accggcttcg cggcggcgag ttatcagcgc | 360 |
| ggtgtccgtt tcattcaagt cccgacgacg ttactgtcgc aggtcgattc ctccgttggc | 420 |
| ggcaaaactg cggtcaacca tcccctcggt aaaaacatga ttggcgcgtt ctaccaacct | 480 |
| gcttcagtgg tggtggatct cgactgtctg aaaacgcttc ccccgcgtga gttagcgtcg | 540 |
| gggctggcag aagtcatcaa atacggcatt attcttgacg gtgcgttttt taactggctg | 600 |
| gaagagaatc tggatgcgtt gttgcgtctg acggtccgg caatgcgta ctgtattcgc | 660 |
| cgttgttgtg aactgaaggc agaagttgtc gccgccgacg agcgcgaaac cgggttacgt | 720 |
| gctttactga atctgggaca ccctttggt catgccattg aagctgaaat ggggtatggc | 780 |
| aattggttac atggtgaagc ggtcgctgcg ggtatggtga tggcggcgcg gacgtcggaa | 840 |
| cgtctcgggc agtttagttc tgccgaaacg cagcgtatta taaccctgct caagcgggct | 900 |
| gggttaccgg tcaatgggcc gcgcgaaatg tccgcgcagg cgtatttacc gcacatgctg | 960 |
| cgtgacaaga aagtccttgc gggagagatg cgcttaattc ttccgttggc aattggtaag | 1020 |
| agtgaagttc gcagcggcgt ttcgcacgag cttgttctta acgccattgc cgattgtcaa | 1080 |
| tcagcgtaa | 1089 |

<210> SEQ ID NO 58
<211> LENGTH: 1098
<212> TYPE: DNA
<213> ORGANISM: Artificial Sequence
<220> FEATURE:
<223> OTHER INFORMATION: Artificial construct

<400> SEQUENCE: 58

| | |
|---|---|
| atgagcgcag tgcagatttt caacaccgtc cacgtcaatg gatcttcccc ctatgatgtc | 60 |

```
cacattggtt ccggcctcaa cgagctcatt gttcagcgcg cagcggaatc aggcgcggag      120
caggtagcga ttttgcacca gcccagcatg gatgacattg catccgagtt ggatgcagca     180
ctagtcgctg ctggtttgaa ggtcctgcac cttaatgttc ccgatgcgga aaacggcaag     240
tccttggaag tagcgggca gtgctgggat gaattgggtg gcgcagcatt cggccgccgc      300
gatatcgtca tcggacttgg tggcggtgct gccacagacc tcgcgggatt cgtcgctgct     360
gcatggatgc gtggcgtgcg cgtcattcag gttccaacca ccttgttggc tatggtggac     420
gctgcggtgg gcggcaagac tggcatcaat accgccgcag gcaagaacct tgtgggcgcg     480
ttccacgagc ctgacgcagt attcattgac accgatcgcc tagccaccct gcctgacgcg     540
gaaatcatcg cgggttccgc cgaaatcatc aaaactggtt tcatcgccga cccagaaatc     600
ctgcgccttt acgaaactga tcccgcagcc tgcctgaaga agaagtcga aggctcccac      660 ctacctgaac tgatttggcg ctccgtcacc gtcaagggct ccgtggtcgg ccaagacctc     720
aaagaatcta gcctgcgcga atcctcaac tacggacaca cctttgccca cgccgtcgaa      780
ctccgcgaaa acttccgctg gcgccacggc aatgccgttg cagtgggcat gatgttcatc     840
gccaacctct cccacaagct cgggcttatc gacgcgcccc tcctcgagcg ccaccgctca    900
atcctggcgg ccatccggtct gcccacttcc tacgaaggcg gagccttcga cgagctttac    960
gacggtatga cccgcgacaa gaaaaaccgc gacggcaaca tccgcttcgt cgcactgacc   1020
gccgtgggcg aggttacccg cattgagggg ccctcaaaac aagatttaca gagtgcttat   1080
gaggcaatca gccactaa                                                1098

<210> SEQ ID NO 59
<211> LENGTH: 525
<212> TYPE: DNA
<213> ORGANISM: Corynebacterium glutamicum

<400> SEQUENCE: 59
atgacacaac ctcttttct gatcgggcct cggggctgtg gtaaaacaac ggtcggaatg      60
gcccttgccg attcgcttaa ccgtcggttt gtcgataccg atcagtggtt gcaatcacag    120
ctcaatatga cggtcgcgga gatcgtcgaa agggaagagt gggcgggatt tcgcgccaga    180
gaaacggcgg cgctggaagc ggtaactgcg ccatccaccg ttatcgctac aggcggcggc    240
attattctga cggaatttaa tcgtcacttc atgcaaaata cgggatcgt ggtttatttg      300 tgtgcgccag tatcagtcct ggttaaccga ctgcaagctg caccggaaga agatttacgg    360
ccaaccttaa cgggaaaacc gctgagcgaa gaagttcagg aagtgctgga agaacgcgat    420
gcgctatatc gcgaagttgc gcatattatc atcgacgcaa caaacgaacc cagccaggtg    480
atttctgaaa ttcgcagcgc cctggcacag acgatcaatt gttga                    525

<210> SEQ ID NO 60
<211> LENGTH: 573
<212> TYPE: DNA
<213> ORGANISM: Corynebacterium glutamicum

<400> SEQUENCE: 60
atggagcgta atgaagtgaa tgatcaaatt cacttagatc atcaatcaga tgacacctct      60
gaatgctcct gcccgatcgt ggttcttgtg ggtttgccag gagctggaaa atccaccatt    120
ggacgtcgat tagcgcgcgc cttaaacact gaactcgtcg actccgacga actgattgag    180
cgcgccaccg gaaaagcctg tggcgccgtg ttcagcgagc tcggcgagcc agccttccgc    240
gagctcgagg ccatccacgt ggccgaagca ctgaaatcct ccggagtggt gagcttggga    300
```

```
ggcggatctg tgctgacaga atccacccgt gaactgctca aaggccagga cgtggtctgg    360
atcgacgtgc cagtagaaga aggcatcagg cgcaccgcaa cgagcgttc ccgcccgtg     420 ctgcaagccg ccgaccccgc cgagcactac cgcaacctgg tgaaagtgcg caccccgttg    480
tacgaagagg tggcaaccta ccgacttcgc accaacaacc gcagccccca gcaagtggtg    540
gcagcagtgt tgcatcatct agaaatcgat taa                                573
```

<210> SEQ ID NO 61
<211> LENGTH: 1434
<212> TYPE: DNA
<213> ORGANISM: Artificial Sequence
<220> FEATURE:
<223> OTHER INFORMATION: Artificial construct

<400> SEQUENCE: 61

```
gtggcgtttg aaaccccgga agaaattgtc aagttcatca aggatgaaaa cgtcgagttc     60
gttgacgttc gattcaccga ccttcccggc accgagcagc acttcagcat cccagctgcc    120
agcttcgatg cagatacaat cgaagaaggt ctcgcattcg acggctcctc gatccgtggc    180
ttcaccacga tcgacgaatc tgacatgaat ctcctgccag acctcggaac ggccaccctt    240
gatccattcc gcaaggcaaa gaccctgaac gttaagttct tcgttcacga tcctttcacc    300
cgcgaggcat tctcccgcga cccacgcaac gtggcacgca aggcagagca gtacctggca    360
tccaccggca ttgcagacac ctgcaacttc ggcgccgagg ctgagttcta cctcttcgac    420
tccgttcgct actccaccga gatgaactcc ggcttctacg aagtagatac cgaagaaggc    480
tggtggaacc gtggcaagga aaccaacctc gacggcaccc caaacctggg cgcaaagaac    540
cgcgtcaagg gtggctactt cccagtagca ccatacgacc aaaccgttga cgtgcgcgat    600
gacatggttc gcaacctcgc agcttccggc ttcgctcttg agcgtttcca ccacgaagtc    660
ggtggcggac agcaggaaat caactaccgc ttcaacacca tgctccacgc ggcagatgat    720
atccagacct tcaagtacat catcaagaac accgctcgcc tccacggcaa ggctgcaacc    780
ttcatgccta agccactggc tggcgacaac ggttccggca tgcacgctca ccagtccctc    840
tggaaggacg gcaagccact cttccacgat gagtccggct acgcaggcct gtccgacatc    900
gcccgctact acatcggcgg catcctgcac cacgcaggcg ctgttctggc gttcaccaac    960
gcaaccctga actcctacca ccgtctggtt ccaggcttcg aggctccaat caacctggtg   1020
tactcacagc gcaaccgttc cgctgctgtc cgtatcccaa tcaccggatc aaacccgaag   1080
gcaaagcgca tcgaattccg cgctccagac ccatcaggca cccataccct gggctttgca   1140
gcgatgatga tggccggcct cgacggcatc aagaaccgca tcgagccaca cgctccagtg   1200
gacaaggacc tctacgaact accaccagag gaagctgcat ccattccaca ggcaccaacc   1260
tccctggaag catccctgaa ggcactgcag gaagacaccg acttcctcac cgagtctgac   1320
gtcttcaccg aggatctcat cgaggcgtac atccagtaca agtacgacaa cgaaatctcc   1380
ccagttcgcc tgcgcccaac cccgcaggaa ttcgaattgt acttcgactg ctaa          1434
```

<210> SEQ ID NO 62
<211> LENGTH: 1341
<212> TYPE: DNA
<213> ORGANISM: Artificial Sequence
<220> FEATURE:
<223> OTHER INFORMATION: Artificial construct

<400> SEQUENCE: 62

| | |
|---|---:|
| atgaacagcg aacaggaatt tgtactcagc gccattgaag aacgcgacat taagtttgtg | 60 |
| cgtctatggt tcactgacat tcttggccac ttgaagtcag tggttgtggc tcctgcagaa | 120 |
| ctagagtctg cgttggaaga aggcatcgga ttcgatggct cagccattga gggctacgcg | 180 |
| cgtatctcgg aagcggacac cattgcccgc ccagatccat cgacattcca ggtcctccca | 240 |
| ctagaagcgg gcatctcaaa actgcaggca gcacgcctgt tttgcgatgt cacgatgcca | 300 |
| gacggacagc catctttttc tgacccgcgc caagtgctgc gcaggcaggt ccaactagct | 360 |
| gcagatgaag gcttgacctg catgatctca ccagagattg agttctattt ggtgcaaagc | 420 |
| cttcgcacca acggactgcc acctgtgccc actgacaacg gcggatattt cgaccaagcc | 480 |
| acattcaatg aggcgccgaa tttccgtcga acgcgatgg tagcgctgga ggaactcggc | 540 |
| atccctgtcg agttctccca ccatgaaact gcacctggcc agcaagaaat cgatttacgc | 600 |
| catgcggatg cgctcactat ggccgacaac atcatgacct tccgctacat catgaaacag | 660 |
| gtggcaaggg accaaggcgt cggggcatca tttatgccca agccattcca agaacatgca | 720 |
| ggctccgcca tgcacacgca catgtcctta tttgagggcg ataccaacgc gttccacgat | 780 |
| ccagacgatt cttacatgct gtccaaaacc gcaaaacagt tcatcgctgg aatcttgcat | 840 |
| cacgctccag aattcaccgc tgtgaccaac cagtgggtca attcctacaa acgcatcgtg | 900 |
| tacgaaaacg aagctccaac tgcggcaacc tggggtgtat ctaatcgttc tgcgctggtt | 960 |
| cgtgttccta cctaccgttt gaataaggag gagtcgcgcc gggtggaggt gcgtcttcct | 1020 |
| gataccgctt gtaacccata tttggcgttt tcagtgatgc tcggcgctgg tttgaaaggc | 1080 |
| attaaagaag ttatgagct cgacgagcca gctgaggacg atatctccaa cttgagcttc | 1140 |
| cgggaacgtc gcgctatggg ctacaacgat ctgccaagca gccttgatca ggcactgcgc | 1200 |
| caaatggaaa agtcagagct tgttgctgac atcctcggtg agcacgtttt tgagtttttc | 1260 |
| ttgcgcaata gtggcgtga atggcgtgac taccaagagc agatcactcc gtgggagctc | 1320 |
| cgaaacaatc ttgattacta g | 1341 |

<210> SEQ ID NO 63
<211> LENGTH: 1880
<212> TYPE: DNA
<213> ORGANISM: Corynebacterium glutamicum

<400> SEQUENCE: 63

| | |
|---|---:|
| atggatatca agagtgcgtt gagccgtatc gtcgggcagt tggacctgac taccgaagaa | 60 |
| atgcgcgagg tcatgcgcca gatcatgacc ggtcagtgca gcgaggcgca gataggcgct | 120 |
| ttcctgatgg gcatgcgcat gaaaagcgaa agcatcgacg aaatcgtcgg tgcggtgtcg | 180 |
| gtgatgcgtg agctggccga aaaggtcgag ctgcaaagcc tcgatggtgt cgtcgatatt | 240 |
| gtcgggaccg gtggtgatgg cgccaacatc ttcaacgtgt ccaccgcttc gtccttcgtc | 300 |
| ctggcggcg cggttgccc ggtggccaag catggtaacc gcgcagtctc gggcaagagc | 360 |
| ggcagtgccg acctgctgga agctgccggc atctacctga actgacgcc aactcaagtg | 420 |
| gcacgctgca tcgacagcct gggcatcggc ttcatgttcg cgcaaagtca ccactcggcc | 480 |
| atgaaacatg ccgctggccc acgtcgagaa ctggggttgc gcaccctgtt caatatgctc | 540 |
| ggcccgctta cgaatccggc cggagtgaag caccaggtgg tcggtgtgtt cgcgcaaacc | 600 |
| ctttgccgcc cgctggctga ggtgctgcag cgcctgggga gcaagcatgt gctggtcgtg | 660 |
| cactcgaagg atggtctgga cgagttcagc ctggctgcac ccaccttcgt cgccgaactg | 720 |
| aaaaatgacg aaatcactga atattgggtc gagccggaag acctcggcat gaagagtcag | 780 |

```
agccttcatg gcctggctgt cgagagcccg caggcttcgc tggagttgat ccgcgatgcg      840
ctgggccggc gcaagaccga gaacggtcag aaggccgccg agatgatcgt gcttaatgct      900
ggcgcggcac tgtatgcagc cgaccatgcc atgagcctga agccggtgt agaactggcc       960 catgatgtac tgcacaccgg cctggcctgg gaaaagctgc aggaattggg tgcctttact     1020
gcagtattca aggtggagaa cgaagcatga gtgtgccgac ggtgctggaa aggatcattg     1080
cccgcaagtt tcaggaagtg gccgagcgca gtgcgcacgt cagcctcgcc gaactggagg     1140
gcctggccaa ggccgctgac gccccgcgag gcttcgccaa cgcgctgatc gagcaggcca     1200
agcgcaagca gcccgcggtg attgccgaaa tcaagaaagc ttcgccaagc aagggcgtga     1260
tccgcgagca cttcgtgcca gcggaaatcg cggtcagcta cgagaagggc ggggccacct     1320
gcctgtcggt gttgaccgat gtcgattatt ccagggtgc cgatgagtac ttgcagcagg      1380
cccgcgcggc ggtttcgctg ccggtgatcc gcaaggactt catggtcgac ccttaccaga     1440
tcgtcgaagc ccgggccctg ggggcagatt gcgtactgct gatcgtgtcg gcgctggatg     1500
acgtgaagat ggctgaactg gccgccactg ccaaggacgt cggcctcgac gtgctggtgg     1560
aagtgcacga tggcgatgaa ctggagcgcg cgctgaaaac cctggatacg ccgctggtgg     1620
gggtgaacaa ccgcaaccct cacaccttcg aggtcagcct ggaaaccacc cttgacctgc     1680
tgccgcgcat tccgcgtgac cgtctggcga ttaccgaaag cggtattctc aaccgggccg     1740
atgtggagct gatggcaatc aacgaggttt actcgttcct ggtgggtgag gcgttcatgc     1800
gcgccgagca gcctggcctg gaattacagc ggctgttctt ccccgagcag gtgaagaaga     1860
ctgttcagca actggactga                                                 1880
```

<210> SEQ ID NO 64
<211> LENGTH: 1104
<212> TYPE: DNA
<213> ORGANISM: Corynebacterium glutamicum

<400> SEQUENCE: 64

```
atggctgaca tgtccgaaca ggagctcaag gcgctgcgcg tacgcatcga cagcctcgac      60
gagaaaattc tcgagctgat cagcgaccgc gcccgctgcg ccgaagaagt ggcccgggtc     120
aagactgcct cgctgaaaga aggcgagaag ccggtgttct accgtcccga gcgtgaagct     180
gcggtgctca agcgcgtgat ggaacgcaac aagggcccgc tggcaacgca agagatggcg     240
cggctgttcc gcgaaatcat gtcgtcgtgc ctggccctgg aagagccgct gaaaatcgcc     300
tacctcggcc tgaaggtac cttcacccag gcggcggcca tgaagcactt cggccacgcg     360
gtgatcagtc ggccgatggc ggccatcgac gaagtgttcc gtgaagtggc ggccggtgcc     420
gtcaacttcg gtgtggtgcc ggtggaaaac tccactgaag gtgcggtcag ccacaccctg     480
gacagcttcc tcgagcatga catggtgatt gcggtgaggg tcgagctgcg tatccaccac     540
cacctgctgg tgggcgagaa caccaagacc gacagcatca cccgcatcta ctcccacgcc     600
cagtcgctgg cccagtgccg aaagtggctg gacgctcact acccgaacgt ggagcgcgtg     660
gccgtttcga gcaatgccga agcggccaag cgggtcaagg gtgagtggaa ctcggcggcg     720
atcgccggcg atatggcggc caacctgtac ggcctgaccc gtctggccga aagatcgaa      780 gaccgcccgg acaactccac gcgcttcctg atgatcggta accaggaagt accgccgacc     840
ggcgacgaca agacctcgat catcgtttcg atgagcaaca agccaggtgc gttgcatgag     900
ttgctggtgc cgttctatca gaacggcatc gacctgaccc gcatcgagac ccgcccgtcg     960
```

```
cgcagcggca agtggaccta cgtgttcttc atcgacttcg tcggccacca ccgcgacccg    1020
ctgatcaagg cggtgctcga gcagatcagc caggaggctg tggcgctgaa ggtgctgggc    1080
tcttatccga aggcggtgct ttga                                           1104
```

<210> SEQ ID NO 65
<211> LENGTH: 8
<212> TYPE: DNA
<213> ORGANISM: Artificial Sequence
<220> FEATURE:
<223> OTHER INFORMATION: The 8 5' nucleotides of pheA gene that overlap
      serC gene

<400> SEQUENCE: 65

```
atggctga                                                                8
```

<210> SEQ ID NO 66
<211> LENGTH: 21
<212> TYPE: DNA
<213> ORGANISM: Artificial Sequence
<220> FEATURE:
<223> OTHER INFORMATION: Artificial construct - synthetic primer

<400> SEQUENCE: 66

```
tatgccgtgt tgaatgccat t                                                21
```

<210> SEQ ID NO 67
<211> LENGTH: 45
<212> TYPE: DNA
<213> ORGANISM: Artificial Sequence
<220> FEATURE:
<223> OTHER INFORMATION: Artificial construct - synthetic primer

<400> SEQUENCE: 67

```
cccgggatcc actaaactta aacacagtgt tgctggagaa gtcat                      45
```

<210> SEQ ID NO 68
<211> LENGTH: 48
<212> TYPE: DNA
<213> ORGANISM: Artificial Sequence
<220> FEATURE:
<223> OTHER INFORMATION: Artificial construct - synthetic primer

<400> SEQUENCE: 68

```
tgtttaagtt tagtggatcc cggggaaaag gagtcttcca atgactag                   48
```

<210> SEQ ID NO 69
<211> LENGTH: 21
<212> TYPE: DNA
<213> ORGANISM: Artificial Sequence
<220> FEATURE:
<223> OTHER INFORMATION: Artificial construct - synthetic primer

<400> SEQUENCE: 69

```
ccagatcgac gttttcctgg c                                                21
```

<210> SEQ ID NO 70
<211> LENGTH: 50
<212> TYPE: DNA
<213> ORGANISM: Artificial Sequence
<220> FEATURE:
<223> OTHER INFORMATION: Artificial construct - synthetic primer

<400> SEQUENCE: 70

```
gccctgcagg taaaaaaagg atttgattca tgacttctcc agcaacactg                 50
```

<210> SEQ ID NO 71
<211> LENGTH: 50
<212> TYPE: DNA
<213> ORGANISM: Artificial Sequence
<220> FEATURE:
<223> OTHER INFORMATION: Artificial construct - synthetic primer

<400> SEQUENCE: 71
gccctgcagg taaaaaaagg atttgattcg tgacttctcc agcaacactg    50

<210> SEQ ID NO 72
<211> LENGTH: 50
<212> TYPE: DNA
<213> ORGANISM: Artificial Sequence
<220> FEATURE:
<223> OTHER INFORMATION: Artificial construct - synthetic primer

<400> SEQUENCE: 72
gccctgcagg taaaaaaagg atttgattct tgacttctcc agcaacactg    50

<210> SEQ ID NO 73
<211> LENGTH: 44
<212> TYPE: DNA
<213> ORGANISM: Artificial Sequence
<220> FEATURE:
<223> OTHER INFORMATION: Artificial construct - synthetic primer

<400> SEQUENCE: 73
gccctgcagg taaaaaaagg attatgactt ctccagcaac actg    44

<210> SEQ ID NO 74
<211> LENGTH: 44
<212> TYPE: DNA
<213> ORGANISM: Artificial Sequence
<220> FEATURE:
<223> OTHER INFORMATION: Artificial construct - synthetic primer

<400> SEQUENCE: 74
gccctgcagg taaaaaaagg attatgactt ctccagcaac actg    44

<210> SEQ ID NO 75
<211> LENGTH: 44
<212> TYPE: DNA
<213> ORGANISM: Artificial Sequence
<220> FEATURE:
<223> OTHER INFORMATION: Artificial construct - synthetic primer

<400> SEQUENCE: 75
gccctgcagg taaaaaaagg attttgactt ctccagcaac actg    44

<210> SEQ ID NO 76
<211> LENGTH: 31
<212> TYPE: DNA
<213> ORGANISM: Artificial Sequence
<220> FEATURE:
<223> OTHER INFORMATION: Artificial construct - synthetic primer

<400> SEQUENCE: 76
cccgggatcc ctagtcattg gaagactcct t    31

<210> SEQ ID NO 77
<211> LENGTH: 45
<212> TYPE: DNA
<213> ORGANISM: Artificial Sequence
<220> FEATURE:
<223> OTHER INFORMATION: Artificial construct - synthetic primer

<400> SEQUENCE: 77 aatcctttt ttacctgcag ggcttagttc gcgagaagct gttcg         45

<210> SEQ ID NO 78
<211> LENGTH: 21
<212> TYPE: DNA
<213> ORGANISM: Artificial Sequence
<220> FEATURE:
<223> OTHER INFORMATION: Artificial construct - synthetic primer

<400> SEQUENCE: 78
aaggagtctt ccaatgacta g                                  21

<210> SEQ ID NO 79
<211> LENGTH: 21
<212> TYPE: DNA
<213> ORGANISM: Artificial Sequence
<220> FEATURE:
<223> OTHER INFORMATION: Artificial construct - synthetic primer

<400> SEQUENCE: 79
gtctccccaa tcaaatcatc a                                  21

<210> SEQ ID NO 80
<211> LENGTH: 42
<212> TYPE: DNA
<213> ORGANISM: Artificial Sequence
<220> FEATURE:
<223> OTHER INFORMATION: Artificial construct - synthetic primer

<400> SEQUENCE: 80
cccgggatcc actaaactta aacagtcacc tgcattagtc at           42

<210> SEQ ID NO 81
<211> LENGTH: 42
<212> TYPE: DNA
<213> ORGANISM: Artificial Sequence
<220> FEATURE:
<223> OTHER INFORMATION: Artificial construct - synthetic primer

<400> SEQUENCE: 81
tgtttaagtt tagtggatcc cgggcgcgga aaactcggat aa           42

<210> SEQ ID NO 82
<211> LENGTH: 21
<212> TYPE: DNA
<213> ORGANISM: Artificial Sequence
<220> FEATURE:
<223> OTHER INFORMATION: Artificial construct - synthetic primer

<400> SEQUENCE: 82
tgatgatgtg cccgtccaca g                                  21

<210> SEQ ID NO 83
<211> LENGTH: 47
<212> TYPE: DNA
<213> ORGANISM: Artificial Sequence
<220> FEATURE:
<223> OTHER INFORMATION: Artificial construct - synthetic primer

<400> SEQUENCE: 83
gccctgcagg acgtggcaga atagtgtgca tgactaatgc aggtgac      47

<210> SEQ ID NO 84

```
<211> LENGTH: 47
<212> TYPE: DNA
<213> ORGANISM: Artificial Sequence
<220> FEATURE:
<223> OTHER INFORMATION: Artificial construct - synthetic primer

<400> SEQUENCE: 84
gccctgcagg acgtggcaga atagtgtgcg tgactaatgc aggtgac          47

<210> SEQ ID NO 85
<211> LENGTH: 47
<212> TYPE: DNA
<213> ORGANISM: Artificial Sequence
<220> FEATURE:
<223> OTHER INFORMATION: Artificial construct - synthetic primer

<400> SEQUENCE: 85
gccctgcagg acgtggcaga atagtgtgct tgactaatgc aggtgac          47

<210> SEQ ID NO 86
<211> LENGTH: 42
<212> TYPE: DNA
<213> ORGANISM: Artificial Sequence
<220> FEATURE:
<223> OTHER INFORMATION: Artificial construct - synthetic primer

<400> SEQUENCE: 86
gccctgcagg acgtggcaga atagatgact aatgcaggtg ac              42

<210> SEQ ID NO 87
<211> LENGTH: 42
<212> TYPE: DNA
<213> ORGANISM: Artificial Sequence
<220> FEATURE:
<223> OTHER INFORMATION: Artificial construct - synthetic primer

<400> SEQUENCE: 87
gccctgcagg acgtggcaga ataggtgact aatgcaggtg ac              42

<210> SEQ ID NO 88
<211> LENGTH: 42
<212> TYPE: DNA
<213> ORGANISM: Artificial Sequence
<220> FEATURE:
<223> OTHER INFORMATION: Artificial construct - synthetic primer

<400> SEQUENCE: 88
gccctgcagg acgtggcaga atagttgact aatgcaggtg ac              42

<210> SEQ ID NO 89
<211> LENGTH: 31
<212> TYPE: DNA
<213> ORGANISM: Artificial Sequence
<220> FEATURE:
<223> OTHER INFORMATION: Artificial construct - synthetic primer

<400> SEQUENCE: 89
cccgggatcc ttatccgagt tttccgcgtc c                          31

<210> SEQ ID NO 90
<211> LENGTH: 45
<212> TYPE: DNA
<213> ORGANISM: Artificial Sequence
<220> FEATURE:
<223> OTHER INFORMATION: Artificial construct - synthetic primer

<400> SEQUENCE: 90
```
aatccttttt ttacctgcag ggcttagttc gcgagaagct gttcg                    45

<210> SEQ ID NO 91
<211> LENGTH: 21
<212> TYPE: DNA
<213> ORGANISM: Artificial Sequence
<220> FEATURE:
<223> OTHER INFORMATION: Artificial construct - synthetic primer

<400> SEQUENCE: 91
aaggagtctt ccaatgacta g                                              21

<210> SEQ ID NO 92
<211> LENGTH: 11
<212> TYPE: DNA
<213> ORGANISM: Artificial Sequence
<220> FEATURE:
<223> OTHER INFORMATION: Artificial construct - synthetic primer

<400> SEQUENCE: 92
agccctgcag g                                                         11

<210> SEQ ID NO 93
<211> LENGTH: 525
<212> TYPE: DNA
<213> ORGANISM: Escherichia coli

<400> SEQUENCE: 93
atgacacaac ctcttttct gatcgggcct cggggctgtg gtaaaacaac ggtcggaatg      60
gccccttgccg attcgcttaa ccgtcggttt gtcgataccg atcagtggtt gcaatcacag   120
ctcaatatga cggtcgcgga gatcgtcgaa agggaagagt gggcgggatt tcgcgccaga   180
gaaacggcgg cgctggaagc ggtaactgcg ccatccaccg ttatcgctac aggcggcggc   240
attattctga cggaatttaa tcgtcacttc atgcaaaata cgggatcgt ggtttatttg    300
tgtgcgccag tatcagtcct ggttaaccga ctgcaagctg caccggaaga agatttacgg   360
ccaaccttaa cgggaaaaacc gctgagcgaa gaagttcagg aagtgctgga agaacgcgat   420
gcgctatatc gcgaagttgc gcatattatc atcgacgcaa caaacgaacc cagccaggtg   480
atttctgaaa ttcgcagcgc cctggcacag acgatcaatt gttga                   525

<210> SEQ ID NO 94
<211> LENGTH: 573
<212> TYPE: DNA
<213> ORGANISM: Corynebacterium glutamicum

<400> SEQUENCE: 94
atggagcgta atgaagtgaa tgatcaaatt cacttagatc atcaatcaga tgacacctct      60
gaatgctcct gcccgatcgt ggttcttgtg ggtttgccag gagctggaaa atccaccatt    120
ggacgtcgat tagcgcgcgc cttaaacact gaactcgtcg actccgacga actgattgag    180
cgcgccaccg gaaaagcctg tgcgccgtg ttcagcgagc tcggcgagcc agccttccgc     240
gagctcgagg ccatccacgt ggccgaagca ctgaaatcct ccggagtggt gagcttggga    300
ggcggatctg tgctgacaga atccacccgt gaactgctca aaggcagga cgtggtctgg    360
atcgacgtgc cagtagaaga aggcatcagg cgcaccgcaa acgagcgttc ccgccccgtg    420
ctgcaagccg ccgaccccgc cgagcactac cgcaacctgg tgaaagtgcg caccccgttg    480
tacgaagagg tggcaaccta ccgacttcgc accaacaacc gcagccccca gcaagtggtg    540
gcagcagtgt tgcatcatct agaaatcgat taa 573

<210> SEQ ID NO 95
<211> LENGTH: 1434
<212> TYPE: DNA
<213> ORGANISM: Corynebacterium glutamicum

<400> SEQUENCE: 95

| | |
|---|---|
| gtggcgtttg aaaccccgga agaaattgtc aagttcatca aggatgaaaa cgtcgagttc | 60 |
| gttgacgttc gattcaccga ccttcccggc accgagcagc acttcagcat cccagctgcc | 120 |
| agcttcgatg cagatacaat cgaagaaggt ctcgcattcg acggatcctc gatccgtggc | 180 |
| ttcaccacga tcgacgaatc tgacatgaat ctcctgccag acctcggaac ggccacccct | 240 |
| gatccattcc gcaaggcaaa gaccctgaac gttaagttct tcgttcacga tcctttcacc | 300 |
| cgcgaggcat tctcccgcga cccacgcaac gtggcacgca aggcagagca gtacctggca | 360 |
| tccaccggca ttgcagacac ctgcaacttc ggcgccgagg ctgagttcta cctcttcgac | 420 |
| tccgttcgct actccaccga gatgaactcc ggcttctacg aagtagatac cgaagaaggc | 480 |
| tggtggaacc gtggcaagga aaccaacctc gacggcaccc caaacctggg cgcaaagaac | 540 |
| cgcgtcaagg gtggctactt cccagtagca ccatacgacc aaaccgttga cgtgcgcgat | 600 |
| gacatggttc gcaacctcgc agcttccggc ttcgctcttg agcgtttcca ccacgaagtc | 660 |
| ggtggcggac agcaggaaat caactaccgc ttcaacacca tgctccacgc ggcagatgat | 720 |
| atccagacct tcaagtacat catcaagaac accgctcgcc tccacggcaa ggctgcaacc | 780 |
| ttcatgccta agccactggc tggcgacaac ggttccggca tgcacgctca ccagtccctc | 840 |
| tggaaggacg gcaagccact cttccacgat gagtccggct acgcaggcct gtccgacatc | 900 |
| gcccgctact acatcggcgg catcctgcac cacgcaggcg ctgttctggc gttcaccaac | 960 |
| gcaaccctga actcctacca ccgtctggtt ccaggcttcg aggctccaat caacctggtg | 1020 |
| tactcacagc gcaaccgttc cgctgctgtc cgtatcccaa tcaccggatc caaccccgaag | 1080 |
| gcaaagcgca tcgaattccg cgctccagac ccatcaggca acccataccb gggctttgca | 1140 |
| gcgatgatga tggccggcct cgacggcatc aagaaccgca tcgagccaca cgctccagtg | 1200 |
| gacaaggacc tctacgaact accaccagag gaagctgcat ccattccaca ggcaccaacc | 1260 |
| tccctggaag catccctgaa ggcactgcag gaagacaccg acttcctcac cgagtctgac | 1320 |
| gtcttcaccg aggatctcat cgaggcgtac atccagtaca agtacgacaa cgagatctcc | 1380 |
| ccagttcgcc tgcgcccaac cccgcaggaa ttcgaattgt acttcgactg ctaa | 1434 |

<210> SEQ ID NO 96
<211> LENGTH: 1857
<212> TYPE: DNA
<213> ORGANISM: Corynebacterium glutamicum

<400> SEQUENCE: 96

| | |
|---|---|
| atgcgtacat ccattgccac tgtttgtttg tccggaactc ttgctgaaaa gctgcgcgca | 60 |
| gctgcagatg ctggatttga tggtgtggaa atcttcgagc aggacttggt ggtttccccg | 120 |
| cattcggcag agcagattcg tcagcgggct caggatttgg gattaaccct ggatctgttc | 180 |
| cagccgtttc gagatttcga aggtgtggaa gaagagcagt ttctgaagaa tctgcaccgc | 240 |
| ttggaagaga agttcaagct gatgaacagg cttggcattg agatgatctt gttgtgttcc | 300 |
| aatgtgggca ccgcgaccat caatgatgat gaccttttcg tggagcagtt gcatcgtgca | 360 |
| gcagatttgg ctgagaagta caacgtcaag attgcttatg aagcgttggc gtggggcaag | 420 |

```
tttgtcaatg attttgagca tgcgcatgca cttgtggaga aggtgaatca caaggcgctg    480
ggaacctgct tggatacgtt ccatattctt tcccgtggtt gggaaaccga cgaggtggaa    540
aacatcccgg cggagaagat tttctttgtt cagttggcgg atgcaccgaa gctgagcatg    600
gacattttgt cctggtcgcg tcaccaccgt gttttccctg gtgaaggcga tttcgatctg    660
gtgaaattca tggttcatct ggccaagacg ggttatgatg cccgatttc tttggaaatc     720 ttcaacgatt ccttccgcaa ggccgaggtt ggtcgcaccg cgattgatgg gttgcgttct    780
ttgcgttggt tggaagatca gacctggcat gcgctaaatg ctgaggatcg tccaagcgca    840
ctagagctgc gtgcacttcc tgaggtcgcg aacctgaag gcgttgattt cattgagatc     900
gccactggac gtttgggtga gaccattcgg gttcttcatc aattgggttt ccgcttgggt    960
ggtcatcact gcagtaagca ggattaccag gtatggaccc agggcgatgt gcgcattgtg   1020
gtgtgtgatc gtggggccac cggggctcca accacgatct ctgcgatggg ctttgacacc   1080
cctgatccag aagccgcgca tgcccgtgcg gaattgctgc gggctcagac aattgatcgt   1140
ccccacatcg agggtgaagt tgaccttaaa ggtgtgtacg cgccggatgg ggtggagctg   1200
tttttcgcgg ggccgagccc cgatggaatg cccgagtggc tgccggagtt cggcgtcgaa   1260
aagcaagaag ctggtctcat tgaagccatc gaccacgtca atttcgccca gccgtggcaa   1320
cattttgatg aggcagtgct gttttacacc gcgctgatgg cgttagagac tgtgcgtgag   1380
gatgagttcc cgagcccaat tggtttggtg cgcaatcagg tgatgcgttc gccgaatgat   1440
gcggtgcggt tgctgctcag cgtggcgccg gaggacggtg agcagggaga tttcctcaac   1500
gcggcctacc cggagcacat tgcgttggcc acggcggaca tcgtggcggt ggctgaacgt   1560
gcgcgcaaac gaggcctgga tttcttgccc gtcccagaga attactacga cgatgtgcag   1620
gcgcgttttg atttgccgca ggagttcttg gacacactca aggaaaacca cctgctttac   1680
gactgcgacg agaacggcga gttcctccac ttttacaccc gcacgttggg cacgctgttc   1740
ttcgaagtgg tggaacgccg cggcggtttt gcaggttggg gcgaaacaaa cgctccggtg   1800
cggttagcgg cgcagtatcg tgaggtgcgg gacctcgagc ggggaatccc caactag     1857
```

<210> SEQ ID NO 97
<211> LENGTH: 39
<212> TYPE: DNA
<213> ORGANISM: Artificial Sequence
<220> FEATURE:
<223> OTHER INFORMATION: Artificial construct - synthetic primer

<400> SEQUENCE: 97

```
ttagaggaga caccatatgg cgtttgaaac cccggaaga                            39
```

<210> SEQ ID NO 98
<211> LENGTH: 42
<212> TYPE: DNA
<213> ORGANISM: Artificial Sequence
<220> FEATURE:
<223> OTHER INFORMATION: Artificial construct - synthetic Primer
      Ex-glnA-2

<400> SEQUENCE: 98

```
gaaccatggg ctagcctcga gttagcagtc gaagtacaat tc                        42
```

<210> SEQ ID NO 99
<211> LENGTH: 50
<212> TYPE: DNA
<213> ORGANISM: Artificial Sequence

```
<220> FEATURE:
<223> OTHER INFORMATION: Artificial construct - synthetic Primer
      Ex-aroL-1

<400> SEQUENCE: 99
ggccctgcag ggaaaggagg cccttcagat gacacaacct cttttctga                 50

<210> SEQ ID NO 100
<211> LENGTH: 31
<212> TYPE: DNA
<213> ORGANISM: Artificial Sequence
<220> FEATURE:
<223> OTHER INFORMATION: Artificial construct - synthetic Primer
      Ex-aroL-2

<400> SEQUENCE: 100
cccgggatcc tcaacaattg atcgtctgtg c                                    31

<210> SEQ ID NO 101
<211> LENGTH: 50
<212> TYPE: DNA
<213> ORGANISM: Artificial Sequence
<220> FEATURE:
<223> OTHER INFORMATION: Artificial construct - synthetic Primer
      Ex-aroK-1

<400> SEQUENCE: 101
ggccctgcag ggaaaggagg cccttcagat gaatgatcaa attcacttag                 50

<210> SEQ ID NO 102
<211> LENGTH: 32
<212> TYPE: DNA
<213> ORGANISM: Artificial Sequence
<220> FEATURE:
<223> OTHER INFORMATION: Artificial construct - synthetic Primer
      Ex-aroK-2

<400> SEQUENCE: 102
cccgggatcc ttaatcgatt tctagatgat gc                                   32

<210> SEQ ID NO 103
<211> LENGTH: 45
<212> TYPE: DNA
<213> ORGANISM: Artificial Sequence
<220> FEATURE:
<223> OTHER INFORMATION: Artificial construct - synthetic Primer JK038f

<400> SEQUENCE: 103
attcgagctc ggtacccggg gatccactac atcgaaaccg gcatc                     45

<210> SEQ ID NO 104
<211> LENGTH: 29
<212> TYPE: DNA
<213> ORGANISM: Artificial Sequence
<220> FEATURE:
<223> OTHER INFORMATION: Artificial construct - synthetic Primer JK039r

<400> SEQUENCE: 104
ctgaactcga gtcagccatg ctccttctc                                       29

<210> SEQ ID NO 105
<211> LENGTH: 34
<212> TYPE: DNA
<213> ORGANISM: Artificial Sequence
<220> FEATURE:
<223> OTHER INFORMATION: Artificial construct - synthetic Primer JK040f
```

```
<400> SEQUENCE: 105
gcatggctga ctcgagttca ggggccttgg ggct                                    34

<210> SEQ ID NO 106
<211> LENGTH: 44
<212> TYPE: DNA
<213> ORGANISM: Artificial Sequence
<220> FEATURE:
<223> OTHER INFORMATION: Artificial construct - synthetic Primer JK041r

<400> SEQUENCE: 106
tagaagcttg catgcctgca ggcagtgagt cgaccaggcc aaag                         44

<210> SEQ ID NO 107
<211> LENGTH: 21
<212> TYPE: DNA
<213> ORGANISM: Artificial Sequence
<220> FEATURE:
<223> OTHER INFORMATION: Artificial construct - synthetic Primer
      Ko-csm-1

<400> SEQUENCE: 107
cttgccgacg agcgtagaaa t                                                  21

<210> SEQ ID NO 108
<211> LENGTH: 21
<212> TYPE: DNA
<213> ORGANISM: Artificial Sequence
<220> FEATURE:
<223> OTHER INFORMATION: Artificial construct - synthetic Primer
      Ko-csm-2

<400> SEQUENCE: 108
gttgaggact accttgactt g                                                  21

<210> SEQ ID NO 109
<211> LENGTH: 54
<212> TYPE: DNA
<213> ORGANISM: Artificial Sequence
<220> FEATURE:
<223> OTHER INFORMATION: Artificial construct - synthetic Primer
      Ex-aroG-1

<400> SEQUENCE: 109
gccctgcagg agatctgaaa ggaggcccct cagatgaatt atcagaacga cgat              54

<210> SEQ ID NO 110
<211> LENGTH: 31
<212> TYPE: DNA
<213> ORGANISM: Artificial Sequence
<220> FEATURE:
<223> OTHER INFORMATION: Artificial construct - synthetic Primer
      Ex-aroG-2

<400> SEQUENCE: 110
cccgggatcc ttacccgcga cgcgcttta c                                        31
```